(12) United States Patent
Braun et al.

(10) Patent No.: US 8,211,892 B2
(45) Date of Patent: Jul. 3, 2012

(54) TETRAHYDROQUINOXALINE UREA DERIVATIVES

(75) Inventors: Alain Jean Braun, Paris (FR); Olivier Crespin, Paris (FR); Claudie Namane, Paris (FR); Eric Nicolai, Paris (FR); Francois Pacquet, Paris (FR); Cecile Pascal, Paris (FR); Christophe Philippo, Paris (FR); Olivier Venier, Paris (FR)

(73) Assignee: Sanofi-Aventis, Paris (FR)

( * ) Notice: Subject to any disclaimer, the term of this patent is extended or adjusted under 35 U.S.C. 154(b) by 169 days.

(21) Appl. No.: 12/843,124

(22) Filed: Jul. 26, 2010

(65) Prior Publication Data

US 2011/0009391 A1    Jan. 13, 2011

Related U.S. Application Data

(63) Continuation of application No. PCT/FR2009/000083, filed on Jan. 27, 2009.

(30) Foreign Application Priority Data

Jan. 28, 2008  (FR) ..................... 08 00429
Aug. 8, 2008  (FR) ..................... 08 04521

(51) Int. Cl.
    *A61K 31/495*  (2006.01)
(52) U.S. Cl. .......... 514/249; 540/575; 544/61; 544/116; 544/238; 544/333; 544/355; 544/359; 346/199; 346/268.1; 548/202; 548/453; 548/518; 549/356; 585/352

(58) Field of Classification Search ............... 514/249; 540/575; 544/61, 116, 238, 333, 355, 359; 546/199, 268.1; 548/202, 453, 518; 549/356; 585/352

See application file for complete search history.

(56) References Cited

FOREIGN PATENT DOCUMENTS

WO   WO2004056745   7/2004
WO   WO2008000951   1/2008

OTHER PUBLICATIONS

International Preliminary Report on Patentability; PCT/FR2009/000083, dated Jan. 27, 2009.

*Primary Examiner* — James O. Wilson
*Assistant Examiner* — Douglas M Willis
(74) *Attorney, Agent, or Firm* — Scully, Scott, Murphy & Presser, P.C.

(57) ABSTRACT

The present invention relates to tetrahydroquinoxaline urea derivatives of Formula (I):

(I)

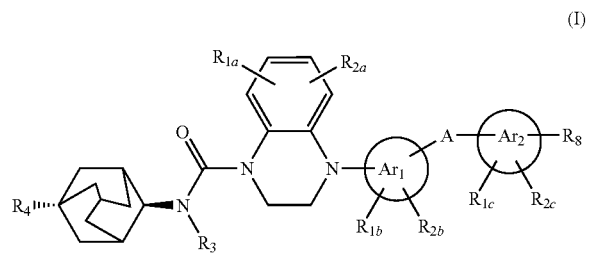

as disclosed herein, to their preparation and to their therapeutic application.

24 Claims, No Drawings

TETRAHYDROQUINOXALINE UREA DERIVATIVES

This application is a Continuation of International Application No. PCT/FR2009/000083, filed Jan. 27, 2009, which is incorporated herein by reference in its entirety.

The present invention relates to tetrahydroquinoxaline urea derivatives, to their preparation and to their therapeutic application.

The compounds according to the invention modulate the activity of 11β-hydroxysteroid dehydrogenase type 1 (11βHSD1) and are of use in the treatment of pathologies in which such a modulation is beneficial, as in the case of metabolic syndrome or non-insulin-dependent type 2 diabetes.

11βHSD1 locally catalyses the conversion of inactive glucocorticoids (cortisone in man) to active glucocorticoids (cortisol in man) in various tissues and organs, mainly the liver and the adipose tissue, but also in the muscles, bones, pancreas, endothelium, ocular tissue and in some parts of the central nervous system. 11βHSD1 acts as a regulator of the action of the glucocorticoids in the tissues and organs where it is expressed (Tomlinson et al., *Endocrine Reviews*, 25(5), 831-866 (2004), Davani et al., *J. Biol. Chem.*, 275, 34841 (2000); Moisan et al., *Endocrinology*, 127, 1450 (1990)).

The main pathologies in which glucocorticoids and inhibition of 11βHSD1 are involved are shown below.

A. Obesity, Type 2 Diabetes and Metabolic Syndrome

The role of 11βHSD1 in obesity, type 2 diabetes and metabolic syndrome (also known under the name of syndrome X or insulin resistance syndrome) where the symptoms include visceral obesity, glucose intolerance, insulin resistance, hypertension, type 2 diabetes and hyperlipidaemia (*Reaven Ann. Rev. Med.*, 44, 121 (1993)) is described in numerous publications. In man, the treatment with carbenoxolone (a non-specific inhibitor of 11βHSD1) improves the insulin sensitivity in thin voluntary patients and in type 2 diabetics (Andrews et al., *J. Clin. Endocrinol. Metab.*, 88, 285 (2003)). Furthermore, the mice whose 11βHSD1 gene has been switched off are resistant to the hyperglycaemia induced by stress and obesity, show an attenuation of the induction of hepatic enzymes of gluconeogenesis (PEPCK and G6P) and exhibit an increase in insulin sensitivity in the adipose tissue (Kotelevstev et al., *Proc. Nat. Acad. Sci.*, 94, 14924 (1997); Morton et al., *J. Biol. Chem.*, 276, 41293 (2001)). Furthermore, transgenic mice where the 11βHSD1 gene has been overexpressed in the adipose tissues exhibit a phenotype similar to that of human metabolic syndrome (Masuzaki et al., *Science*, 294, 2166 (2001)). It should be noted that the phenotype observed exists without an increase in the total of the circulating glucocorticoids but is induced by the specific increase in active glucocorticoids in the adipose deposits.

Furthermore, novel categories of specific 11βHSD1 inhibitors have recently appeared:
  arylsulphonamidothiazoles have shown that they improve insulin sensitivity and reduce the level of glucose in the blood of mice exhibiting hyperglycaemia (Barf et al., *J. Med. Chem.*, 45, 3813 (2002)). Furthermore, in a recent study, it has been shown that compounds of this type reduce food intake and the increase in weight by obese mice (Wang et al., *Diabetologia*, 49, 1333 (2006));
  triazoles have shown that they improve the metabolic syndrome and slow down the progression of atherosclerosis in mice (Hermanowski-Vosatka et al., *J. Exp. Med.*, 202, 517 (2005)).

A2. Microvascular Complications of Diabetes

The presence of chronic complications in the type 2 diabetic patient is often associated with the severity and with the duration of diabetes. Functional and structural microvascular disorders in large part explain the development of certain pathologies observed in the diabetic patient, such as neuropathy, retinopathy and nephropathy (Rayman, Diabetes Review 7, 261-274, 1999; Gärtner and Eigentler, Clin. Nephrol., 70, 1-9, 2008; Zent and Pozzi, Sem. Nephrol., 27, 161-171, 2007; Malecki et al., EJCI 38, 925-930, 2008). Chronic elevation of glycaemia, or glucose intolerance, represent major risk factors of these microvascular complications (Robinson Singleton et al., Diabetes, 52, 2867-2873, 2003; Lachin et al., Diabetes, 57, 995-1001, 2008). By making possible better control of glycaemia, by virtue of a fall in hepatic gluconeogenesis and an increase in insulin sensitivity of the body (see "Obesity, type 2 diabetes and metabolic syndrome" section), 11βHSD1 inhibitors can prevent the progression towards microvascular complications observed in the diabetic patient. However, strict control of glycaemia does not make it possible to completely prevent the development of microvascular complications and makes it necessary to discover novel treatments which make possible a more comprehensive treatment of diabetic and dyslipidaemic patients (Girach et al., Int. J. Clin. Pract., 60 (11), 1471-1483, 2006; Taylor, Curr. Diab. Rep., 8 (5), 345-352, 2008). Advantageously, a study by Chiodini et al. (Diabetes Care, 30, 83-88, 2007) has shown that the secretion of cortisol in diabetic patients was directly associated with the presence of chronic macro- or microvascular complications. Furthermore, the microvascular reactivity and the endothelial function are detrimentally affected in the patient suffering from Cushing's syndrome, exhibiting hypercortisolism (Prazny et al., Physiol. Rev., 57, 13-22, 2008).

More particularly, Bhatia et al. (Ann. Opthalmol., 15, 128-130, 1983) have shown an association between the high plasma cortisol levels and retinopathy in the diabetic patient.

Koh et al. have shown that the treatment by adrenalectomy of patients affected by Cushing's syndrome, which makes it possible to reverse hypercortisolism, improves the renal function.

The clinical parameters of polyneuropathies (sensory perception, cardiac autonomic neuropathy) are associated with an increase in the secretion of cortisol in diabetic patients (Tsigos et al., J. Clin. Endocrinol. Metab., 76, 554-558, 1993).

All these elements show that a decrease in the impact of cortisol by local inhibition of its regeneration via 11βHSD1 inhibitors might have a favourable role in disorders of microcirculation associated with diabetes (polyneuropathy, retinopathy and nephropathy).

B. Cognition and Dementia

Mild cognitive disorders are phenomena common to elderly people and to type 1 and 2 diabetic patients and can gradually result in depression or dementia (Messier et al., *Neurobiol. Aging*, 26, 26; Greenwood et al. (2005), *Neurobiol. Aging*, 26, 45 (2005)). Both in the case of elderly animals and of elderly humans, the differences in individuals for the general cognitive functions have been related to the differences in long-term exposure to glucocorticoids (Lupien et al., *Nat. Neurosci.*, 1, 69 (1998)). Furthermore, the deregulation of the HPA (hypothalamic-pituitary-adrenal) axis resulting in the chronic exposure to glucocorticoids of certain subregions of the brain has been proposed as contributing to the decline in the cognitive functions (McEwen et al., *Curr. Opin. Neurobiol.*, 5, 205, 1995). 11βHSD1 is abundant in the brain and is expressed in numerous subregions, including the hypothalamus, the frontal cortex and the cerebellum (Sandeep et al., *Proc. Natl. Acad. Sci.*, 101, 6734 (2004)). Mice deficient in 11βHSD1 are protected against the dysfunctionings of the hypothalamus associated with glucocorticoids which are related to old age (Yau et al., *Proc. Natl. Acad. Sci.*, 98, 4716, (2001)). Furthermore, in studies in man, it has been shown that the administration of carbenoxolone improves verbal fluidity and verbal memory in elderly people (Yau et al., *Proc. Natl. Acad. Sci.*, 98, 4716 (2001), Sandeep et al., *Proc. Natl. Acad. Sci.*, 101, 6734 (2004)). Finally, the use of selective 11βHSD1 inhibitors of triazole type has shown that they extend the retention of memory in elderly mice (Rocha et al., Abstract 231 *ACS Meeting*, Atlanta, 26-30 Mar. 2006). Furthermore, it has been shown, in diabetic rodent models, that the level of corticosterone contributed to the development of cognitive pathologies induced by diabetes (Stranhan et al., Nature Neurosc., 11, 309 (2008)). Thus, 11βHSD1 inhibitors, which make possible a reduction in the regeneration of cortisol in the hippocampus, might have a beneficial role on the cognitive functions in elderly diabetic patients (Sandeep et al., *Proc. Natl. Acad. Sci.*, 101, 6734 (2004)).

C. Intraocular Pressure

Glucocorticoids can be used by the topical route or systemic route for a great variety of pathologies of clinical ophthalmology. A particular complication of these treatments is the glaucoma induced by the use of corticosteroids. This pathology is characterized by the increase in the intraocular pressure (IOP). In the most severe cases and for the untreated forms, the IOP can result in partial loss of field of vision and possibly in complete loss of vision. The IOP is the result of an imbalance between the production of aqueous humour and its drainage. The aqueous humour is produced in the nonpigmented epithelial cells and the drainage is carried out through the cells of the trabecular network. The 11βHSD1 is located in the nonpigmented epithelial calls and its function is clearly the amplification of the activity of the glucocorticoids in these cells (Stokes et al., *Invest. Opthalmol. Vis. Sci.*, 41, 1629 (2000)). This notion is confirmed by the observation that the concentration of free cortisol is in high excess with respect to the cortisone in the aqueous humour (ratio 14/1). The functional activity of 11βHSD1 in the eyes was evaluated by studying the action of carbenoxolone in healthy volunteers. After treating with carbenoxolone for seven days, the IOP is reduced by 18% (Rauz et al., *Invest. Ophtamol. Vis. Sci.*, 42, 2037 (2001)). The inhibition of 11βHSD1 in the eyes is thus predicted as reducing the local concentration of glucocorticoids and the IOP, producing a beneficial effect in the treatment of glaucoma and other disorders of vision.

D. Hypertension

The hypertensive substances resulting from the adipocytes, such as leptin and angiotensinogen, have been proposed as being key components in the hypertension pathologies related to obesity (Wajchenberg et al., *Endocr. Rev.*, 21, 697 (2000)). Leptin, which is secreted in excess in transgenic aP2-11βHSD1 mice (Masuzaki et al., *J. Clinical Invest.*, 112, 83 (2003)), can activate various networks of sympathetic neuronal systems, including those which regulate the arterial pressure (Matsuzawa et al., *Acad. Sci.*, 892, 146 (1999)). Furthermore, the renin-angiotensin system (RAS) has been identified as being a determining route in the variation in arterial pressure. Angiotensinogen, which is produced in the liver and the adipose tissue, is a key substrate for renin and is the cause of the activation of the RAS. The plasma angiotensinogen level is significantly high in transgenic aP2-11βHSD1 mice, as are those of angiotensin II and of aldosterone (Masuzaki et al., *J. Clinical Invest.*, 112, 83 (2003)); these components result in the elevation of the arterial pressure. The treatment of these mice with low doses of an angiotensin II receptor antagonist does away with this hypertension (Masuzaki et al., *J. Clinical Invest.*, 112, 83 (2003)). These items of information illustrate the importance of the local activation of the glucocorticoids in the adipose tissue and the liver and suggest that this hypertension can be caused or exacerbated by the activity of 11βHSD1 in these tissues. The inhibition of 11βHSD1 and the reduction in the level of glucocorticoids in the adipose tissue and/or in the liver is thus predicted as having a beneficial role in the treatment of hypertension and the associated cardiovascular pathologies.

D2. Salt-Sensitive Arterial Hypertension

It is estimated that approximately 30 to 50% of the general population exhibits a specific sensitivity to salt. Much evidence suggests a connection between sensitivity to salt and arterial hypertension and cardiovascular risks (Weinberger M H, Curr. Opin. Cardiol., 2004, 19, 353-356). It has been shown that subjects sensitive to salt exhibit a reduced variability in heart rate, and also an increased arterial pressure and an increased production of cortisol during mental stress, in comparison with nonsensitive subjects (Weber C S et al., Journal of Human Hypertension, 2008, 22, 423-431). Furthermore, a recent study by Liu Y et al. (Physiol. Genomics, 2008, Sep. 30) has demonstrated, in the Dahl salt-sensitive rat, that the specific inhibition of the expression of renal medullary 11βHSD1, by the use of shRNA, makes it possible to very markedly reduce, in animals, the elevation in the mean arterial pressure brought about by a salty diet. These elements suggest that an inhibitor of the 11βHSD1 enzyme would very probably have a beneficial effect on this form of arterial hypertension.

E. Osteoporosis

The development of the skeleton and the bone functions are also regulated by the action of the glucocorticoids. 11βHSD1 is present in the osteoclasts and osteoblasts. The treatment of healthy volunteers with carbenoxolone has shown a reduction in the bone resorption markers without change in the bone formation markers (Cooper et al., Bone, 27, 375 (2000)). The inhibition of 11βHSD1 and the reduction in the level of glucocorticoids in the bones might thus be used as a protective mechanism in the treatment of osteoporosis.

F. Highly Active Antiretroviral Therapy (HAART) Associated Lipodystrophy or HAL Syndrome The use of an intensive antiretroviral treatment for patients affected by AIDS often results in a lipodystrophy (HAL) syndrome resembling Cushing's syndrome and associating increase in the abdominal fatty mass, hypertriglyceridaemia and insulin resistance. It has been shown (Sutinen et al., Diabetologia, 47, 1668 (2004)) that this lipodystrophy (HAL) was associated with an increase in the expression of 11βHSD1 in the adipose tissue of the patients. 11β-HSD1 inhibitors, which make possible a reduction in the regeneration of cortisol in the adipose tissue, might thus have a beneficial role in patients affected by lipodystrophy associated with an intensive treatment of AIDS by antiretrovirals (HAL syndrome).

G. Infectious Diseases

Some infections, such as tuberculosis, are associated with disturbances to the immune response (Ellner J J, J. Lab. Clin. Med., 130, 469 (1997)). This distinctive feature, which is generally accompanied by the increase in the secretion of certain cytokines (IL-10, TNFα) and/or the response to certain cytokines, appears to be at least partially caused by local tissue exposure of the immune cells to glucocorticoids. Furthermore, the administration of synthetic glucocorticoids to man or animals brings about the reactivation of tuberculosis in man and in animals (Haanas O C et al., Eur. J. Respir. Dis., 64, 294 (1998), Brown et al., Infect. Immun., 63, 2243

(1995)). Likewise, the various stresses which are activators of the HPA axis have as a consequence a reactivation of this infection.

Apart from these specific cases, the circulating levels of glucocorticoids and the activation of the HPA axis appear to be normal in patients affected by tuberculosis (Baker et al., Am. J. Resp. Grit. Care Med., 162, 1641 (2000)). On the other hand, the levels of cortisol versus cortisone in the bronchoalveolar fluid appear increased, reflecting an adjustment in the metabolism of the glucocorticoids towards the active form (dependent in particular on the activity of 11βHSD1). The inhibition of 11βHSD1 in the peripheral tissues and in particular the lungs might consequently produce a beneficial effect on the stabilization and then the reversion of the infection.

H. Cardiac Hypertrophy and Cardiac Insufficiency

Cardiovascular diseases represent the leading cause of morbidity and mortality in industrialized countries, and left ventricular hypertrophy (LVH) is a risk factor independent of cardiovascular mortality (Havranek E P, Am. J. Med., 121, 870-875, 2008). Apart from genetic causes, pathological conditions, such as arterial hypertension, myocardial infarction or renal insufficiency, can result in compensatory hypertrophy, subsequently progressing towards chronic cardiac insufficiency. The 11βHSD1 activity, which makes possible the conversion of 11-dehydrocorticosterone to corticosterone, is expressed in the cardiomyocytes of neonate rats and contributes to the modulating activity of glucocorticoids and aldosterone in the heart (Sheppard and Autelitano, Endocrinology, 143, 198-204, 2002). By using these cells, Lister et al. (Cardiovascular Research, 70, 555-565, 2006) have shown that the hypertrophy of the cardiomyocytes induced by pharmacological agents was accompanied by an increase in the activity of enzyme 11βHSD1. In the same study, the use of RU-486, a specific antagonist of glucocorticoid receptors, made it possible to reduce the hypertrophy of the cells.

Inhibitors of the 11βHSD1 activity might therefore limit cardiac hypertrophy and thus prevent the progression towards cardiac insufficiency.

I. Liver Diseases:

I1. Hepatic Steatosis:

Studies in severely obese patients (BMI>35 kg/m$^2$) report a prevalence of 91% for steatosis and 37% for steatohepatitis (Neuschwander-Tetri & Caldwell, Hepatology, 37, 1202-1219, 2003). Type 2 diabetes is another major factor associated with steatosis with a prevalence of 70% reported with regard to a sample of 3000 diabetic patients in Italy (Targher et al., Diabetes Care, 30, 1212-1218, 2007). Furthermore, an association between insulin resistance and hepatic steatosis independently of obesity has been observed in patients affected by non-alcoholic hepatic steatosis (Manchesini et al., Diabetes, 50, 1844-1850, 2001). In obese patients, the 11βHSD1 activity appears modified, as is testified by the activation of orally administered cortisone, the urinary excretion of cortisol metabolites or the hepatic tissue expression of 11βHSD1 (Tomlinson et al., Endocrine Rev., 25, 831-866, 2004; Rask et al., J. Clin. Endocrin. Metab., 86, 1418-1421, 2001; Stewart et al., J. Clin. Endocrin. Metabol., 84, 1022-1027, 1999; Valsamakis et al., J. Clin. Endocrinol. Metabol., 89, 4755-4761, 2004). Transgenic mice overexpressing 11βHSD1 in the adipose tissue or in the liver develop hepatic steatosis and dyslipidaemia (Masuzaki et al., Sciences, 294, 2166-2170, 2001; Paterson et al., PNAS, 101, 7088-7093, 2004). 11βHSD1 inhibition in rats reduces fasting triglyceridaemia following a reduction in the secretion of hepatic triglycerides and following an increase in the uptake and tissue oxidation of fatty acids, which is also reflected in the liver by a significant reduction in triglycerides (Berthiaume et al., Am. J. Physiol. Endocrinol. Metab., 293, 1045-1052, 2007). The local reduction of active glucocorticoid by inhibition of the 11βHSD1 activity is thus envisaged in order to reduce the insulin-resistance and lipid effects of glucocorticoids and thus to reduce hepatic steatosis.

I2. Metabolic Steatohepatitis:

Metabolic steatohepatitis represents a stage in the development of metabolic hepatic steatosis in some people. A correlation is described between urinary cortisol, the concentration of post-dexamethasone cortisol and the grade of hepatic necroinflammation and fibrosis in subjects affected by metabolic steatohepatitis, suggesting the existence of a subclinic or local hypercorticolism (Targher et al., Clin. Endocrinol., 64, 337-341, 2006). A general and local correction (in the centrilobular region) of the insulin resistance as well as an improvement in the oxidation of hepatic fatty acids by inhibition of the 11βHSD1 activity, and also the reduction in the profibrotic effects of cortisol, are thus predictive of an improvement in the development of the pathology.

I3. Liver Regeneration:

The liver exhibits a high ability to regenerate which is entirely necessary in the case of attacks of infectious or non-infectious origins, in particular originating from the digestive tract. For example, hepatic apoptosis or hepatic necrosis can result from medicinal, viral, alcoholic, metabolic, cholestatic or vascular ischaemic toxicity. Glucocorticoids inhibit hepatocyte proliferation and liver tissue regeneration (Tsukamoto & Kojo, Gut, 30, 387-390, 1989; Nagy et al., Hepatology, 28, 423-429, 1998; Tannuri et al., Pediatr. Transplantation, 12, 73-79, 2008). Inhibition of the 11βHSD1 reductase activity might in this context reduce the negative local effects of cortisol on liver regeneration and are to be lined up with the proangiogenic effects of these inhibitors and with their positive action on certain growth factors.

J. Healing of Chronic Skin Wounds:

The healing of chronic wounds depends on the underlying pathological context which modifies and desynchronizes the physiological stages of healing. In the chronic ulcer of the diabetic patient, the potential advantage of 11βHSD1 inhibitors should be seen simultaneously in the correction of the outward signs of diabetes, taking into account the local pathological role of the endogenous corticoids at the wound and the state of progression of the pathology. A certain amount of evidence exists showing that endogenous corticoids are directly involved in the detrimental change in the healing of wounds in man and in rodent animal models (Goforth et al., J. Foot Surgery, 19, 199-2002, 1980; Dostal et al, Arch. Surg., 125, 636-640, 1990; Bitard, Am. J. Pathology, 152, 547-554, 1998). Local production of cortisol is predicted by the presence of an 11βHSD1 reductase activity in the endothelial, fibroblast or cutaneous region in man and in rodents (Gong et al., Steroids, 73, 1187-1196, 2008; Hammami et al., J. Clin. Endocrinol. Metabol., 73, 326-334, 1991; Cooper et al., ENDO 2003; Teelucksingh et al., Lancet, 335, 1060-1063, 1990). Cortisol and other glucocorticoids inhibit the healing of the skin ulcer via numerous mechanisms and at different stages: detrimental change in microcirculatory vasomotricity, inhibition of the inflammatory phase, in particular with regard to the synthesis of prostaglandins, leukotrienes, cytokines, such as TNFα and the production of IL-1β, IL-4, and the like, and the signalling of IFNγ, increase in infection, reduction in cell motility and proliferation of keratinocytes, reduction in the expression of proangiogenic factors, such as VEGF, suppression of the expression of TGFβ1 and 2, which are essential in the production of collagen by fibroblasts and their conversion to myofibroblasts, suppression of the expression of MMP1, 2, 9 and 10 and induction of TIMP, thus blocking the remodelling, promotion of epidermal terminal differentiation but inhibition of the first stages of differentiation, the consequence of which is a weakening of the epidermis (Bitard, *Am. J. Pathology*, 152, 547-554, 1998; Beer et al., *Vitam. Horm.*, 59, 217-239, 2000; Rosen & Miner, *Endocrine Review*, 26, 452-464, 2005; Stojadinovic et al., *J. Biol. Chem.*, 282, 4021-4034, 2007). Conversely and as expected, inhibition of the 11βHSD1 reductase activity is described in order to induce vasodilatation and a proangiogenic and antiinfective effect (see the corresponding sections) and, in some inflammatory situations, in order to produce a heightening in and an overexpression of growth factors, such as TGFβ (Zhang et al., *J. Immunology*, 179, 6325-6335, 2007). 11HSD1 inhibitors should thus make it possible, by acting in this way, to improve the healing of chronic skin wounds.

Tetrahydroquinoxaline urea derivatives carrying an adamantane nucleus which modulate the activity of 11βHSD1 have now been found.

A subject-matter of the present invention is compounds corresponding to the formula (I):

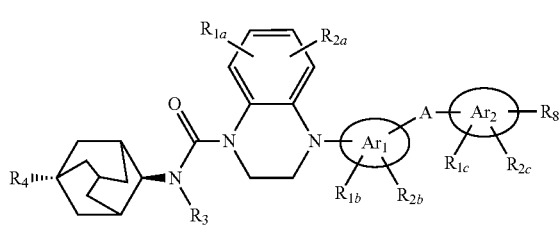

in which:
- A represents a bond, an oxygen atom or an —O—$CH_2$— group,
- $Ar_1$ represents a phenyl or heteroaryl group,
- $Ar_2$ represents a phenyl group, a heteroaryl group or a heterocycloalkyl group,
- $R_{1a,b,c}$ and $R_{2a,b,c}$, which are identical or different, each represent a hydrogen or halogen atom or an alkyl, cycloalkyl, -alkylcycloalkyl optionally substituted by one or more halogen atoms, —$OR_5$ (hydroxyl or alkoxy), hydroxyalkyl, alkoxyalkyl, alkoxyalkoxy, haloalkyl, —O-haloalkyl, oxo, —CO-alkyl, —CO-alkyl-$NR_6R_7$, —CO-haloalkyl, —$COOR_5$, -alkyl-$COOR_5$, —O-alkyl-$COOR_5$, —$SO_2$-alkyl, —$SO_2$-cycloalkyl, —$SO_2$-alkylcycloalkyl, —$SO_2$-alkyl-$OR_5$, —$SO_2$-alkyl-$COOR_5$, —$SO_2$-alkyl-$NR_6R_7$, —$SO_2$-haloalkyl, -alkyl-$SO_2$-alkyl, —$SO_2$—$NR_6R_7$, —$SO_2$-alkylalkoxyalkoxy, —$CONR_6R_7$, -alkyl-$CONR_6R_7$ or —O-alkyl-$NR_6R_7$ group, or also $R_{1a}$, $R_{1b}$ and $R_{1c}$ are respectively bonded to $R_{2a}$, $R_{2b}$ and $R_{2c}$ and to the carbon atom which carries them and represent —O-alkyl-O—;
- $R_3$ represents a hydrogen atom or an alkyl group,
- $R_4$ represents a hydrogen or halogen atom or a cyano, —$OR_5$, hydroxyalkyl, —$COOR_5$, —$NR_6R_7$, —$CONR_6R_7$, —$SO_2$-alkyl, —$SO_2$—$NR_6R_7$, —$NR_6$—$COOR_5$, —$NR_6$—$COR_5$ or —CO—$NR_6$-alkyl-$OR_5$ group;
- $R_5$, $R_6$ and $R_7$, which are identical or different, each represent a hydrogen atom, an alkyl group or an -alkylphenyl group, and
- $R_8$ represents a hydrogen atom, an alkyl group or a group of formula —B-Het, where B can be absent or can represent a bond, an oxygen atom or a —CO— or —$SO_2$—$(CH_2)_n$— group with n equal to 0, 1 or 2 and where Het represents a heteroaryl or a heterocycloalkyl optionally substituted by 1 to 3 groups chosen from alkyl, —$SO_2$-alkyl and —$COOR_5$ groups.

The compounds of formula (I) can comprise one or more asymmetric carbon atoms. They can therefore exist in the form of enantiomers or diastereoisomers. These enantiomers or diastereoisomers, and their mixtures, including racemic mixtures, come within the invention.

The compounds of formula (I) can exist in the form of bases or acids or be salified by acids or bases, in particular pharmaceutically acceptable acids or bases. Such addition salts come within the invention. These salts are advantageously prepared with pharmaceutically acceptable acids or bases but the salts of other acids or bases, for example of use in the purification or the isolation of the compounds of formula (I), also come within the invention.

The compounds of formula (I) can also exist in the form of hydrates or solvates, namely in the form of combinations or associations with one or more molecules of solvent. Such solvates also come within the invention.

In the context of the present invention and unless otherwise mentioned in the text:
- a halogen atom is understood to mean a fluorine, a chlorine, a bromine or an iodine;
- an alkyl group is understood to mean a saturated, linear or branched, aliphatic group comprising from 1 to 5 carbon atoms. Mention may be made, by way of examples, of the methyl, ethyl, propyl, methylpropyl, isopropyl, butyl, isobutyl, tert-butyl or pentyl groups;
- a cycloalkyl group is understood to mean a cyclic alkyl group comprising from 3 to 6 carbon atoms. Mention may be made, by way of examples, of the cyclopropyl, cyclobutyl or cyclopentyl groups;
- an alkoxy group is understood to mean a radical of the formula —O-alkyl where the alkyl group is as defined above;
- a hydroxyalkyl group is understood to mean a radical of formula -alkyl-OH where the alkyl group is as defined above;
- an alkoxyalkyl group is understood to mean a radical of formula -alkyl-O-alkyl where the identical or different alkyl groups are as defined above. Mention may be made, by way of examples, of —$(CH_2)_2$—O—$CH_3$, —$(CH_2)_3$—O—$CH_3$ or —CH—$(CH_2$—O—$CH_3)_2$;
- an alkoxyalkoxy group is understood to mean a radical of formula —O-alkyl-O-alkyl where the identical or different alkyl groups are as defined above;
- a haloalkyl group is understood to mean an alkyl group as defined above substituted by 1 to 5 halogen atoms as defined above. Mention will be made, for example, of the trifluoromethyl group;
- a heteroaryl group is understood to mean an aromatic group comprising from 5 to 9 atoms, including from 1 to 3 heteroatoms, such as nitrogen, oxygen or sulphur. Mention may in particular be made of the pyridinyl, pyrimidinyl, pyridazinyl or thiazolyl groups; and
- a heterocycloalkyl is understood to mean an optionally bridged mono- or bicyclic alkyl group comprising from 4 to 9 atoms or optionally partially unsaturated, one or two atoms of which are heteroatoms, such as oxygen, nitrogen or sulphur. Mention may in particular be made of the pyrrolidinyl, piperidinyl, piperazinyl, tetrahydropyranyl, morpholinyl, homopiperazinyl, 3,8-diazabicyclo[3.2.1]octyl, thiomorpholinyl, thiomorpholinyl 1,1- dioxide, octahydropyrrolo[3,4-c]pyrrolyl, 1,2,3,6-tetrahydropyridinyl or 2,5-diazabicyclo[2.2.1]heptyl groups;

a carbonyl functional group can be represented by CO.

In the context of the present invention, $R_{1a,b,c}$ denotes the $R_{1a}$, $R_{1b}$ and $R_{1c}$ groups and $R_{2a,b,c}$ denotes the $R_{2a}$, $R_{2b}$ and $R_{2c}$ groups. When $Ar_2$ represents a heterocycloalkyl group, the $R_{1c}$, $R_{2c}$ and $R_8$ groups can be carried by any atom of the said heterocycle, whether a carbon atom or a heteroatom (for example a nitrogen atom), including by the same atom of the said heterocycloalkyl (for example when a sulphur atom is involved).

Mention may be made, among the compounds of formula (I) according to the invention, of a subgroup of compounds in which:

A represents a bond, an oxygen atom or an —O—$CH_2$— group, $Ar_1$ represents a phenyl or heteroaryl group, $Ar_2$ represents a phenyl group, a heteroaryl group or a heterocycloalkyl group, $R_{1a,b,c}$ and $R_{2a,b,c}$, which are identical or different, each represent a hydrogen or halogen atom or an alkyl, —$OR_5$, hydroxyalkyl, alkoxyalkyl, alkoxyalkoxy, haloalkyl, —O-haloalkyl, oxo, —CO-alkyl, —CO-haloalkyl, —$COOR_5$, -alkyl-$COOR_5$, —O-alkyl-$COOR_5$, —$SO_2$-alkyl, —$SO_2$-haloalkyl, -alkyl-$SO_2$-alkyl, —$SO_2$—$NR_6R_7$, —$CONR_6R_7$, -alkyl-$CONR_6R_7$ or —O-alkyl-$NR_6R_7$ group, $R_3$ represents a hydrogen atom or an alkyl group, $R_4$ represents a hydrogen or halogen atom or a cyano, —$OR_5$, hydroxyalkyl, —$COOR_5$, —$NR_6R_7$, —$CONR_6R_7$, —$SO_2$-alkyl or —$SO_2$—$NR_6R_7$ group, $R_5$, $R_6$ and $R_7$, which are identical or different, each represent a hydrogen atom or an alkyl group, and $R_8$ represents a hydrogen atom or a group of formula —B-Het, where B can be absent or can represent a bond, an oxygen atom or a —CO— or —$SO_2$— group and where Het represents a heterocycloalkyl optionally substituted by 1 to 3 groups chosen from alkyl, —$SO_2$-alkyl and —$COOR_5$ groups.

Mention may be made, among the compounds of formula (I) according to the invention, of a subgroup of compounds in which:

A represents a bond, an oxygen atom or an —O—$CH_2$— group, $Ar_1$ represents a phenyl or heteroaryl group, $Ar_2$ represents a phenyl group, a heteroaryl group or a heterocycloalkyl group, $R_{1a,b,c}$ and $R_{2a,b,c}$, which are identical or different, each represent a hydrogen or halogen atom or an alkyl, cycloalkyl, —$OR_5$ (hydroxyl or alkoxy), hydroxyalkyl, alkoxyalkyl, alkoxyalkoxy, haloalkyl, —O-haloalkyl, oxo, —CO-alkyl, —CO-alkyl-$NR_6R_7$, —CO-haloalkyl, —$COOR_5$, -alkyl-$COOR_5$, —O-alkyl-$COOR_5$, —$SO_2$-alkyl, —$SO_2$-cycloalkyl, —$SO_2$-alkylcycloalkyl, —$SO_2$-alkyl-$OR_5$, —$SO_2$-alkyl-$COOR_5$, —$SO_2$-alkyl-$NR_6R_7$, —$SO_2$-haloalkyl, -alkyl-$SO_2$-alkyl, —$SO_2$—$NR_6R_7$, —$SO_2$-alkyl-O-alkyl-$OR_5$, —$CONR_6R_7$, -alkyl-$CONR_6R_7$ or —O-alkyl-$NR_6R_7$ group, or also $R_{1a}$, $R_{1b}$ and $R_{1c}$ are respectively bonded to $R_{2a}$, $R_{2b}$ and $R_{2c}$ and to the carbon atom which carries them and represent —O-alkyl-O—;

$R_3$ represents a hydrogen atom or an alkyl group, $R_4$ represents a hydrogen or halogen atom or a cyano, —$OR_5$, hydroxyalkyl, —$COOR_5$, —$NR_6R_7$, —$CONR_6R_7$, —$SO_2$-alkyl, —$SO_2$—$NR_6R_7$, —$NR_6$—$COOR_5$ or —CO—$NR_6$-alkyl-$OR_5$ group;

$R_5$, $R_6$ and $R_7$, which are identical or different, each represent a hydrogen atom, an alkyl group or an -alkylphenyl group, and $R_8$ represents a hydrogen atom, an —$SO_2$-alkyl group or a group of formula —B-Het, where B can be absent or can represent a bond, an oxygen atom or a —CO— or —$SO_2$—$(CH_2)_n$— group with n equal to 0, 1 or 2 and where Het represents a heteroaryl or a heterocycloalkyl optionally substituted by 1 to 3 groups chosen from alkyl, —$SO_2$-alkyl and —$COOR_5$ groups.

Mention may be made, among the compounds of formula (I) according to the invention, of a subgroup of compounds in which:

A represents a bond, an oxygen atom or an —O—$CH_2$— group, $Ar_1$ represents a phenyl or heteroaryl group, $Ar_2$ represents a phenyl group, a heteroaryl group or a heterocycloalkyl group, $R_{1a,b,c}$ and $R_{2a,b,c}$, which are identical or different, each represent a hydrogen or halogen atom or an alkyl, cycloalkyl, -alkylcycloalkyl optionally substituted by one or more halogen atoms, —$OR_5$ (hydroxyl or alkoxy), hydroxyalkyl, alkoxyalkyl, haloalkyl, —O-haloalkyl, oxo, —CO-alkyl, —CO-alkyl-$NR_6R_7$, —$COOR_5$, -alkyl-$COOR_5$, —$SO_2$-alkyl, —$SO_2$-cycloalkyl, —$SO_2$-alkylcycloalkyl, —$SO_2$-alkyl-$OR_5$, —$SO_2$-alkyl-$COOR_5$, —$SO_2$-alkyl-$NR_6R_7$, —$SO_2$-haloalkyl, -alkyl-$SO_2$-alkyl, —$SO_2$-alkylalkoxyalkoxy, —$CONR_6R_7$ or —O-alkyl-$NR_6R_7$ group, or also $R_{1a}$, $R_{1b}$ and $R_{1c}$ are respectively bonded to $R_{2a}$, $R_{2b}$ and $R_{2c}$ and to the carbon atom which carries them and represent —O-alkyl-O—;

$R_3$ represents a hydrogen atom or an alkyl group, $R_4$ represents a hydrogen or halogen atom or a cyano, —$OR_5$, hydroxyalkyl, —$COOR_5$, —$CONR_6R_7$, —$NR_6$—$COOR_5$, —$NR_6$—$COR_5$ or —CO—$NR_6$-alkyl-$OR_5$ group;

$R_5$, $R_6$ and $R_7$, which are identical or different, each represent a hydrogen atom, an alkyl group or an -alkylphenyl group, and $R_8$ represents a hydrogen atom, an alkyl group or a group of formula —B-Het, where B can be absent or can represent a bond, an oxygen atom or a —CO— or —$SO_2$—$(CH_2)_n$— group with n equal to 0, 1 or 2 and where Het represents a heteroaryl or a heterocycloalkyl optionally substituted by 1 to 3 groups chosen from alkyl, —$SO_2$-alkyl and —$COOR_5$ groups.

Mention may be made, among the compounds of formula (I) according to the invention, of a subgroup of compounds in which:

A represents a bond, an oxygen atom or an —O—$CH_2$— group, and/or $Ar_1$ represents a phenyl or heteroaryl group, and/or $Ar_2$ represents a phenyl group, a heteroaryl group or a heterocycloalkyl group, and/or $R_{1a,b,c}$ and $R_{2a,b,c}$, which are identical or different, each represent a hydrogen or halogen atom or an alkyl, cycloalkyl, -alkylcycloalkyl optionally substituted by one or more halogen atoms, —$OR_5$ (hydroxyl or alkoxy), hydroxyalkyl, alkoxyalkyl, haloalkyl, —O-haloalkyl, oxo, —CO-alkyl, —CO-alkyl-$NR_6R_7$, —$COOR_5$, -alkyl-$COOR_5$, —$SO_2$-alkyl, —$SO_2$-cycloalkyl, —$SO_2$-alkylcycloalkyl, —$SO_2$-alkyl-$OR_5$, —$SO_2$-alkyl-$COOR_5$, —$SO_2$-alkyl-$NR_6R_7$, —$SO_2$-haloalkyl, -alkyl-$SO_2$-alkyl, —$SO_2$-alkylalkoxyalkoxy, —$CONR_6R_7$ or —O-alkyl-$NR_6R_7$ group, or also $R_{1a}$, $R_{1b}$ and $R_{1c}$ are respectively bonded to $R_{2a}$, $R_{2b}$ and $R_{2c}$ and to the carbon atom which carries them and represent —O-alkyl-O—;

and/or $R_3$ represents a hydrogen atom or an alkyl group, and/or $R_4$ represents a hydrogen or halogen atom or a cyano, —$OR_5$, hydroxyalkyl, —$COOR_5$, —$CONR_6R_7$, —$NR_6$—$COOR_5$, —$NR_6$—$COR_5$ or —CO—$NR_6$-alkyl-$OR_5$ group;

and/or $R_5$, $R_6$ and $R_7$, which are identical or different, each represent a hydrogen atom, an alkyl group or an -alkylphenyl group, and/or $R_8$ represents a hydrogen atom, an alkyl group or a group of formula —B-Het, where B can be absent or can represent a bond, an oxygen atom or a —CO— or —$SO_2$—$(CH_2)_n$— group with n equal to 0, 1 or 2 and where Het represents a heteroaryl or a heterocycloalkyl optionally substituted by 1 to 3 groups chosen from alkyl, —$SO_2$-alkyl and —$COOR_5$ groups.

Mention may be made, among the compounds of formula (I) according to the invention, of a subgroup of compounds in which A represents a bond.

Another subgroup of compounds of formula (I) according to the invention is such that $Ar_1$ represents a phenyl group.

Another subgroup of compounds of formula (I) according to the invention is such that $Ar_1$ represents a heteroaryl group. Advantageously, $Ar_1$ represents a pyridinyl, pyrimidinyl or thiazolyl group.

Another subgroup of compounds of formula (I) according to the invention is such that $Ar_1$ represents a phenyl, pyridinyl, pyrimidinyl, pyridazinyl or thiazolyl group. Advantageously, $Ar_1$ represents a phenyl, pyridinyl, pyrimidinyl or thiazolyl group.

Another subgroup of compounds of formula (I) according to the invention is such that $Ar_2$ represents a phenyl group.

Another subgroup of compounds of formula (I) according to the invention is such that $Ar_2$ represents a heteroaryl group.

Another subgroup of compounds of formula (I) according to the invention is such that $Ar_2$ represents a heterocycloalkyl group.

Another subgroup of compounds of formula (I) according to the invention is such that $Ar_2$ represents a phenyl, pyridinyl, pyrimidinyl, piperidinyl, piperazinyl, homopiperazinyl, 3,8-diazabicyclo[3.2.1]octyl, morpholinyl, thiomorpholinyl, octahydropyrrolo[3,4-c]pyrrolyl, 1,2,3,6-tetrahydropyridinyl or 2,5-diazabicyclo[2.2.1]heptyl group. Advantageously, $Ar_2$ represents a phenyl, pyridinyl, pyrimidinyl, piperidinyl or piperazinyl group.

Mention may be made, among the compounds of formula (I) according to the invention in which $Ar_1$ represents a phenyl group or a 6-membered heteroaryl, of those in which the bond between the A-$Ar_2$ and $Ar_1$ nuclei is in the para position with respect to the bond between $Ar_1$ and the nitrogen atom of the tetrahydroquinoxaline nucleus to which it is bonded.

Mention may be made, among the compounds of formula (I) according to the invention in which $Ar_2$ represents a heteroaryl or heterocycloalkyl group, of those which are bonded to the group A via a heteroatom.

Another subgroup of compounds of formula (I) according to the invention is such that $R_{1a}$, $R_{2a}$, $R_{1b}$ and $R_{2b}$, which are identical or different, each represent a hydrogen or halogen atom or an alkyl or alkoxy group. Advantageously, $R_{1a}$ and $R_{2a}$, which are identical or different, each represent a hydrogen or halogen atom and $R_{1b}$ and $R_{2b}$ each represent a hydrogen atom.

Another subgroup of compounds of formula (I) according to the invention is such that $R_{1c}$ and $R_{2c}$, which are identical or different, each represent a hydrogen or halogen atom or an alkyl, alkoxy, —$SO_2$-alkyl or —$SO_2$-cycloalkyl group.

Another subgroup of compounds of formula (I) according to the invention is such that $R_3$ represents a hydrogen atom.

Another subgroup of compounds of formula (I) according to the invention is such that $R_4$ represents a hydrogen or halogen atom or a cyano, hydroxyl, hydroxyalkyl, —$COOR_5$ or —$CONH_2$ group.

Another subgroup of compounds of formula (I) according to the invention is such that $R_8$ represents a hydrogen atom, an alkyl group or a group of formula —B-Het, where B can be absent or can represent a bond, an oxygen atom or a —CO— or —$SO_2$—$(CH_2)_n$— group with n equal to 0, 1 or 2 and where Het represents a pyrrolidinyl, piperidinyl, piperazinyl, tetrahydropyranyl, morpholinyl or pyridinyl group, the said Het group optionally being substituted by 1 to 3 groups chosen from alkyl, —$SO_2$-alkyl and —$COOR_5$ groups.

Furthermore, B can be absent and the Het group can occur in the spiro position on the $Ar_2$ nucleus, when the latter represents a heterocycloalkyl group.

The subgroups defined above, taken separately or in combination, also come within the invention.

Mention may in particular be made of the subgroup of compounds of formula (I) according to the invention in which:

A represents a bond, an oxygen atom or an —O—$CH_2$— group, $Ar_1$ represents a phenyl, pyridinyl, pyrimidinyl, pyridazinyl or thiazolyl group, $Ar_2$ represents a phenyl, pyridinyl, pyrimidinyl, piperidinyl, piperazinyl, homopiperazinyl, 3,8-diazabicyclo[3.2.1]octyl, morpholinyl, thiomorpholinyl, octahydropyrrolo[3,4-c]pyrrolyl, 1,2,3,6-tetrahydropyridinyl or 2,5-diazabicyclo[2.2.1]heptyl group, $R_{1a,b,c}$ and $R_{2a,b,c}$, which are identical or different, each represent a hydrogen or halogen atom or an alkyl, cycloalkyl, -alkylcycloalkyl optionally substituted by one or more halogen atoms, —$OR_5$ (hydroxyl or alkoxy), hydroxyalkyl, alkoxyalkyl, haloalkyl, —O-haloalkyl, oxo, —CO-alkyl, —CO-alkyl-$NR_6R_7$, —$COOR_5$, -alkyl-$COOR_5$, —$SO_2$-alkyl, —$SO_2$-cycloalkyl, —$SO_2$-alkylcycloalkyl, —$SO_2$-alkyl-$OR_5$, —$SO_2$-alkyl-$COOR_5$, —$SO_2$-alkyl-$NR_6R_7$, —$SO_2$-haloalkyl, -alkyl-$SO_2$-alkyl, —$SO_2$-alkylalkoxyalkoxy, —$CONR_6R_7$ or —O-alkyl-$NR_6R_7$ group, or also $R_{1a}$, $R_{1b}$ and $R_{1c}$ are respectively bonded to $R_{2a}$, $R_{2b}$ and $R_{2c}$ and to the carbon atom which carries them and represent —O-alkyl-O—, $R_3$ represents a hydrogen atom or an alkyl group, $R_4$ represents a hydrogen or halogen atom or a cyano, —$OR_5$, hydroxyalkyl, —$COOR_5$, —$CONR_6R_7$, —$NR_6$—$COOR_5$, —$NR_6$—$COR_5$ or —CO—$NR_6$-alkyl-$OR_5$ group, $R_5$, $R_6$ and $R_7$, which are identical or different, each represent a hydrogen atom, an alkyl group or an -alkylphenyl group, and $R_8$ represents a hydrogen atom, an alkyl group or a group of formula —B-Het, where B can be absent or can represent a bond, an oxygen atom or a —CO— or —$SO_2$—$(CH_2)_n$— group with n equal to 0, 1 or 2 and where Het represents a pyrrolidinyl, piperidinyl, piperazinyl, tetrahydropyranyl, morpholinyl or pyridinyl group, the said Het group optionally being substituted by 1 to 3 groups chosen from alkyl, —SO$_2$-alkyl and —COOR$_5$ groups.

Mention may also be made of the subgroup of compounds of formula (I) according to the invention in which:

A represents a bond, an oxygen atom or an —O—CH$_2$— group,

Ar$_1$ represents a phenyl or heteroaryl group,

Ar$_2$ represents a phenyl group,

R$_{1a,b,c}$ and R$_{2a,b,c}$, which are identical or different, each represent a hydrogen or halogen atom or an alkyl, cycloalkyl, -alkylcycloalkyl optionally substituted by one or more halogen atoms, —OR$_5$ (hydroxyl or alkoxy), hydroxyalkyl, alkoxyalkyl, haloalkyl, —O-haloalkyl, oxo, —CO-alkyl, —CO-alkyl-NR$_6$R$_7$, —COOR$_5$, -alkyl-COOR$_5$, —SO$_2$-alkyl, —SO$_2$-cycloalkyl, —SO$_2$-alkylcycloalkyl, —SO$_2$-alkyl-OR$_5$, —SO$_2$-alkyl-COOR$_5$, —SO$_2$-alkyl-NR$_6$R$_7$, —SO$_2$-haloalkyl, -alkyl-SO$_2$-alkyl, —SO$_2$-alkylalkoxyalkoxy, —CONR$_6$R$_7$ or —O-alkyl-NR$_6$R$_7$ group, or also R$_{1a}$, R$_{1b}$ and R$_{1c}$ are respectively bonded to R$_{2a}$, R$_{2b}$ and R$_{2c}$ and to the carbon atom which carries them and represent —O-alkyl-O—, R$_3$ represents a hydrogen atom or an alkyl group, R$_4$ represents a hydrogen or halogen atom or a cyano, —OR$_5$, hydroxyalkyl, —COOR$_5$, —CONR$_6$R$_7$, —NR$_6$—COOR$_5$, —NR$_6$—COR$_5$ or —CO—NR$_6$-alkyl-OR$_5$ group, R$_5$, R$_6$ and R$_7$, which are identical or different, each represent a hydrogen atom, an alkyl group or an -alkylphenyl group, and R$_8$ represents a hydrogen atom, an alkyl group or a group of formula —B-Het, where B can be absent or can represent a bond, an oxygen atom or a —CO— or —SO$_2$—(CH$_2$)$_n$— group with n equal to 0, 1 or 2 and where Het represents a pyrrolidinyl, piperidinyl, piperazinyl, tetrahydropyranyl, morpholinyl or pyridinyl group, the said Het group optionally being substituted by 1 to 3 groups chosen from alkyl, —SO$_2$-alkyl and —COOR$_5$ groups.

Mention may also be made of the subgroup of compounds of formula (I) according to the invention in which:

A represents a bond, an oxygen atom or an —O—CH$_2$— group,

Ar$_1$ represents a phenyl or heteroaryl group,

Ar$_2$ represents a heteroaryl group (such as a pyridinyl or pyrimidinyl group), R$_{1a,b,c}$ and R$_{2a,b,c}$, which are identical or different, each represent a hydrogen or halogen atom or an alkyl, cycloalkyl, -alkylcycloalkyl optionally substituted by one or more halogen atoms, —OR$_5$ (hydroxyl or alkoxy), hydroxyalkyl, alkoxyalkyl, haloalkyl, —O-haloalkyl, oxo, —CO-alkyl, —CO-alkyl-NR$_6$R$_7$, —COOR$_5$, -alkyl-COOR$_5$, —SO$_2$-alkyl, —SO$_2$-cycloalkyl, —SO$_2$-alkylcycloalkyl, —SO$_2$-alkyl-OR$_5$, —SO$_2$-alkyl-COOR$_5$, —SO$_2$-alkyl-NR$_6$R$_7$, —SO$_2$-haloalkyl, -alkyl-SO$_2$-alkyl, —SO$_2$-alkylalkoxyalkoxy, —CONR$_6$R$_7$ or —O-alkyl-NR$_6$R$_7$ group, or also R$_{1a}$, R$_{1b}$ and R$_{1c}$ are respectively bonded to R$_{2a}$, R$_{2b}$ and R$_{2c}$ and to the carbon atom which carries them and represent —O-alkyl-O—, R$_3$ represents a hydrogen atom or an alkyl group, R$_4$ represents a hydrogen or halogen atom or a cyano, —OR$_5$, hydroxyalkyl, —COOR$_5$, —CONR$_6$R$_7$, —NR$_6$—COOR$_5$, —NR$_6$—COR$_5$ or —CO—NR$_6$-alkyl-OR$_5$ group, R$_5$, R$_6$ and R$_7$, which are identical or different, each represent a hydrogen atom, an alkyl group or an -alkylphenyl group, and R$_8$ represents a hydrogen atom, an alkyl group or a group of formula —B-Het, where B can be absent or can represent a bond, an oxygen atom or a —CO— or —SO$_2$—(CH$_2$)$_n$— group with n equal to 0, 1 or 2 and where Het represents a pyrrolidinyl, piperidinyl, piperazinyl, tetrahydropyranyl, morpholinyl or pyridinyl group, the said Het group optionally being substituted by 1 to 3 groups chosen from alkyl, —SO$_2$-alkyl and —COOR$_5$ groups.

Mention may be made of the subgroup of compounds of formula (I) according to the invention in which:

A represents a bond, an oxygen atom or an —O—CH$_2$— group,

Ar$_1$ represents a phenyl or heteroaryl group,

Ar$_2$ represents a heterocycloalkyl group (such as a piperidinyl, piperazinyl, homopiperazinyl, 3,8-diazabicyclo[3.2.1]octyl, morpholinyl, thiomorpholinyl, octahydropyrrolo[3,4-c]pyrrolyl, 1,2,3,6-tetrahydropyridinyl or 2,5-diazabicyclo[2.2.1]heptyl group), R$_{1a,b,c}$ and R$_{2a,b,c}$, which are identical or different, each represent a hydrogen or halogen atom or an alkyl, cycloalkyl, -alkylcycloalkyl optionally substituted by one or more halogen atoms, —OR$_5$ (hydroxyl or alkoxy), hydroxyalkyl, alkoxyalkyl, haloalkyl, —O-haloalkyl, oxo, —CO-alkyl, —CO-alkyl-NR$_6$R$_7$, —COOR$_5$, -alkyl-COOR$_5$, —SO$_2$-alkyl, —SO$_2$-cycloalkyl, —SO$_2$-alkylcycloalkyl, —SO$_2$-alkyl-OR$_5$, —SO$_2$-alkyl-COOR$_5$, —SO$_2$-alkyl-NR$_6$R$_7$, —SO$_2$-haloalkyl, -alkyl-SO$_2$-alkyl, —SO$_2$-alkylalkoxyalkoxy, —CONR$_6$R$_7$ or —O-alkyl-NR$_6$R$_7$ group, or also R$_{1a}$, R$_{1b}$ and R$_{1c}$ are respectively bonded to R$_{2a}$, R$_{2b}$ and R$_{2c}$ and to the carbon atom which carries them and represent —O-alkyl-O—, R$_3$ represents a hydrogen atom or an alkyl group, R$_4$ represents a hydrogen or halogen atom or a cyano, —OR$_5$, hydroxyalkyl, —COOR$_5$, —CONR$_6$R$_7$, —NR$_6$—COOR$_5$, —NR$_6$—COR$_5$ or —CO—NR$_6$-alkyl-OR$_5$ group;

R$_5$, R$_6$ and R$_7$, which are identical or different, each represent a hydrogen atom, an alkyl group or an -alkylphenyl group, and R$_8$ represents a hydrogen atom, an alkyl group or a group of formula —B-Het, where B can be absent or can represent a bond, an oxygen atom or a —CO— or —SO$_2$—(CH$_2$)$_n$— group with n equal to 0, 1 or 2 and where Het represents a pyrrolidinyl, piperidinyl, piperazinyl, tetrahydropyranyl, morpholinyl or pyridinyl group, the said Het group optionally being substituted by 1 to 3 groups chosen from alkyl, —SO$_2$-alkyl and —COOR$_5$ groups.

Finally, mention may be made of the subgroup of compounds of formula (I) according to the invention in which:

A represents a bond,

Ar$_1$ represents a phenyl or heteroaryl group,

Ar$_2$ represents a heterocycloalkyl group,

R$_{1a,b,c}$ and R$_{2a,b,c}$, which are identical or different, each represent a hydrogen or halogen atom or an alkyl, cycloalkyl, -alkylcycloalkyl optionally substituted by one or more halogen atoms, —OR$_5$ (hydroxyl or alkoxy), hydroxyalkyl, alkoxyalkyl, haloalkyl, —O-haloalkyl, oxo, —CO-alkyl, —CO-alkyl-NR$_6$R$_7$, —COOR$_5$, -alkyl-COOR$_5$, —SO$_2$-alkyl, —SO$_2$-cycloalkyl, —SO$_2$-alkylcycloalkyl, —SO$_2$-alkyl-OR$_5$, —SO$_2$-alkyl-COOR$_5$, —SO$_2$-alkyl-NR$_6$R$_7$, —SO$_2$-haloalkyl, -alkyl-SO$_2$-alkyl, —SO$_2$-alkylalkoxyalkoxy, —CONR$_6$R$_7$ or —O-alkyl-NR$_6$R$_7$ group, or also R$_{1a}$, R$_{1b}$ and R$_{1c}$ are respectively bonded to R$_{2a}$, R$_{2b}$ and R$_{2c}$ and to the carbon atom which carries them and represent —O-alkyl-O—, R$_3$ represents a hydrogen atom, R$_4$ represents an OH or —CONH$_2$ group, R$_5$, R$_6$ and R$_7$, which are identical or different, each represent a hydrogen atom, an alkyl group or an -alkylphenyl group, and R$_8$ represents a hydrogen atom.

Mention may in particular be made, among the compounds of formula (I) which are subject-matters of the invention, of the following compounds:

.4-(4-(Pyridin-2-yl)phenyl)-3-4-dihydro-2H-quinoxaline-1-carboxylic acid adamantan-2-ylamide, .4-{4-[1-(Tetrahydropyran-4-carbonyl)piperidin-4-yloxy]phenyl}-3,4-dihydro-2H-quinoxaline-1-carboxylic acid adamantan-2-ylamide, .4-[4-(Pyrimidin-2-ylmethoxy)phenyl]-3,4-dihydro-2H-quinoxaline-1-carboxylic acid adamantan-2-ylamide, .4-{4-[1-(Morpholine-4-carbonyl)piperidin-4-yl]phenyl}-3,4-dihydro-2H-quinoxaline-1-carboxylic acid adamantan-2-ylamide, .4-[4-(4-Methoxypyrimidin-2-yloxy)phenyl]-3,4-dihydro-2H-quinoxaline-1-carboxylic acid adamantan-2-ylamide, .4-{4-[4-(Morpholine-4-carbonyl)phenyl]thiazol-2-yl}-3,4-dihydro-2H-quinoxaline-1-carboxylic acid adamantan-2-ylamide, .4-[5-(4-Methoxyphenyl)pyrimidin-2-yl]-3,4-dihydro-2H-quinoxaline-1-carboxylic acid adamantan-2-ylamide, .4-[5-(4-Methoxyphenyl)pyrimidin-2-yl]-3,4-dihydro-2H-quinoxaline-1-carboxylic acid (5-hydroxyadamantan-2-yl)amide, .trans-4-[4-(4-(Methanesulphonyl)piperazin-1-yl)phenyl]-3,4-dihydro-2H-quinoxaline-1-carboxylic acid (5-hydroxyadamantan-2-yl)amide, .Methyl ester of 4-({4-[4-(4-(Methanesulphonyl)piperazin-1-yl)phenyl]-3,4-dihydro-2H-quinoxaline-1-carbonyl}amino)adamantane-1-carboxylic acid .4-({4-[4-(4-(Methanesulphonyl)piperazin-1-yl)phenyl]-3,4-dihydro-2H-quinoxaline-1-carbonyl}amino)adamantane-1-carboxylic acid .4-[4-(4-(Methanesulphonyl)piperazin-1-yl)phenyl]-3,4-dihydro-2H-quinoxaline-1-carboxylic acid (5-carbamoyladamantan-2-yl)amide, .trans-4-[4-(Pyridin-2-yloxy)phenyl]-3,4-dihydro-2H-quinoxaline-1-carboxylic acid (5-hydroxyadamantan-2-yl)amide, .trans-4-[4-(4-(Trifluoromethyl)pyrimidin-2-yloxy)phenyl]-3,4-dihydro-2H-quinoxaline-1-carboxylic acid (5-hydroxyadamantan-2-yl)amide, .trans-4-[4-(1-(Methanesulphonyl)-1,2,3,6-tetrahydropyridin-4-yl)phenyl]-3,4-dihydro-2H-quinoxaline-1-carboxylic acid (5-hydroxyadamantan-2-yl)amide, .trans-4-[4-(4-Hydroxy-1-(Methanesulphonyl)piperidin-4-yl)phenyl]-3,4-dihydro-2H-quinoxaline-1-carboxylic acid (5-hydroxyadamantan-2-yl)amide, .trans-4-[2-(4-(Methanesulphonyl)piperazin-1-yl)pyrimin-5-yl]-3,4-dihydro-2H-quinoxaline-1-carboxylic acid (5-hydroxyadamantan-2-yl)amide, .trans-4-[5-(4-(Methanesulphonyl)piperazin-1-yl)pyrimidin-2-yl]-3,4-dihydro-2H-quinoxaline-1-carboxylic acid (5-hydroxyadamantan-2-yl)amide, .trans-4-{4-[1-(Morpholine-4-carbonyl)piperidin-4-yl]phenyl}-3,4-dihydro-2H-quinoxaline-1-carboxylic acid (5-hydroxyadamantan-2-yl)amide, .trans-4-{4-[4-(5-Hydroxyadamantan-2-ylcarbamoyl)-3,4-dihydro-2H-quinoxalin-1-yl]phenyl}piperazine-1-carboxylic acid benzyl ester, .trans-4-[4-(4-(Methanesulphonyl)piperazin-1-yl)phenyl]-3,4-dihydro-2H-quinoxaline-1-carboxylic acid (5-(hydroxymethyl)adamantan-2-yl)amide, .trans-4-[4-(5-Fluoropyrimidin-2-yloxy)phenyl]-3,4-dihydro-2H-quinoxaline-1-carboxylic acid (5-hydroxyadamantan-2-yl)amide, .trans-4-[4-(1-(Methanesulphonyl)piperidin-4-yloxy)phenyl]-3,4-dihydro-2H-quinoxaline-1-carboxylic acid (5-hydroxyadamantan-2-yl)amide, .trans-4-(4-(Morpholin-4-yl)phenyl)-3,4-dihydro-2H-quinoxaline-1-carboxylic acid (5-hydroxyadamantan-2-yl)amide, .trans-4-[4-(1,1-Dioxo-1$\lambda^6$-thiomorpholin-4-yl)phenyl]-3,4-dihydro-2H-quinoxaline-1-carboxylic acid (5-hydroxyadamantan-2-yl)amide, .trans-4-[4-(5-Isopropoxypyridin-2-yl)phenyl]-3,4-dihydro-2H-quinoxaline-1-carboxylic acid (5-hydroxyadamantan-2-yl)amide, .trans-4-{4-[5-(4-Isopropylpiperazine-1-carbonyl)pyridin-2-yl]phenyl}-3,4-dihydro-2H-quinoxaline-1-carboxylic acid (5-hydroxyadamantan-2-yl)amide, .trans-4-[6-(4-(Methanesulphonyl)piperazin-1-yl)pyridin-3-yl]-3,4-dihydro-2H-quinoxaline-1-carboxylic acid (5-hydroxyadamantan-2-yl)amide, .trans-4-(4-(piperazin-1-yl)phenyl)-3,4-dihydro-2H-quinoxaline-1-carboxylic acid (5-hydroxyadamantan-2-yl)amide, .trans-4-[4-(4,4-Difluoropiperidin-1-yl)phenyl]-3,4-dihydro-2H-quinoxaline-1-carboxylic acid (5-hydroxyadamantan-2-yl)amide, .trans-4-[5-(4-(Methanesulphonyl)piperazin-1-yl)pyridin-2-yl]-3,4-dihydro-2H-quinoxaline-1-carboxylic acid (5-hydroxyadamantan-2-yl)amide, .trans-4-[5-(4-(Methanesulphonyl)piperazin-1-yl)pyridin-2-yl]-3,4-dihydro-2H-quinoxaline-1-carboxylic acid (5-hydroxyadamantan-2-yl)amide, .trans-4-[2-(1-(Methanesulphonyl)piperidin-4-yloxy)pyrimidin-5-yl]-3,4-dihydro-2H-quinoxaline-1-carboxylic acid (5-hydroxyadamantan-2-yl)amide, .trans-4-[5-(5-Isopropoxypyridin-2-yl)pyrimidin-2-yl]-3,4-dihydro-2H-quinoxaline-1-carboxylic acid (5-hydroxyadamantan-2-yl)amide, .trans-4-[4-(4-(Ethanesulphonyl)piperazin-1-yl)phenyl]-3,4-dihydro-2H-quinoxaline-1-carboxylic acid (5-hydroxyadamantan-2-yl)amide, .trans-4-{4-[4-(2,2,2-Trifluoroethanesulphonyl)piperazin-1-yl]phenyl}-3,4-dihydro-2H-quinoxaline-1-carboxylic acid (5-hydroxyadamantan-2-yl)amide, .trans-4-{4-[4-(Propane-2-sulphonyl)piperazin-1-yl]phenyl}-3,4-dihydro-2H-quinoxaline-1-carboxylic acid (4-hydroxyadamantan-1-yl)amide, .trans-4-(4-{4-[4-(5-Hydroxyadamantan-2-ylcarbamoyl)-3,4-dihydro-2H-quinoxalin-1-yl]phenyl}piperazine-1-sulphonyl)piperidine-1-carboxylic acid benzyl ester, .trans-4-{4-[4-(Piperidine-4-sulphonyl)piperazin-1-yl]phenyl}-3,4-dihydro-2H-quinoxaline-1-carboxylic acid (5-hydroxyadamantan-2-yl)amide, .trans-4-[4-(4-(Cyclopropanesulphonyl)piperazin-1-yl)phenyl]-3,4-dihydro-2H-quinoxaline-1-carboxylic acid (5-hydroxyadamantan-2-yl)amide, .trans-4-[4-(4-(Methanesulphonyl)piperazin-1-yl)phenyl]-3,4-dihydro-2H-quinoxaline-1-carboxylic acid (5-fluoroadamantan-2-yl)amide,

- trans-4-[4-(4-(Cyclobutanesulphonyl)piperazin-1-yl)phenyl]-3,4-dihydro-2H-quinoxaline-1-carboxylic acid (5-hydroxyadamantan-2-yl)amide,
- trans-4-{4-[4-(Propane-1-sulphonyl)piperazin-1-yl]phenyl}-3,4-dihydro-2H-quinoxaline-1-carboxylic acid (5-hydroxyadamantan-2-yl)amide,
- trans-4-{4-[4-(Butane-1-sulphonyl)piperazin-1-yl]phenyl}-3,4-dihydro-2H-quinoxaline-1-carboxylic acid (5-hydroxyadamantan-2-yl)amide,
- trans-4-{4-[4-(Morpholine-4-sulphonyl)piperazin-1-yl]phenyl}-3,4-dihydro-2H-quinoxaline-1-carboxylic acid (5-hydroxyadamantan-2-yl)amide,
- trans-4-[4-(4-(Trifluoromethanesulphonyl)piperazin-1-yl)phenyl]-3,4-dihydro-2H-quinoxaline-1-carboxylic acid (5-hydroxyadamantan-2-yl)amide,
- trans-4-[4-(1,4-Dioxa-8-azaspiro[4.5]dec-8-yl)phenyl]-3,4-dihydro-2H-quinoxaline-1-carboxylic acid (5-hydroxyadamantan-2-yl)amide,
- trans-4-[4-(4-Methanesulphonyl-3,3-dimethylpiperazin-1-yl)phenyl]-3,4-dihydro-2H-quinoxaline-1-carboxylic acid (5-hydroxyadamantan-2-yl)amide,
- trans-4-[4-((3R,5S)-4-Methanesulphonyl-3,5-dimethylpiperazin-1-yl)phenyl]-3,4-dihydro-2H-quinoxaline-1-carboxylic acid (5-hydroxyadamantan-2-yl)amide,
- trans-(4-{4-[4-(5-Hydroxyadamantan-2-ylcarbamoyl)-3,4-dihydro-2H-quinoxalin-1-yl]phenyl}piperazine-1-sulphonyl)acetic acid,
- trans-(4-{4-[4-(5-Hydroxyadamantan-2-ylcarbamoyl)-3,4-dihydro-2H-quinoxalin-1-yl]phenyl}piperazine-1-sulphonyl)acetic acid ethyl ester,
- trans-4-[4-(4-Hydroxypiperidin-1-yl)phenyl]-3,4-dihydro-2H-quinoxaline-1-carboxylic acid (5-hydroxyadamantan-2-yl)amide,
- trans-4-[4-(4-Methanesulphonyl-1,4-diazepan-1-yl)phenyl]-3,4-dihydro-2H-quinoxaline-1-carboxylic acid (5-hydroxyadamantan-2-yl)amide,
- trans-2-(4-{4-[4-(5-Hydroxyadamantan-2-ylcarbamoyl)-3,4-dihydro-2H-quinoxalin-1-yl]phenyl}piperazin-1-yl)-2-methylpropionic acid ethyl ester,
- trans-3-(4-{4-[4-(5-Hydroxyadamantan-2-ylcarbamoyl)-3,4-dihydro-2H-quinoxalin-1-yl]phenyl}piperazine-1-sulphonyl)propionic acid methyl ester,
- trans-4-[4-(5-Methoxypyrimidin-2-yl)phenyl]-3,4-dihydro-2H-quinoxaline-1-carboxylic acid (5-hydroxyadamantan-2-yl)amide,
- trans-4-{4-[4-(2-(Morpholin-4-yl)ethanesulphonyl)piperazin-1-yl]phenyl}-3,4-dihydro-2H-quinoxaline-1-carboxylic acid (5-hydroxyadamantan-2-yl)amide,
- trans-4-[6-(4-(Methanesulphonyl)piperazin-1-yl)pyridazin-3-yl]-3,4-dihydro-2H-quinoxaline-1-carboxylic acid (5-hydroxyadamantan-2-yl)amide,
- trans-4-[4-(4-(Methanesulphonyl)piperazin-1-yl)phenyl]-3,4-dihydro-2H-quinoxaline-1-carboxylic acid (5-hydroxyadamantan-2-yl)(methyl)amide,
- trans-4-[4-(4-Methanesulphonyl-3,5-dimethylpiperazin-1-yl)phenyl]-3,4-dihydro-2H-quinoxaline-1-carboxylic acid (5-hydroxyadamantan-2-yl)amide,
- trans-4-{4-[4-(2-(Diethylamino)ethanesulphonyl)piperazin-1-yl]phenyl}-3,4-dihydro-2H-quinoxaline-1-carboxylic acid (5-hydroxyadamantan-2-yl)amide,
- trans-4-[4-(3-Methanesulphonyl-3,8-diazabicyclo[3.2.1]oct-8-yl)phenyl]-3,4-dihydro-2H-quinoxaline-1-carboxylic acid (5-hydroxyadamantan-2-yl)amide,
- trans-4-[5-(4-Methoxyphenyl)pyrimidin-2-yl]-3,4-dihydro-2H-quinoxaline-1-carboxylic acid (5-carbamoyladamantan-2-yl)amide,
- trans-4-{4-[4-(2-Methoxyethanesulphonyl)piperazin-1-yl]phenyl}-3,4-dihydro-2H-quinoxaline-1-carboxylic acid (5-hydroxyadamantan-2-yl)amide,
- trans-4-[4-(4-Isopropoxypiperidin-1-yl)phenyl]-3,4-dihydro-2H-quinoxaline-1-carboxylic acid (5-hydroxyadamantan-2-yl)amide,
- trans-4-[5-(4-Hydroxyphenyl)pyrimidin-2-yl]-3,4-dihydro-2H-quinoxaline-1-carboxylic acid (5-hydroxyadamantan-2-yl)amide,
- trans-4-(4-(piperazin-1-yl)phenyl)-3,4-dihydro-2H-quinoxaline-1-carboxylic acid (5-carbamoyladamantan-2-yl)amide,
- trans-4-[4-(5-Bromopyrimidin-2-yloxy)phenyl]-3,4-dihydro-2H-quinoxaline-1-carboxylic acid (5-hydroxyadamantan-2-yl)amide,
- trans-4-[4-(4-(Cyclopropanesulphonyl)piperazin-1-yl)phenyl]-3,4-dihydro-2H-quinoxaline-1-carboxylic acid (5-carbamoyladamantan-2-yl)amide,
- trans-4-[4-(4-(Cyclopropanesulphonyl)piperazin-1-yl)phenyl]-3,4-dihydro-2H-quinoxaline-1-carboxylic acid (5-carbamoyladamantan-2-yl)amide,
- trans-6-Chloro-4-[4-(4-(Methanesulphonyl)piperazin-1-yl)phenyl]-3,4-dihydro-2H-quinoxaline-1-carboxylic acid (5-hydroxyadamantan-2-yl)amide,
- trans-4-[4-(5-(Methanesulphonyl)hexahydropyrrolo[3,4-c]pyrrol-2-yl)phenyl]-3,4-dihydro-2H-quinoxaline-1-carboxylic acid (5-hydroxyadamantan-2-yl)amide,
- trans-4-{4-[4-(2-Aminoethanesulphonyl)piperazin-1-yl]phenyl}-3,4-dihydro-2H-quinoxaline-1-carboxylic acid (5-hydroxyadamantan-2-yl)amide,
- trans-4-(4-(Morpholin-4-yl)phenyl)-3,4-dihydro-2H-quinoxaline-1-carboxylic acid (5-carbamoyladamantan-2-yl)amide,
- trans-4-{4-[5-(Piperidin-4-yloxy)pyridin-2-yl]phenyl}-3,4-dihydro-2H-quinoxaline-1-carboxylic acid (5-hydroxyadamantan-2-yl)amide,
- trans-4-{4-[5-(2-Aminoethoxy)pyridin-2-yl]phenyl}-3,4-dihydro-2H-quinoxaline-1-carboxylic acid (5-hydroxyadamantan-2-yl)amide,
- trans-4-{4-[4-(2-Hydroxyethanesulphonyl)piperazin-1-yl]phenyl}-3,4-dihydro-2H-quinoxaline-1-carboxylic acid (5-hydroxyadamantan-2-yl)amide,
- trans-4-[4-(8-Methanesulphonyl-3,8-diazabicyclo[3.2.1]oct-3-yl)phenyl]-3,4-dihydro-2H-quinoxaline-1-carboxylic acid (5-carbamoyladamantan-2-yl)amide,
- trans-4-[4-(8-Methanesulphonyl-3,8-diazabicyclo[3.2.1]oct-3-yl)phenyl]-3,4-dihydro-2H-quinoxaline-1-carboxylic acid (5-hydroxyadamantan-2-yl)amide,
- trans-4-[5-(4-Isopropoxyphenyl)pyrimidin-2-yl]-3,4-dihydro-2H-quinoxaline-1-carboxylic acid (5-hydroxyadamantan-2-yl)amide,
- trans-4-{5-[4-(2,2,2-Trifluoroethanesulphonyl)piperazin-1-yl]pyridin-2-yl}-3,4-dihydro-2H-quinoxaline-1-carboxylic acid (5-hydroxyadamantan-2-yl)amide,
- trans-4-{5-[4-(2,2,2-Trifluoroethanesulphonyl)piperazin-1-yl]pyridin-2-yl}-3,4-dihydro-2H-quinoxaline-1-carboxylic acid (5-carbamoyladamantan-2-yl)amide,
- trans-3-(4-{4-[4-(5-Hydroxyadamantan-2-ylcarbamoyl)-3,4-dihydro-2H-quinoxalin-1-yl]phenyl}piperazine-1-sulphonyl)propionic acid,
- trans-4-[4-(4-(Methanesulphonyl)piperazin-1-yl)phenyl]-3,4-dihydro-2H-quinoxaline-1-carboxylic acid [5-(2-hydroxyethylcarbamoyl)adamantan-2-yl]amide,
- trans-4-[4-(5-Isobutoxypyridin-2-yl)phenyl]-3,4-dihydro-2H-quinoxaline-1-carboxylic acid (5-hydroxyadamantan-2-yl)amide, trans-4-[4-(5-(sec-Butoxy)pyridin-2-yl)phenyl]-3,4-dihydro-2H-quinoxaline-1-carboxylic acid (5-hydroxyadamantan-2-yl)amide, trans-4-[4-(5-Isopropoxypyridin-2-yl)phenyl]-3,4-dihydro-2H-quinoxaline-1-carboxylic acid (5-carbamoyladamantan-2-yl)amide, trans-[4-({4-[4-(4-(Methanesulphonyl)piperazin-1-yl)phenyl]-3,4-dihydro-2H-quinoxaline-1-carbonyl]amino)adamantan-1-yl}carbamic acid methyl ester, trans-4-[5-(4-(Ethanesulphonyl)piperazin-1-yl)pyridin-2-yl]-3,4-dihydro-2H-quinoxaline-1-carboxylic acid (5-hydroxyadamantan-2-yl)amide, trans-4-[5-(4-(Cyclopropanesulphonyl)piperazin-1-yl)pyridin-2-yl]-3,4-dihydro-2H-quinoxaline-1-carboxylic acid (5-hydroxyadamantan-2-yl)amide, trans-4-[5-(4-(Cyclopropanesulphonyl)piperazin-1-yl)pyridin-2-yl]-3,4-dihydro-2H-quinoxaline-1-carboxylic acid (5-carbamoyladamantan-2-yl)amide, trans-4-{5-[4-(Propane-2-sulphonyl)piperazin-1-yl]pyridin-2-yl}-3,4-dihydro-2H-quinoxaline-1-carboxylic acid (5-hydroxyadamantan-2-yl)amide, trans-4-{4-[4-(Pyridin-4-yloxy)piperidin-1-yl]phenyl}-3,4-dihydro-2H-quinoxaline-1-carboxylic acid (5-hydroxyadamantan-2-yl)amide, trans-4-{4-[4-(2-Methoxyethanesulphonyl)piperazin-1-yl]phenyl}-3,4-dihydro-2H-quinoxaline-1-carboxylic acid (5-carbamoyladamantan-2-yl)amide, trans-4-{4-[4-(2-Aminoethanesulphonyl)piperazin-1-yl]phenyl}-3,4-dihydro-2H-quinoxaline-1-carboxylic acid (5-carbamoyladamantan-2-yl)amide, trans-4-{4-[4-(2-(Diethylamino)ethanesulphonyl)piperazin-1-yl]phenyl}-3,4-dihydro-2H-quinoxaline-1-carboxylic acid (5-carbamoyladamantan-2-yl)amide, trans-4-{4-[4-(Piperidine-4-sulphonyl)piperazin-1-yl]phenyl}-3,4-dihydro-2H-quinoxaline-1-carboxylic acid (5-carbamoyladamantan-2-yl)amide, trans-4-[4-(4-(tert-Butyl)piperazin-1-yl)phenyl]-3,4-dihydro-2H-quinoxaline-1-carboxylic acid (5-carbamoyladamantan-2-yl)amide, trans-4-[5-(4-(Methanesulphonyl)piperazin-1-yl)pyridin-2-yl]-3,4-dihydro-2H-quinoxaline-1-carboxylic acid (5-carbamoyladamantan-2-yl)amide, trans-4-{5-[4-(Propane-1-sulphonyl)piperazin-1-yl]pyridin-2-yl}-3,4-dihydro-2H-quinoxaline-1-carboxylic acid (5-hydroxyadamantan-2-yl)amide, trans-4-{5-[4-(2-Methylpropane-1-sulphonyl)piperazin-1-yl]pyridin-2-yl}-3,4-dihydro-2H-quinoxaline-1-carboxylic acid (5-hydroxyadamantan-2-yl)amide, trans-4-(5-(Morpholin-4-yl)pyridin-2-yl)-3,4-dihydro-2H-quinoxaline-1-carboxylic acid (5-hydroxyadamantan-2-yl)amide, trans-4-{4-[4-(2-Hydroxyethanesulphonyl)piperazin-1-yl]phenyl}-3,4-dihydro-2H-quinoxaline-1-carboxylic acid (5-carbamoyladamantan-2-yl)amide, trans-4-{4-[4-(Piperidin-4-yloxy)piperidin-1-yl]phenyl}-3,4-dihydro-2H-quinoxaline-1-carboxylic acid (5-hydroxyadamantan-2-yl)amide, trans-4-[4-(4-(Dimethylcarbamoyl)piperazin-1-yl)phenyl]-3,4-dihydro-2H-quinoxaline-1-carboxylic acid (5-hydroxyadamantan-2-yl)amide, trans-4-[6-(4-(Cyclopropanesulphonyl)piperazin-1-yl)pyridin-3-yl]-3,4-dihydro-2H-quinoxaline-1-carboxylic acid (5-carbamoyladamantan-2-yl)amide, trans-4-[4-(4-(Ethanesulphonyl)piperazin-1-yl)phenyl]-3,4-dihydro-2H-quinoxaline-1-carboxylic acid (5-carbamoyladamantan-2-yl)amide, trans-4-{4-[4-(2,2,2-Trifluoroethanesulphonyl)piperazin-1-yl]phenyl}-3,4-dihydro-2H-quinoxaline-1-carboxylic acid (5-carbamoyladamantan-2-yl)amide, trans-4-{4-[4-(2-Aminoacetyl)piperazin-1-yl]phenyl}-3,4-dihydro-2H-quinoxaline-1-carboxylic acid (5-carbamoyladamantan-2-yl)amide, trans-4-[4-(5-(Hydroxymethyl)pyridin-2-yl)phenyl]-3,4-dihydro-2H-quinoxaline-1-carboxylic acid (5-carbamoyladamantan-2-yl)amide, trans-4-[5-(4-(Cyclopentanesulphonyl)piperazin-1-yl)pyridin-2-yl]-3,4-dihydro-2H-quinoxaline-1-carboxylic acid (5-hydroxyadamantan-2-yl)amide, trans-4-[4-(4-Isopropoxypiperidin-1-yl)phenyl]-3,4-dihydro-2H-quinoxaline-1-carboxylic acid (5-carbamoyladamantan-2-yl)amide, trans-4-{4-[5-(2,2,2-Trifluoroethoxy)pyridin-2-yl]phenyl}-3,4-dihydro-2H-quinoxaline-1-carboxylic acid (5-hydroxyadamantan-2-yl)amide, trans-4-{4-[5-(2,2,2-Trifluoroethoxy)pyridin-2-yl]phenyl}-3,4-dihydro-2H-quinoxaline-1-carboxylic acid (5-carbamoyladamantan-2-yl)amide, trans-4-[5-(4-Isopropoxyphenyl)pyrimidin-2-yl]-3,4-dihydro-2H-quinoxaline-1-carboxylic acid (5-carbamoyladamantan-2-yl)amide, trans-4-{5-[4-(Piperidin-4-yloxy)phenyl]pyrimidin-2-yl}-3,4-dihydro-2H-quinoxaline-1-carboxylic acid (5-carbamoyladamantan-2-yl)amide, trans-4-[5-(4-(Trifluoromethanesulphonyl)piperazin-1-yl)pyridin-2-yl]-3,4-dihydro-2H-quinoxaline-1-carboxylic acid (5-hydroxyadamantan-2-yl)amide, trans-4-[5-(4-(tert-Butyl)piperazin-1-yl)pyridin-2-yl]-3,4-dihydro-2H-quinoxaline-1-carboxylic acid (5-hydroxyadamantan-2-yl)amide, trans-4-[6-(4-(Ethanesulphonyl)piperazin-1-yl)pyridin-3-yl]-3,4-dihydro-2H-quinoxaline-1-carboxylic acid (5-carbamoyladamantan-2-yl)amide, trans-4-[5-(4-Cyclopropylpiperazin-1-yl)pyridin-2-yl]-3,4-dihydro-2H-quinoxaline-1-carboxylic acid (5-hydroxyadamantan-2-yl)amide, trans-4-[5-(4-(Cyclobutanesulphonyl)piperazin-1-yl)pyridin-2-yl]-3,4-dihydro-2H-quinoxaline-1-carboxylic acid (5-hydroxyadamantan-2-yl)amide, trans-4-[5-(4-Acetylpiperazin-1-yl)pyridin-2-yl]-3,4-dihydro-2H-quinoxaline-1-carboxylic acid (5-hydroxyadamantan-2-yl)amide, trans-4-{4-[4-(1-Ethylpropyl)piperazin-1-yl]phenyl}-3,4-dihydro-2H-quinoxaline-1-carboxylic acid (5-carbamoyladamantan-2-yl)amide, trans-4-{5-[4-(2-Methylpropane-1-sulphonyl)piperazin-1-yl]pyridin-2-yl}-3,4-dihydro-2H-quinoxaline-1-carboxylic acid (5-carbamoyladamantan-2-yl)amide, trans-4-{5-[4-(3,3,3-Trifluoropropane-1-sulphonyl)piperazin-1-yl]pyridin-2-yl}-3,4-dihydro-2H-quinoxaline-1-carboxylic acid (5-hydroxyadamantan-2-yl)amide, trans-4-{4-[4-(2,2,2-Trifluoroethyl)piperazin-1-yl]phenyl}-3,4-dihydro-2H-quinoxaline-1-carboxylic acid (5-carbamoyladamantan-2-yl)amide, trans-4-(4-{4-[2-(2-Methoxyethoxy)ethanesulphonyl]piperazin-1-yl}phenyl)-3,4-dihydro-2H-quinoxaline-1-carboxylic acid (5-carbamoyladamantan-2-yl)amide, trans-4-{5-[4-(2-Isopropoxyethanesulphonyl)piperazin-1-yl]pyridin-2-yl}-3,4-dihydro-2H-quinoxaline-1-carboxylic acid (5-carbamoyladamantan-2-yl)amide, 4-[5-(4-(Cyclopropylmethanesulphonyl)piperazin-1-yl)pyridin-2-yl]-3,4-dihydro-2H-quinoxaline-1-carboxylic acid (5-hydroxyadamantan-2-yl)amide,

- trans-4-[5-(4-(tert-Butyl)piperazin-1-yl)pyridin-2-yl]-3,4-dihydro-2H-quinoxaline-1-carboxylic acid (5-carbamoyladamantan-2-yl)amide,
- trans-4-[5-(4-Cyclopropylpiperazin-1-yl)pyridin-2-yl]-3,4-dihydro-2H-quinoxaline-1-carboxylic acid (5-carbamoyladamantan-2-yl)amide,
- trans-4-{4-[4-(Tetrahydropyran-4-yl)piperazin-1-yl]phenyl}-3,4-dihydro-2H-quinoxaline-1-carboxylic acid (5-carbamoyladamantan-2-yl)amide,
- trans-4-{5-[4-(2-Methoxyethanesulphonyl)piperazin-1-yl]pyridin-2-yl}-3,4-dihydro-2H-quinoxaline-1-carboxylic acid (5-carbamoyladamantan-2-yl)amide,
- trans-4-[4-(7-Methanesulphonyl-2,7-diazaspiro[4.4]non-2-yl)phenyl]-3,4-dihydro-2H-quinoxaline-1-carboxylic acid (5-hydroxyadamantan-2-yl)amide,
- trans-4-{5-[4-(2,2-Dimethylpropyl)piperazin-1-yl]pyridin-2-yl}-3,4-dihydro-2H-quinoxaline-1-carboxylic acid (5-hydroxyadamantan-2-yl)amide,
- trans-4-{5-[4-(2-Methoxy-1-(methoxymethyl)ethyl)piperazin-1-yl]pyridin-2-yl}-3,4-dihydro-2H-quinoxaline-1-carboxylic acid (5-hydroxyadamantan-2-yl)amide,
- trans-4-{5-[4-(3-Methoxypropyl)piperazin-1-yl]pyridin-2-yl}-3,4-dihydro-2H-quinoxaline-1-carboxylic acid (5-hydroxyadamantan-2-yl)amide,
- trans-4-{5-[4-(3-Methylbutyryl)piperazin-1-yl]pyridin-2-yl}-3,4-dihydro-2H-quinoxaline-1-carboxylic acid (5-hydroxyadamantan-2-yl)amide,
- trans-4-[4-(4-(Methanesulphonyl)piperazin-1-yl)phenyl]-3,4-dihydro-2H-quinoxaline-1-carboxylic acid (5-(acetylamino)adamantan-2-yl)amide,
- trans-4-{5-[4-(2-Methoxyethanesulphonyl)piperazin-1-yl]pyridin-2-yl}-3,4-dihydro-2H-quinoxaline-1-carboxylic acid (5-hydroxyadamantan-2-yl)amide,
- trans-4-{5-[4-(2,2-Dimethylpropionyl)piperazin-1-yl]pyridin-2-yl}-3,4-dihydro-2H-quinoxaline-1-carboxylic acid (5-hydroxyadamantan-2-yl)amide,
- trans-4-(4,4-Difluoro-3,4,5,6-tetrahydro-2H-1,3'-bipyridinyl-6'-yl)-3,4-dihydro-2H-quinoxaline-1-carboxylic acid (5-hydroxyadamantan-2-yl)amide,
- trans-4-(4-(Pyrrolidin-1-yl)-3,4,5,6-tetrahydro-2H-1,3'-bipyridinyl-6'-yl)-3,4-dihydro-2H-quinoxaline-1-carboxylic acid (5-hydroxyadamantan-2-yl)amide,
- trans-4-[5-(5-Cyclopropanesulphonyl-2,5-diazabicyclo[2.2.1]hept-2-yl)pyridin-2-yl]-3,4-dihydro-2H-quinoxaline-1-carboxylic acid (5-hydroxyadamantan-2-yl)amide,
- trans-4-{6-[4-(5-Hydroxyadamantan-2-ylcarbamoyl)-3,4-dihydro-2H-quinoxalin-1-yl]-pyridin-3-yl}piperazine-1-carboxylic acid tert-butyl ester,
- trans-4-{4-[4-(2-Methoxyethyl)piperazin-1-yl]phenyl}-3,4-dihydro-2H-quinoxaline-1-carboxylic acid (5-carbamoyladamantan-2-yl)amide,
- trans-4-[5-(4-(Methanesulphonyl)piperazin-1-yl)-3-methylpyridin-2-yl]-3,4-dihydro-2H-quinoxaline-1-carboxylic acid (5-carbamoyladamantan-2-yl)amide,
- trans-2-(4-{4-[4-(5-Carbamoyladamantan-2-ylcarbamoyl)-3,4-dihydro-2H-quinoxalin-1-yl]-phenyl}piperazin-1-yl)-2-methylpropionic acid,
- trans-4-(4-(tert-Butyl)-3,4,5,6-tetrahydro-2H-1,3'-bipyridinyl-6'-yl)-3,4-dihydro-2H-quinoxaline-1-carboxylic acid (5-carbamoyladamantan-2-yl)amide,
- trans-4-(4-(Pyrrolidin-1-yl)-3,4,5,6-tetrahydro-2H-1,3'-bipyridinyl-6'-yl)-3,4-dihydro-2H-quinoxaline-1-carboxylic acid (5-carbamoyladamantan-2-yl)amide,
- trans-4-[5-(4-(Ethanesulphonyl)piperazin-1-yl)pyridin-2-yl]-3,4-dihydro-2H-quinoxaline-1-carboxylic acid (5-carbamoyladamantan-2-yl)amide,
- trans-4-[5-(4-(Methanesulphonyl)piperazin-1-yl)-6-methylpyridin-2-yl]-3,4-dihydro-2H-quinoxaline-1-carboxylic acid (5-carbamoyladamantan-2-yl)amide,
- trans-4-(4,4-Difluoro-3,4,5,6-tetrahydro-2H-1,3'-bipyridinyl-6'-yl)-3,4-dihydro-2H-quinoxaline-1-carboxylic acid (5-carbamoyladamantan-2-yl)amide,
- trans-4-{4-[4-(2-Hydroxy-1,1-dimethylethyl)piperazin-1-yl]phenyl}-3,4-dihydro-2H-quinoxaline-1-carboxylic acid (5-carbamoyladamantan-2-yl)amide,
- trans-4-{5-[4-(Propane-2-sulphonyl)piperazin-1-yl]-pyridin-2-yl}-3,4-dihydro-2H-quinoxaline-1-carboxylic acid (5-carbamoyladamantan-2-yl)amide,
- trans-4-(5-(Morpholin-4-yl)-pyridin-2-yl)-3,4-dihydro-2H-quinoxaline-1-carboxylic acid (5-carbamoyladamantan-2-yl)amide,
- trans-4-[5-(4-(Methanesulphonyl)piperazin-1-yl)-4-methylpyridin-2-yl]-3,4-dihydro-2H-quinoxaline-1-carboxylic acid (5-carbamoyladamantan-2-yl)amide,
- trans-4-(4-Trifluoromethyl-3,4,5,6-tetrahydro-2H-1,3'-bipyridinyl-6'-yl)-3,4-dihydro-2H-quinoxaline-1-carboxylic acid (5-carbamoyladamantan-2-yl)amide,
- trans-4-(4-(tert-Butyl)-3,4,5,6-tetrahydro-2H-1,3'-bipyridinyl-6'-yl)-3,4-dihydro-2H-quinoxaline-1-carboxylic acid (5-hydroxyadamantan-2-yl)amide,
- trans-4-[5-(4-Isobutylpiperazin-1-yl)pyridin-2-yl]-3,4-dihydro-2H-quinoxaline-1-carboxylic acid (5-carbamoyladamantan-2-yl)amide,
- trans-4-[5-(4-(Cyclopropylmethyl)piperazin-1-yl)pyridin-2-yl]-3,4-dihydro-2H-quinoxaline-1-carboxylic acid (5-carbamoyladamantan-2-yl)amide,
- trans-4-{5-[4-(2,2,2-Trifluoroethyl)piperazin-1-yl]pyridin-2-yl}-3,4-dihydro-2H-quinoxaline-1-carboxylic acid (5-carbamoyladamantan-2-yl)amide,
- trans-4-[5-(4-(tert-Butyl)piperazin-1-yl)pyridin-2-yl]-3,4-dihydro-2H-quinoxaline-1-carboxylic acid (5-(hydroxymethyl)adamantan-2-yl)amide,
- trans-4-[5-(4-(tert-Butyl)piperazin-1-yl)pyridin-2-yl]-6,7-difluoro-3,4-dihydro-2H-quinoxaline-1-carboxylic acid (5-carbamoyladamantan-2-yl)amide,
- trans-4-{5-[4-(2,2-Dimethylpropionyl)piperazin-1-yl]pyridin-2-yl}-3,4-dihydro-2H-quinoxaline-1-carboxylic acid (5-carbamoyladamantan-2-yl)amide,
- trans-4-[5-(4-(tert-Butyl)piperazin-1-yl)pyrimidin-2-yl]-3,4-dihydro-2H-quinoxaline-1-carboxylic acid (5-carbamoyladamantan-2-yl)amide,
- trans-4-[5-(4-(Cyclopropanesulphonyl)piperazin-1-yl)pyridin-2-yl]-3,4-dihydro-2H-quinoxaline-1-carboxylic acid (5-cyanoadamantan-2-yl)amide,
- trans-4-[5-(1-(tert-Butyl)piperidin-4-yloxy)pyridin-2-yl]-3,4-dihydro-2H-quinoxaline-1-carboxylic acid (5-carbamoyladamantan-2-yl)amide,
- trans-{6'-[4-(5-Carbamoyladamantan-2-ylcarbamoyl)-3,4-dihydro-2H-quinoxalin-1-yl]-3,4,5,6-tetrahydro-2H-1,3'-bipyridinyl-4-yl}-acetic acid methyl ester,
- trans-6'-[4-(5-Carbamoyladamantan-2-ylcarbamoyl)-3,4-dihydro-2H-quinoxalin-1-yl]-3,4,5,6-tetrahydro-2H-1,3'-bipyridinyl-4-carboxylic acid ethyl ester,
- trans-4-[5-(4-Isopropylpiperazin-1-yl)pyridin-2-yl]-3,4-dihydro-2H-quinoxaline-1-carboxylic acid (5-carbamoyladamantan-2-yl)amide,
- trans-4-(1'-(tert-Butyl)-1',2',3',4',5',6'-hexahydro-3,4'-bipyridinyl-6-yl)-3,4-dihydro-2H-quinoxaline-1-carboxylic acid (5-carbamoyladamantan-2-yl)amide,
- trans-{6'-[4-(5-Carbamoyladamantan-2-ylcarbamoyl)-3,4-dihydro-2H-quinoxalin-1-yl]-3,4,5,6-tetrahydro-2H-1,3'-bipyridinyl-4-yl}acetic acid, trans-6'-[4-(5-Carbamoyladamantan-2-ylcarbamoyl)-3,4-dihydro-2H-quinoxalin-1-yl]-3,4,5,6-tetrahydro-2H-1,3'-bipyridinyl-4-carboxylic acid, trans-2-(4-{6-[4-(5-Carbamoyladamantan-2-ylcarbamoyl)-3,4-dihydro-2H-quinoxalin-1-yl]-pyridin-3-yl}-piperazin-1-yl)-2-methylpropionic acid ethyl ester, trans-4-(4,4-Dimethyl-3,4,5,6-tetrahydro-2H-1,3'-bipyridinyl-6'-yl)-3,4-dihydro-2H-quinoxaline-1-carboxylic acid (5-carbamoyladamantan-2-yl)amide, trans-4-{5-[4-(2,2-Difluorocyclopropylmethyl)piperazin-1-yl]pyridin-2-yl}-3,4-dihydro-2H-quinoxaline-1-carboxylic acid (5-carbamoyladamantan-2-yl)amide, trans-4-{5-[4-(Difluoromethanesulphonyl)piperazin-1-yl]pyridin-2-yl}-3,4-dihydro-2H-quinoxaline-1-carboxylic acid (5-carbamoyladamantan-2-yl)amide, trans-4-{5-[4-(3,3,3-Trifluoropropyl)piperazin-1-yl]pyridin-2-yl}-3,4-dihydro-2H-quinoxaline-1-carboxylic acid (5-carbamoyladamantan-2-yl)amide, trans-4-{5-[4-(2-(Methanesulphonyl)ethyl)piperazin-1-yl]pyridin-2-yl}-3,4-dihydro-2H-quinoxaline-1-carboxylic acid (5-carbamoyladamantan-2-yl)amide, trans-4-{5-[4-(1-Ethylpropyl)piperazin-1-yl]pyridin-2-yl}-3,4-dihydro-2H-quinoxaline-1-carboxylic acid (5-carbamoyladamantan-2-yl)amide, trans-4-[5-(1,1-Dioxo-1$\lambda^6$-thiomorpholin-4-yl)pyridin-2-yl]-3,4-dihydro-2H-quinoxaline-1-carboxylic acid (5-carbamoyladamantan-2-yl)amide, trans-4-{5-[4-(Tetrahydropyran-4-yl)piperazin-1-yl]pyridin-2-yl}-3,4-dihydro-2H-quinoxaline-1-carboxylic acid (5-carbamoyladamantan-2-yl)amide, trans-4-[5-(4-(Cyclopropanesulphonyl)piperazin-1-yl)-3-methylpyridin-2-yl]-3,4-dihydro-2H-quinoxaline-1-carboxylic acid (5-carbamoyladamantan-2-yl)amide, trans-4-{5-[4-(2-Hydroxy-1,1-dimethylethyl)-piperazin-1-yl]pyridin-2-yl}-3,4-dihydro-2H-quinoxaline-1-carboxylic acid (5-carbamoyladamantan-2-yl)amide, trans-4-{5-[4-(2-Fluoro-1,1-dimethylethyl)-piperazin-1-yl]pyridin-2-yl}-3,4-dihydro-2H-quinoxaline-1-carboxylic acid (5-carbamoyladamantan-2-yl)amide, trans-4-[5-(4-(Trifluoromethanesulphonyl)piperazin-1-yl)pyridin-2-yl]-3,4-dihydro-2H-quinoxaline-1-carboxylic acid (5-carbamoyladamantan-2-yl)amide.

It should be noted that the above compounds were named in IUPAC nomenclature via the AutoNom software (Beilstein Information System).

In that which follows, the term "protective group" (PG) is understood to mean a group which makes it possible, on the one hand, to protect a reactive functional group, such as a hydroxyl or amine, during a synthesis and, on the other hand, to regenerate the reactive functional group intact at the end of the synthesis. Examples of protective groups and protecting and deprotecting methods are given in "Protective Groups in Organic Synthesis", Green et al., 3$^{rd}$ Edition (John Wiley & Sons Inc., New York).

The term "leaving group" (Lg, E, J, V, X, Z) is understood to mean, in that which follows, a group which can be easily split from a molecule by cleavage of a heterolytic bond with departure of an electron pair. This group can thus be easily replaced by another group, for example during a substitution reaction. Such leaving groups are, for example, halogens or an activated hydroxyl group, such as a mesyl, tosyl, triflate, acetyl, para-nitrophenyl and the like. Examples of leaving groups and methods for their preparation are given in "Advances in Organic Chemistry", J. March, 3$^{rd}$ Edition, Wiley Interscience, pp. 310-316.

In accordance with the invention, the compounds of general formula (I) can be prepared according to the following processes.

Scheme 1 (Method No. 1):

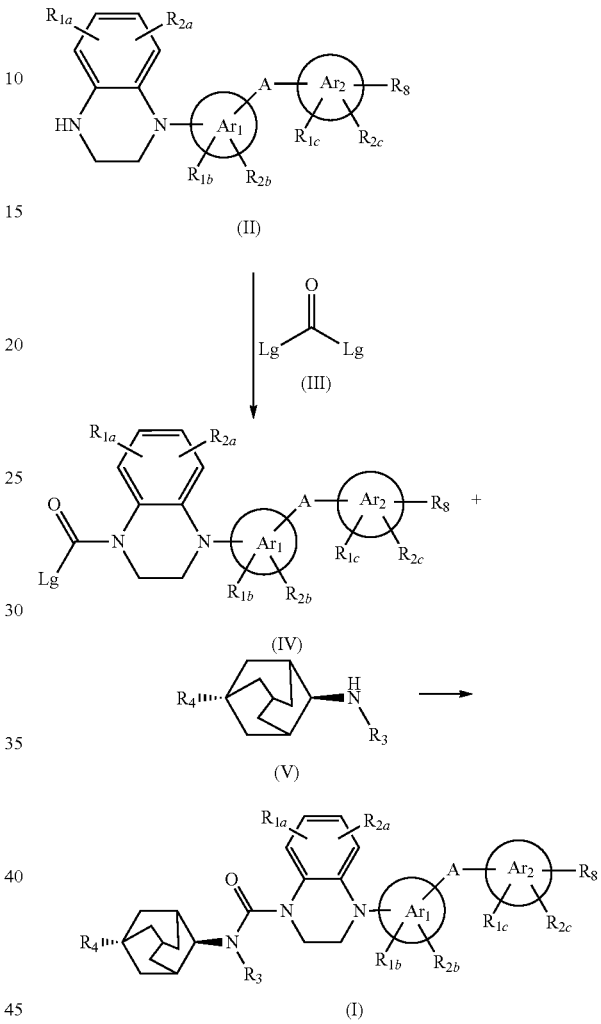

In Scheme 1, the compounds of formula (IV) can be prepared by reaction between the intermediates of formula (II) and a carbonyl of formula (III) exhibiting two leaving groups Lg (for example, a chlorine atom, a trichloromethoxy group, a para-nitrophenyl group or an imidazole or methylimidazolium group) in the presence of a base, such as triethylamine or diisopropylamine, in a solvent, such as dichloromethane or tetrahydrofuran, and at a temperature varying from ambient temperature to 80° C. The compounds of formula (I) are subsequently obtained by coupling between the activated derivatives (IV) and the amines (V) in the presence or absence of a base, such as triethylamine or potassium carbonate, in a solvent, such as tetrahydrofuran, dichloromethane, acetonitrile, dimethylformamide or water, at a temperature varying from ambient temperature to 100° C.

In some cases, when $R_1$ or $R_2$ is an alcohol or a primary or secondary amine or if $Ar_1$ or $Ar_2$ exhibits, in the compound (I), a secondary amine functional group, it is then necessary to carry out Method No. 1 with a derivative (II) where the abovementioned functional groups are rendered nonreactive by the presence of a protective group (for example, for an amine, a Boc, Bn or CBz group, for an alcohol, a Bn group, or, for an acid, an ester group). Finally, in order to obtain the desired functionality, it is subsequently necessary to carry out a deprotection reaction under conditions known to a person skilled in the art.

The heterocycles of general formula (V) are commercially available or can be prepared by methods described in the literature (for example, WO 2007/077949, US 2005/0215784 A1, US 2005/0245745 A1, Journal of Organic Chemistry (2005), 70(20), 7919-7924).

Scheme 2 explains in detail a synthesis of the compounds of formula (II).

Scheme 2:

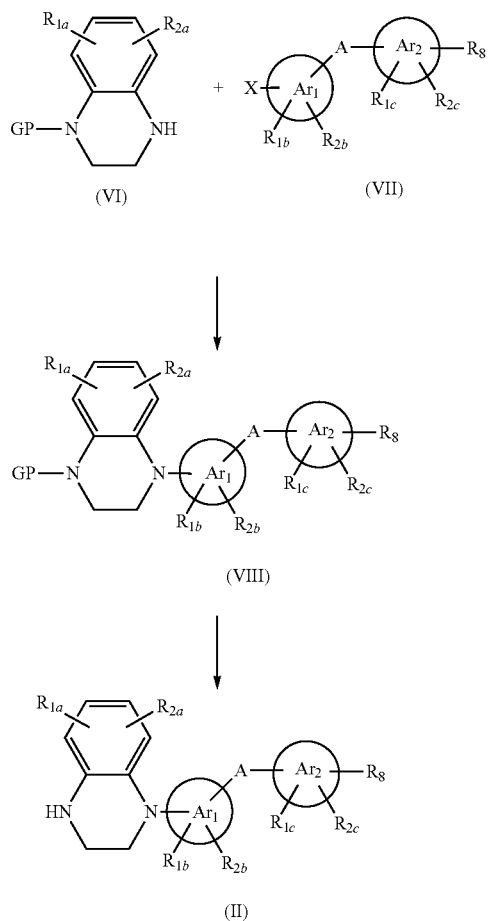

The heterocycles of general formula (VI) are commercially available or can be prepared by methods chosen from those known to a person skilled in the art; they comprise, inter alia, the use of trifluoroacetic acid or hydrochloric acid in dichloromethane, dioxane, tetrahydrofuran or diethyl ether, in the case of protection by a Boc group, and of piperidine, for a Fmoc group, at temperatures varying from −10 to 100° C.

The heterocycles of general formula (VI) are commercially available or can be prepared by methods described in the literature (for example, "Comprehensive Heterocyclic Chemistry", Katritzky et al., $2^{nd}$ Edition (Pergamon Press); Krchnak, V. et coll., Tet. Lett (2001), 42, 2443-2446; Eary, C. T. et al. Tet. Lett. (2006), 47, 6899-6902; Savrides, E.-M. et al., J. Het. Chem. (2005), 42, 1031-1034; De Selms, R. C. et al., J. Het. Chem. (1974), 11(4), 595-7.

The compounds of general formula (VII) are commercially available or can be prepared by methods described in the literature (for example, Z. Sui et al., Bioorg. Med. Chem. Lett. (2003), 13, 761-765; Chopa, A. B. et al., J. Organomet. Chem. (2005), 690(17), 3865-3877; Duggeli, M. et al., Org. Biomol. Chem. (2003), 1(11), 1894-1899; Gros, P. et al., J. Org. Chem. (2003), 68(5), 2028-2029; Bouillon, A. et al., Tet. (2002), 58(14), 2885-2890; Balle, T. et al., J. Med. Chem. (2006), 49(11), 3159-3171; M. A. Ismail et al., J. Med. Chem. (2006), 49(17), 5324-5332; Gu, Y. G. et al., J. Med. Chem. (2006), 49(13), 3770-3773; Serafin, B. et al., Eur. J. Med. Chem. (1977), 12(4), 325-31; Schmidt, H.-W. et al., J. Het. Chem. (1987), 24(5), 1305-7; Walsh, D. A. et al., J. Med. Chem. (1990), 33(7), 2028-32; WO 2005/042521; EP 0 277 725).

Scheme 3 explains in detail a synthesis of the compounds of formula (VIII) in which $Ar_1$ represents a pyridine nucleus (Y=CH) or a pyrimidine nucleus (Y=N); these compounds will be referred to hereinafter as compounds of formula (IX).

Scheme 3:

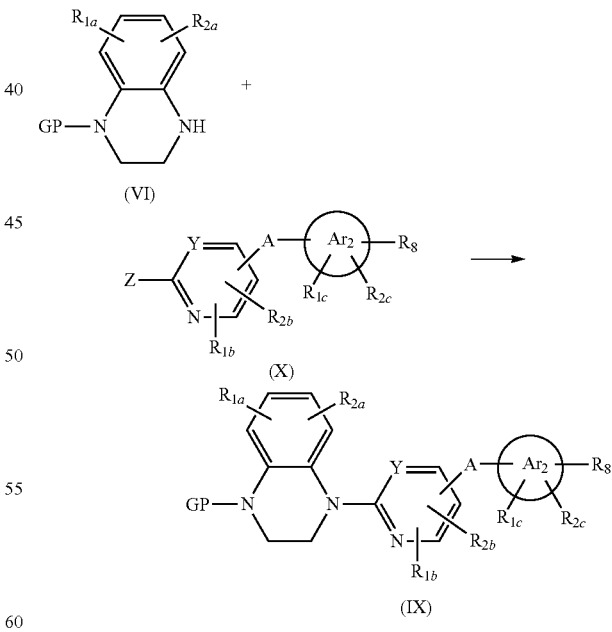

In Scheme 2, the compounds of formula (VIII) can be prepared by coupling between a monoprotected tetrahydroquinoxaline of formula (VI) and a derivative (VII) exhibiting a leaving group X (for example, a halogen or a tosylate, triflate or nonaflate group) in the presence of an organometallic catalyst, such as a palladium derivative, in the presence or absence of a phosphine, such as tri(tert-butyl)phosphine or triphenylphosphine, in the presence of a base, such as potassium carbonate, potassium fluoride, potassium tert-butoxide or potassium phosphate, in a solvent or mixture of solvents, such as dioxane, ethylene glycol dimethyl ether, toluene, tetrahydrofuran or water, at a temperature varying from ambient temperature to 100° C. The amines (II) are obtained by protection of the amine functional group of the compounds of In Scheme 3, the compounds of formula (IX) can be prepared by a nucleophilic aromatic substitution reaction between a monoprotected tetrahydroquinoxaline of formula (VI) and a derivative (X) exhibiting a leaving group Z (for example, a halogen or an alkylsulphonyl group) in the presence of a base, such as the lithium salt of hexamethyldisilazane or sodium hydride, in a solvent, such as tetrahydrofuran, N-methylpyrrolidinone, dimethyl sulphoxide or dimethylformamide, at a temperature varying from ambient temperature to 100° C.

Scheme 4 explains in detail a synthesis of the compounds of formula (VIII) in which $Ar_1$ represents a phenyl nucleus and A represents a bond; these compounds will be referred to hereinafter as compounds of formula (XI).

Scheme 4:

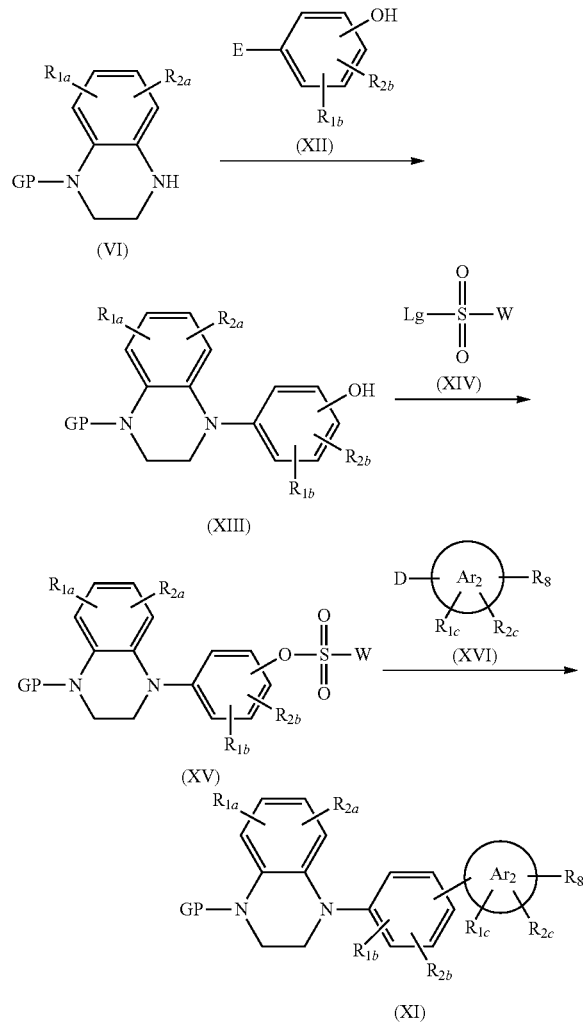

In Scheme 4, the compounds of formula (XIII) can be prepared by a coupling reaction between a monoprotected tetrahydroquinoxaline of formula (VI) and a derivative (XII) exhibiting a leaving group E (for example, a halogen, triflate or nonaflate) in the presence of an organometallic catalyst, such as a palladium derivative, in the presence or absence of a phosphine, such as tri(tert-butyl)phosphine or triphenylphosphine, in the presence of a base, such as potassium carbonate, caesium carbonate, potassium fluoride, potassium tert-butoxide or potassium phosphate, in a solvent or mixture of solvents, such as dioxane, ethylene glycol dimethyl ether, toluene, tetrahydrofuran or water, at a temperature varying from ambient temperature to 100° C. The phenol functional group is subsequently converted to a sulphonic ester (XV) by the action of a sulphonic derivative (XIV), where Lg represents, for example, a tosylate, triflate or nonaflate group, such as a sulphonic anhydride ($Lg=OSO_2W$), a sulphonic acid fluoride (Lg=F) or a sulphonic acid chloride (Lg=Cl), in the presence of a base or of a mixture of bases, such as triethylamine, pyridine, dimethylaminopyridine, diisopropylethylamine or potassium carbonate, in a solvent or mixture of solvents, such as dichloromethane, chloroform, toluene, tetrahydrofuran, dimethylformamide or acetonitrile, at a temperature varying from −78° C. to 100° C. Finally, the derivatives (XI) can be obtained by a coupling reaction between a derivative (XV) and a compound (XVI) exhibiting an organometallic derivative D (for example, a boron derivative, a tin derivative or an organozinc compound) in the presence of an organometallic entity, such as a palladium derivative, in the presence or absence of a phosphine, such as tricyclohexylphosphine or triphenylphosphine, in the presence of a base, such as potassium carbonate or potassium fluoride, in a solvent or mixture of solvents, such as dioxane, dimethylformamide, ethylene glycol dimethyl ether, tetrahydrofuran or water, at a temperature varying from ambient temperature to 100° C.

Scheme 5 presents an alternative synthesis of the compounds of formula (XI).

Scheme 5:

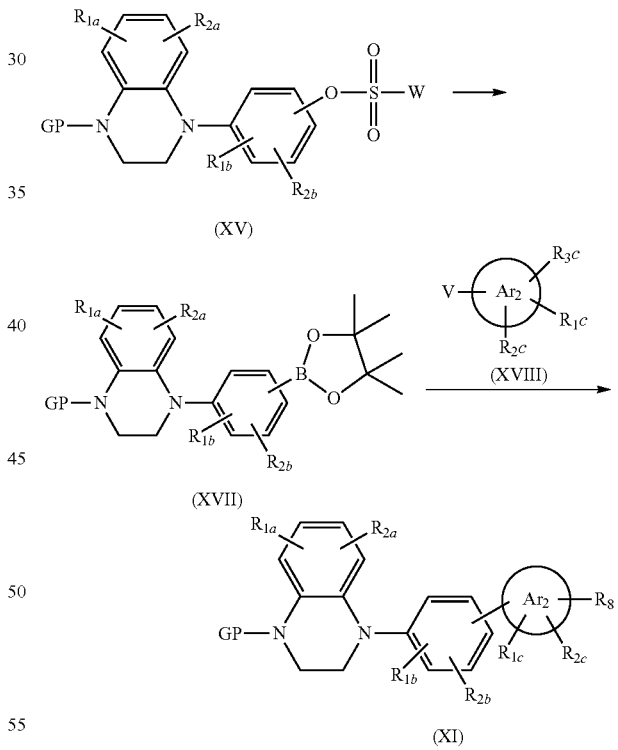

In Scheme 5, the compounds of formula (XVII) can be prepared by conversion of the sulphonic ester functional group of the compounds (XV) to a boronic ester derivative (XVII) by reaction with bis(pinacolato)diboron in the presence of a palladium complex, such as [1,1′-bis(diphenylphosphino)ferrocene]dichloropalladium(II), in the presence of a base, such as potassium acetate and lithium chloride, in a solvent or mixture of solvents, such as dichloromethane, dioxane or dimethyl sulphoxide, at a temperature varying from ambient temperature to 100° C. In a second stage, the derivatives (XI) can be obtained by a coupling reaction between the derivative (XVII) and a compound (XVIII) exhibiting a leaving group V (for example, a halogen, a triflate or a nonaflate) in the presence of an organometallic catalyst, such as a palladium derivative, in the presence or absence of a phosphine, such as tricyclohexylphosphine or triphenylphosphine, in the presence of a base, such as sodium carbonate, potassium carbonate or potassium fluoride, in a solvent or mixture of solvents, such as dioxane, dimethylformamide, ethylene glycol dimethyl ether, tetrahydrofuran or water, at a temperature varying from ambient temperature to 100° C.

Scheme 6 explains in detail a synthesis of the compounds of formula (VIII) in which $Ar_1$ represents a pyridine nucleus (just one of the two Y atoms is a nitrogen and the other is a carbon) and A represents a bond; these compounds will be referred to hereinafter as compounds of formula (XIX).

Scheme 6:

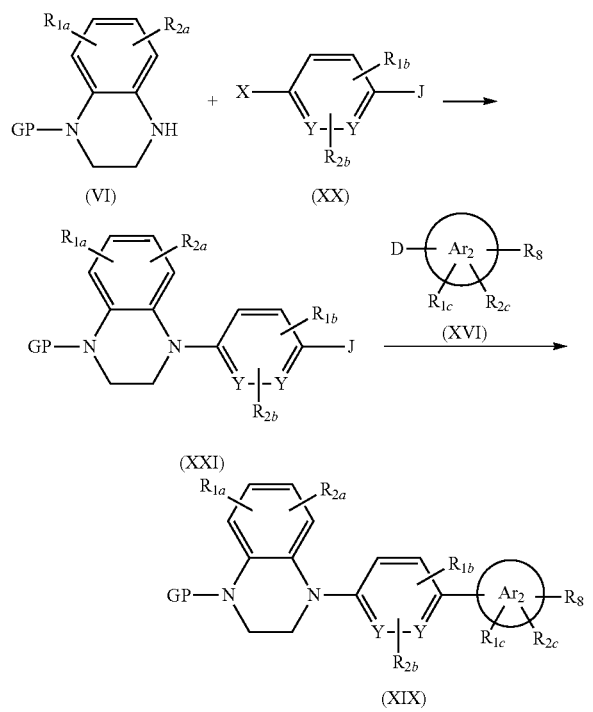

In Scheme 6, the compounds of formula (XXI) can be prepared by a nucleophilic aromatic substitution reaction between a monoprotected tetrahydroquinoxaline of formula (VI) and a derivative (XX) exhibiting a leaving group X (for example, a fluorine atom) and a leaving group J (for example, a bromine atom) in the presence of a base, such as potassium tert-butoxide or sodium hydride, in a solvent, such as N-methylpyrrolidinone or dimethylformamide, at a temperature varying from ambient temperature to 100° C. Finally, the derivatives (XIX) can be obtained by a coupling reaction between a derivative (XXI) and a compound (XVI) exhibiting an organometallic group D (for example, a boron derivative, a tin derivative or an organozinc compound) in the presence of an organometallic catalyst, such as a palladium derivative, in the presence or absence of a phosphine, such as tricyclohexylphosphine or triphenylphosphine, in the presence of a base, such as potassium carbonate, caesium carbonate, potassium triphosphate or potassium fluoride, in a solvent or mixture of solvents, such as toluene, dioxane, dimethylformamide, ethylene glycol dimethyl ether, tetrahydrofuran or water, at a temperature varying from ambient temperature to 100° C.

Scheme 7 explains in detail a synthesis of the compounds of formula (VIII) in which A is an oxygen atom or an —O—$CH_2$— group; these compounds will be referred to hereinafter as compounds of formula (XXII).

Scheme 7:

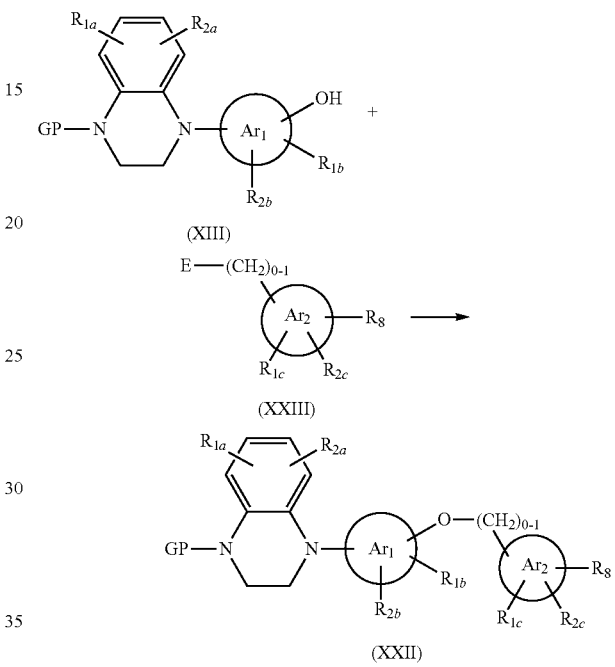

In Scheme 7, the compounds of formula (XXII) can be prepared by a nucleophilic aromatic or aliphatic substitution reaction between a quinoxaline of formula (XIII) and a derivative (XXIII) exhibiting a leaving group E (for example, a halogen) in the presence of a base, such as potassium tert-butoxide, sodium hydride or potassium carbonate, in a solvent, such as dimethylformamide, at a temperature varying from ambient temperature to 150° C. In some cases, during the reaction, the protective group PG can be removed simultaneously with the nucleophilic substitution (in particular if PG is a Boc group).

Scheme 8 explains in detail a synthesis of the compounds of formula (VIII) in which A is a bond, $Ar_1$ is a phenyl group and $Ar_2$ is a piperidinyl group; these compounds will be referred to hereinafter as compounds of formula (XXVIII).

Scheme 8:

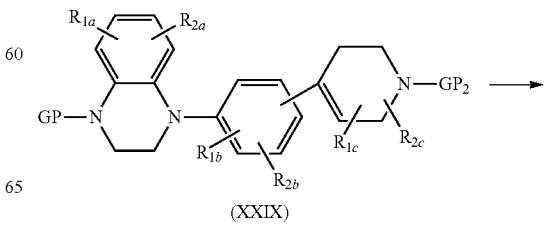

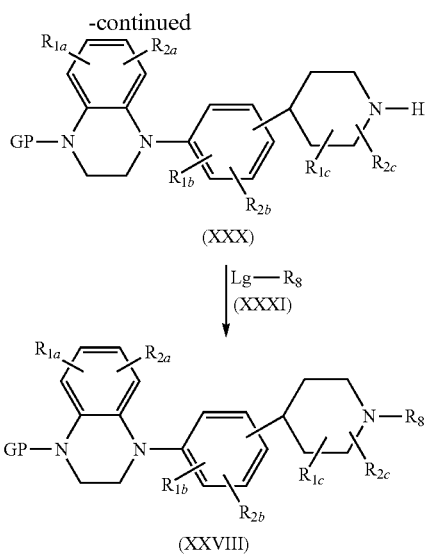

(XXX)

↓ Lg—R₈ (XXXI)

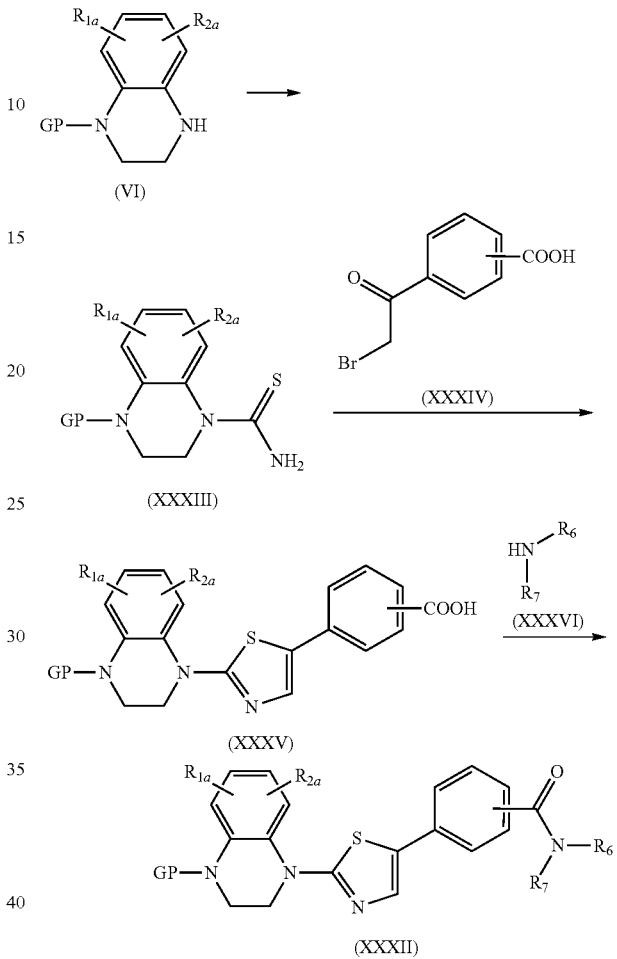

In Scheme 8, in order to result in the derivatives (XXX), the compound of formula (XXIX), where the amine functional group of the 1,2,3,6-tetrahydropiperidine is protected by a protective group PG₂ of benzyl or benzyloxycarbonyl type (the PG group being either the Fmoc group or the Boc group), can undergo a hydrogenation reaction of the double bond and hydrogenolysis of the protective group PG₂ in the presence of an organometallic catalyst, such as a palladium derivative (for example, 10% Pd deposited on charcoal or Pd(OAc)₂), in a solvent or mixture of solvents, such as methanol, ethanol or ethyl acetate, at a temperature varying from ambient temperature to 80° C. In the final stage, the compound (XXVIII) can be prepared according to different methods. The compound (XXXI) can be a carboxylic acid derivative and the derivative (XXVIII) can then be obtained by reaction between (XXX) and (XXXI) under conventional peptide coupling conditions using, as coupling agent, for example dicyclohexylcarbodiimide, 1-(3-dimethylaminopropyl)-3-ethylcarbodiimide hydrochloride or bromotripyrrolidinophosphonium hexafluorophosphate, in the presence or absence of hydroxybenzotriazole, and by using, as organic base, triethylamine or diisopropylethylamine, in a solvent or mixture of solvents, such as dioxane, dichloromethane or acetonitrile. The compound (XXXI) can be an acid derivative, such as an acid chloride, bromide or fluoride, an isocyanate, a carbamoyl chloride or also a sulphonic acid chloride and the derivative (XXVIII) can then be obtained by reaction between (XXX) and (XXXI) in the presence of a base, such as triethylamine, diisopropylamine or pyridine, without solvent or in a solvent or mixture of solvents, such as dichloromethane, tetrahydrofuran, acetonitrile or dimethylformamide, at a temperature varying from 0° C. to 160° C. The compound (XXXI) can also be a ketone and the derivative (XXVIII) can then be obtained by a reductive amination reaction between (XXX) and (XXXI) using a reducing agent, such as sodium borohydride, sodium triacetoxyborohydride or sodium cyanoborohydride, in the presence or absence of a Brönsted acid (such as hydrochloric acid) or Lewis acid (such as titanium tetraisopropoxide), in a solvent, such as dichloroethane, dichloromethane, acetic acid or methanol, at temperatures of between −10° C. and 30° C.

Scheme 9 explains in detail a synthesis of the compounds of formula (VIII) in which A is a bond, $Ar_1$ is a thiazolyl group and $Ar_2$ is a phenyl group substituted by a —$CONR_6R_7$ group; these compounds will be referred to hereinafter as compounds of formula (XXXII).

Scheme 9:

In Scheme 9, the compounds of formula (XXXIII) can be prepared by a methodology as described in Patent Application WO 2005/007601. The thiazole derivative (XXXV) can be obtained conventionally (cf. Koti, R. S. et al., Synthetic Communications (2007), 37(1), 99-105; Duggineni, S. et al., Tetrahedron (2006), 62(14), 3228-3241; Balavoine, F. et al., Bioorganic & Medicinal Chemistry Letters (2007), 17(13), 3754-3759) by condensation of the thiourea derivative (XXXIII) with an α-bromoketone derivative (XXXIV) in a solvent, such as ethanol, acetone or tetrahydrofuran, at temperatures of between ambient temperature and 80° C. Finally, the derivative (XXXII) can be obtained by reaction between (XXXV) and (XXXVI) under conventional peptide coupling conditions by using, as coupling agent, for example dicyclohexylcarbodiimide, 1-(3-dimethylaminopropyl)-3-ethylcarbodiimide hydrochloride or bromotripyrrolidinophosphonium hexafluorophosphate, in the presence or absence of hydroxybenzotriazole, and by using, as organic base, triethylamine or diisopropylethylamine, in a solvent or mixture of solvents, such as dioxane, dichloromethane or acetonitrile.

Scheme 10 explains in detail an alternative synthesis of the compounds of formula (I) in which A represents a bond.

Scheme 10 (Method No. 2):

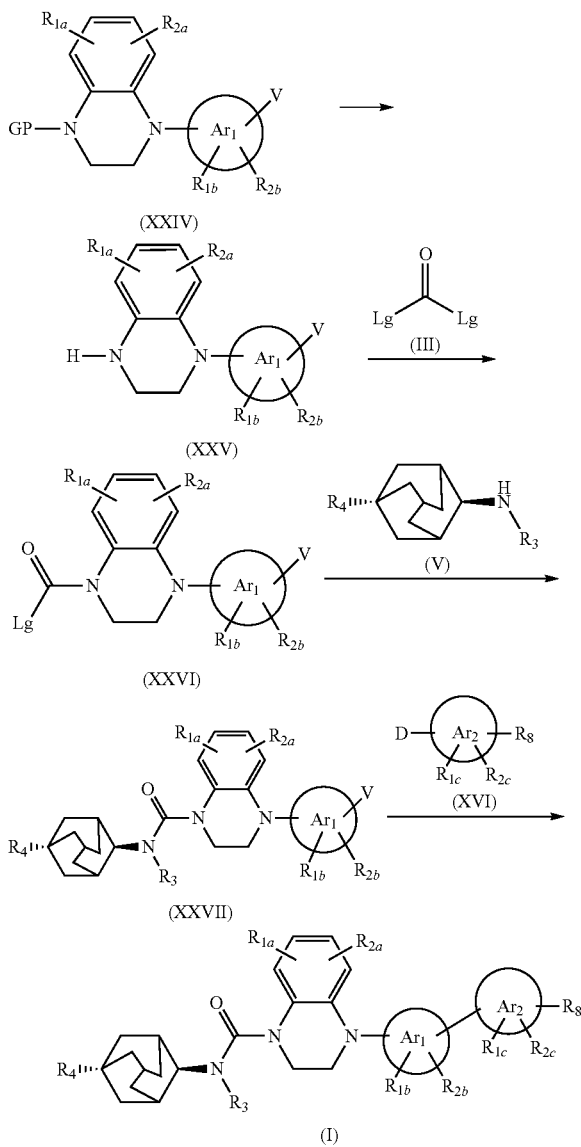

In Scheme 10, the amines (XXV) exhibiting a leaving group V (for example, a halogen, a triflate or a nonaflate) are obtained by deprotection of the amine functional group of the compounds of formula (XXIV) by methods chosen from those known to a person skilled in the art. They comprise, inter alia, the use of trifluoroacetic acid or hydrochloric acid in dichloromethane, dioxane, tetrahydrofuran or diethyl ether, in the case of protection by a Boc group, and of piperidine, for a Fmoc group, at temperatures varying from −10 to 100° C. In a following stage, the compounds of formula (XXVI) can be prepared by reaction between the intermediates of formula (XXV) and a carbonyl of formula (III) exhibiting two leaving groups Lg (chosen, for example, from chlorine atoms or trichloromethoxy, para-nitrophenyl, imidazole or methylimidazolium groups) in the presence of a base, such as triethylamine or diisopropylamine, in a solvent, such as dichloromethane or tetrahydrofuran, at a temperature varying from ambient temperature to 80° C. The compounds of formula (XXVII) are subsequently obtained by coupling between the activated derivatives (XXVI) and the amines (V) in the presence or absence of a base, such as triethylamine or potassium carbonate, in a solvent, such as tetrahydrofuran, dichloromethane, acetonitrile, dimethylformamide or water, at a temperature varying from ambient temperature to 100° C. Finally, the compounds (I) can be obtained by a coupling reaction between a derivative (XXVII) and a compound (XVI) exhibiting an organometallic group D (for example, a boron derivative, a tin derivative or an organozinc compound) in the presence of an organometallic catalyst, such as a palladium derivative (for example 2'-(dimethylamino)-2-biphenylylpalladium(II) chloride dinorbornylphosphine), in the presence or absence of a phosphine, such as tricyclohexylphosphine or triphenylphosphine, in the presence of a base, such as potassium carbonate, caesium carbonate, potassium triphosphate or potassium fluoride, in a solvent or mixture of solvents, such as toluene, dioxane, dimethylformamide, ethylene glycol dimethyl ether, tetrahydrofuran or water, at a temperature varying from ambient temperature to 100° C., under thermal or microwave heating.

Scheme 11 explains in detail a synthesis of the compounds of formula (I) in which $R_4$ represents an amide functional group; these compounds will be referred to hereinafter as compounds of formula (XXXVII).

Scheme 11 (Method No. 3):

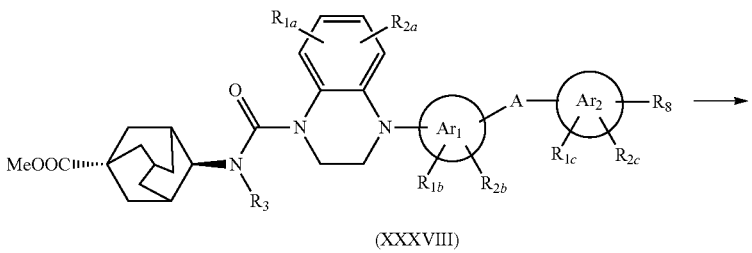

(XXXVIII)

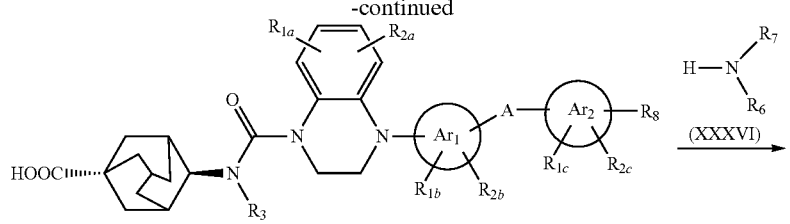
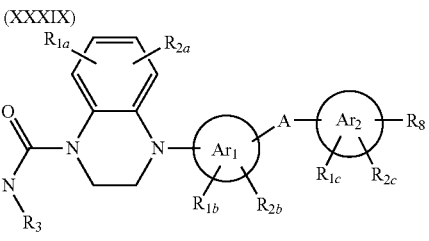
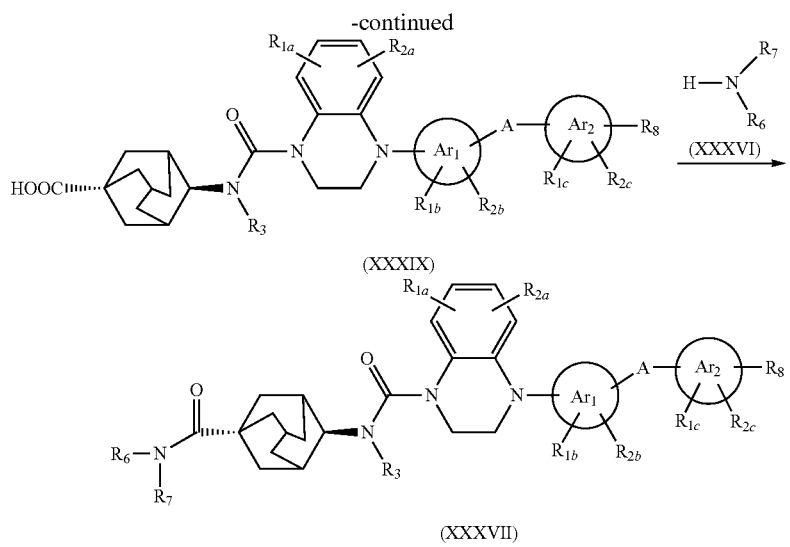

In Scheme 11, the ester functional group of the compound (XXXVIII) is saponified to give the acid functional group using sodium hydroxide, potassium hydroxide or lithium hydroxide in a solvent or mixture of solvents, such as an alcohol, water or tetrahydrofuran, at a temperature varying from ambient temperature to 100° C., to result in the acid (XXXIX). In the final stage, the compound (XXXVII) can be prepared by condensation between the acid intermediate of formula (XXXIX) and an amine (XXXVI) under conventional peptide coupling conditions by using, as coupling agent, for example dicyclohexylcarbodiimide, 1-(3-dimethylaminopropyl)-3-ethylcarbodiimide hydrochloride or bromotripyrrolidinophosphonium hexafluorophosphate, in the presence or absence of hydroxybenzotriazole, and by using, as organic base, triethylamine or diisopropylethylamine, in a solvent or mixture of solvents, such as dioxane, dichloromethane or acetonitrile.

Scheme 12 explains in detail an alternative synthesis of the compounds of formula (I).

Scheme 12 (Method No. 4):

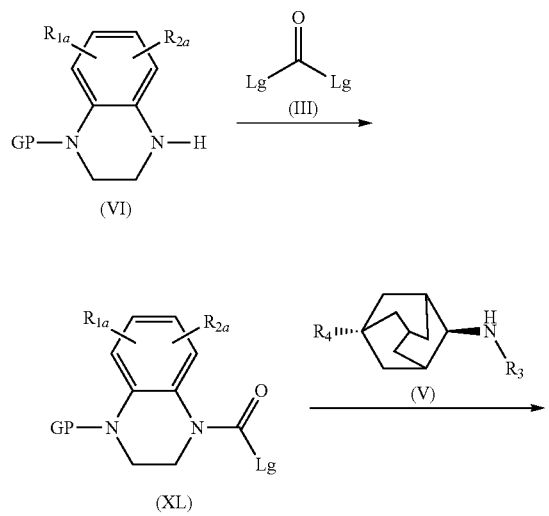
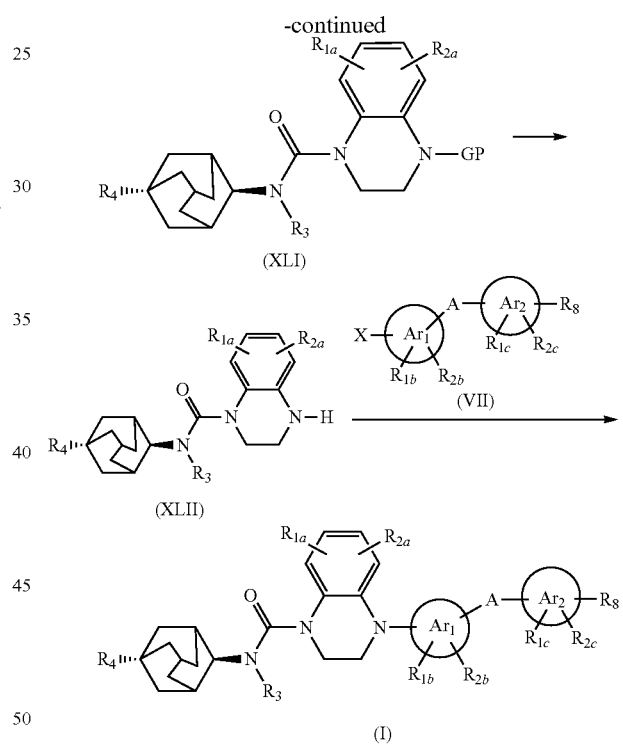

In Scheme 12, the compounds of formula (XL) can be prepared by reaction between the intermediates of formula (VI) and a carbonyl of formula (III) exhibiting two leaving groups Lg (chosen, for example, from chlorine atoms or trichloromethoxy, para-nitrophenyl, imidazole or methylimidazolium groups) in the presence of a base, such as triethylamine or diisopropylamine, in a solvent, such as dichloromethane or tetrahydrofuran, at a temperature varying from ambient temperature to 80° C. The compounds of formula (XLI) are subsequently obtained by coupling between the activated derivatives (XL) and the amines (V) in the presence or absence of a base, such as triethylamine or potassium carbonate, in a solvent, such as tetrahydrofuran, dichloromethane, acetonitrile, dimethylformamide or water, at a temperature varying from ambient temperature to 100° C.

The amines (XLII) are subsequently obtained by deprotection of the amine functional group of the compounds of formula (XLI) by methods chosen from those known to a person skilled in the art; they comprise, inter alia, the use of trifluoroacetic acid or hydrochloric acid in dichloromethane, dioxane, tetrahydrofuran or diethyl ether, in the case of protection by a Boc group, and of piperidine, for a Fmoc group, at temperatures varying from −10 to 100° C. Finally, the compounds (I) can be obtained by coupling between the derivative (XLII) and a derivative (VII) exhibiting a leaving group X (for example, a halogen or a tosylate, triflate or nonaflate group) in the presence of an organometallic catalyst, such as a palladium derivative, in the presence or absence of a phosphine, such as tri(tert-butyl)phosphine or triphenylphosphine, in the presence of a base, such as potassium carbonate, potassium fluoride, potassium tert-butoxide or potassium phosphate, in a solvent or mixture of solvents, such as dioxane, ethylene glycol dimethyl ether, toluene, tetrahydrofuran or water, at a temperature varying from ambient temperature to 100° C.

Scheme 13 explains in detail a synthesis of the compounds of formula (VIII) in which $Ar_1$ represents a pyridine nucleus (one of the two Y groups is a nitrogen and the other is a carbon) or a pyrimidine nucleus (both Y groups are nitrogens) and A represents a bond; these compounds will be referred to hereinafter as compounds of formula (XLIII).

Scheme 13:

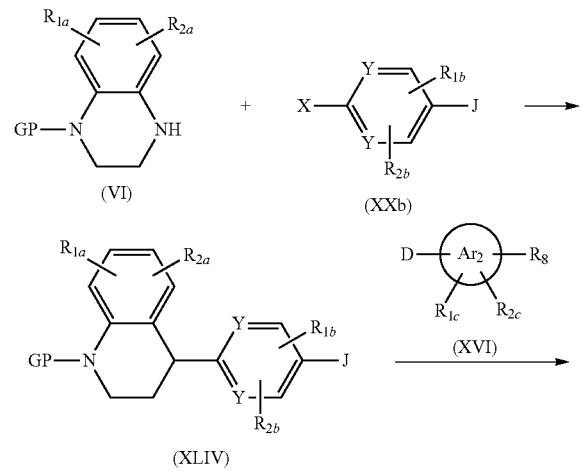

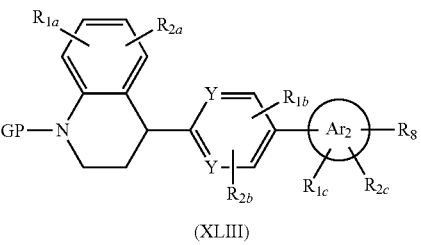

In Scheme 13, the compounds of formula (XLIV) can be prepared by a nucleophilic aromatic substitution reaction between a monoprotected tetrahydroquinoxaline of formula (VI) and a derivative (XXb) exhibiting a leaving group X (for example a fluorine or chlorine atom or an $SO_2Me$ group) and another leaving group J (for example a bromine or iodine atom) in the presence of a base, such as potassium tert-butoxide, n-butyllithium or sodium hydride, in a solvent, such as N-methylpyrrolidinone, tetrahydrofuran or dimethylformamide, at a temperature varying from −70° C. to 100° C. Finally, the derivatives (XLIII) can be obtained by a coupling reaction between a derivative (XLIV) and a compound (XVI) in which D is either an organometallic group (for example a boron derivative, a tin derivative or an organozinc compound) or a hydrogen atom of a cyclic secondary amine (for example $Ar_2$ is a piperazine or piperidine derivative) in the presence of an organometallic catalyst, such as a palladium derivative, in the presence or absence of a phosphine, such as tricyclohexylphosphine, tri(tert-butyl)phosphine, triphenylphosphine or 2-dicyclohexylphosphino-2',6'-dimethoxybiphenyl, in the presence of a base, such as potassium carbonate, caesium carbonate, potassium triphosphate or potassium fluoride, in a solvent or mixture of solvents, such as toluene, dioxane, dimethylformamide, ethylene glycol dimethyl ether, tetrahydrofuran or water, at a temperature varying from ambient temperature to 100° C.

Scheme 14 explains in detail a synthesis of the compounds of formula (I) in which $R_4$ represents a $CH_2OH$ group; these compounds will be referred to hereinafter as compounds of formula (XLV).

Scheme 14 (Method No. 5):

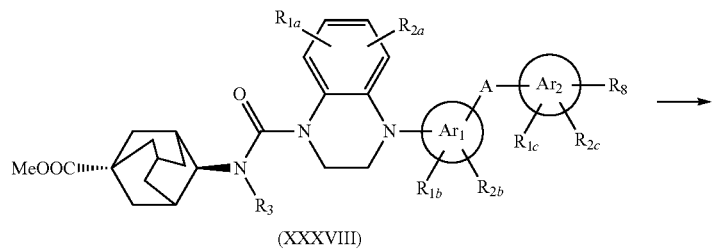

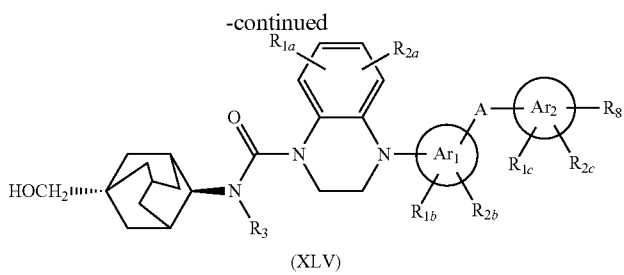

(XLV)

In Scheme 14, the derivatives (XLV) are obtained by reduction of the ester functional group of the compound (XXXVIII) to give an alcohol functional group using a hydride, such as $LiAlH_4$, $LiBH_4$ or DIBAL, in a solvent or mixture of solvents, such as tetrahydrofuran, ether or toluene, at a temperature varying from −78° C. to 40° C.

Scheme 15 explains in detail a synthesis of the compounds of formula (I) in which $Ar_2$ is a piperazine group, A is a single bond directly connected to one of the two nitrogens of the piperazine and $R_{1c}$ is connected to the other nitrogen atom of the piperazine; these compounds will be referred to hereinafter as compounds of formula (XLVI). The same reaction scheme can also be applied to the synthesis of compounds where the position between $R_{1c}$ and $R_8$ is interchanged. The groups $Lg$-$R_{1c}$ and $O$=$R_{1c}$ are then replaced respectively by the groups $Lg$-$R_8$ and $O$=$R_8$.

Scheme 15 (Method No. 6):

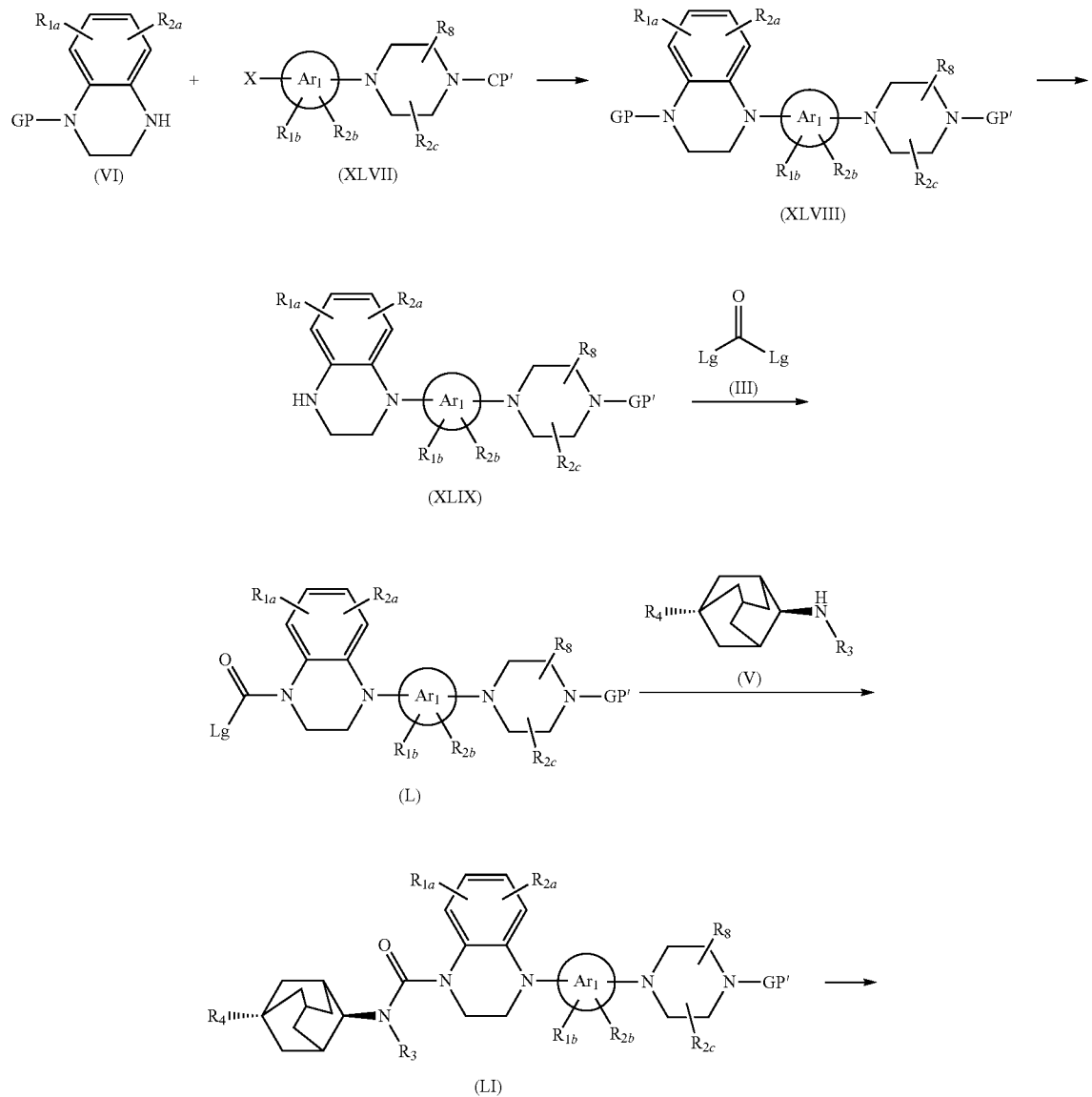

-continued

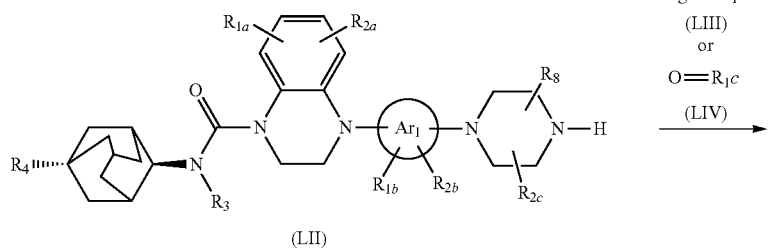

(LII)

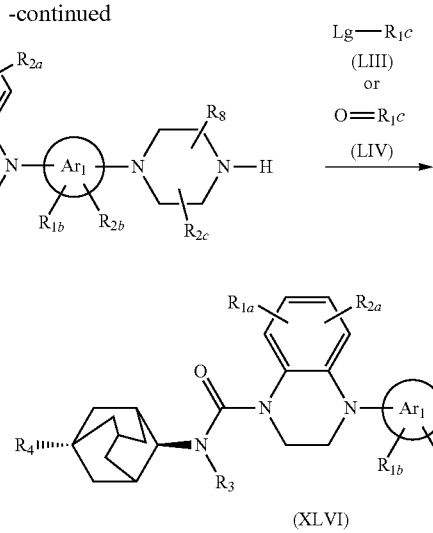

(XLVI)

In Scheme 12, the compounds of formula (XLVIII) can be prepared by coupling between a monoprotected tetrahydroquinoxaline of formula (VI) and a derivative (XLVII) exhibiting a leaving group X (for example a halogen or a tosylate, triflate or nonaflate group) in the presence of an organometallic catalyst, such as a palladium derivative, in the presence or absence of a phosphine, such as tri(tert-butyl)phosphine or triphenylphosphine, in the presence of a base, such as potassium carbonate, potassium fluoride, potassium tert-butoxide or potassium phosphate, in a solvent or mixture of solvents, such as dioxane, ethylene glycol dimethyl ether, toluene, tetrahydrofuran or water, at a temperature varying from ambient temperature to 100° C. The two compounds (VI) and (XLVII) exhibit two protected amine functional groups. In order to obtain selective deprotection of the compound (XLVIII), it is necessary for the two protective groups carried by the compounds (VI) and (XLVII) to be different. Furthermore, each protective group must be able to be resistant to the conditions for deprotection of its neighbour. For example, PG can be a Boc or Fmoc group and PG' can be a benzyl or benzyloxycarbonyl group. The amines (XLIX) are obtained by selective deprotection from the PG groups of the compounds of formula (XLVIII) by methods chosen from those known to a person skilled in the art; they comprise, inter alia, the use of trifluoroacetic acid or hydrochloric acid in dichloromethane, dioxane, tetrahydrofuran or diethyl ether, in the case of protection by a Boc group, and of piperidine, for a Fmoc group, at temperatures varying from −10 to 100° C. In the following stage, the compounds of formula (L) can be prepared by reaction between the intermediates of formula (XLIX) and a carbonyl of formula (III) exhibiting two leaving groups Lg (for example chosen from chlorine atoms or trichloromethoxy, para-nitrophenyl, imidazole or methylimidazolium groups) in the presence of a base, such as triethylamine or diisopropylamine, in a solvent, such as dichloromethane or tetrahydrofuran, at a temperature varying from ambient temperature to 80° C. The compounds of formula (LI) are subsequently obtained by coupling between the activated derivatives (L) and the amines (V) in the presence or absence of a base, such as triethylamine or potassium carbonate, in a solvent, such as tetrahydrofuran, dichloromethane, acetonitrile, dimethylformamide or water, at a temperature varying from ambient temperature to 100° C. The amines (LII) are subsequently obtained by deprotection of the amine functional group of the compounds of formula (LI); for example, if PG' is a benzyl or benzyloxycarbonyl group, the possible deprotection methods comprise, inter alia, the use of hydrogen in the presence of a palladium-derived catalyst, in order to carry out a hydrogenolysis reaction, in a solvent or mixture of solvents, such as methanol, ethanol, ethyl acetate or tetrahydrofuran, under a hydrogen pressure of between 1 and 10 bar at a temperature varying from ambient temperature to 80° C. An alternative method for carrying out a hydrogenolysis of the Bn or Cbz group is to use catalysis with palladium (for example with palladium adsorbed on charcoal) in the presence of ammonium formate at reflux of a solvent, such as methanol. In the final stage, the compounds (XLVI) can be obtained according to different reactions:

The compound (LII) can be reacted with a derivative (LIII) of sulphonyl chloride, acid chloride or carbamoyl chloride type (Lg is then a chlorine atom) in the presence of a base, such as triethylamine, diisopropylethylamine or pyridine, with or without solvent, such as dichloromethane, chloroform, tetrahydrofuran or dioxane, at a temperature varying from 0 to 40° C.

An alkylation reaction is also possible between the compound (LII) and a substituted or unsubstituted alkyl group (LIII) in which Lg is, for example, a chlorine, bromine or iodine atom or a tosylate or triflate group, in the presence of a base, such as triethylamine, or diisopropylethylamine, in a solvent, such as tetrahydrofuran or dioxane, at a temperature varying from 0 to 80° C.

A reductive amination reaction can also be carried out between the compound (LII) and a derivative (LIV) of aldehyde or ketone type by using a reducing agent, such as sodium borohydride, sodium triacetoxyborohydride or sodium cyanoborohydride, in the presence or absence of a Brönsted acid (such as hydrochloric acid) or Lewis acid (such as titanium tetraisopropoxide) in a solvent, such as dichloroethane, dichloromethane, acetic acid or methanol, at temperatures of between −10° C. and 30° C. In some cases, an additional deprotection stage is necessary in order to obtain the desired functionality on $R_{1c}$ or $R_8$ (for example, an alcohol or primary or secondary amine functional group).

Scheme 16 explains in detail a synthesis of the compounds of formula (I) in which $R_4$ represents a halogen atom, such as a fluorine atom; these compounds will be referred to hereinafter as compounds of formula (LV).

Scheme 16 (Method No. 7):

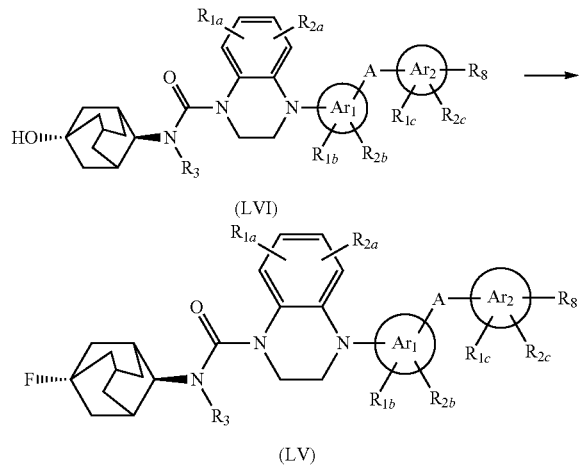

(LVI)

(LV)

In Scheme 16, the derivatives (LV) are obtained by conversion of the alcohol functional group of the compound (LVI) to a halogen atom, such as a fluorine atom, using a halogenating reagent, such as (diethylamino)sulphur trifluoride (DAST) or bis(2-methoxyethyl)aminosulphur trifluoride (Deoxo-Fluor®), in a solvent, such as dichloromethane or toluene, at a temperature varying from −78° C. to ambient temperature.

Scheme 17 explains in detail a synthesis of the compounds of formula (I) in which $R_{1c}$ represents an —SO$_2$—(CH$_2$)$_{1-3}$—CO$_2$H group; these compounds will be referred to hereinafter as compounds of formula (LVI).

Scheme 17 (Method No. 8):

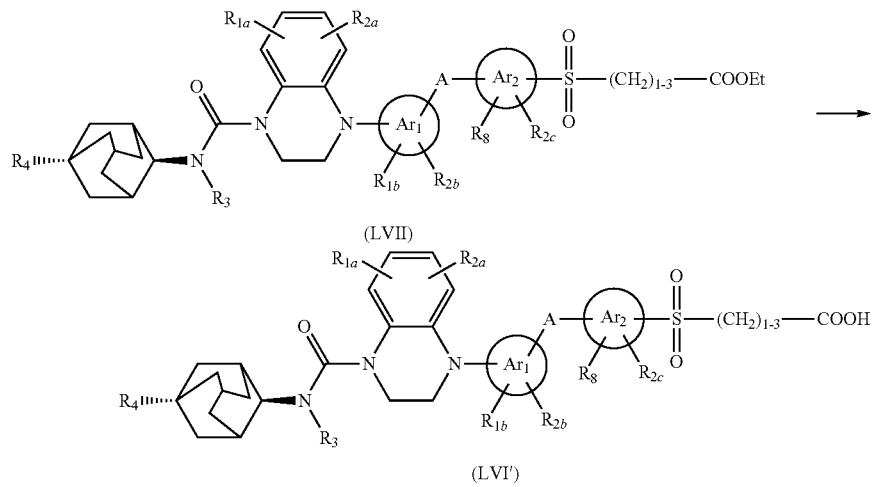

(LVII)

(LVI')

In Scheme 17, the derivatives (LVI) are obtained by hydrolysis of the ester functional group (for example ethyl ester) of the compound (LVII) using an inorganic base, such as sodium hydroxide, potassium hydroxide or lithium hydroxide, in a solvent, such as an alcohol or water, at a temperature varying from ambient temperature to 100° C., in order to result in the acids (LVI).

Scheme 18 explains in detail a synthesis of the compounds of formula (I) in which Ar$_2$ is a piperidine group, A is a single bond directly connected to the nitrogen of the piperidine and $R_{1c}$ is an alcohol functional group and is connected in the 4 position with regard to the nitrogen atom of the piperidine; these compounds will be referred to hereinafter as compounds of formula (LVIII).

Scheme 18 (Method No. 9):

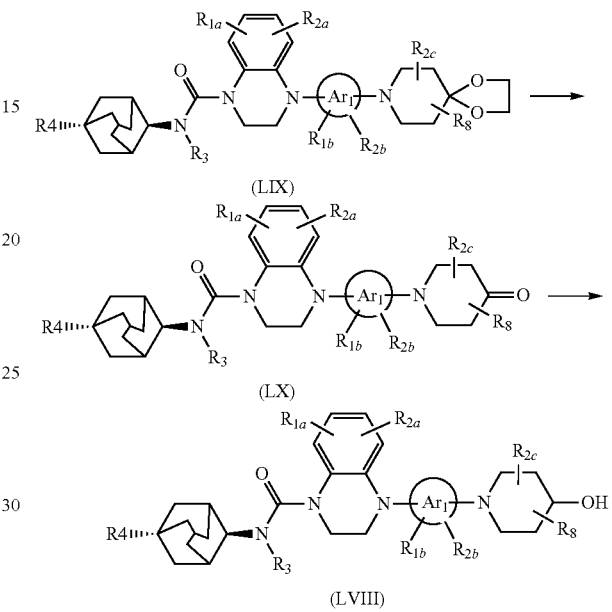

(LIX)

(LX)

(LVIII)

In Scheme 18, the derivatives (LX) are obtained by hydrolysis of the cyclic acetal functional group of the compound (LIX) using an acid, such as hydrochloric acid, in a solvent or mixture of solvents, such as water, an alcohol or dioxane, at a temperature varying from ambient temperature to 100° C., to result in the ketones (LX). The final stage consists in reducing the carbonyl group to give an alcohol functional group using a reducing agent, such as a hydride, for example sodium borohydride or lithium aluminium hydride, in a solvent, such as methanol or ethanol, at a temperature varying from 0° C. to ambient temperature, in order to result in the compounds (LVIII).

Scheme 19 explains in detail a synthesis of the compounds of formula (VIII) in which $Ar_2$ is a piperazine group, A is a single bond directly connected to one of the two nitrogens of the piperazine and $R_{1c}$ is an —$SO_2(CH_2)_2$-Nu group (Nu is an $OR_5$ or $NR_6R_7$ group) and is connected to the other nitrogen atom of the piperazine; these compounds will be referred to hereinafter as compounds of formula (LXI).

with palladium, results in the monoprotected derivative (LXII). In the following stage, the compound (LXIII) is obtained by reacting the derivative (LXII) with 2-chloroethanesulphonic acid chloride according to the conditions described by Golding et al. in the paper Org. Biomol. Chem., 2007, 5 (132-138). The intermediates (LXI) are finally obtained after a reaction of Michael type between the derivative (LXIII) and the nucleophiles H-Nu (LXIV). The nucleophiles (LXIV) can be of various natures, such as secondary amines, alcohols or phthalimides, and the reaction can be carried out under conditions described by B. T. Golding et al.

Scheme 19:

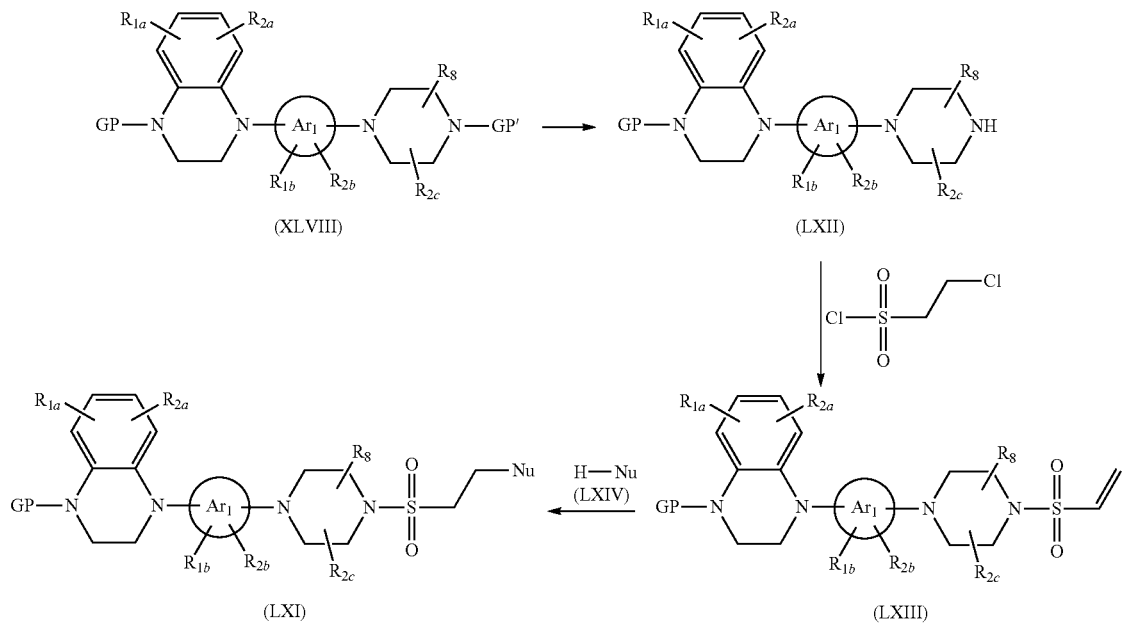

In Scheme 19, the compounds of formula (LXII) can be obtained by a selective deprotection of the PG' group with respect to the PG group. For example, if PG is a Boc group and PG' is a CBz group, a hydrogenolysis reaction on the derivative (XLVIII), for example carried out either under hydrogen pressure or with ammonium formate with catalysis in the paper Org. Biomol. Chem., 2007, 5 (132-138), or by J. Marchand-Brynaert in the paper Tet., 1996, 52 (5591-5606).

Scheme 20 explains in detail a synthesis of the compounds of formula (I) in which $R_{1c}$ represents an —$SO_2(CH_2)_{2-3}$ $CH_2OH$ group; these compounds will be referred to hereinafter as compounds of formula (LXV).

Scheme 20 (Method No. 10):

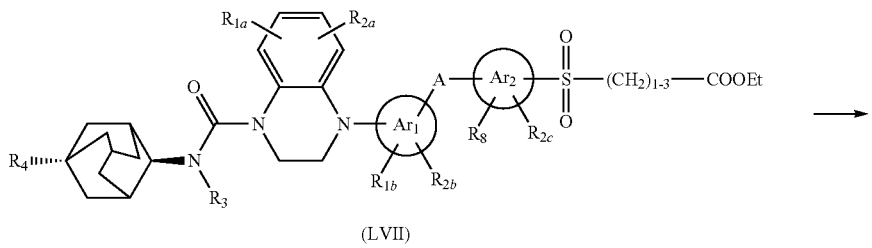

(LVII)

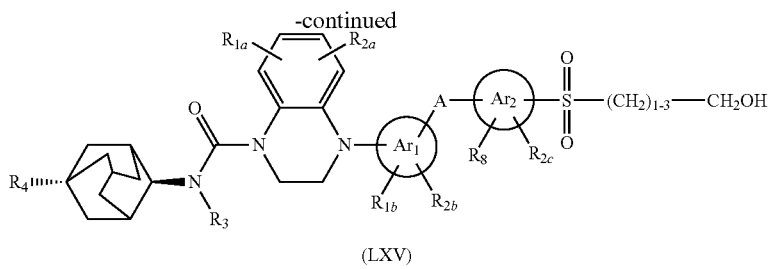

(LXV)

In Scheme 20, the derivatives (LXV) are obtained by reduction of the ester functional group of the compound (LVII) to give an alcohol functional group using a reducing agent, such as a hydride, for example LiAlH$_4$, LiBH$_4$, DIBAL, in a solvent or mixture of solvents, such as tetrahydrofuran, ether or toluene, at a temperature varying from −78° C. to 40° C.

Scheme 21 explains in detail a synthesis of the compounds of formula (I) in which R$_8$ represents a 4-hydroxypiperidine group and R$_8$ is connected to Ar$_2$ via the oxygen atom; these compounds will be referred to hereinafter as compounds of formula (LXVI).

Scheme 21 (Method No. 11):

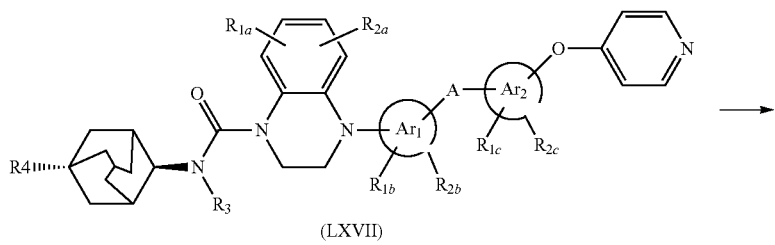

(LXVII)

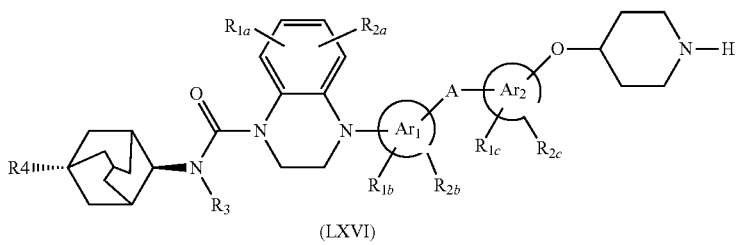

(LXVI)

In Scheme 21, the derivatives (LXVI) are obtained by reduction of the pyridine nucleus of the compound (LXVII) to give a piperidine using a catalyst, such as palladium or platinum derivatives, in the presence or absence of an acid, such as para-toluenesulphonic acid, HCl or H$_2$SO$_4$, under a hydrogen pressure of between 1 and 50 bar in a solvent or mixture of solvents, such as an alcohol or water.

Scheme 22 explains in detail a synthesis of the compounds of formula (VIII) in which Ar$_2$ is a piperazine group, A is a single bond directly connected to one of the two nitrogens of the piperazine and R$_{1c}$ is connected to the other nitrogen atom of the piperazine; these compounds will be referred to hereinafter as compounds of formula (LXVIII).

Scheme 22:

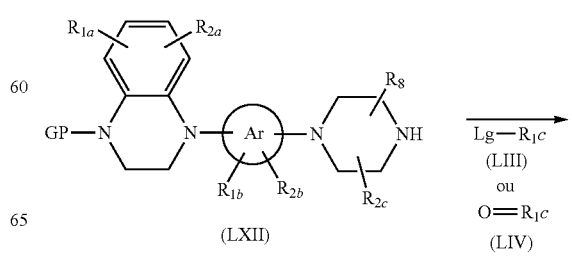

(LXII)           (LIV)

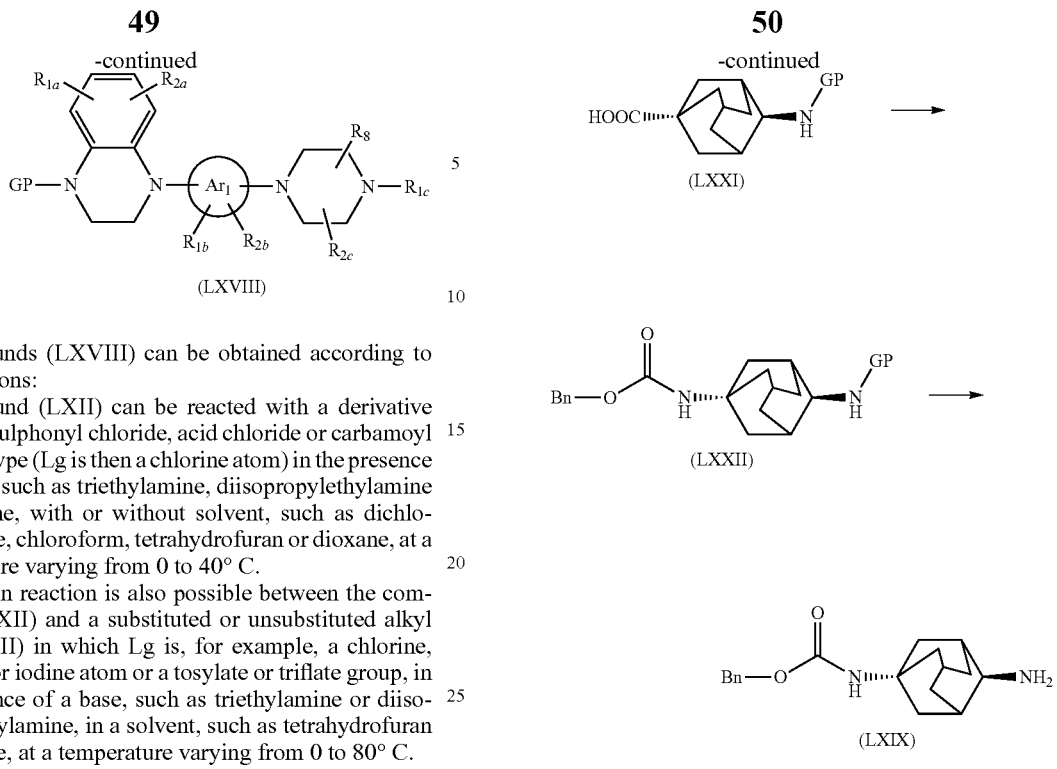

The compounds (LXVIII) can be obtained according to different reactions:

- The compound (LXII) can be reacted with a derivative (LIII) of sulphonyl chloride, acid chloride or carbamoyl chloride type (Lg is then a chlorine atom) in the presence of a base, such as triethylamine, diisopropylethylamine or pyridine, with or without solvent, such as dichloromethane, chloroform, tetrahydrofuran or dioxane, at a temperature varying from 0 to 40° C.
- An alkylation reaction is also possible between the compound (LXII) and a substituted or unsubstituted alkyl group (LIII) in which Lg is, for example, a chlorine, bromine or iodine atom or a tosylate or triflate group, in the presence of a base, such as triethylamine or diisopropylethylamine, in a solvent, such as tetrahydrofuran or dioxane, at a temperature varying from 0 to 80° C.
- A reductive amination reaction can also be carried out between the compound (LXII) and a derivative (LIV) of aldehyde or ketone type using a reducing agent, such as sodium borohydride, sodium triacetoxyborohydride or sodium cyanoborohydride, in the presence or absence of a Bronsted acid (such as hydrochloric acid) or Lewis acid (such as titanium tetraisopropoxide) in a solvent, such as dichloroethane, dichloromethane, acetic acid or methanol, at temperatures of between −10° C. and 30° C.

Scheme 23 explains in detail a synthesis of the compounds of formula (V) in which $R_3$ is a hydrogen and $R_4$ is a benzyl carbamate group; these compounds will be referred to hereinafter as compounds of formula (LXIX).

Scheme 23:

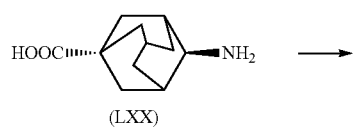

(LXX)

In Scheme 23, the derivatives (LXXI) are obtained by protecting the amine functional group of the derivative (LXX), for example with a Boc group, by means of methods known to a person skilled in the art. In a second stage, the acid functional group of the derivatives (LXXI) is subjected to a Curtius reaction, such as, for example, described with adamantane derivatives in Maison et al., J. Org. Chem. 2008, pp. 1056, or Broadhurst et al., J. Med. Chem., 2004, pp. 4975. The amines (LXIX) are obtained by deprotecting the amine functional group of the compounds of formula (LXXII) by methods chosen from those known to a person skilled in the art; they comprise, inter alia, the use of trifluoroacetic acid or of hydrochloric acid in dichloromethane, dioxane, tetrahydrofuran or diethyl ether, in the case of protection by a Boc group, and of piperidine, for a Fmoc group, at temperatures varying from −10 to 100° C.

Scheme 24 explains in detail a synthesis of the compounds of formula (I) in which $R_3$ is a hydrogen and $R_4$ is an —NH-$COR_6$ group; these compounds are referred to hereinafter as compounds of formula (LXXIII).

Scheme 24 (Method No. 12):

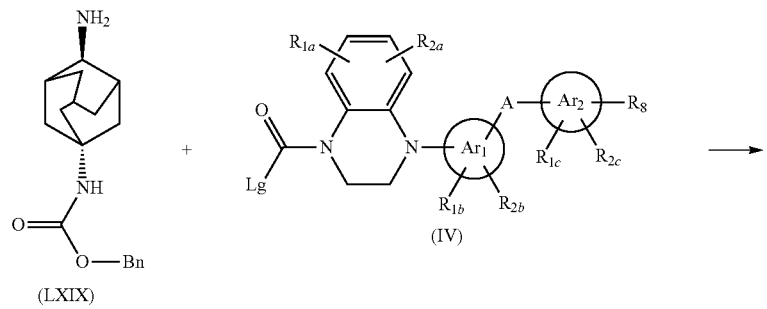

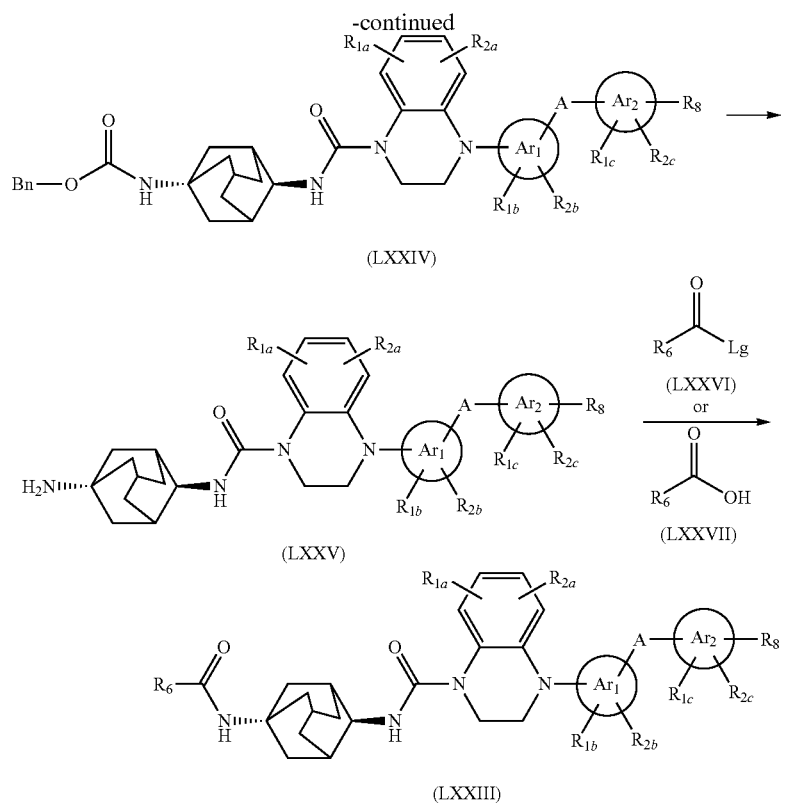

(LXXIV)

(LXXV)

(LXXIII)

In Scheme 24, the derivatives (LXXIV) are obtained by coupling between the activated derivatives (IV) and the amine (LXIX) in the presence or absence of a base, such as triethylamine or potassium carbonate, in a solvent, such as tetrahydrofuran, dichloromethane, acetonitrile, dimethylformamide or water, at a temperature varying from ambient temperature to 100° C. The amines (LXXV) are subsequently obtained by deprotection of the benzyloxycarbonyl functional group. The possible deprotection methods comprise, inter alia, the use of hydrogen in the presence of a palladium-derived catalyst, in order to carry out a hydrogenolysis reaction, in a solvent or mixture of solvents, such as methanol, ethanol, ethyl acetate or tetrahydrofuran, under a hydrogen pressure of between 1 and 10 bar at a temperature varying from ambient temperature to 80° C. An alternative method for carrying out a hydrogenolysis of the Cbz group is to use catalysis with palladium (for example with palladium adsorbed on charcoal) in the presence of ammonium formate at reflux in a solvent, such as methanol. In the final stage, the formation of the amide bond of the compounds (LXXIII) can be obtained either by the reaction of the amines (LXXV) with an acid derivative of formula (LXXVI) exhibiting a leaving group Lg (for example a chlorine atom, a trichloromethoxy group, a para-nitrophenyl group or an imidazole or methylimidazolium group) in the presence of a base, such as triethylamine or diisopropylamine, in a solvent, such as dichloromethane or tetrahydrofuran, at a temperature varying from ambient temperature to 80° C.; or by condensation between the acids of formula (LXXVII) and the amines (LXXV) under conventional peptide coupling conditions by using, for example, as coupling agent, dicyclohexylcarbodiimide, 1-(3-dimethylaminopropyl)-3-ethylcarbodiimide hydrochloride or bromotris(pyrrolidino)phosphonium hexafluorophosphate, in the presence or absence of hydroxybenzotriazole, and by using, as organic base, triethylamine or diisopropylethylamine, in a solvent or mixture of solvents, such as dioxane, dichloromethane or acetonitrile.

Scheme 25 explains in detail a synthesis of the compounds of formula (I) in which $R_{1c}$ represents an -alkyl-$CO_2H$ group; these compounds will be referred to hereinafter as compounds of formula (LXXVIII).

Scheme 25 (Method No. 13):

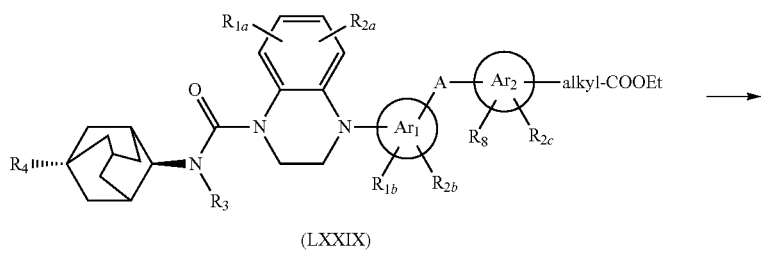

(LXXIX)

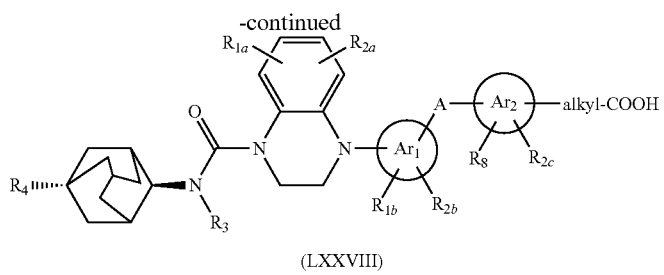

(LXXVIII)

In Scheme 25, the derivatives (LXXVIII) are obtained by hydrolysis of the ester functional group (for example an ethyl ester) of the compound (LXXIX) using an inorganic base, such as sodium hydroxide, potassium hydroxide or lithium hydroxide, in a solvent, such as an alcohol or water, at a temperature varying from ambient temperature to 100° C.

Scheme 26 explains in detail a synthesis of the compounds of formula (I) in which $R_{1c}$ represents an -alkyl-$CH_2OH$ group; these compounds will be referred to hereinafter as compounds of formula (LXXX).

agent, such as a hydride, for example $LiAlH_4$, $LiBH_4$ or DIBAL, in a solvent or mixture of solvents, such as tetrahydrofuran, ether or toluene, at a temperature varying from −78° C. to 40° C.

Scheme 27 explains in detail a synthesis of the compounds of formula (I) in which $R_3$ is a hydrogen and $R_4$ is a —CN group; these compounds are referred to hereinafter as compounds of formula (LXXXI).

Scheme 26 (Method No. 14):

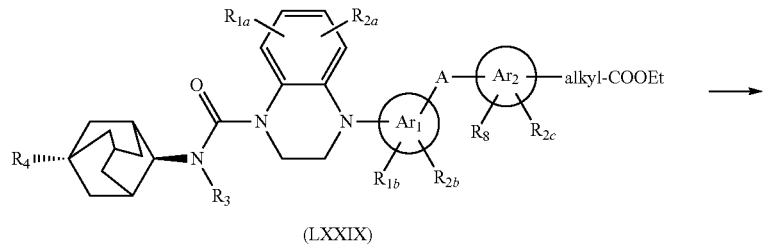

(LXXIX)

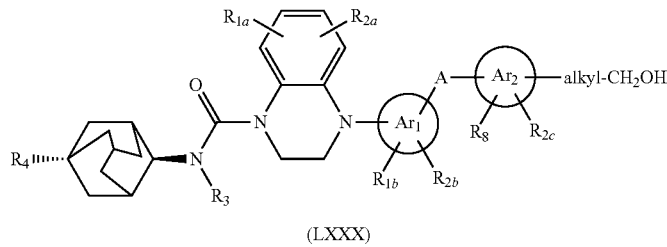

(LXXX)

In Scheme 26, the derivatives (LXXX) are obtained by reduction of the ester functional group of the compound (LXXIX) to give an alcohol functional group using a reducing Scheme 27 (Method No. 15):

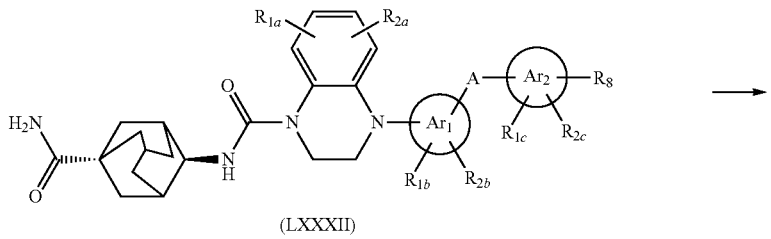

(LXXXII)

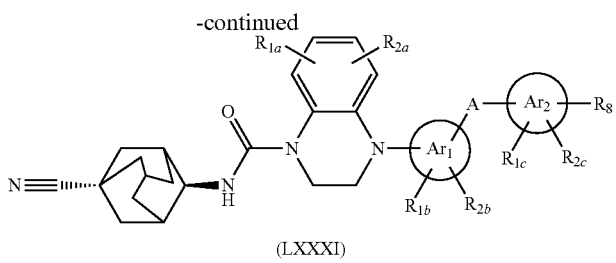

(LXXXI)

In Scheme 27, the derivatives (LXXXI) are obtained by dehydration of the primary amide functional group of the compound (LXXXII) to give a nitrile functional group using a dehydrating agent, such as trifluoroacetic anhydride, trifluoromethanesulphonic anhydride, $SOCl_2$, $POCl_3$ or $P_2O_5$, in a solvent or mixture of solvents, such as dichloromethane, dioxane, dichloroethane or dimethylformamide, in the presence or absence of a base, such as pyridine or triethylamine, at a temperature varying from –0° C. to 70° C.

Scheme 28 explains in detail a synthesis of the compounds of formula (VIII) in which A is a bond, $Ar_1$ is a pyridine group and $Ar_2$ is a piperidine group; these compounds will be referred to hereinafter as compounds of formula (LXXXIII).

tion between the derivative (LXXXV) and a compound (LXXXVI) exhibiting a leaving group V (for example a halogen, a triflate or a nonaflate) in the presence of an organometallic catalyst, such as a palladium derivative, in the presence or absence of a phosphine, such as tricyclohexylphosphine or triphenylphosphine, in the presence of a base, such as sodium carbonate, potassium carbonate or potassium fluoride, in a solvent or mixture of solvents, such as dioxane, dimethylformamide, ethylene glycol dimethyl ether, tetrahydrofuran or water, at a temperature varying from ambient temperature to 100° C. In the final stage, the double bond of the compound (LXXXVII) is subjected to a hydrogenation reaction in the presence of an organometallic catalyst, such as a palladium Scheme 28:

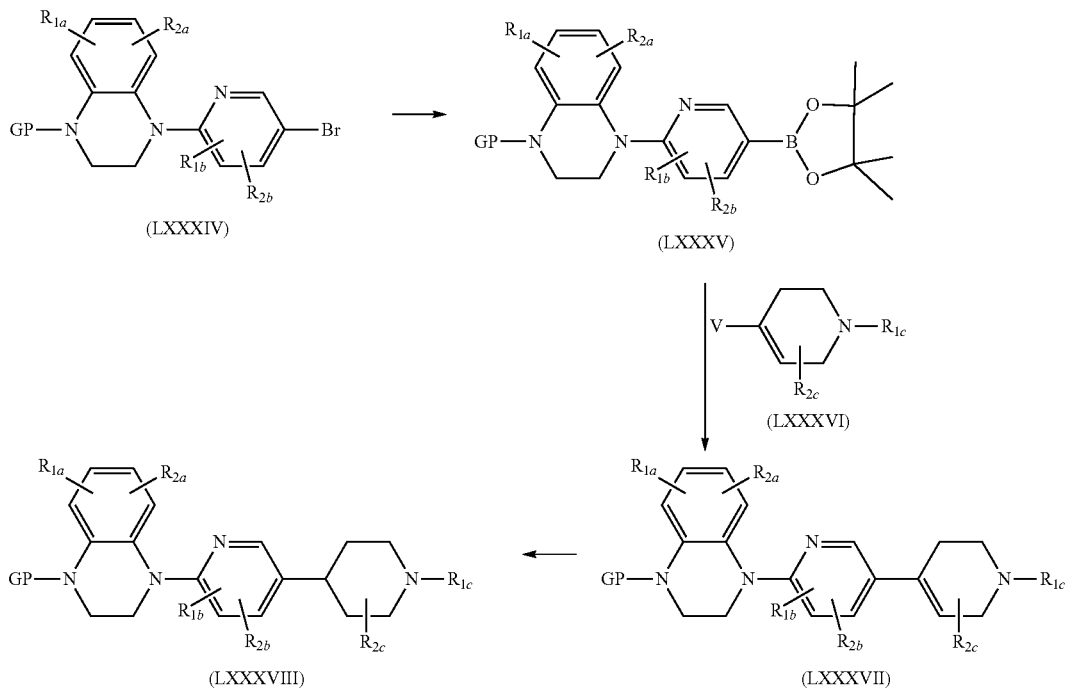

In Scheme 27, the compounds of formula (LXXXV) can be prepared by conversion of the bromo functional group of the compounds (LXXXIV) to a boronic ester derivative (LXXXV) by reaction with bis(pinacolato)diboron in the presence of a palladium complex, such as [1,1'-bis(diphenylphosphino)ferrocene]dichloropalladium(II), in the presence of a base, such as potassium acetate and lithium chloride, in a solvent or mixture of solvents, such as dichloromethane, dioxane or dimethyl sulphoxide, at a temperature varying from ambient temperature to 100° C. In a second stage, the derivatives (LXXXVII) can be obtained by a coupling reacderivative (for example 10% Pd deposited on charcoal, or Pd $(OAc)_2$), in a solvent or mixture of solvents, such as methanol, ethanol or ethyl acetate, at a temperature varying from ambient temperature to 80° C.

Scheme 29 explains in detail a synthesis of the compounds of formula (VIII) in which $Ar_2$ is a piperazine group, A is a single bond directly connected to one of the two nitrogens of the piperazine and $R_{1c}$ is an alkyl sulphone group connected to the other nitrogen atom of the piperazine; these compounds will be referred to hereinafter as compounds of formula (LXXXVIII).

Scheme 29:

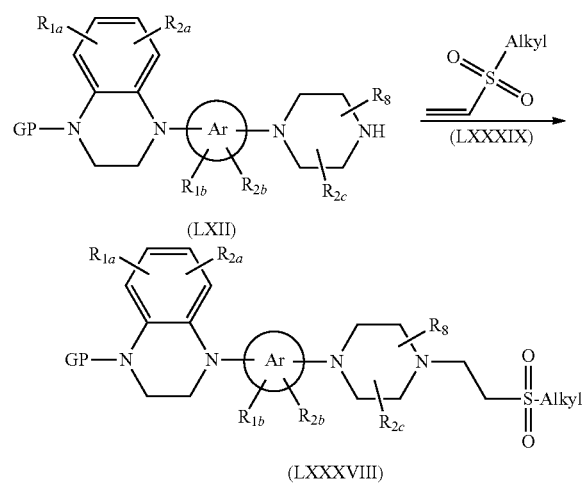

In Scheme 29, the derivatives (LXXXVIII) are obtained by a reaction of Michael type between the compound (LXII) and the Michael acceptor (LXXXIX) in the presence or absence of a base, such as triethylamine, in a solvent, such as an alcohol, at a temperature varying from 0° C. to ambient temperature, in order to result in the derivatives (LXXXVIII).

In the preceding schemes, the starting compounds and the reactants, when their method of preparation is not described, are commercially available or are described in the literature or else can be prepared according to methods which are described therein or which are known to a person skilled in the art.

The invention, according to another of its aspects, also has as subject-matter the compounds of formulae (II), (IV), (XX-VII), (XXXIX), (XXXVIII), (XLI), (XLII), (LI), (LII), (LVI), (LVII), (LX), (LXIII), (LXVII), (LXXIV) and (LXXV) defined above. These compounds are of use as intermediates in the synthesis of the compounds of formula (I).

The following examples describe the preparation of some compounds in accordance with the invention. These examples are not limiting and serve only to illustrate the present invention. The numbers of the compounds exemplified refer to those given in the table below, in which the chemical structures and the physical properties of some compounds according to the invention are illustrated.

The following abbreviations and molecular formulae are used:

| | |
|---|---|
| ° C. | Degrees Celsius |
| DME | dimethoxyethane |
| DMF | dimethylformamide |
| DMSO | dimethyl sulphoxide |
| h | hour(s) |
| $H_2$ | dihydrogen |
| $H_2O$ | water |
| HCl | hydrochloric acid |
| $K_2CO_3$ | potassium carbonate |
| LC/MS | liquid chromatography/mass spectrometry |
| ml | millilitre(s) |
| mmol | millimole(s) |
| MHz | megahertz |
| $MgSO_4$ | magnesium sulphate |
| N | normal |
| NMP | N-methylmorpholine |
| $NaHCO_3$ | sodium hydrogencarbonate |
| Pd/C | palladium-on-charcoal |
| $P_2O_5$ | phosphorus pentoxide |
| ppm | parts per million |
| psi | pounds per square inch |
| $SO_2$ | sulphur dioxide |

EXAMPLE 1

4-[4-(Pyrimidin-2-ylmethoxy)Phenyl]-3,4-dihydro-2H-quinoxaline-1-carboxylic Acid adamantan-2-ylamide (Compound No. 3)

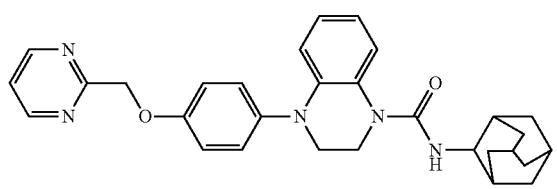

1.1: tert-Butyl Ester of 4-(4-hydroxyphenyl)-3,4-dihydro-2H-quinoxaline-1-carboxylic Acid 0.3 g of 3,4-dihydro-2H-quinoxaline-1-carboxylic acid tert-butyl ester, 0.183 g of 4-bromophenol, 0.0079 g of 2'-(dimethylamino)-2-biphenylyl-palladium(II) chloride dinorbornylphosphine complex and 0.363 g of potassium triphosphate in 3.4 ml of ethylene glycol dimethyl ether are placed under an inert atmosphere. 4.16 ml of lithium bis(trimethylsilyl)amide and 2.17 ml of ethylene glycol dimethyl ether are added. The reaction mixture is stirred at 80° C. for 4 h. After cooling, the reaction medium is taken up in dichloromethane. A 1N aqueous hydrochloric acid solution is added to pH 1, the pH is then brought back to 8 with a saturated aqueous sodium hydrogencarbonate solution and the mixture is extracted with dichloromethane. The organic phases are combined, washed with water and with a saturated aqueous sodium chloride solution, and dried over magnesium sulphate. After concentrating to dryness, the crude product obtained is chromatographed on silica gel, elution being carried out with a gradient of methanol in dichloromethane varying from 0% to 2.5%. 0.34 g of the tert-butyl ester of 4-(4-hydroxyphenyl)-3,4-dihydro-2H-quinoxaline-1-carboxylic acid is obtained.

$M+H^+=327$ 1.2: 1-[4-(Pyrimidin-2-ylmethoxy)Phenyl]-1,2,3,4-tetrahydroquinoxaline 0.3 g of the tert-Butyl ester of 4-(4-hydroxyphenyl)-3,4-dihydro-2H-quinoxaline-1-carboxylic acid is placed in 4.6 ml of dimethylformamide under nitrogen. 0.167 g of 2-(chloromethyl)pyrimidine and 0.508 g of potassium carbonate are added. The reaction medium is heated at 100° C. for 4 h. 0.254 g of potassium carbonate is added and heating is maintained for 1 h 30. After hydrolysis, the reaction medium is extracted with ethyl acetate until the aqueous phase has been completely extracted. The organic phases are combined, washed with a saturated aqueous sodium chloride solution, dried over magnesium sulphate and concentrated to dryness. The crude product obtained is chromatographed on silica gel, elution being carried out with a gradient of methanol in dichloromethane varying from 0% to 9/1. 0.095 g of 1-[4-(pyrimidin-2-ylmethoxy)phenyl]-1,2,3,4-tetrahydroquinoxaline is obtained.

M+H$^+$=319

1.3: 4-[4-(Pyrimidin-2-ylmethoxy)Phenyl]-3,4-dihydro-2H-quinoxaline-1-carboxylic Acid Adamantan-2-ylamide 0.095 g of 1-[4-(pyrimidin-2-ylmethoxy)phenyl]-1,2,3,4-tetrahydroquinoxaline is placed in 3 ml of dichloromethane at 0° C. under nitrogen. 0.09 ml of triethylamine and 0.031 g of triphosgene are added. The mixture is stirred at ambient temperature for 2 h 30, 0.01 g of triphosgene is then added and stirring is maintained for 2 h. 0.12 ml of triethylamine and 0.062 g of adamantan-2-ylamine hydrochloride are then added. Stirring is maintained at ambient temperature for 1 h. After hydrolysis, the reaction medium is extracted with ethyl acetate until the aqueous phase has been completely extracted. The organic phases are combined, washed with a saturated aqueous sodium chloride solution, dried over magnesium sulphate and concentrated to dryness. The crude product obtained is chromatographed on silica gel, elution being carried out with a gradient of methanol in dichloromethane varying from 0% to 9/1. 0.03 g of 4-[4-(pyrimidin-2-ylmethoxy)phenyl]-3,4-dihydro-2H-quinoxaline-1-carboxylic acid adamantan-2-ylamide is obtained, which is triturated from a mixture of ethyl acetate and diisopropyl ether.

Melting point=123-125° C.; M+H$^+$=496; $^1$H NMR (d$_6$-DMSO, 400 MHz), δ (ppm): 1.91 (bd, J=12 Hz, 2H); 1.66-1.97 (m, 11H); 2.09 (bd, J=12 Hz, 2H); 3.69 (m, 4H); 4.72 (s, 2H); 6.4 (m, 1H); 6.64-6.53 (m, 3H); 7.07 (m, J=9 Hz, 2H); 7.15 (m, J=9 Hz, 2H); 7.39 (t, J=4.9 Hz, 1H); 7.76 (d, J=7 Hz, 1H), 8.79 (d, J=4.8 Hz, 2H).

EXAMPLE 2

Trans-4-[4-(4-(Methanesulphonyl)Piperazin-1-yl)Phenyl]-3,4-dihydro-2H-quinoxaline-1-carboxylic Acid (5-hydroxyadamantan-2-yl)Amide (Compound No. 9)

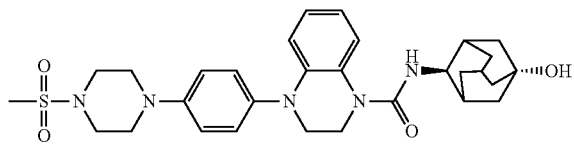

2.1: 1-(4-Bromophenyl)-4-(methanesulphonyl)Piperazine 7.7 ml of methanesulphonyl chloride are added to a solution of 20 g of 1-(4-bromophenyl)piperazine and 17.34 ml of triethylamine in 394 ml of dichloromethane. The reaction medium is stirred at ambient temperature for 4 h. Water is subsequently added and the organic phase is washed twice with water and dried over magnesium sulphate and then the solvent is evaporated under reduced pressure to result in 26.2 g of 1-(4-bromophenyl)-4-(methanesulphonyl)piperazine. The product is subsequently used as is without other purification.

M+H$^+$=321.4

2.2: tert-Butyl Ester of 4-[4-(4-(methanesulphonyl)Piperazin-1-yl)Phenyl]-3,4-dihydro-2H-quinoxaline-1-carboxylic Acid 11.8 g of sodium tert-butoxide, 0.737 g of palladium diacetate and 0.664 g of tri(tert-butyl)phosphine are added to a solution of 19.23 g of 3,4-dihydro-2H-quinoxaline-1-carboxylic acid tert-butyl ester and 26.2 g of 1-(4-bromophenyl)-4-(methanesulphonyl)piperazine in 410 ml of xylene. The reaction medium is heated at 150° C. for 4 h and then water and ethyl acetate are subsequently added. The organic phase is washed twice with water and dried over magnesium sulphate and then the solvent is evaporated under reduced pressure. The residue is chromatographed on silica gel with a gradient of heptane/ethyl acetate mixture from 8/2 to 0/1. 31.5 g of tert-butyl ester of 4-[4-(4-(methanesulphonyl)piperazin-1-yl)phenyl]-3,4-dihydro-2H-quinoxaline-1-carboxylic acid are obtained.

M+H$^+$=473.0

2.3: 1-[4-(4-(Methanesulphonyl)Piperazin-1-yl)Phenyl]-1,2,3,4-tetrahydro-quinoxaline 31.5 g of the tert-butyl ester of 4-[4-(4-(methanesulphonyl)piperazin-1-yl)phenyl]-3,4-dihydro-2H-quinoxaline-1-carboxylic acid are placed in 400 ml of dichloromethane and then 333 ml of 4N hydrochloric acid in dioxane are added. After stirring for 16 h under an inert atmosphere, the solvents are evaporated under reduced pressure. Water, a saturated aqueous sodium hydrogencarbonate solution and dichloromethane are added. The aqueous sodium phase is extracted twice with dichloromethane. The organic phases are combined, washed with water and dried over magnesium sulphate and then the solvent is evaporated under reduced pressure. 23.2 g of 1-[4-(4-(methanesulphonyl)piperazin-1-yl)phenyl]-1,2,3,4-tetrahydroquinoxaline are obtained. The product is subsequently used as is without other purification.

M+H$^+$=373.5

2.4: trans-4-[4-(4-(Methanesulphonyl)Piperazin-1-yl)Phenyl]-3,4-dihydro-2H-quinoxaline-1-carboxylic Acid (5-hydroxyadamantan-2-yl)Amide 0.6 g of 1-[4-(4-(methanesulphonyl)piperazin-1-yl)phenyl]-1,2,3,4-tetrahydro-quinoxaline is placed in 5 ml of dichloromethane at 0° C. under nitrogen. 0.45 ml of triethylamine and 0.192 g of triphosgene are added. The mixture is stirred at ambient temperature for 3 h, 15 ml of dimethylformamide, 0.45 ml of triethylamine and 0.427 g of 4-aminoadamantan-1-ol hydrochloride are then added and stirring is maintained for 18 h. After hydrolysis, the reaction medium is extracted with ethyl acetate until the aqueous phase has been completely extracted. The organic phases are combined, washed with a saturated aqueous sodium chloride solution, dried over magnesium sulphate and concentrated to dryness. The crude product obtained is chromatographed on silica gel, elution being carried out with a gradient of methanol and ethyl acetate in dichloromethane varying from 0/0/1 to 2.5/0.5/7. 0.24 g of trans-4-[4-(4-(methanesulphonyl)piperazin-1-yl)phenyl]-3,4-dihydro-2H-quinoxaline-1-carboxylic acid (5-hydroxyadamantan-2-yl)amide is obtained, which product is triturated from a mixture of ethyl acetate and diisopropyl ether.

Melting point=160° C.; M+H$^+$=566; $^1$H NMR (d$_6$-DMSO, 400 MHz), δ (ppm): 1.38 (bd, J=12 Hz, 2H); 1.58-1.737 (m, 9H); 2.02 (m, 2H); 2.94 (s, 3H); 3.27 (m, 8H); 3.53 (m, 2H), 3.71 (m, 1H), 3.78 (m, 1H), 4.4 (s, 1H), 5.95 (d, J=6.1 Hz), 6.52 (dd, J=8.2 and 1.3 Hz, 1H); 6.67 (m, J=7.5 and 1.4 Hz, 1H); 6.84 (m, J=7.8 and 1.5 Hz, 1H); 7.05 (m, J=9 Hz, 2H); 7.16 (m, J=9 Hz, 1H); 7.28 (d, J=7.9 and 1.5 Hz, 1H).

EXAMPLE 3 trans-4-[4-(4-(Ethanesulphonyl)Piperazin-1-yl)Phenyl]-3,4-dihydro-2H-quinoxaline-1-carboxylic Acid (5-hydroxyadamantan-2-yl)Amide (Compound No. °34)

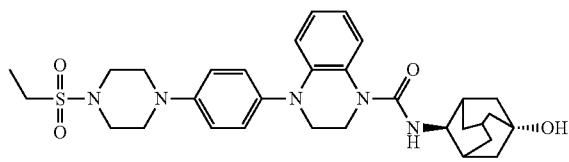

3.1: 4-(4-Bromophenyl)Piperazine-1-carboxylic Acid Benzyl Ester 5 g of 4-bromophenylpiperazine are placed in a 500 ml three-necked flask under a nitrogen atmosphere. 4.34 ml of triethylamine are added. The mixture is cooled in an ice bath and 3.24 ml of benzyl chloroformate are added. The mixture is allowed to return to ambient temperature. It is diluted with dichloromethane and then gentle hydrolysis is carried out. The aqueous phase is extracted with dichloromethane. The organic phases are combined, washed with a saturated NaCl solution, dried over sodium sulphate, then filtered through a sintered glass filter and concentrated under vacuum. 8.43 g of 4-(4-bromophenyl)piperazine-1-carboxylic acid benzyl ester are obtained.

M+H$^+$=376

3.2: 4-[4-(4-(Benzyloxycarbonyl)piperazin-1-yl)Phenyl]-3,4-dihydro-2H-quinoxaline-1-carboxylic Acid tert-butyl Ester 8.43 g of 4-(4-bromophenyl)piperazine-1-carboxylic acid benzyl ester are placed in a 500 ml three-necked flask under a nitrogen atmosphere. 170 ml of anhydrous o-xylene, 5.01 g of 3,4-dihydro-2H-quinoxaline-1-carboxylic acid tert-butyl ester and then 3.08 g of sodium tert-butoxide are added, followed by 0.48 g of palladium acetate, and then the addition is completed with 0.53 ml of tri(tert-butyl)phosphine. The reaction mixture is heated at 150° C. for 18 h. Heating is halted and the mixture is brought back to ambient temperature. The o-xylene is evaporated and the mixture is taken up in ethyl acetate before filtering it through celite. The organic phase is washed with water and then with a saturated aqueous sodium chloride solution. The aqueous phase is extracted with ethyl acetate. The organic phases are combined and then dried over sodium sulphate, filtered through a sintered glass filter and concentrated under vacuum. 8.9 g of 4-[4-(4-(Benzyloxycarbonyl)piperazin-1-yl)phenyl]-3,4-dihydro-2H-quinoxaline-1-carboxylic acid tert-butyl ester are obtained after purification on a silica column, elution being carried out with a gradient of heptane/ethyl acetate solvent varying from 95/5 to 60/40).

M+H$^+$=529

3.3: 4-[4-(3,4-Dihydro-2H-quinoxalin-1-yl)Phenyl]piperazine-1-carboxylic Acid Benzyl Ester 8.9 g of 4-[4-(4-(benzyloxycarbonyl)piperazin-1-yl)phenyl]-3,4-dihydro-2H-quinoxaline-1-carboxylic acid tert-butyl ester are placed in 220 ml of dichloromethane. 55 ml of a 4N solution of hydrochloric acid in dioxane are slowly added at 0° C. The mixture is stirred for 5 minutes under cold conditions and then it is allowed to return to ambient temperature. The reaction mixture is stirred at ambient temperature for 18 h and is then diluted with dichloromethane. A saturated aqueous sodium carbonate solution is added and then the addition is continued with solid sodium carbonate until a pH=7-8 is reached. The aqueous phase is extracted with dichloromethane. The organic phases are combined, washed with water, dried over sodium sulphate, filtered through a sintered glass filter and concentrated under vacuum. 7.2 g of 4-[4-(3,4-dihydro-2H-quinoxalin-1-yl)phenyl]piperazine-1-carboxylic acid benzyl ester are obtained in the form of an oil.

M+H$^+$=429

3.4: Trans-4-{4-[4-(5-Hydroxyadamantan-2-ylcarbamoyl)-3,4-dihydro-2H-quinoxalin-1-yl]phenyl}piperazine-1-carboxylic Acid Benzyl Ester 4 g of 4-[4-(3,4-dihydro-2H-quinoxalin-1-yl)phenyl]piperazine-1-carboxylic acid benzyl ester are introduced into 93 ml of anhydrous dichloromethane in a 250 ml three-necked flask under an inert nitrogen atmosphere. 5.2 ml of triethylamine are added at 0° C. 1.11 g of triphosgene are subsequently added. The mixture is stirred at ambient temperature for 1 h and 1.56 of trans-4-aminoadamantan-1-ol and 15 ml of anhydrous dimethylformamide are subsequently added. The mixture is stirred at ambient temperature for 18 h. The solvents are evaporated and the residue is taken up in water. Dilution is carried out with dichloromethane and washing is carried out with water and then with a saturated sodium hydrogencarbonate solution. The aqueous phase is extracted with dichloromethane. The organic phases are combined, washed with water, dried over sodium sulphate, filtered through a sintered glass filter and evaporated to dryness. 2.34 g of trans-4-{4-[4-(5-hydroxyadamantan-2-ylcarbamoyl)-3,4-dihydro-2H-quinoxalin-1-yl]phenyl}piperazine-1-carboxylic acid benzyl ester are obtained.

M+H$^+$=622

3.5: Trans-4-(4-(Piperazin-1-yl)Phenyl)-3,4-dihydro-2H-quinoxaline-1-carboxylic Acid (5-hydroxyadamantan-2-yl)Amide 4.1 g of trans-4-{4-[4-(5-hydroxyadamantan-2-ylcarbamoyl)-3,4-dihydro-2H-quinoxalin-1-yl]phenyl}piperazine-1-carboxylic acid benzyl ester are placed in a 250 ml three-necked flask under inert atmosphere. 66 ml of methanol, then 1.66 g of ammonium formate, followed by 1.40 g of 10% Pd/C (50% in water), are added. The mixture is brought to reflux of the methanol for one hour and then brought back to ambient temperature. The mixture is filtered through a Whatman filter under an inert atmosphere and then the filter is rinsed numerous times with methanol. The methanol is evaporated under reduced pressure. The residue is taken up in dichloromethane and the organic phase is washed with the minimum amount of water. The organic phase is dried over sodium sulphate, filtered through a sintered glass filter and evaporated under reduced pressure. 3.15 g of trans-4-(4-(piperazin-1-yl)phenyl)-3,4-dihydro-2H-quinoxaline-1-carboxylic acid (5-hydroxyadamantan-2-yl)amide are obtained in the form of a white solid.

M+H⁺=488

3.6: Trans-4-[4-(4-(Ethanesulphonyl)piperazin-1-yl) Phenyl]-3,4-dihydro-2H-quinoxaline-1-carboxylic Acid (5-hydroxyadamantan-2-yl)Amide 0.2 g of trans-4-(4-(piperazin-1-yl)phenyl)-3,4-dihydro-2H-quinoxaline-1-carboxylic acid (5-hydroxyadamantan-2-yl)amide is placed in a 25 ml round-bottom flask. 4 ml of dichloromethane, then 0.09 ml of triethylamine and, finally, 0.04 ml of ethylsulphonyl chloride are added. The reaction mixture is stirred at ambient temperature for 18 h, then diluted with dichloromethane and washed with a 1N aqueous HCl solution. The aqueous phase is extracted with dichloromethane and then the organic phases are combined. The organic phases are washed with water, dried over sodium sulphate, filtered through a sintered glass filter and evaporated under reduced pressure. 0.21 g of trans-4-[4-(4-(ethanesulphonyl)piperazin-1-yl)phenyl]-3,4-dihydro-2H-quinoxaline-1-carboxylic acid (5-hydroxyadamantan-2-yl)amide is obtained in the form of a white solid, after purification on a silica column, elution being carried out with a heptane/ethyl acetate gradient ranging from 95/5 to 40/60, followed by crystallization from ethyl ether.

Melting point=138-160° C.; M+H⁺=579; ¹H NMR (400 MHz, d₆-DMSO), δ ppm: 7.28 (dd, J=7.8 and 1.5 Hz, 1H); 7.16 (m, J=9 Hz, 2H); 7.04 (m, J=9 Hz, 2H); 6.84 (m, J=7.8 and 1.5 Hz, 1H); 6.67 (m, J=7.8 and 1.4 Hz, 1H); 6.52 (dd, J=8.2 and 1.3 Hz, 1H); 5.94 (d, J=6.1 Hz, 1H); 4.4 (s, 1H); 3.79 (m, 2H); 3.71 (m, 1H); 3.53 (m, 2H); 3.36-3.27 (m, 4H); 3.24 (m, 4H); 3.13 (q, J=7.9 Hz, 2H); 2.08-1.96 (m, 3H); 1.74-1.57 (m, 8H); 1.38 (m, 2H); 1.26 (t, J=7.9 Hz, 3H).

EXAMPLE 4

Trans-4-{4-[4-(2-Methoxyethanesulphonyl)Piperazin-1-yl]phenyl}-3,4-dihydro-2H-quinoxaline-1-carboxylic Acid (5-hydroxyadamantan-2-yl)Amide (Compound No. 63)

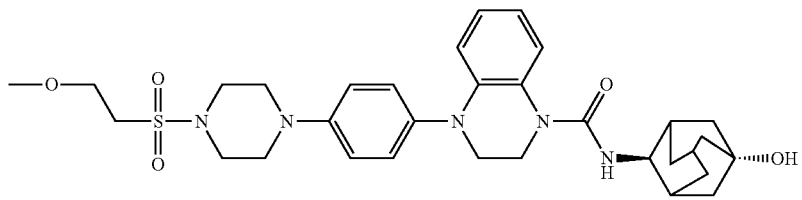

4.1: 4-(4-(piperazin-1-yl)Phenyl)-3,4-dihydro-2H-quinoxaline-1-carboxylic Acid tert-butyl Ester 3.5 g of 4-[4-(4-(benzyloxycarbonyl)piperazin-1-yl)phenyl]-3,4-dihydro-2H-quinoxaline-1-carboxylic acid tert-butyl ester are placed in a 250 ml three-necked flask under an inert atmosphere. 66 ml of MeOH, then 1.67 g of ammonium formate followed by 1.41 g of 10% Pd/C (50% in water), are added. The mixture is brought to reflux of the methanol for 1 h 30 minutes and then brought back to ambient temperature. It is filtered on a Whatman filter under an inert atmosphere and then rinsing is carried out numerous times with methanol. The methanol is evaporated under reduced pressure. The mixture is taken up in dichloromethane and the organic phase is washed with the minimum amount of water. The organic phase is dried over sodium sulphate, filtered through a sintered glass filter and evaporated under reduced pressure. 2.5 g of 4-(4-(piperazin-1-yl)phenyl)-3,4-dihydro-2H-quinoxaline-1-carboxylic acid tert-butyl ester are obtained in the form of a white solid.

M+H⁺=395

4.2: 4-[4-(4-(Ethenesulphonyl)Piperazin-1-yl)Phenyl]-3,4-dihydro-2H-quinoxaline-1-carboxylic Acid tert-butyl Ester 2 g of 4-(4-(piperazin-1-yl)phenyl)-3,4-dihydro-2H-quinoxaline-1-carboxylic acid tert-butyl ester are placed in a 250 ml round-bottomed flask under an inert atmosphere. 72 ml of anhydrous dichloromethane are added and then, at 0° C., 1.22 ml of chloroethylsulphonyl chloride are added, followed by 3.67 ml of triethylamine. The reaction mixture is allowed to return gently to ambient temperature. The reaction mixture is stirred at ambient temperature for 3 h before being diluted with dichloromethane. The organic phase is washed with a saturated aqueous sodium hydrogencarbonate solution and the aqueous phase is extracted with dichloromethane. The organic phases are combined and washed with water, then dried over sodium sulphate, filtered through a sintered glass filter and concentrated under reduced pressure. 1.01 g of 4-[4-(4-(ethenesulphonyl)piperazin-1-yl)phenyl]-3,4-dihydro-2H-quinoxaline-1-carboxylic acid tert-butyl ester are obtained in the form of a white solid, after purification on a silica column, elution being carried out with a heptane/ethyl acetate gradient varying from 95/5 to 40/60.

M+H⁺=485

4.3: 4-{4-[4-(2-Methoxyethanesulphonyl)Piperazin-1-yl]phenyl}-3,4-dihydro-2H-quinoxaline-1-carboxylic Acid tert-butyl Ester 0.3 g of 4-[4-(4-(ethenesulphonyl)piperazin-1-yl)phenyl]-3,4-dihydro-2H-quinoxaline-1-carboxylic acid tert-butyl ester is placed in a 100 ml three-necked flask under an inert atmosphere. 23.5 ml of 0.5N sodium methoxide in methanol are slowly added. The mixture is stirred at reflux (65° C.) for 1 h and then heating is halted. The methanol is evaporated and the mixture is taken up in dichloromethane. The organic phase is washed with a saturated aqueous ammonium chloride solution. The aqueous phase is extracted with dichloromethane. The combined organic phases are washed with water, dried over sodium sulphate, filtered through a sintered glass filter and concentrated under vacuum. 0.3 g of 4-{4-[4-(2-methoxyethanesulphonyl)piperazin-1-yl]-phenyl}-3,4-dihydro-2H-quinoxaline-1-carboxylic acid tert-butyl is obtained in the form of a white solid.

M+H⁺=517

4.4: 1-{4-[4-(2-Methoxyethanesulphonyl)Piperazin-1-yl]phenyl}-1,2,3,4-tetrahydroquinoxaline 0.35 g of 4-{4-[4-(2-methoxyethanesulphonyl)piperazin-1-yl]phenyl}-3,4-dihydro-2H-quinoxaline-1-carboxylic acid tert-butyl ester is placed in 7 ml of dichloromethane. 2.5 ml of a 4N solution of HCl in dioxane are slowly added at 0° C. The mixture is stirred for 5 minutes under cold conditions and then the mixture is allowed to return to ambient temperature. The reaction mixture is stirred at ambient temperature for 18 h and is then diluted with dichloromethane. A saturated aqueous sodium hydrogencarbonate solution is added until a pH=7-8 is reached. The aqueous phase is extracted with dichloromethane. The organic phases are combined, washed with water, dried over sodium sulphate, filtered through a sintered glass filter and concentrated under reduced pressure. 0.246 g of 1-{4-[4-(2-methoxyethanesulphonyl)piperazin-1-yl]phenyl}-1,2,3,4-tetrahydroquinoxaline is obtained in the form of an oil.

M+H$^+$=417

4.5: trans-4-{4-[4-(2-Methoxyethanesulphonyl)Piperazin-1-yl]phenyl}-3,4-dihydro-2H-quinoxaline-1-carboxylic Acid (5-hydroxyadamantan-2-yl)Amide 0.246 g of 1-{4-[4-(2-methoxyethanesulphonyl)piperazin-1-yl]phenyl}-1,2,3,4-tetrahydroquinoxaline is placed in 6 ml of anhydrous dichloromethane in a 50 ml three-necked flask under an inert atmosphere. 0.33 ml (2.36 mmol, 4 eq.) of triethylamine is added at 0° C., followed by addition of 0.07 g (0.24 mmol, 0.4 eq.) of triphosgene. The mixture is stirred at ambient temperature for 1 h and then 0.4 g of trans-4-aminoadamantan-1-ol and 15 ml of anhydrous dimethylformamide are added. The reaction mixture is stirred at ambient temperature overnight, the mixture of solvents is then evaporated under reduced pressure and the residue is taken up in water. Dilution is carried out with dichloromethane. The organic phase is washed with water and then with a saturated aqueous sodium hydrogencarbonate solution. The aqueous phase is extracted with dichloromethane. The combined organic phases are washed with water, dried over sodium sulphate, filtered through a sintered glass filter and evaporated under reduced pressure. 0.04 g of trans-4-{4-[4-(2-methoxyethanesulphonyl)piperazin-1-yl]phenyl}-3,4-dihydro-2H-quinoxaline-1-carboxylic acid (5-hydroxyadamantan-2-yl) amide is obtained in the form of a white solid, after purification on a silica column, elution being carried out with a dichloromethane/methanol/aqueous ammonia gradient varying from 1/0/0 to 99/1/0.1.

M+H$^+$=610; $^1$H NMR (400 MHz, d$_6$-DMSO) δ ppm: 7.28 (dd, J=7.9 and 1.5 Hz, 1H); 7.16 (m, J=9 Hz, 2H); 7.04 (m, J=9 Hz, 2H); 6.84 (m, J=7.8 and 1.6 Hz, 1H); 6.67 (m, J=7.6 and 1.6 Hz, 1H); 6.51 (dd, J=8.3 and 1.4 Hz, 1H); 5.94 (d, J=6.3 Hz, 1H); 4.40 (s, 1H); 3.79 (m, 2H); 3.70 (m, 3H); 3.53 (m, 2H); 3.39 (t, J=6 Hz, 2H); 3.34-3.27 (m, 7H); 3.24 (m, 4H); 2.02 (m, 3H); 1.74-1.58 (m, 8H); 1.38 (m, 2H).

EXAMPLE 5

4-[4-(4-(Methanesulphonyl)Piperazin-1-yl)phenyl]-3,4-dihydro-2H-quinoxaline-1-carboxylic Acid (5-carbamoyladamantan-2-yl)Amide (Compound No. 12)

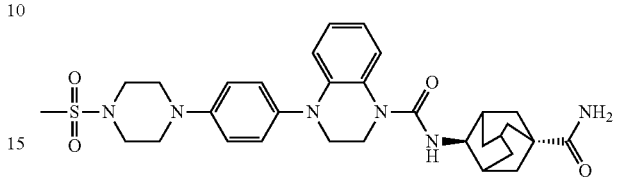

5.1: 4-Aminoadamantane-1-carboxylic Acid Methyl Ester 5 g of 4-oxoadamantane-1-carboxylic acid methyl ester are placed in 26 ml of methanol under nitrogen. 86 ml of a 7N solution of ammonia in methanol are added. The reaction medium is stirred for 18 h, 4 g of sodium borohydride are then added at 0° C. and the reaction medium is stirred for a further 3 h. After concentrating to dryness under reduced pressure and adding water and ethyl acetate, the aqueous phase is extracted three times in ethyl acetate. The organic phases are combined, dried over magnesium sulphate and concentrated to dryness. The crude product obtained is chromatographed on silica gel, elution being carried out with a gradient of heptane/acetone/methanol/NH$_4$OH solvent from 1/0/0 to 4/5/1/0.1. 1.5 g of 4-aminoadamantane-1-carboxylic acid methyl ester are obtained in the form of a mixture of cis/trans (1/3) isomers.

M+H$^+$=210

5.2: 4-({4-[4-(4-(Methanesulphonyl)Piperazin-1-yl) Phenyl]-3,4-dihydro-2H-quinoxaline-1-carbonyl}amino)Adamantane-1-carboxylic Acid Methyl Ester 1.2 g of 1-[4-(4-(methanesulphonyl)piperazin-1-yl)phenyl]-1,2,3,4-tetrahydroquinoxaline are placed in 32 ml of dichloromethane at 0° C. under nitrogen. 0.99 ml of triethylamine and 0.38 g of triphosgene are added. The mixture is stirred at ambient temperature for 4 h, then 24 ml of dimethylformamide, 1.35 ml of triethylamine and 0.742 g of a cis/trans-4-amino-adamantane-1-carboxylic acid methyl ester (1/3) mixture are added and stirring is maintained for 18 h. After hydrolysis, the reaction medium is extracted three times with ethyl acetate. The organic phases are combined, washed with a saturated aqueous sodium chloride solution, dried over magnesium sulphate and concentrated to dryness. The crude product obtained is chromatographed on silica gel, elution being carried out with a gradient of heptane/ethyl acetate/methanol solvent from 1/0/0 to 4/5/1. 1.91 g of a cis/trans (1/3) mixture of 4-({4-[4-(4-(methanesulphonyl)piperazin-1-yl)phenyl]-3,4-dihydro-2H-quinoxaline-1-carbonyl}amino)adamantane-1-carboxylic acid methyl ester are obtained.

M+H$^+$=608

5.3: Trans-4-({4-[4-(4-(Methanesulphonyl)Piperazin-1-yl)Phenyl]-3,4-dihydro-2H-quinoxaline-1-carbonyl}amino)Adamantane-1-carboxylic Acid 1.65 g of 4-({4-[4-(4-(methanesulphonyl)piperazin-1-yl)phenyl]-3,4-dihydro-2H-quinoxaline-1-carbonyl}amino)adamantane-1-carboxylic acid methyl ester are placed in 27 ml of a tetrahydrofuran/methanol/water (1/1/1) mixture and 0.193 g of lithium hydroxide monohydrate is added. The reaction medium is stirred for 18 h, then a further 0.04 g of lithium hydroxide monohydrate is added and stirring is resumed for 20 minutes. The organic solvents are evaporated under reduced pressure and water and dichloromethane are added. The aqueous phase is acidified down to a pH=1 with a concentrated aqueous hydrochloric acid solution and subsequently extracted with dichloromethane and then twice with ethyl acetate. The organic phases are combined, dried over magnesium sulphate and concentrated to dryness. The crude product obtained is chromatographed on silica gel, elution being carried out with a heptane/ethyl acetate/methanol (4/5/1) mixture, and is then rechromatographed on silica gel, elution being carried out with a gradient of dichloromethane/acetone/methanol solvent from 1/0/0 to 4/5/1. After crystallizing from ethyl acetate, 0.5 g of trans-4-({4-[4-(4-(methanesulphonyl)piperazin-1-yl)phenyl]-3,4-dihydro-2H-quinoxaline-1-carbonyl}amino)adamantane-1-carboxylic acid is obtained.

$M+H^+=594$

5.4: 4-[4-(4-(Methanesulphonyl)Piperazin-1-yl)Phenyl]-3,4-dihydro-2H-quinoxaline-1-carboxylic Acid (5-carbamoyladamantan-2-yl)Amide 10.3 g of trans-4-({4-[4-(4-(methanesulphonyl)piperazin-1-yl)phenyl]-3,4-dihydro-2H-quinoxaline-1-carbonyl}amino)adamantane-1-carboxylic acid are placed in 8.5 ml of dimethylformamide, and 0.3 ml of a 7.5N solution of ammonia in water, 0.136 g of 1-hydroxybenzotriazole, 0.29 g of 1-ethyl-3-(3-dimethylaminopropyl)carbodiimide hydrochloride and 0.17 ml of diisopropylethylamine are added. The reaction medium is stirred for 3 h and then water is added. The aqueous phase is extracted twice with ethyl acetate. The organic phases are combined, dried over magnesium sulphate and concentrated to dryness. The crude product obtained is chromatographed on silica gel, elution being carried out with a gradient of dichloromethane/acetone/methanol solvent from 1/0/0 to 70/25/5. 0.171 g of trans-4-[4-(4-(methanesulphonyl)piperazin-1-yl)phenyl]-3,4-dihydro-2H-quinoxaline-1-carboxylic acid (5-carbamoyladamantan-2-yl)amide is obtained.

Melting point=247-250° C.; $M+H^+=593$; $^1H$ NMR (300 MHz, $d_6$-DMSO) δ ppm: 7.29 (d, J=7.9 Hz, 1H); 7.16 (m, 2H); 7.04 (m, 2H); 6.97 (m, 1H); 6.83 (m, 1H); 6.68 (m, 2H); 6.5 (m, J=8.5 Hz, 1H); 6.0 (d, J=6.6 Hz, 1H); 3.77 (m, 3H); 3.53 (m, 2H); 3.25 (m, 8H); 2.94 (s, 3H); 2.02-1.63 (m, 11H); 1.46 (m, 2H).

EXAMPLE 6

Trans-4-[4-(4-(Methanesulphonyl)Piperazin-1-yl)Phenyl]-3,4-dihydro-2H-quinoxaline-1-carboxylic Acid (5-fluoroadamantan-2-yl)Amide (Compound No. 40)

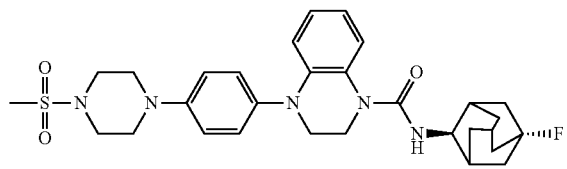

0.2 g of trans-4-[4-(4-(methanesulphonyl)piperazin-1-yl)phenyl]-3,4-dihydro-2H-quinoxaline-1-carboxylic acid (5-hydroxyadamantan-2-yl)amide (Example 2) is placed in 7 ml of dichloromethane at 0° C. under nitrogen. 0.09 ml of (diethylamino)sulphur trifluoride is added. The mixture is stirred at ambient temperature for 2 h and then ice and a saturated sodium hydrogencarbonate solution are added. The mixture is extracted three times with dichloromethane. The organic phases are combined, washed with water and then with a saturated aqueous sodium chloride solution, dried over magnesium sulphate and concentrated to dryness. The crude product obtained is chromatographed on silica gel, elution being carried out with a gradient of dichloromethane/ethyl acetate/methanol solvent varying from 1/0/0 to 7/2, 5/0.5. After crystallizing from ethyl acetate, 0.07 g of trans-4-[4-(4-(methanesulphonyl)piperazin-1-yl)phenyl]-3,4-dihydro-2H-quinoxaline-1-carboxylic acid (5-fluoroadamantane-2-yl)amide is obtained.

Melting point=165-200° C.; $M+H^+=568$; $^1H$ NMR (400 MHz, $d_6$-DMSO) δ ppm: 7.30 (dd, J=7.8 and 1.5 Hz, 1H); 7.17 (m, J=9 Hz, 2H); 7.05 (m, J=9, 2H); 6.83 (m, J=7.7 and 1.5 Hz, 1H); 6.67 (m, J=7.7 and 1.5 Hz, 1H); 6.51 (dd, J=8.1 and 1.3 Hz, 1H); 6.03 (d, J=5.8 Hz, 1H); 3.79 (m, 3H); 3.54 (m, 2H); 3.27 (m, 8H); 2.94 (s, 3H); 2.24-2.12 (m, 3H); 1.99-1.82 (m, 6H); 1.70 (m, 2H); 1.43 (m, 2H).

EXAMPLE 7

Trans-(4-{4-[4-(5-Hydroxyadamantan-2-ylcarbamoyl)-3,4-dihydro-2H-quinoxalin-1-yl]phenyl}piperazine-1-sulphonyl)Acetic Acid (Compound No. 49)

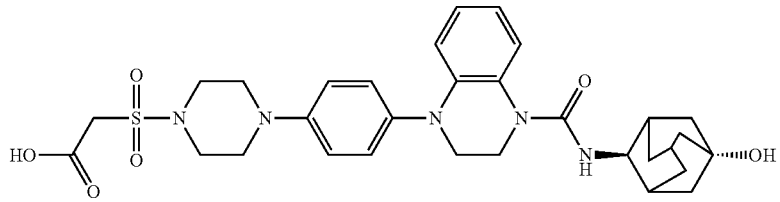

7.1: trans-(4-{4-[4-(5-Hydroxyadamantan-2-ylcarbamoyl)-3,4-dihydro-2H-quinoxalin-1-yl]phenyl}piperazine-1-sulphonyl)acetic acid ethyl ester 0.35 g of trans-4-(4-(piperazin-1-yl)phenyl)-3,4-dihydro-2H-quinoxaline-1-carboxylic acid (5-hydroxyadamantan-2-yl)amide (intermediate 3.5) is placed in 5.5 ml of dichloromethane. 0.15 ml of triethylamine and then 0.154 g of chlorosulphonylacetic acid ethyl ester are added. The mixture is stirred at ambient temperature for 3 h, is then diluted with dichloromethane and washed with water. The organic phase is dried over sodium sulphate and then evaporated under reduced pressure. 0.055 g of trans-(4-{4-[4-(5-hydroxyadamantan-2-ylcarbamoyl)-3,4-dihydro-2H-quinoxalin-1-yl]phenyl}piperazine-1-sulphonyl)acetic acid ethyl ester is obtained in the form of a white solid, after purification on a silica column, elution being carried out with a dichloromethane/methanol/aqueous ammonia gradient varying from 99/1/0.1 to 94/6/0.6, and C18 reverse phase purification, elution being carried out with a water/acetonitrile gradient varying from 90/10 to 5/95.

M+H$^+$=638

7.2: Trans-(4-{4-[4-(5-Hydroxyadamantan-2-ylcarbamoyl)-3,4-dihydro-2H-quinoxalin-1-yl]phenyl}piperazine-1-sulphonyl)Acetic Acid 0.041 g of trans-(4-{4-[4-(5-hydroxyadamantan-2-ylcarbamoyl)-3,4-dihydro-2H-quinoxalin-1-yl]-phenyl}piperazine-1-sulphonyl)acetic acid ethyl ester is placed in 1 ml of a tetrahydrofuran/methanol/water (2/1/1) mixture and 0.008 g of lithium hydroxide monohydrate is added. The reaction medium is stirred for 2 h. The organic solvents are evaporated under reduced pressure and water is added. The mixture is acidified with a 10% aqueous citric acid solution until a pH=6 has been reached and is then extracted with dichloromethane. The organic phase is dried over sodium sulphate and concentrated to dryness under reduced pressure. 0.015 g of trans-(4-{4-[4-(5-hydroxyadamantan-2-ylcarbamoyl)-3,4-dihydro-2H-quinoxalin-1-yl]phenyl}piperazine-1-sulphonyl)acetic acid is obtained.

M+H$^+$=610; $^1$H NMR (400 MHz, d$_6$-DMSO) δ ppm: 13.28 (s, 1H), 7.29 (dd, J=7.8 and 1.5 Hz, 1H); 7.17 (m, J=9 Hz, 2H); 7.05 (m, J=9 Hz, 2H); 6.84 (m, J=7.8 and 1.5 Hz, 1H); 6.67 (m, J=7.5 and 1.3 Hz, 1H); 6.52 (dd, J=8.3 and 1.4 Hz, 1H); 5.95 (d, J=6.1 Hz, 1H); 4.40 (s, 1H); 4.21 (s, 2H); 3.79 (m, 2H); 3.71 (m, 1H); 3.53 (m, 2H); 3.39 (m, 4H); 3.25 (m, 4H); 2.02 (m, 3H); 1.75-1.56 (m, 8H); 1.37 (m, 2H).

EXAMPLE 8

Trans-4-[4-(4-(Methanesulphonyl)Piperazin-1-yl)Phenyl]-3,4-dihydro-2H-quinoxaline-1-carboxylic Acid (5-(hydroxymethyl)Adamantan-2-yl)Amide (Compound No. 21)

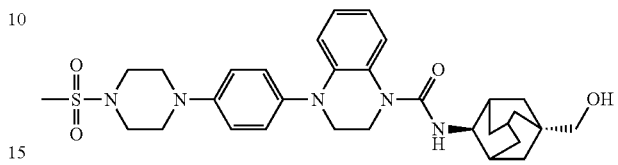

0.7 g of intermediate 5.2 is placed in 11 ml of tetrahydrofuran and then 2.3 ml of a 1N solution of lithium aluminium hydride in ether are added at 0° C. The reaction medium is stirred at ambient temperature for 2 h. Water and ethyl acetate are added. The aqueous phase is extracted three times with ethyl acetate. The organic phases are combined, washed with water, dried over magnesium sulphate and concentrated to dryness. The crude product obtained is chromatographed twice on silica gel, elution being carried out, for the first purification, with a gradient of dichloromethane/acetone/methanol solvent varying from 1/0/0 to 85/15/3 and then, for the second purification, with a gradient of dichloromethane/acetone/methanol solvent varying from 1/0/0 to 90/10/2. After crystallizing from ethanol, 0.415 g of trans-4-[4-(4-(methanesulphonyl)piperazin-1-yl)phenyl]-3,4-dihydro-2H-quinoxaline-1-carboxylic acid (5-(hydroxymethyl)adamantan-2-yl)amide is obtained.

Melting point=160° C.; M+H$^+$=580; $^1$H NMR (400 MHz, d$_6$-DMSO) δ ppm: 7.28 (dd, J=7.9 and 1.5 Hz, 1H); 7.15 (m, J=9 Hz, 2H); 7.03 (m, J=9 Hz, 2H); 6.83 (m, J=7.7 and 1.5 Hz, 1H); 6.66 (m, J=7.6 and 1.4 Hz, 1H); 6.51 (dd, J=8.3 and 1.3 Hz, 1H); 5.96 (d, J=6.7 Hz, 1H); 4.31 (m, 1H); 3.77 (m, 2H); 3.69 (m, 1H); 3.52 (m, 2H); 3.25 (m, 8H); 2.99 (d, J=5.8 Hz, 2H); 2.93 (s, 3H); 1.94 (m, 2H); 1.82 (m, 1H); 1.69 (m, 2H); 1.54-1.37 (m, 8H).

EXAMPLE 9

Trans-4-{4-[4-(2-Hydroxyethanesulphonyl)Piperazin-1-yl]phenyl}-3,4-dihydro-2H-quinoxaline-1-carboxylic Acid (5-hydroxyadamantan-2-yl)Amide (Compound No. 75)

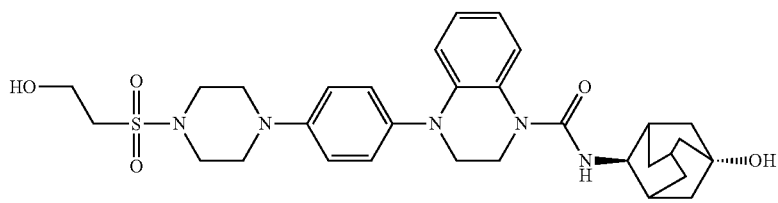

0.145 g of intermediate 7.1 is placed in 2.3 ml of tetrahydrofuran and then 0.14 ml of a 2N solution of lithium aluminium hydride in tetrahydrofuran is added at 0° C. The reaction medium is stirred at ambient temperature for 18 h. 5 ml of a 10% solution of potassium hydrogensulphate in water are subsequently added at 0° C. and the medium is left stirring at the same temperature for 20 minutes. The heterogeneous mixture is filtered and then the aqueous phase is extracted with ethyl acetate. The organic phase is washed with water, dried over magnesium sulphate and concentrated under reduced pressure. The crude product obtained is chromatographed on silica gel, elution being carried out with a gradient of dichloromethane/methanol/aqueous ammonia solvent from 1/0/0 to 90/10/1. 0.003 g of trans-4-{4-[4-(2-hydroxyethanesulphonyl)piperazin-1-yl]phenyl}-3,4-dihydro-2H-quinoxaline-1-carboxylic acid (5-hydroxyadamantan-2-yl)amide is obtained.

M+H$^+$=596; $^1$H NMR (400 MHz, d$_6$-DMSO) δ ppm: 7.28 (dd, J=7.8 and 1.5 Hz, 1H); 7.16 (m, J=9 Hz, 2H); 7.04 (m, J=9 Hz, 2H); 6.84 (m, J=7.8 and 1.5 Hz, 1H); 6.67 (m, J=1.3 Hz, 1H); 6.51 (dd, J=8.3 and 1.4 Hz, 1H); 5.94 (d, J=6.2 Hz, 1H); 5.04 (t, J=5.4 Hz, 1H); 4.40 (s, 1H); 3.79 (m, 3H); 3.71 (m, 1H); 3.53 (m, 2H); 3.46-3.17 (m, 10H); 2.02 (m, 3H); 1.74-1.57 (m, 8H); 1.38 (m, 2H).

EXAMPLE 10

Trans-4-[4-(4-Hydroxypiperidin-1-yl)Phenyl]-3,4-dihydro-2H-quinoxaline-1-carboxylic Acid (5-hydroxyadamantan-2-yl)Amide (Compound No. 51)

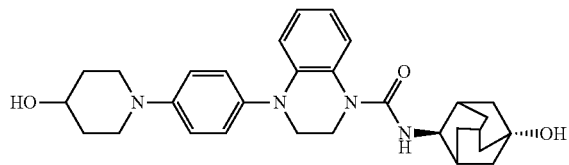

10.1: 8-(4-Bromophenyl)-1,4-dioxa-8-azaspiro[4.5]decane 0.5 g of 1-bromo-4-iodobenzene and 0.3 g of 1,4-dioxa-8-azaspiro[4.5]decane are placed in 10 ml of toluene and then 0.08 g of tris(dibenzylideneacetone)dipalladium(0), 0.061 g of 4,5-bis(diphenylphosphino)-9,9-dimethylxanthene and 0.255 g of sodium tert-butoxide are added. The reaction medium is brought to reflux of the solvent for 4 h. Ethyl acetate is subsequently added and the mixture is washed twice with water and once with a saturated aqueous sodium chloride solution. The organic phase is dried over magnesium sulphate and concentrated under reduced pressure. The crude product obtained is chromatographed on silica gel, elution being carried out with a heptane/ethyl acetate (4/1) solvent mixture. 0.31 g of 8-(4-bromophenyl)-1,4-dioxa-8-azaspiro[4.5]decane is obtained.

M+H$^+$=300

10.2: 4-[4-(1,4-Dioxa-8-azaspiro[4.5]dec-8-yl)Phenyl]-3,4-dihydro-2H-quinoxaline-1-carboxylic Acid tert-butyl Ester 0.31 g of 8-(4-bromophenyl)-1,4-dioxa-8-azaspiro[4.5] decane is placed in 5 ml of anhydrous o-xylene. 0.24 g of 3,4-dihydro-2H-quinoxaline-1-carboxylic acid tert-butyl ester is added, then 0.15 g of sodium tert-butoxide is added, followed by 0.009 g of palladium acetate, and then the addition is completed with 0.0084 g of tri(tert-butyl)phosphine. The reaction mixture is heated at 150° C. for 4 h, then the heating is halted and the mixture is brought back to ambient temperature. Ethyl acetate is added and the mixture is washed twice with water and then twice with a saturated aqueous sodium chloride solution. The organic phase is dried over sodium sulphate and concentrated under reduced pressure. The crude product obtained is chromatographed on silica gel, elution being carried out with a heptane/ethyl acetate (4/1) solvent mixture. 0.27 g of 4-[4-(1,4-dioxa-8-azaspiro[4.5]dec-8-yl)phenyl]-3,4-dihydro-2H-quinoxaline-1-carboxylic acid tert-butyl ester is obtained.

M+H$^+$=452

10.3: 1-[4-(1,4-Dioxa-8-azaspiro[4.5]dec-8-yl)Phenyl]-1,2,3,4-tetrahydroquinoxaline 0.27 g of 4-[4-(1,4-dioxa-8-azaspiro[4.5]dec-8-yl)phenyl]-3,4-dihydro-2H-quinoxaline-1-carboxylic acid tert-butyl ester is placed in 3 ml of a 4N solution of hydrochloric acid in dioxane. The mixture is stirred at ambient temperature for 28 h. The reaction mixture is diluted with dichloromethane and then a saturated aqueous sodium hydrogencarbonate solution is added. The aqueous phase is extracted three times with dichloromethane. The organic phases are combined, dried over sodium sulphate and concentrated under vacuum. 0.21 g of 1-[4-(1,4-dioxa-8-azaspiro[4.5]dec-8-yl)phenyl]-1,2,3,4-tetrahydroquinoxaline is obtained.

M+H$^+$=352

10.4: Trans-4-[4-(1,4-Dioxa-8-azaspiro[4.5]dec-8-yl) Phenyl]-3,4-dihydro-2H-quinoxaline-1-carboxylic Acid (5-hydroxyadamantan-2-yl)Amide 0.21 g of trans-1-[4-(1,4-dioxa-8-azaspiro[4.5]dec-8-yl)phenyl]-1,2,3,4-tetrahydroquinoxaline is placed in 5 ml of dichloromethane at 0° C. under nitrogen. 0.33 ml of triethylamine and 0.071 g of triphosgene are added. The mixture is stirred at ambient temperature for 3 h, 1 ml of dimethylformamide and 0.1 g of trans-4-aminoadamantan-1-ol are then added and stirring is maintained for 3 days. The reaction medium is washed with a saturated aqueous sodium hydrogencarbonate solution. The organic phase is dried over magnesium sulphate and concentrated to dryness. The crude product obtained is chromatographed on silica gel, elution being carried out with a gradient of a dichloromethane/methanol (99/1 to 96/4) mixture. 0.21 g of trans-4-[4-(1,4-dioxa-8-azaspiro[4.5]dec-8-yl)phenyl]-3,4-dihydro-2H-quinoxaline-1-carboxylic acid (5-hydroxyadamantan-2-yl)amide is obtained.

M+H$^+$=545.7

10.5: Trans-4-[4-(4-Oxopiperidin-1-yl)Phenyl]-3,4-dihydro-2H-quinoxaline-1-carboxylic Acid (5-hydroxyadamantan-2-yl)Amide 0.20 g of trans-4-[4-(1,4-dioxa-8-azaspiro[4.5]dec-8-yl)phenyl]-3,4-dihydro-2H-quinoxaline-1-carboxylic acid (5-hydroxyadamantan-2-yl)amide is placed in 4 ml of a 5N solution of hydrochloric acid in water. The reaction medium is stirred for 36 h and then neutralized at 0° C. with a saturated aqueous sodium hydrogencarbonate solution. The aqueous phase is extracted three times with dichloromethane. The organic phases are combined, dried over sodium sulphate and concentrated under vacuum. The crude product obtained is chromatographed on silica gel, elution being carried out with a gradient of a dichloromethane/methanol (98/2 to 97/3) mixture. 0.145 g of trans 4-[4-(4-oxopiperidin-1-yl)phenyl]-3,4-dihydro-2H-quinoxaline-1-carboxylic acid (5-hydroxyadamantan-2-yl)amide is obtained.

M+H$^+$=519.7 (hydrate)

10.6: Trans-4-[4-(4-Hydroxypiperidin-1-yl)Phenyl]-3,4-dihydro-2H-quinoxaline-1-carboxylic Acid (5-hydroxyadamantan-2-yl)Amide 0.145 g of trans-4-[4-(4-oxopiperidin-1-yl)phenyl]-3,4-dihydro-2H-quinoxaline-1-carboxylic acid (5-hydroxyadamantan-2-yl)amide is placed in 2.9 ml of methanol and then 0.015 g of sodium borohydride is added at 0° C. The reaction medium is stirred at ambient temperature for 4 h. Water is subsequently added at 0° C. and the mixture is concentrated under reduced pressure. The crude product obtained is chromatographed on silica gel with a dichloromethane/methanol (98/2 to 96/4) solvent gradient. 0.058 g of trans-4-[4-(4-hydroxypiperidin-1-yl)phenyl]-3,4-dihydro-2H-quinoxaline-1-carboxylic acid (5-hydroxyadamantan-2-yl)amide is obtained.

Melting point=131° C.; M+H$^+$=503; $^1$H NMR (400 MHz, d$_6$-DMSO) δ ppm: 7.27 (dd, J=7.7 and 1.5 Hz, 1H); 7.10 (m, J=9 Hz, 2H); 6.99 (m, J=9 Hz, 2H); 6.83 (m, J=7.8 and 1.5 Hz, 1H); 6.66 (m, J=7.6 and 1.3 Hz, 1H); 6.49 (dd, J=8.3 and 1.3 Hz, 1H); 5.93 (d, J=6.2 Hz, 1H); 4.66 (d, J=4.5 Hz, 1H); 4.40 (s, 1H), 3.78 (m, 2H); 3.71 (m, 1H); 3.64 (m, 1H); 3.53 (m, 4H); 3.28 (m, 4H); 2.86 (m, 2H); 2.02 (m, 3H); 1.84 (m, 2H); 1.74-1.57 (m, 8H); 1.49 (m, 2H); 1.38 (m, 2H).

EXAMPLE 11

Trans-4-[4-(4-Hydroxy-1-(methanesulphonyl)Piperidin-4-yl)Phenyl]-3,4-dihydro-2H-quinoxaline-1-carboxylic Acid (5-hydroxy-adamantan-2-yl)Amide (Compound No. 16)

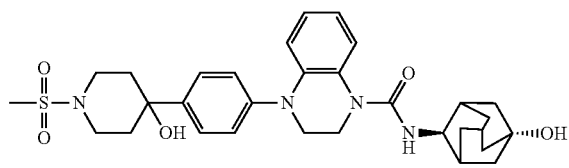

11.1: 4-(4-Bromophenyl)-1-(methanesulphonyl)Piperidin-4-ol 1 g of 4-(4-bromophenyl)piperidin-4-ol is placed in 20 ml of dichloromethane. 0.65 ml of triethylamine and then 0.33 ml of methanesulphonyl chloride are added. The reaction mixture is stirred at ambient temperature for 2 h. It is washed with water and then with a saturated aqueous sodium chloride solution. The organic phase is dried over sodium sulphate and then evaporated under reduced pressure. The crude product obtained is chromatographed on silica gel, elution being carried out with a dichloromethane/methanol (99/1) solvent mixture. 1.1 g of 4-(4-bromophenyl)-1-(methanesulphonyl)piperidin-4-ol are obtained.

M+H$^+$=335

11.2: Trans-4-(5-Hydroxyadamantan-2-ylcarbamoyl)-3,4-dihydro-2H-quinoxaline-1-carboxylic Acid tert-butyl Ester 0.4 g of 3,4-dihydro-2H-quinoxaline-1-carboxylic acid tert-butyl ester is placed in 8 ml of dichloromethane at 0° C. under nitrogen. 0.69 ml of triethylamine and 0.202 g of triphosgene are added. The mixture is stirred at ambient temperature for 3 h, then 1 ml of dimethylformamide and 0.285 g of trans 4-aminoadamantan-1-ol are added and stirring is maintained for 18 h. The reaction medium is washed with a saturated aqueous sodium hydrogencarbonate solution. The organic phase is dried over magnesium sulphate and concentrated to dryness. The crude product obtained is chromatographed on silica gel, elution being carried out with a gradient of a dichloromethane/methanol (99/1 to 95/5) mixture. 0.54 g of trans-4-(5-hydroxyadamantan-2-ylcarbamoyl)-3,4-dihydro-2H-quinoxaline-1-carboxylic acid tert-butyl ester is obtained.

M+H$^+$=428

11.3: Trans-3,4-Dihydro-2H-quinoxaline-1-carboxylic Acid (5-hydroxyadamantan-2-yl)Amide 0.54 g of trans-4-(5-hydroxyadamantan-2-ylcarbamoyl)-3,4-dihydro-2H-quinoxaline-1-carboxylic acid tert-butyl ester is placed in 5 ml of a 4N solution of hydrochloric acid in dioxane. The reaction mixture is stirred at ambient temperature for 3.5 h. It is diluted with dichloromethane. A saturated aqueous sodium hydrogencarbonate solution is added. The aqueous phase is extracted three times with dichloromethane. The organic phases are combined, dried over sodium sulphate and concentrated under vacuum. 0.41 g of trans-3,4-dihydro-2H-quinoxaline-1-carboxylic acid (5-hydroxyadamantan-2-yl)amide is obtained.

M+H$^+$=328

11.4: Trans-4-[4-(4-Hydroxy-1-(methanesulphonyl)Piperidin-4-yl)Phenyl]-3,4-dihydro-2H-quinoxaline-1-carboxylic Acid (5-hydroxyadamantan-2-yl)Amide 0.210 g of 4-(4-bromophenyl)-1-(methanesulphonyl)piperidin-4-ol is placed in 4 ml of dioxane. 0.206 g of trans-3,4-dihydro-2H-quinoxaline-1-carboxylic acid (5-hydroxyadamantan-2-yl)amide is added and then 0.4 g of K$_3$PO$_4$ is added, followed by 0.0353 g of chloro(di-2-norbornylphosphino)(2'-dimethylamino-1,1'-biphenyl-2-yl)palladium(II). The reaction mixture is heated at reflux of the solvent for 20 h. Heating is subsequently halted and the reaction mixture is brought back to ambient temperature. Water and ethyl acetate are added and then the aqueous phase is extracted twice with ethyl acetate. The organic phases are combined, washed with a saturated aqueous sodium chloride solution, dried over sodium sulphate and concentrated under reduced pressure. The crude product obtained is chromatographed on silica gel, elution being carried out with a gradient of a dichloromethane/methanol (99/1 to 95/5) mixture. 0.114 g of trans-4-[4-(4-hydroxy-1-(methanesulphonyl)piperidin-4-yl)phenyl]-3,4-dihydro-2H-quinoxaline-1-carboxylic acid (5-hydroxyadamantan-2-yl)amide is obtained. Melting point=160° C.; M+H$^+$=581; $^1$H NMR (400 MHz, d$_6$-DMSO) δ ppm: 7.54 (m, J=8.8 Hz, 2H); 7.35 (dd, J=7.9 and 1.5 Hz, 1H); 7.24 (m, J=8.8 Hz, 2H); 6.88 (m, J=7.7 and 1.5 Hz, 1H); 6.75 (m, J=7.5 and 1.4 Hz, 1H); 6.70 (dd, J=8.2 and 1.4 Hz, 1H); 5.99 (dd, J=6 Hz, 1H); 5.12 (s, 1H); 4.40 (s, 1H); 3.80

(m, 2H); 3.71 (m, 1H); 3.61 (m, 2H); 3.49 (m, 2H); 3.28 (m, 8H); 3.13 (m, 2H); 2.92 (s, 3H); 2.08-1.94 (m, 6H); 1.79-1.59 (m, 9H); 1.37 (m, 2H).

EXAMPLE 12

Trans-4-{4-[4-(Piperidin-4-yloxy)Piperidin-1-yl] phenyl}-3,4-dihydro-2H-quinoxaline-1-carboxylic Acid (5-hydroxyadamantan-2-yl)Amide (Compound No. 102)

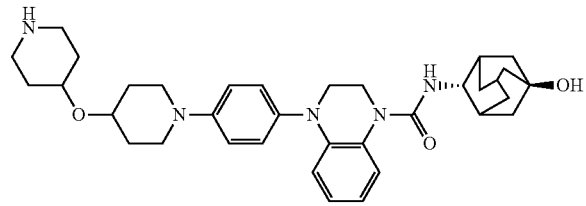

12.1: 4-[1-(4-Bromophenyl)Piperidin-4-yloxy]pyridine 2 g of 1-bromo-4-iodobenzene and 1.386 g of 4-(piperidin-4-yloxy)pyridine are placed in 35 ml of toluene and then 0.324 g of tris(dibenzylideneacetone)dipalladium(0), 0.245 g of 4,5-bis(diphenylphosphino)-9,9-dimethylxanthene and 1.019 g of sodium tert-butoxide are added. The reaction medium is heated at 110° C. for 18 h. Ethyl acetate is subsequently added and the mixture is washed twice with water and once with a saturated aqueous sodium chloride solution. The organic phase is dried over magnesium sulphate and concentrated under reduced pressure. The crude product obtained is chromatographed on silica gel, elution being carried out with a gradient of a dichloromethane/methanol (99/1 to 98/2) mixture. 1.2 g of 4-[1-(4-bromophenyl)piperidin-4-yloxy]pyridine are obtained.

M+H$^+$=335

12.2: 4-{4-[4-(Pyridin-4-yloxy)Piperidin-1-yl]phenyl}-3,4-dihydro-2H-quinoxaline-1-carboxylic Acid tert-butyl Ester 1.2 g of 4-[1-(4-bromophenyl)piperidin-4-yloxy]pyridine are placed in 20 ml of anhydrous o-xylene. 0.844 g of 3,4-dihydro-2H-quinoxaline-1-carboxylic acid tert-butyl ester is added, then 0.519 g of sodium tert-butoxide is added, followed by 0.032 g of palladium acetate, and then addition is completed with 0.029 g of tri(tert-butyl)phosphine. The reaction mixture is heated at 150° C. for 6 h. Heating is subsequently halted, the mixture is brought back to ambient temperature and ethyl acetate is added. The mixture is washed twice with water and then twice with a saturated aqueous sodium chloride solution. The organic phase is dried over sodium sulphate and concentrated under reduced pressure. The crude product obtained is chromatographed on silica gel, elution being carried out with a gradient of a dichloromethane/methanol (99/1 to 97/3) mixture. 1.1 g of 4-{4-[4-(pyridin-4-yloxy)piperidin-1-yl]phenyl}-3,4-dihydro-2H-quinoxaline-1-carboxylic acid tert-butyl ester are obtained.

M+H$^+$=487

12.3: 1-{4-[4-(Pyridin-4-yloxy)Piperidin-1-yl]phenyl}-1,2,3,4-tetrahydroquinoxaline 1.1 g of trans-4-{4-[4-(pyridin-4-yloxy)piperidin-1-yl]phenyl}-3,4-dihydro-2H-quinoxaline-1-carboxylic acid tert-butyl ester are placed in 15 ml of a 4N solution of hydrochloric acid in dioxane. The reaction mixture is stirred at ambient temperature for 3 h. It is diluted with dichloromethane and then a saturated aqueous sodium hydrogencarbonate solution is added. The aqueous phase is extracted three times with dichloromethane. The organic phases are combined, dried over sodium sulphate and concentrated under vacuum. 0.87 g of 1-{4-[4-(pyridin-4-yloxy)piperidin-1-yl]phenyl}-1,2,3,4-tetrahydroquinoxaline is obtained.

M+H$^+$=387

12.4: Trans-4-{4-[4-(Pyridin-4-yloxy)Piperidin-1-yl]phenyl}-3,4-dihydro-2H-quinoxaline-1-carboxylic Acid (5-hydroxyadamantan-2-yl)Amide 0.4 g of 1-{4-[4-(pyridin-4-yloxy)piperidin-1-yl]phenyl}-1,2,3,4-tetrahydroquinoxaline is placed in 6 ml of dichloromethane at 0° C. 0.58 ml of triethylamine and 0.123 g of triphosgene are added. The mixture is stirred at ambient temperature for 3 h, then 1.5 ml of dimethylformamide and 0.173 g of trans-4-aminoadamantan-1-ol are added and stirring is maintained for 22 h. The reaction medium is washed with a saturated aqueous sodium hydrogencarbonate solution. The organic phase is dried over magnesium sulphate and concentrated to dryness. The crude product obtained is chromatographed on silica gel, elution being carried out with a gradient of a dichloromethane/methanol (98/2 to 90/10) mixture. 0.045 g of trans-4-{4-[4-(pyridin-4-yloxy)piperidin-1-yl]phenyl}-3,4-dihydro-2H-quinoxaline-1-carboxylic acid (5-hydroxyadamantan-2-yl)amide is obtained.

M+H$^+$=580

12.5: Trans-4-{4-[4-(Piperidin-4-yloxy)Piperidin-1-yl]phenyl}-3,4-dihydro-2H-quinoxaline-1-carboxylic Acid (5-hydroxyadamantan-2-yl)Amide 0.045 g of trans-4-{4-[4-(pyridin-4-yloxy)piperidin-1-yl]phenyl}-3,4-dihydro-2H-quinoxaline-1-carboxylic acid (5-hydroxyadamantan-2-yl)amide is placed in 7 ml of ethanol in a Parr bottle. 0.005 g of platinum oxide and 0.015 g of para-toluenesulphonic acid monohydrate are added. The reaction medium is stirred under 50 psi of hydrogen at ambient temperature for 12 h and then at 40° C. for 22 h. The reaction medium is poured at 0° C. over 2 ml of a 2N aqueous sodium hydroxide solution, filtered and then concentrated under reduced pressure. Water and dichloromethane are added. The aqueous phase is extracted twice with dichloromethane. The organic phases are combined, dried over magnesium sulphate and concentrated to dryness. The crude product obtained is chromatographed on silica gel, elution being carried out with a gradient of a dichloromethane/methanol/aqueous ammonia (98/2/0.2 to 90/10/1) mixture. 0.003 g of trans-4-{4-[4-(piperidin-4-yloxy)piperidin-1-yl]phenyl}-3,4-dihydro-2H-quinoxaline-1-carboxylic acid (5-hydroxyadamantan-2-yl)amide is obtained.

M+H$^+$=586; $^1$H NMR (400 MHz, d$_6$-DMSO) δ ppm: 7.27 (d, J=7.9 Hz, 1H); 7.11 (m, 2H); 7 (m, 2H), 6.83 (m, J=7.8 and 1.5 Hz, 1H); 6.66 (m, 1H); 6.49 (m, J=8.2 Hz, 1H); 5.93 (d, J=6.2 Hz, 1H); 4.40 (m, 1H); 3.84-3.42 (m, 9H); 3.21-2.73 (m, 6H); 2.12-1.11 (m, 21H).

EXAMPLE 13

Trans-4-[4-(4-(Methanesulphonyl)Piperazin-1-yl) Phenyl]-3,4-dihydro-2H-quinoxaline-1-carboxylic Acid (5-acetylaminoadamantan-2-yl)Amide (Compound No. 137)

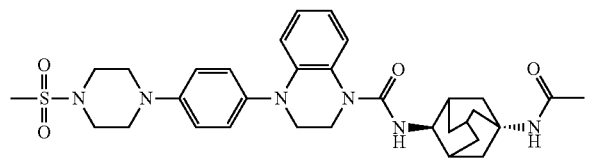

13.1: Trans-4-Aminoadamantane-1-carboxylic Acid

4-Oxoadamantane-1-carboxylic acid (8 g, 41.2 mmol) is stirred for 19 h under an $H_2$ atmosphere in the presence of 10% palladium-on-charcoal (0.5 g) in 160 ml of a 7N methanolic ammonia solution. The suspended solid is first of all filtered off and washed with methanol, then it is taken up in 200 ml of water and the palladium-on-charcoal is filtered off. The filtrate is concentrated to dryness, the residue is taken up in a small amount of methanol and then the white solid is filtered off and subsequently dried over $P_2O_5$. 5.4 g of the expected trans-4-aminoadamantane-1-carboxylic acid are obtained.

[M+H$^+$]=196

13.2: Trans-4-(tert-Butoxycarbonylamino)Adamantane-1-carboxylic Acid trans-4-Aminoadamantane-1-carboxylic acid (7.74 g, 39.6 mmol) is dissolved in 70 ml of a 1N aqueous sodium hydroxide solution and then 70 ml of dioxane are added. Di(t-butyl) carbonate (25.9 g, 118.9 mmol) is added. The reaction medium is stirred at ambient temperature for 16 h. After evaporating the dioxane, the aqueous phase is extracted with dichloromethane. A 1N aqueous HCl solution is then added until a pH of 4 is reached. Extraction is carried out with dichloromethane. The organic phase is dried over MgSO$_4$ and concentrated to dryness. 10.5 g of the expected trans-4-(t-butoxycarbonylamino)adamantane-1-carboxylic acid are obtained.

[M+H$^+$]=296

13.3: Trans-(4-(tert-Butoxycarbonylamino)Adamantan-1-yl)Carbamic Acid Benzyl Ester trans-4-(t-Butoxycarbonylamino)adamantane-1-carboxylic acid (2.0 g, 6.77 mmol) is placed in 13 ml of anhydrous toluene under nitrogen. Triethylamine (1.04 ml, 7.45 mmol) is added, followed by diphenylphosphoryl azide (1.61 ml, 7.45 mmol). The reaction medium is heated at reflux for 2 h. 1N sodium benzyloxide in benzyl alcohol (3.4 ml, 3.39 mmol) is then added. Heating at reflux is continued for 4 h. After hydrolysis and extraction with ethyl acetate, the organic phase is washed with a saturated aqueous sodium chloride solution, dried over MgSO$_4$ and concentrated to dryness. The crude product obtained is chromatographed on silica gel, elution being carried out with a gradient of dichloromethane/ethyl acetate/methanol in heptane varying from 100/0/0/0 to 0/7/2.5/0.5. 1.85 g of trans-(4-(tert-butoxycarbonylamino) adamantan-1-yl)carbamic acid benzyl ester are obtained as a mixture with 0.5 mol of benzyl alcohol.

[M+H$^+$]=456

13.4: Trans-(4-Aminoadamantan-1-yl)Carbamic Acid Benzyl Ester Hydrochloride trans-(4-(tert-Butoxycarbonylamino)adamantan-1-yl)carbamic acid benzyl ester (1.85 g, 4.07 mmol) is placed in 4N HCl in dioxane (17 ml, 69 mmol). The reaction medium is stirred at ambient temperature for 4 h. The precipitate obtained is filtered off and rinsed with dioxane. 1.85 g of trans-(4-aminoadamantan-1-yl)carbamic acid benzyl ester hydrochloride are obtained.

[M+H$^+$]=301

13.5: Trans-[4-({4-[4-(4-(Methanesulphonyl)Piperazin-1-yl)Phenyl]-3,4-dihydro-2H-quinoxaline-1-carbonyl]amino)Adamantan-1-yl}carbamic Acid Benzyl Ester 1-[4-(4-(Methanesulphonyl)piperazin-1-yl)phenyl]-1,2,3, 4-tetrahydroquinoxaline (1.1 g, 2.95 mmol) is placed in 90 ml of a 50/50 mixture of dichloromethane/saturated aqueous NaHCO$_3$ solution at 0° C. 20% phosgene in toluene (2.33 ml, 2.95 mmol) is added. After stirring for 1 h 30, the aqueous phase is extracted with dichloromethane. The organic phase is dried over MgSO$_4$. The crude product obtained is placed in 45 ml of anhydrous NMP under nitrogen. Triethylamine (0.82 ml, 5.91 mmol) is added, followed by trans-(4-aminoadamantan-1-yl)carbamic acid benzyl ester hydrochloride (1.15 g, 2.95 mmol). The reaction medium is stirred for 48 h and is then heated at 50° C. for 2 h. After hydrolysis and extraction with ethyl acetate, the organic phase is washed with a saturated aqueous sodium chloride solution and dried over MgSO$_4$. After concentrating to dryness, the crude product obtained is chromatographed on silica gel, elution being carried out with a gradient of methanol in dichloromethane varying from 0% to 10%. 0.37 g of [4-({4-[4-(4-(methanesulphonyl)piperazin-1-yl)phenyl]-3,4-dihydro-2H-quinoxaline-1-carbonyl]amino)adamantan-1-yl}carbamic acid benzyl ester is obtained.

[M+H$^+$]=699

13.6: Trans-4-[4-(4-(Methanesulphonyl)piperazin-1-yl)Phenyl]-3,4-dihydro-2H-quinoxaline-1-carboxylic Acid (Trans-5-aminoadamantan-2-yl)Amide trans-[4-({4-[4-(4-(Methanesulphonyl)piperazin-1-yl) phenyl]-3,4-dihydro-2H-quinoxaline-1-carbonyl]amino) adamantan-1-yl}carbamic acid benzyl ester (1.34 g, 1.92 mmol) is placed in 19 ml of methanol. 10% Pd/C comprising 50% water (0.27 g) and ammonium formate (1.21 g, 19.2 mmol) are added. The reaction medium is heated at reflux for 2 h. The Pd/C is filtered off and then rinsed with methanol. Furthermore, the Pd/C, as a mixture with the expected product, is taken up in a mixture of water and dichloromethane. The heterogeneous mixture is filtered and then rinsing is carried out with dichloromethane. The aqueous phase of the filtrate is basified with a saturated aqueous sodium hydrogencarbonate solution and is then extracted with dichloromethane. The collection of organic phases is combined, dried over magnesium sulphate and then concentrated under reduced pressure. The crude product obtained is chromatographed on silica gel, elution being carried out with a gradient of methanol/aqueous ammonia in dichloromethane varying from 100/0/0 to 90/10/1 (dichloromethane/methanol/aqueous ammonia). 0.77 g of 4-[4-(4-(methanesulphonyl)piperazin-1-yl)phenyl]-3,4-dihydro-2H-quinoxaline-1-carboxylic acid (trans-5-aminoadamantan-2-yl)amide is obtained.
[M+H⁺]=565

13.7: Trans-4-[4-(4-(Methanesulphonyl)Piperazin-1-yl)Phenyl]-3,4-dihydro-2H-quinoxaline-1-carboxylic Acid (Trans-5-acetylaminoadamantan-2-yl)Amide 4-[4-(4-(Methanesulphonyl)piperazin-1-yl)phenyl]-3,4-dihydro-2H-quinoxaline-1-carboxylic acid (trans-5-aminoadamantan-2-yl)amide (0.26 g, 0.46 mmol) is placed in 4 ml of anhydrous dichloromethane under nitrogen. Diisopropylethylamine (0.18 ml, 1.01 mmol) and acetyl chloride (0.03 ml, 0.48 mmol) are then added. The reaction medium is stirred at ambient temperature for 18 h. After hydrolysis with a saturated aqueous sodium hydrogencarbonate solution, the aqueous phase is extracted with ethyl acetate. The organic phases are combined, then washed with a saturated aqueous sodium chloride solution, dried over MgSO₄ and concentrated to dryness. The crude product obtained is chromatographed on silica gel, elution being carried out with a gradient of methanol in dichloromethane varying from 0% to 10%. After trituration from acetonitrile, 0.184 g of 4-[4-(4-(methanesulphonyl)piperazin-1-yl)phenyl]-3,4-dihydro-2H-quinoxaline-1-carboxylic acid (trans-5-acetylaminoadamantan-2-yl)amide is obtained.
M.p.: 250° C.; [M+H⁺]=607; ¹H NMR (400 MHz, d₆-DMSO) δ ppm: 7.34 (m, 1H), 7.29 (double doublet, J=8 Hz and 1.4 Hz, 1H), 7.16 (m, 2H), 7.05 (m, 2H), 6.83 (m, J=7.8 Hz and 1.5 Hz, 1H), 6.77 (m, J=7.7 Hz and 1.4 Hz, 1H), 6.52 (double doublet, J=8.2 Hz and 1.4 Hz, 1H), 5.98 (d, J=6.1 Hz, 1H), 3.79 (m, 2H), 3.75 (m, 1H), 3.54 (m, 2H), 3.27 (m, 8H), 2.94 (s, 3H), 2.06 to 1.90 (m, 9H), 1.76 (s, 3H), 1.67 (m, 2H), 1.45 (m, 2H).

EXAMPLE 14

Trans-4-[5-(4-(Ethanesulphonyl)Piperazin-1-yl)Pyridin-2-yl]-3,4-dihydro-2H-quinoxaline-1-carboxylic Acid (5-carbamoyladamantan-2-yl)Amide (Compound No. 149)

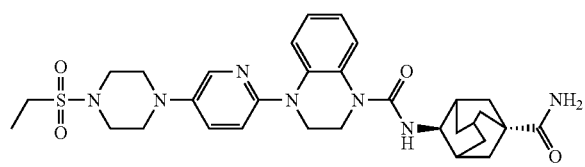

14.1: 4-(5-Bromopyridin-2-yl)-3,4-dihydro-2H-quinoxaline-1-carboxylic Acid tert-butyl Ester 30 g of 3,4-dihydro-2H-quinoxaline-1-carboxylic acid tert-butyl ester are placed in 430 ml of N-methylpyrrolidinone at 0° C. under nitrogen. 30 g of potassium tert-butoxide are added portionwise while maintaining a temperature below 10° C. The mixture is stirred at ambient temperature for 1 h 30 and then, at 0° C., 850 ml of water and 800 ml of ethyl ether are added. The aqueous phase is extracted with 800 ml of ethyl ether and then with 400 ml of ethyl ether. The organic phases are combined, then dried over magnesium sulphate and concentrated to dryness. 300 ml of pentane are added to the crude reaction product and the heterogeneous mixture obtained is subjected to ultrasound for 5 min. The mixture is placed at 5° C. for 48 h and then the solid is filtered off, washed three times with pentane and then dried at 40° C. for 5 h. 35 g of 4-(5-bromopyridin-2-yl)-3,4-dihydro-2H-quinoxaline-1-carboxylic acid tert-butyl ester are obtained.
M+H⁺=392.0

14.2: 4-[5-(4-(Benzyloxycarbonyl)Piperazin-1-yl)Pyridin-2-yl]-3,4-dihydro-2H-quinoxaline-1-carboxylic Acid tert-butyl Ester 10.12 g of 4-(5-bromopyridin-2-yl)-3,4-dihydro-2H-quinoxaline-1-carboxylic acid tert-butyl ester and 5.7 g of 4-(benzyloxycarbonyl)piperazine are placed in 118 ml of toluene and then 0.95 g of tris(dibenzylideneacetone)dipalladium(0), 1.7 g of 2-dicyclohexylphosphino-2',6'-dimethoxybiphenyl and 3.5 g of sodium tert-butoxide are added. The reaction medium is heated at 110° C. for 3 h. Ethyl acetate is subsequently added and the mixture is washed once with water and once with a saturated aqueous sodium chloride solution. The organic phase is dried over magnesium sulphate and concentrated under reduced pressure. The crude product obtained is chromatographed on silica gel, elution being carried out with a gradient of a mixture of heptane/ethyl acetate (90/10 to 0/100). 10.16 g of 4-[5-(4-(benzyloxycarbonyl)piperazin-1-yl)pyridin-2-yl]-3,4-dihydro-2H-quinoxaline-1-carboxylic acid tert-butyl ester are obtained.
M+H⁺=530.5

14.3: 4-(5-(Piperazin-1-yl)Pyridin-2-yl)-3,4-dihydro-2H-quinoxaline-1-carboxylic Acid tert-butyl Ester 5.08 g of 4-[5-(4-(benzyloxycarbonyl)piperazin-1-yl)pyridin-2-yl]-3,4-dihydro-2H-quinoxaline-1-carboxylic acid tert-butyl ester are placed in 240 ml of ethanol in a Parr bottle. 2 g of 10% Pd/C (50% in water) are added. The reaction medium is stirred at 35° C. under 45 psi hydrogen for 3.5 h. It is filtered on a Whatman filter under an inert atmosphere and then the filter residue is washed many times with methanol. The methanol is evaporated under reduced pressure. 3.57 g of 4-(5-(piperazin-1-yl)pyridin-2-yl)-3,4-dihydro-2H-quinoxaline-1-carboxylic acid tert-butyl ester are obtained.
M+H⁺=396.6

14.4: 4-[5-(4-(Ethanesulphonyl)Piperazin-1-yl)Pyridin-2-yl]-3,4-dihydro-2H-quinoxaline-1-carboxylic Acid tert-butyl Ester 0.8 g of 4-(5-(piperazin-1-yl)-pyridin-2-yl)-3,4-dihydro-2H-quinoxaline-1-carboxylic acid tert-butyl ester is placed in a 25 ml round-bottomed flask. 10 ml of dichloromethane are added, followed by 0.37 ml of triethylamine and finally 0.23 ml of ethylsulphonyl chloride. The reaction mixture is stirred at ambient temperature for 3 h, then washed twice with water and once with a saturated sodium chloride solution and then evaporated under reduced pressure. 0.98 g of 4-[5-(4-(ethanesulphonyl)piperazin-1-yl)pyridin-2-yl]-3,4-dihydro-2H-quinoxaline-1-carboxylic acid tert-butyl ester is obtained.
M+H⁺=488.0

14.5: 1-[5-(4-(Ethanesulphonyl)Piperazin-1-yl)Pyridin-2-yl]-1,2,3,4-tetrahydro-quinoxaline 0.98 g of 4-[5-(4-(ethanesulphonyl)piperazin-1-yl)pyridin-2-yl]-3,4-dihydro-2H-quinoxaline-1-carboxylic acid tert-butyl ester is placed in 3 ml of a 4N solution of hydrochloric acid in dioxane. The reaction mixture is stirred at ambient temperature for 3 h. It is subsequently evaporated under reduced pressure and then a saturated aqueous sodium hydrogencarbonate solution is added. The aqueous phase is extracted three times with dichloromethane. The organic phases are combined, dried over sodium sulphate and concentrated under vacuum. 0.7 g of 1-[5-(4-(ethanesulphonyl)piperazin-1-yl)pyridin-2-yl]-1,2,3,4-tetrahydroquinoxaline is obtained.

M+H⁺=388.6

14.6: Trans-4-[5-(4-(Ethanesulphonyl)Piperazin-1-yl)Pyridin-2-yl]-3,4-dihydro-2H-quinoxaline-1-carboxylic Acid (5-carbamoyladamantan-2-yl)Amide 0.33 g of 1-[5-(4-(ethanesulphonyl)piperazin-1-yl)pyridin-2-yl]-1,2,3,4-tetrahydro-quinoxaline is placed in a mixture of 14 ml of a saturated aqueous sodium hydrogencarbonate solution and 14 ml of dichloromethane at 0° C. 0.67 ml of a 20% solution of phosgene in toluene is added. The mixture is stirred at ambient temperature for 15 min and then the two phases are separated by settling. The aqueous phase is extracted with dichloromethane. The organic phases are combined, dried over magnesium sulphate and concentrated under vacuum. The crude reaction product is taken up in 18 ml of dimethylformamide and then 0.74 ml of diisopropylethylamine and also 0.22 g of trans-4-aminoadamantane-1-carboxylic acid amide hydrochloride are added. The mixture is stirred at ambient temperature for 48 h and then water is added. The aqueous phase is extracted twice with ethyl acetate. The organic phases are combined, washed three times with water, dried over sodium sulphate and concentrated under vacuum. The crude product obtained is chromatographed on silica gel, elution being carried out with a gradient of a dichloromethane/methanol mixture (99/1 to 90/10). 0.185 g of trans-4-[5-(4-(ethanesulphonyl)piperazin-1-yl)pyridin-2-yl]-3,4-dihydro-2H-quinoxaline-1-carboxylic acid (5-carbamoyladamantan-2-yl)amide is obtained after triturating from a mixture of ethyl acetate and ethyl ether.

Melting point=175° C.; M+H⁺=608; ¹H NMR (400 MHz, d₆-DMSO) δ ppm: 8.07 (d, J=3 Hz, 1H), 7.47 (double doublet, J=8 Hz and 1.6 Hz, 1H), 7.42 (double doublet, J=9 Hz and 3 Hz, 1H), 7.17 to 7.11 (m, 2H), 6.99 to 6.85 (m, 3H), 6.69 (broad singlet, 1H), 6.07 (d, J=6 Hz, 1H), 3.81 (s, 4H), 3.75 (m, 1H), 3.34 (m, 4H), 3.20 (m, 4H), 3.13 (q, J=7.4 Hz, 2H), 1.99 (m, 2H), 1.91 to 1.72 (m, 9H), 1.45 (m, 2H), 1.26 (t, J=7.4 Hz, 3H)

EXAMPLE 15

Trans-2-(4-{4-[4-(5-Carbamoyladamantan-2-ylcarbamoyl)-3,4-dihydro-2H-quinoxalin-1-yl]-phenyl}piperazin-1-yl)-2-methylpropionic Acid (Compound No. 146)

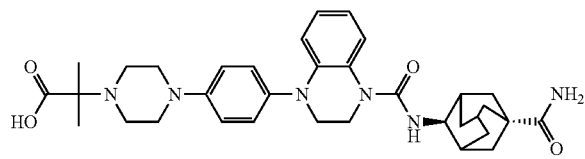

15.1: Trans-4-{4-[4-(5-Carbamoyladamantan-2-ylcarbamoyl)-3,4-dihydro-2H-quinoxalin-1-yl]phenyl}piperazine-1-carboxylic Acid Benzyl Ester 1.17 g of intermediate 3.3 are introduced into 28 ml of anhydrous dichloromethane in a 100 ml three-necked flask under an inert nitrogen atmosphere. 0.56 ml of triethylamine is added at 0° C. 0.32 g of triphosgene is subsequently added. The mixture is stirred at ambient temperature for 2 h, diluting is carried out with dichloromethane and washing is carried out with a saturated sodium hydrogencarbonate solution and then with water. The organic phase is dried over sodium sulphate, filtered through a sintered glass filter and evaporated to dryness. The crude product is subsequently dissolved in 25 ml of dimethylformamide and subsequently 1.56 g of trans-4-aminoadamantane-1-carboxylic acid amide hydrochloride are added. The mixture is stirred at ambient temperature for 18 h. The solvents are evaporated and the residue is taken up in water. The aqueous phase is extracted with dichloromethane. The organic phase is dried over sodium sulphate, filtered through a sintered glass filter and evaporated to dryness. The crude product obtained is chromatographed on silica gel, elution being carried out with a gradient of a dichloromethane/methanol/aqueous ammonia mixture (99/1/0.1 to 92/8/0.8). 1.09 g of trans-4-{4-[4-(5-carbamoyladamantan-2-ylcarbamoyl)-3,4-dihydro-2H-quinoxalin-1-yl]phenyl}piperazine-1-carboxylic acid benzyl ester are obtained.

M+H⁺=649

15.2: Trans-4-(4-(Piperazin-1-yl)Phenyl)-3,4-dihydro-2H-quinoxaline-1-carboxylic Acid (5-carbamoyladamantan-2-yl)Amide 1.08 g of trans-4-{4-[4-(5-carbamoyladamantan-2-ylcarbamoyl)-3,4-dihydro-2H-quinoxalin-1-yl]phenyl}piperazine-1-carboxylic acid benzyl ester are placed in a 100 ml three-necked flask under an inert atmosphere. 15 ml of methanol are added, followed by 0.42 g of ammonium formate, followed by 0.35 g of 10% Pd/C (50% in water). The mixture is brought to reflux of the methanol for one hour and is then brought back to ambient temperature. It is filtered through a Whatman filter under an inert atmosphere and then the filter residue is rinsed many times with methanol. The methanol is evaporated under reduced pressure. The residue is taken up in dichloromethane and the organic phase is washed with the minimum amount of water. The organic phase is dried over sodium sulphate, filtered through a sintered glass filter and evaporated under reduced pressure. 0.7 g of trans-4-(4-(piperazin-1-yl)phenyl)-3,4-dihydro-2H-quinoxaline-1-carboxylic acid (5-carbamoyladamantan-2-yl)amide is obtained.

M+H⁺=515

15.3: Trans-2-(4-{4-[4-(5-Carbamoyladamantan-2-ylcarbamoyl)-3,4-dihydro-2H-quinoxalin-1-yl]phenyl}piperazin-1-yl)-2-methylpropionic Acid Ethyl Ester 0.7 g of trans-4-(4-(piperazin-1-yl)phenyl)-3,4-dihydro-2H-quinoxaline-1-carboxylic acid (5-carbamoyladamantan-2-yl)amide is placed in a 100 ml round-bottomed flask under an inert atmosphere. 14 ml of dimethylformamide, 0.36 g of potassium carbonate and then 0.21 ml of 2-bromo-2-methyl-propionic acid ethyl ester are added. The mixture is stirred at ambient temperature for 4 h and is then heated at 50° C. for 18 hours. 0.36 g of potassium carbonate is added, followed by 0.2 ml of 2-bromo-2-methylpropionic acid ethyl ester, and then the mixture is heated at 50° C. for 32 hours. The solvents are evaporated and the residue is taken up in water. The aqueous phase is extracted with dichloromethane. The organic phase is washed with water, dried over sodium sulphate, filtered through a sintered glass filter and evaporated to dryness. The crude product obtained is chromatographed on silica gel, elution being carried out with a gradient of a dichloromethane/methanol/aqueous ammonia mixture (99/1/0.1 to 95/5/0.5). 0.37 g of trans-2-(4-{4-[4-(5-carbamoyladamantan-2-ylcarbamoyl)-3,4-dihydro-2H-quinoxalin-1-yl]phenyl}piperazin-1-yl)-2-methylpropionic acid ethyl ester is obtained.

M+H⁺=629

15.4: Trans-2-(4-{4-[4-(5-Carbamoyladamantan-2-ylcarbamoyl)-3,4-dihydro-2H-quinoxalin-1-yl]phenyl}piperazin-1-yl)-2-methylpropionic Acid 0.15 g of trans-2-(4-{4-[4-(5-carbamoyladamantan-2-ylcarbamoyl)-3,4-dihydro-2H-quinoxalin-1-yl]phenyl}piperazin-1-yl)-2-methylpropionic acid ethyl ester is placed in a 25 ml round-bottomed flask. 2 ml of tetrahydrofuran and 1 ml of ethanol are added. A solution of 0.031 g of lithium hydroxide in 1 ml of water is added at 0° C. The mixture is stirred at ambient temperature for 24 hours and is then heated at 50° C. for 8 hours. The solvents are evaporated, the residue is taken up in water and then the solution is basified using a 1N aqueous sodium hydroxide solution. Acidification is subsequently carried out down to pH=1 using a 6% solution of SO₂ in water. The aqueous phase is extracted with dichloromethane. The organic phase is dried over sodium sulphate, filtered through a sintered glass filter and evaporated to dryness. The crude product obtained is chromatographed on silica gel, elution being carried out with a gradient of a dichloromethane/methanol/aqueous ammonia mixture (99/1/0.1 to 80/20). 0.01 g of trans-2-(4-{4-[4-(5-carbamoyladamantan-2-ylcarbamoyl)-3,4-dihydro-2H-quinoxalin-1-yl]phenyl}piperazin-1-yl)-2-methylpropionic acid is obtained after triturating from ether.

M+H⁺=601; ¹H NMR (400 MHz, d₆-DMSO) δ ppm: 7.29 (m, 1H), 7.22 to 6.94 (m, 5H), 6.84 (m, 1H), 6.74 to 6.22 (m, 2H), 6.51 (m, 1H), 6 (m, 1H), 3.77 (m, 3H), 3.56 to 3.02 (m, 8H), 2.77 (m, 2H), 1.99 (m, 2H), 1.94 to 1.64 (m, 11H), 1.47 (m, 2H), 1.27 (m, 6H).

EXAMPLE 16

Trans-4-{4-[4-(2-Hydroxy-1,1-dimethylethyl)Piperazin-1-yl]phenyl}-3,4-dihydro-2H-quinoxaline-1-carboxylic Acid (5-carbamoyladamantan-2-yl)Amide (Compound No. 152)

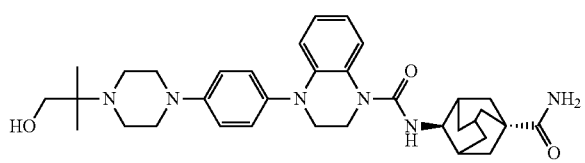

0.19 g of intermediate 15.3 is placed in 3 ml of tetrahydrofuran and then 0.36 ml of a 2N solution of lithium aluminium hydride in tetrahydrofuran is added at 0° C. The reaction medium is stirred at a temperature of 0-5° C. for 2 h. 1.5 ml of a 10% solution of potassium hydrogen sulphate in water are subsequently added at 0° C. and the medium is left stirring at the same temperature for 10 minutes. The aqueous phase is extracted with ethyl acetate. The organic phases are combined, washed with water, dried over sodium sulphate and concentrated under reduced pressure. The crude product obtained is chromatographed on silica gel, elution being carried out with a dichloromethane/methanol/aqueous ammonia solvent gradient from 99/1/0.1 to 95/5/0.5. 0.071 g of trans-4-{4-[4-(2-hydroxy-1,1-dimethylethyl)piperazin-1-yl]phenyl}-3,4-dihydro-2H-quinoxaline-1-carboxylic acid (5-carbamoyladamantan-2-yl)amide is obtained after triturating from ether.

Melting point=194-200° C.; M+H⁺=587; ¹H NMR (400 MHz, d₆-DMSO) δ ppm: 8.02 (s, 1H), 7.45 (d, J=8 Hz, 1H), 7.36 (d, J=8.4 Hz, 1H), 7.10 (m, 2H), 7 to 6.82 (m, 3H), 6.68 (s, 1H), 6.05 (d, J=5.9 Hz, 1H), 4.26 (m, 1H), 3.79 (s, 4H), 3.75 (m, 1H), 3.32 (m, 2H), 3.10 (m, 4H), 2.71 (m, 4H), 2.02 to 1.70 (m, 11H), 1.45 (m, 2H), 0.99 (s, 6H).

EXAMPLE 17

Trans-4-[5-(4-Isobutylpiperazin-1-yl)Pyridin-2-yl]-3,4-dihydro-2H-quinoxaline-1-carboxylic Acid (5-carbamoyladamantan-2-yl)Amide (Compound No. 158)

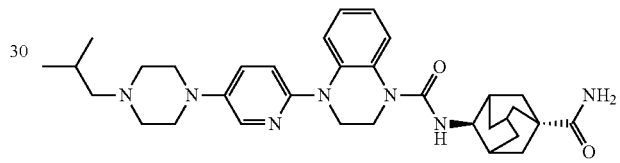

17.1: 4-[5-(4-Isobutylpiperazin-1-yl)Pyridin-2-yl]-3,4-dihydro-2H-quinoxaline-1-carboxylic Acid tert-butyl Ester Intermediate 14.3 (0.4 g, 1.01 mmol) is placed in 5 ml of dichloromethane. Isobutyraldehyde (0.090 ml, 1.01 mmol) and sodium triacetoxyborohydride (0.279 g, 1.31 mmol) are added. The reaction medium is stirred at ambient temperature under nitrogen for 18 h. After hydrolysis and extraction with dichloromethane, the organic phase is dried over MgSO₄ and concentrated to dryness. The crude product obtained is chromatographed on silica gel, elution being carried out with a gradient of methanol in dichloromethane varying from 0% to 5%. 0.39 g of 4-[5-(4-isobutylpiperazin-1-yl)pyridin-2-yl]-3,4-dihydro-2H-quinoxaline-1-carboxylic acid tert-butyl ester is obtained.

[M+H⁺]=452

17.2: 1-[5-(4-Isobutylpiperazin-1-yl)Pyridin-2-yl]-1,2,3,4-tetrahydroquinoxaline 4-[5-(4-Isobutylpiperazin-1-yl)pyridin-2-yl]-3,4-dihydro-2H-quinoxaline-1-carboxylic acid tert-butyl ester (0.39 g, 0.86 mmol) is placed in 1.7 ml of dichloromethane and then 4N HCl in dioxane (3.24 ml, 12.95 mmol) is added. The reaction medium is stirred at ambient temperature for 18 h. After hydrolysis with a 1N aqueous sodium hydroxide solution up to a pH of 10, extraction is carried out with dichloromethane. The organic phase is washed with a saturated aqueous sodium chloride solution and then dried over MgSO₄ and concentrated to dryness. The crude product obtained is chromatographed on silica gel, elution being carried out with a gradient of methanol in dichloromethane varying from 0% to 10%. 0.27 g of 1-[5-(4-isobutylpiperazin-1-yl)pyridin-2-yl]-1,2,3,4-tetrahydroquinoxaline is obtained.
[M+H$^+$]=352

17.3: 4-[5-(4-Isobutylpiperazin-1-yl)Pyridin-2-yl]-3,4-dihydro-2H-quinoxaline-1-carboxylic Acid (5-carbamoyladamantan-2-yl)Amide 1-[5-(4-Isobutylpiperazin-1-yl)pyridin-2-yl]-1,2,3,4-tetrahydroquinoxaline (0.25 g, 0.71 mmol) is placed in 7 ml of dichloromethane at 0° C. under nitrogen. Triethylamine (0.2 ml, 1.43 mmol) and then triphosgene (0.084 g, 0.28 mmol) are added. The reaction medium is stirred at ambient temperature for 3 h. 7.1 ml of DMF, diisopropylamine (0.31 ml, 1.78 mmol) and then 4-aminoadamantane-1-carboxylic acid amide (0.164 g, 0.71 mmol) are then added. The reaction medium is heated at 50° C. for 18 h under nitrogen. After hydrolysis on 50 ml of ice and extraction with ethyl acetate, the organic phase is washed with water and then with a saturated aqueous sodium chloride solution, dried over MgSO$_4$ and concentrated to dryness. The crude product obtained is chromatographed on silica gel, elution being carried out with an ethyl acetate/methanol/aqueous ammonia gradient in dichloromethane varying from 100/0/0/0 to 7/2.5/0.5/0.5 (dichloromethane/ethyl acetate/methanol/aqueous ammonia). 0.236 g of 4-[5-(4-isobutylpiperazin-1-yl)pyridin-2-yl]-3,4-dihydro-2H-quinoxaline-1-carboxylic acid (5-carbamoyladamantan-2-yl)amide is obtained, subsequently triturated from diethyl ether. The crystals obtained are filtered off and dried.
[M+H$^+$]=572; M.p.: 209° C.; $^1$H NMR (400 MHz, d$_6$-DMSO) δ ppm: 8.03 (d, J=3 Hz, 1H); 7.45 (double doublet, J=8 Hz and 1.5 Hz, 1H); 7.38 (double doublet, J=8.9 Hz and 3 Hz, 1H); 7.10 (m, 2H); 6.97 (m, 1H); 6.94 (m, J=7.6 Hz and 1.5 Hz, 1H); 6.86 (m, J=7.6 Hz and 1.5 Hz, 1H); 6.69 (m, 1H); 6.06 (d, J=6 Hz, 1H); 3.79 (s, 4H); 3.74 (m, 1H); 3.13 (m, 4H); 2.49 (m, 4H); 2.10 (d, J=7.2 Hz, 2H); 1.99 (m, 2H); 1.91 to 1.71 (m, 10H); 1.45 (m, 2H); 0.89 (d, J=6.5 Hz, 6H);

EXAMPLE 18

Trans-4-(1'-(tert-Butyl)-1',2',3',4',5',6'-hexahydro-[3,4']bipyridinyl-6-yl)-3,4-dihydro-2H-quinoxaline-1-carboxylic Acid (5-carbamoyladamantan-2-yl)Amide (Compound No. 170)

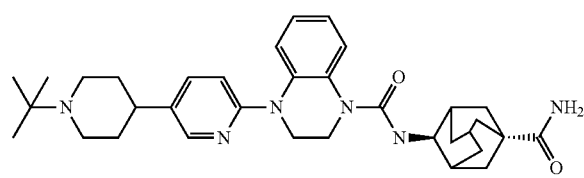

18.1: 4-[5-(4,4,5,5-Tetramethyl-1,3,2-dioxaborolan-2-yl)Pyridin-2-yl]-3,4-dihydro-2H-quinoxaline-1-carboxylic Acid tert-butyl Ester 4-(5-Bromopyridin-2-yl)-3,4-dihydro-2H-quinoxaline-1-carboxylic acid tert-butyl ester (2 g, 5.12 mmol) is placed in 25 ml of DME. Bis(pinacolato)diboron (1.56 g, 6.15 mmol), potassium acetate (1.51 g, 15.4 mmol) and [1,1'-bis(diphenylphosphino)ferrocene]dichloropalladium(II) (0.418 g, 0.51 mmol) are added. The reaction medium is heated at reflux for 2 h. After hydrolysis and addition of ethyl acetate, the mixture is filtered through Celite®, the aqueous phase is extracted with ethyl acetate, and the organic phases are combined and then washed with a saturated aqueous sodium chloride solution, dried over MgSO$_4$ and concentrated to dryness. The crude product obtained is chromatographed on silica gel, elution being carried out with a gradient of ethyl acetate in heptane varying from 10% to 30%. 1.75 g of 4-[5-(4,4,5,5-tetramethyl-1,3,2-dioxaborolan-2-yl)pyridin-2-yl]-3,4-dihydro-2H-quinoxaline-1-carboxylic acid tert-butyl ester are obtained.
[M+H$^+$]=438

18.2: 4-(1'-(tert-Butyl)-1',2',3',6'-tetrahydro-3,4'-bipyridinyl-6-yl)-3,4-dihydro-2H-quinoxaline-1-carboxylic Acid tert-butyl Ester 4-[5-(4,4,5,5-Tetramethyl-1,3,2-dioxaborolan-2-yl)pyridin-2-yl]-3,4-dihydro-2H-quinoxaline-1-carboxylic acid tert-butyl ester (0.3 g, 0.69 mmol), 1-(tert-butyl)-1,2,3,6-tetrahydropyridin-4-yl ester of methanesulphonic acid (0.22 g, 0.75 mmol), tetrakis(triphenylphosphine)palladium (0.04 g, 0.03 mmol) and a 2N aqueous sodium hydrogencarbonate solution (1.03 ml, 2.06 mmol) are placed in 2.3 ml of DME. The reaction medium is heated for 20 min at 100° C. using a Biotage® microwave synthesizer. After addition of 50 ml of H$_2$O and extraction with ethyl acetate, the organic phase is washed with a saturated aqueous sodium chloride solution, dried over MgSO$_4$ and concentrated to dryness. The crude product obtained is chromatographed on silica gel, elution being carried out with a gradient of methanol and dichloromethane varying from 0% to 10%. 0.44 g of 4-(1'-(tert-butyl)-1',2',3',6'-tetrahydro-3,4'-bipyridinyl-6-yl)-3,4-dihydro-2H-quinoxaline-1-carboxylic acid tert-butyl ester is obtained.
[M+H$^+$]=448

18.3: 4-(1'-(tert-Butyl)-1',2',3',4',5',6'-hexahydro-3,4'-bipyridinyl-6-yl)-3,4-dihydro-2H-quinoxaline-1-carboxylic Acid tert-butyl Ester 4-(1'-(tert-Butyl)-1',2',3',6'-tetrahydro-3,4'-bipyridinyl-6-yl)-3,4-dihydro-2H-quinoxaline-1-carboxylic acid tert-butyl ester (0.44 g, 0.98 mmol) is placed in 60 ml of ethyl acetate in a Parr apparatus bottle. Platinum oxide (0.089 g, 0.39 mmol) is added. After stirring for 4 h under 32 psi H$_2$, the catalyst is filtered off and rinsed with ethyl acetate. The filtrate is concentrated to dryness and then the residue is again stirred in 60 ml of ethyl acetate in the presence of 90 mg of platinum oxide under 35 psi for 18 h. The operation is repeated for 5 h and then 7 h. After filtering off the catalyst and rinsing with ethyl acetate, the filtrate is concentrated and then chromatographed on silica gel, elution being carried out with a methanol/aqueous ammonia gradient in dichloromethane varying from 100/0/0 to 9/1/0.1 (dichloromethane/methanol/aqueous ammonia). 0.166 g of 4-(1'-(tert-butyl)-1',2',3',4',5',6'-hexahydro-3,4'-bipyridinyl-6-yl)-3,4-dihydro-2H-quinoxaline-1-carboxylic acid tert-butyl ester is obtained.
[M+H$^+$]=451

18.4: 1-(1'-(tert-Butyl)-1',2',3',4',5',6'-hexahydro-3,4'-bipyridinyl-6-yl)-1,2,3,4-tetrahydroquinoxaline 4-(1'-(tert-Butyl)-1',2',3',4',5',6'-hexahydro-3,4'-bipyridinyl-6-yl)-3,4-dihydro-2H-quinoxaline-1-carboxylic acid tert-butyl ester (0.166 g, 0.37 mmol) is placed in 0.65 ml of dichloromethane at 0° C. and then 4N HCl in dioxane (1.4 ml, 5.59 mmol) is added. The reaction medium is stirred at ambient temperature for 18 h. After concentrating to dryness, the reaction medium is hydrolysed with 20 ml of H₂O and then K₂CO₃ is added until a pH of 10 is reached. The aqueous phase is extracted with ethyl acetate. The organic phase is then washed with a saturated aqueous sodium chloride solution, then dried over MgSO₄ and concentrated to dryness. 0.12 g of 1-(1'-(tert-butyl)-1',2',3',4',5',6'-hexahydro-3,4'-bipyridinyl-6-yl)-1,2,3,4-tetrahydroquinoxaline is obtained.
[M+H$^+$]=351

18.5: 4-(1'-(tert-Butyl)-1',2',3',4',5',6'-Hexahydro-3,4'-bipyridinyl-6-yl)-3,4-dihydro-2H-quinoxaline-1-carboxylic Acid (5-carbamoyladamantan-2-yl)Amide 1-(1'-(tert-Butyl)-1',2',3',4',5',6'-hexahydro-3,4'-bipyridinyl-6-yl)-1,2,3,4-tetrahydroquinoxaline (0.12 g, 0.35 mmol) is placed in 3.5 ml of dichloromethane at 0° C. Triethylamine (0.10 ml, 0.7 mmol) and then triphosgene (0.041 g, 0.14 mmol) are added. The reaction medium is stirred at ambient temperature for 3 h. 3.5 ml of DMF, diisopropylethylamine (0.15 ml, 0.87 mmol) and then 4-aminoadamantane-1-carboxylic acid amide hydrochloride (0.08 g, 0.35 mmol) are then added. The reaction medium is heated at 50° C. for 18 h under nitrogen. After hydrolysing on 40 ml of H₂O and extracting with ethyl acetate, the organic phase is washed with water and then with a saturated aqueous sodium chloride solution, dried over MgSO₄ and concentrated to dryness. The crude product obtained is chromatographed on silica gel, elution being carried out with an ethyl acetate/methanol/aqueous ammonia gradient in dichloromethane varying from 100/0/0/0 to 7/2.5/0.5/0.5 (dichloromethane/ethyl acetate/methanol/aqueous ammonia). 0.09 g of 4-(1'-(tert-butyl)-1',2',3',4',5',6'-hexahydro-3,4'-bipyridinyl-6-yl)-3,4-dihydro-2H-quinoxaline-1-carboxylic acid (5-carbamoyladamantan-2-yl)amide is obtained and is subsequently triturated from diethyl ether. The crystals obtained are filtered off and dried.

[M+H$^+$]=571; M.p.: 228° C.; $^1$H NMR (400 MHz, d$_6$-DMSO) δ ppm: 8.16 (d, J=2.5 Hz, 1H), 7.55 (m, 2H), 7.33 (m, 1H), 7.10 (d, J=8.6 Hz, 2H), 7.02 to 6.94 (m, 3H), 6.68 (broad singlet, 1H), 6.10 (d, J=6 Hz, 1H), 3.91 (m, 2H), 3.81 (m, 2H), 3.74 (m, 1H), 3.11 (m, 1H), 2.44 (m, 1H), 2.13 (m, 2H), 1.98 (m, 2H), 1.93 to 1.71 (m, 10H), 1.59 (m, 2H), 1.44 (m, 2H), 1.06 (s, 9H)

EXAMPLE 19

Trans-4-[5-(4-(Cyclopropanesulphonyl)Piperazin-1-yl)Pyridin-2-yl]-3,4-dihydro-2H-quinoxaline-1-carboxylic Acid (5-cyanoadamantan-2-yl)Amide (Compound No. 165)

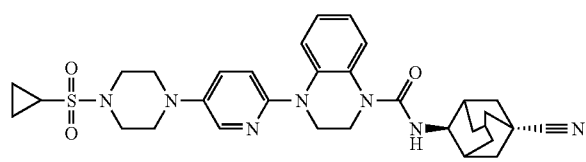

19.1: 4-[5-(4-(Cyclopropylsulphonyl)Piperazin-1-yl)Pyridin-2-yl]-3,4-dihydro-2H-quinoxaline-1-carboxylic Acid tert-butyl Ester 10 g of 4-(5-(piperazin-1-yl)pyridin-2-yl)-3,4-dihydro-2H-quinoxaline-1-carboxylic acid tert-butyl ester are placed in a 500 ml round-bottomed flask. 126 ml of dichloromethane are added, followed by 4.23 ml of triethylamine and, finally, 2.7 ml of cyclopropylsulphonyl chloride. The reaction mixture is stirred at ambient temperature for 16 h, then washed with water and once with a saturated sodium chloride solution, dried over magnesium sulphate and then evaporated under reduced pressure. The crude product obtained is chromatographed on silica gel, elution being carried out with a gradient of methanol in dichloromethane varying from 0% to 10%. 10.9 g of 4-[5-(4-(cyclopropylsulphonyl)piperazin-1-yl)pyridin-2-yl]-3,4-dihydro-2H-quinoxaline-1-carboxylic acid tert-butyl ester are obtained.
M+H$^+$=500.6

19.2: 4-[5-(4-(Cyclopropylsulphonyl)Piperazin-1-yl)Pyridin-2-yl]-3,4-dihydro-2H-quinoxaline 10.3 g of 4-[5-(4-(cyclopropylsulphonyl)piperazin-1-yl)pyridin-2-yl]-3,4-dihydro-2H-quinoxaline-1-carboxylic acid tert-butyl ester are placed in 204 ml of a 4N solution of hydrochloric acid in dioxane. The reaction mixture is stirred at ambient temperature for 1.5 h. It is subsequently evaporated under reduced pressure and then a saturated aqueous sodium hydrogencarbonate solution is added. The aqueous phase is extracted three times with dichloromethane. The organic phases are combined, dried over sodium sulphate and concentrated under vacuum. 7.96 g of 4-[5-(4-(cyclopropylsulphonyl)piperazin-1-yl)pyridin-2-yl]-3,4-dihydro-2H-quinoxaline are obtained.
M+H$^+$=400.5

19.3: Trans-4-[5-(4-(Cyclopropylsulphonyl)Piperazin-1-yl)Pyridin-2-yl]-3,4-dihydro-2H-quinoxaline-1-carboxylic Acid (5-carbamoyladamantan-2-yl)Amide 0.39 g of 4-[5-(4-(cyclopropylsulphonyl)piperazin-1-yl)pyridin-2-yl]-3,4-dihydro-2H-quinoxaline is placed in 6.1 ml of dichloromethane and 0.54 ml of triethylamine. 0.12 g of triphosgene is subsequently added at 0° C. The reaction medium is stirred at ambient temperature for 2 h and is then washed with a saturated aqueous sodium hydrogencarbonate solution. The organic phase is dried over sodium sulphate and concentrated under vacuum. The crude reaction product is diluted with 8 ml of dimethylformamide and then 0.34 ml of triethylamine and also 0.25 g of trans-4-aminoadamantane-1-carboxylic acid amide hydrochloride are added. The mixture is stirred at ambient temperature for 16 h and then water and ethyl acetate are added. The organic phase is washed three times with water and once with a saturated aqueous sodium hydrogencarbonate solution, dried over sodium sulphate and concentrated under vacuum. The crude product obtained is chromatographed on silica gel, elution being carried out with a gradient of a dichloromethane/acetone/methanol mixture (88/10/2 to 70/25/5). 0.34 g of trans-4-[5-(4-(cyclopropylsulphonyl)piperazin-1-yl)pyridin-2-yl]-3,4-dihydro-2H-quinoxaline-1-carboxylic acid (5-carbamoyladamantan-2-yl)amide is obtained after triturating from a mixture of ethyl acetate and ethyl ether.
M+H$^+$=620.8

19.4: Trans-4-[5-(4-(Cyclopropanesulphonyl)Piperazin-1-yl)Pyridin-2-yl]-3,4-dihydro-2H-quinoxaline-1-carboxylic Acid (5-cyanoadamantan-2-yl)Amide 0.1 g of intermediate 19.3 is placed in 0.85 ml of dichloromethane at 0° C. 0.04 ml of triethylamine and then 0.03 ml of trifluoroacetic anhydride are added. The reaction medium is stirred at 0° C. for 2 h 20. The reaction medium is hydrolysed with a saturated aqueous sodium hydrogencarbonate solution and then dichloromethane is added. The aqueous phase is extracted three times with dichloromethane and then the organic phase is dried over MgSO$_4$ and concentrated to dryness. The crude product obtained is chromatographed on silica gel, elution being carried out with a gradient of methanol in dichloromethane varying from 100/0 to 90/10 (dichloromethane/methanol). 0.045 g of trans-4-[5-(4-(cyclopropanesulphonyl)piperazin-1-yl)pyridin-2-yl]-3,4-dihydro-2H-quinoxaline-1-carboxylic acid (5-cyanoadamantan-2-yl) amide is obtained.

[M+H$^+$]=602; M.p.: 188° C.; $^1$H NMR (400 MHz, d$_6$-DMSO) δ ppm: 8.07 (m, 1H), 7.47 (m, J=8 Hz, 1H), 7.42 (m, J=9.2 Hz, 1H), 7.14 (m, 2H), 6.94 (m, 1H), 6.87 (m, 1H), 6.16 (d, J=5.7 Hz, 1H), 3.87 to 3.74 (m, 5H), 3.41 to 3.16 (m, 8H), 2.67 (m, 1H), 2.13 to 1.94 (m, 8H), 1.90 (broad singlet, 1H), 1.81 (m, 2H), 1.52 (m, 2H), 1.08 to 0.93 (m, 4H)

EXAMPLE 20

Trans-4-{5-[4-(2-(Methanesulphonyl)Ethyl)Piperazin-1-yl]-pyridin-2-yl}-3,4-dihydro-2H-quinoxaline-1-carboxylic Acid (5-carbamoyladamantan-2-yl) Amide (Compound No. 178)

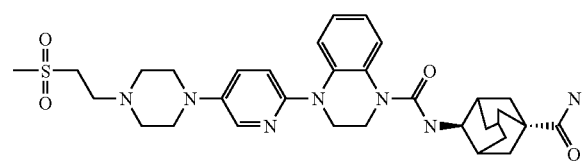

20.1: 4-{5-[4-(2-(Methanesulphonyl)Ethyl)Piperazin-1-yl]pyridin-2-yl}-3,4-dihydro-2H-quinoxaline-1-carboxylic Acid tert-butyl Ester Intermediate 14.3 (0.3 g, 0.76 mmol) is placed in 7.5 ml of methanol. Methyl vinyl sulphone (0.17 ml, 1.94 mmol) is added. The reaction medium is stirred at ambient temperature under nitrogen for 18 h. The reaction medium is concentrated to dryness and then chromatographed on silica gel, elution being carried out with a gradient of methanol in dichloromethane varying from 1% to 10%. 0.38 g of 4-{5-[4-(2-(methanesulphonyl)ethyl)piperazin-1-yl]pyridin-2-yl}-3,4-dihydro-2H-quinoxaline-1-carboxylic acid tert-butyl ester is obtained.

[M+H$^+$]=502

20.2: 1-{5-[4-(2-(Methanesulphonyl)Ethyl)Piperazin-1-yl]pyridin-2-yl}-1,2,3,4-tetrahydroquinoxaline 4-{5-[4-(2-(Methanesulphonyl)ethyl)piperazin-1-yl]pyridin-2-yl}-3,4-dihydro-2H-quinoxaline-1-carboxylic acid tert-butyl ester (0.38 g, 0.76 mmol) is placed in 5 ml of dioxane and then 4N HCl in dioxane (2.84 ml, 11.36 mmol) is added. The reaction medium is stirred at ambient temperature for 18 h. 4N HCl in dioxane (2.84 ml, 11.36 mmol) is again added and the reaction medium is stirred at ambient temperature for an additional 18 h. After concentrating to dryness, the reaction medium is diluted with 50 ml of 1N HCl in water and extracted with 100 ml of diethyl ether. The organic phase is again washed with 50 ml of 1N HCl in water. The aqueous phases are combined, basified with K$_2$CO$_3$ powder up to a pH of 10 and extracted 3 times with 50 ml of dichloromethane. The resulting organic phases are combined, washed with a saturated aqueous sodium chloride solution, dried over MgSO$_4$ and concentrated to dryness. 0.3 g of 1-{5-[4-(2-(methanesulphonyl)ethyl)piperazin-1-yl]pyridin-2-yl}-1,2,3,4-tetrahydroquinoxaline is obtained.

[M+H$^+$]=402

20.3: Trans-4-{5-[4-(2-(Methanesulphonyl)Ethyl)Piperazin-1-yl]pyridin-2-yl}-3,4-dihydro-2H-quinoxaline-1-carboxylic Acid (5-carbamoyladamantan-2-yl)Amide 1-{5-[4-(2-(Methanesulphonyl)ethyl)piperazin-1-yl]pyridin-2-yl}-1,2,3,4-tetrahydroquinoxaline (0.3 g, 0.75 mmol) is placed in 5 ml of dichloromethane at 0° C. Triethylamine (0.21 ml, 1.50 mmol) and then triphosgene (0.09 g, 0.3 mmol) are added. The reaction medium is stirred under nitrogen at 0° C. for 30 min and then at ambient temperature for 3 hours. 4-Aminoadamantane-1-carboxylic acid amide hydrochloride (0.19 g, 0.82 mmol), triethylamine (0.26 ml, 1.89 mmol) and 5 ml of DMF are then added. The reaction medium is stirred at ambient temperature under nitrogen for 18 h. After hydrolysis with 100 ml of H$_2$O, the medium is extracted twice with 50 ml of dichloromethane. The organic phases are combined, washed twice with 100 ml of H$_2$O and then with 100 ml of a saturated aqueous sodium chloride solution, dried over MgSO$_4$ and concentrated to dryness. The crude product obtained is chromatographed on silica gel, elution being carried out with a gradient of methanol in dichloromethane varying from 1% to 10%. After triturating from diethyl ether, filtering and drying, 0.23 g of trans-4-{5-[4-(2-(methanesulphonyl)ethyl)piperazin-1-yl]pyridin-2-yl}-3,4-dihydro-2H-quinoxaline-1-carboxylic acid (5-carbamoyladamantan-2-yl)amide is obtained.

[M+H$^+$]=622; M.p.=204° C.; $^1$H NMR (400 MHz, d$_6$-DMSO) δ ppm: 8.05 (s, 1H), 7.45 (d, J=8.2 Hz, 1H), 7.40 (d, J=9 Hz, 1H), 7.11 (d, J=8.4 Hz, 2H), 7-6.82 (m, 3H), 6.68 (s, 1H), 6.06 (d, J=5.8 Hz, 1H), 3.79 (s, 4H), 3.75 (broad singlet, 1H), 3.75 (m, 2H), 3.15 (m, 4H), 3.06 (s, 3H), 2.78 (broad triplet, J=6 Hz, 2H), 2.61 (m, 4H), 2.03 to 1.70 (m, 11H), 1.45 (m, 2H).

The chemical structures and the physical properties of some compounds according to the invention which correspond to the formula (Ia), in which R$_{1b}$ and R$_{2b}$ represent hydrogen atoms, and which are provided in the form of free bases (nonsalified compounds), except for compound No. 155, which is provided in the form of an equimolar hydrochloride, are illustrated in the following table. In this table:

in the "A" column, "-" represents a single bond;
Me represents a methyl group;
Et represents an ethyl group;
iPr represents an isopropyl group;
tBu represents a tert-butyl group;
Ph represents a phenyl group;
M.p. represents the melting point of the compound, expressed in degrees Celsius;
M+H$^+$ represents the weight of the compound, obtained by LC-MS (Liquid Chromatography-Mass Spectroscopy).

TABLE (Ia)
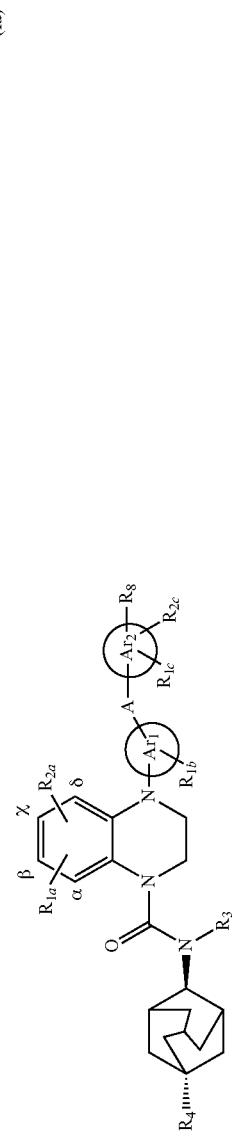
| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M + H+ | Synthesis |
|---|---|---|---|---|---|---|---|---|---|---|---|---|---|---|
| 1 | — | H | H | H | H | H | H | H | H | phenyl | pyridyl | 73-82 | 465 | Method 1 |
| 2 | —O— | H | H | H | H | H | H | H | tetrahydropyranyl | phenyl | piperidinyl-N-R_8 | 110 | 599 | Method 1 |
| 3 | —O—CH_2— | H | H | H | H | H | H | H | H | phenyl | pyridyl | 123-125 | 496 | Method 1 |
| 4 | — | H | H | H | H | H | H | H | morpholinyl-CO | phenyl | piperidinyl-N-R_8 | 110 | 584 | Method 1 |
| 5 | —O— | H | H | H | —OMe | H | H | H | H | phenyl | pyrimidinyl | 72 | 512 | Method 1 |

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+ H+ | Synthesis |
|---|---|---|---|---|---|---|---|---|---|---|---|---|---|---|
| 6 | — | H | H | H | H | H | H | H | morpholine-C(O)- | thiazole | phenyl-$R_8$ | 163-169 | 584 | Method 1 |
| 7 | — | H | H | H | —OMe | H | H | H | H | pyrimidine | phenyl-$R_{1c}$ | 140-144 | 496 | Method 1 |
| 8 | — | H | H | H | —OMe | H | H | —OH | H | pyrimidine | phenyl-$R_{1c}$ | >200 | 512 | Method 1 |
| 9 | — | H | H | H | —SO$_2$Me | H | H | —OH | H | phenyl | piperazine-$R_{1c}$ | 160 | 566 | Method 1 |
| 10 | — | H | H | H | —SO$_2$Me | H | H | —CO$_2$Me | H | phenyl | piperazine-$R_{1c}$ | 191-194 | 608 | Method 1 |
| 11 | — | H | H | H | —SO$_2$Me | H | H | —CO$_2$H | H | phenyl | piperazine-$R_{1c}$ | 194-198 | 594 | Method 3 |
| 12 | — | H | H | H | —SO$_2$Me | H | H | —CONH$_2$ | H | phenyl | piperazine-$R_{1c}$ | 247-250 | 593 | Method 3 |

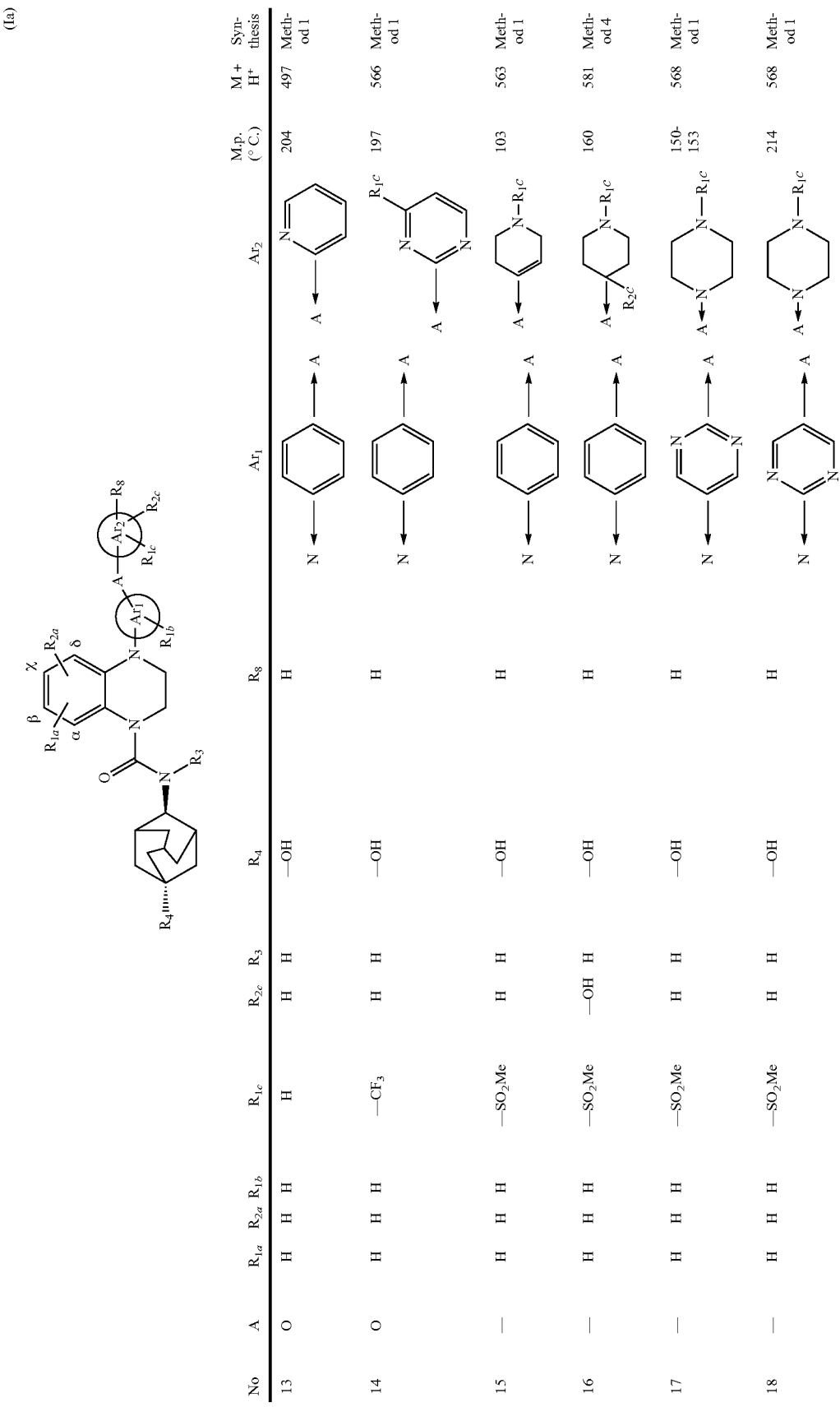

TABLE-continued

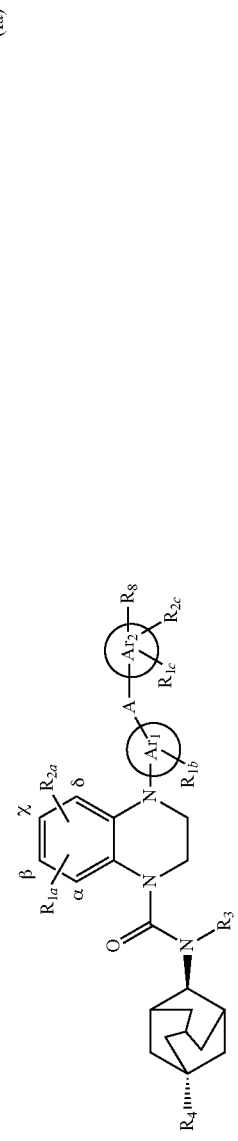

(Ia)

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+H+ | Synthesis |
|----|---|------|------|------|------|------|-----|------|-----|-----|-----|------|------|-----------|
| 19 | — | H | H | H | H | H | H | —OH | morpholine-C(O)- | phenyl-N→A | piperidine N-R8 | 105 | 600 | Method 1 |
| 20 | — | H | H | H | PhCH2OC(O)- | H | H | —OH | H | phenyl-N→A | piperazine N-R1c | 94-101 | 622 | Method 1 |
| 21 | — | H | H | H | —SO2Me | H | H | —CH2OH | H | phenyl-N→A | piperazine N-R1c | 160 | 580 | Method 5 |
| 22 | O | H | H | H | F | H | H | —OH | H | phenyl-N→A | pyrimidine | 215 | 516 | Method 1 |
| 23 | O | H | H | H | —SO2Me | H | H | —OH | H | phenyl-N→A | piperazine N-R1c | 115 | 581 | Method 1 |
| 24 | — | H | H | H | H | H | H | —OH | H | phenyl-N→A | morpholine | 214 | 489 | Method 1 |
| 25 | — | H | H | H | H | H | H | —OH | H | phenyl-N→A | thiomorpholine dioxide | 218 | 537 | Method 1 |

TABLE-continued (Ia)

| No | A | R$_{1a}$ | R$_{2a}$ | R$_{1b}$ | R$_{1c}$ | R$_{2c}$ | R$_3$ | R$_4$ | R$_8$ | Ar$_1$ | Ar$_2$ | M.p. (°C.) | M+H$^+$ | Synthesis |
|---|---|---|---|---|---|---|---|---|---|---|---|---|---|---|
| 26 | — | H | H | H | —O-iPr | H | H | —OH | H | phenyl | pyridyl-R$_{1c}$ | 113-115 | 539 | Method 1 |
| 27 | — | H | H | H | H | H | H | —OH | N-isopropyl-piperazinyl-C(O)- | phenyl | pyridyl-R$_8$ | 127 | 635 | Method 1 |
| 28 | — | H | H | H | —SO$_2$Me | H | H | —OH | H | pyridyl | piperazinyl-N-R$_{1c}$ | 114 | 567 | Method 1 |
| 29 | — | H | H | H | H | H | H | —OH | H | phenyl | piperazinyl-N-H | 116 | 488 | Method 1 |
| 30 | — | H | H | H | F | F | H | —OH | H | phenyl | piperidinyl-R$_{1c}$,R$_{2c}$ | 95 | 523 | Method 1 |
| 31 | — | H | H | H | —SO$_2$Me | H | H | —OH | H | pyridyl | piperazinyl-N-R$_{1c}$ | 125 | 567 | Method 1 |
| 32 | O | H | H | H | —SO$_2$Me | H | H | —OH | H | pyrimidyl | piperazinyl-N-R$_{1c}$ | 120 | 583 | Method 1 |

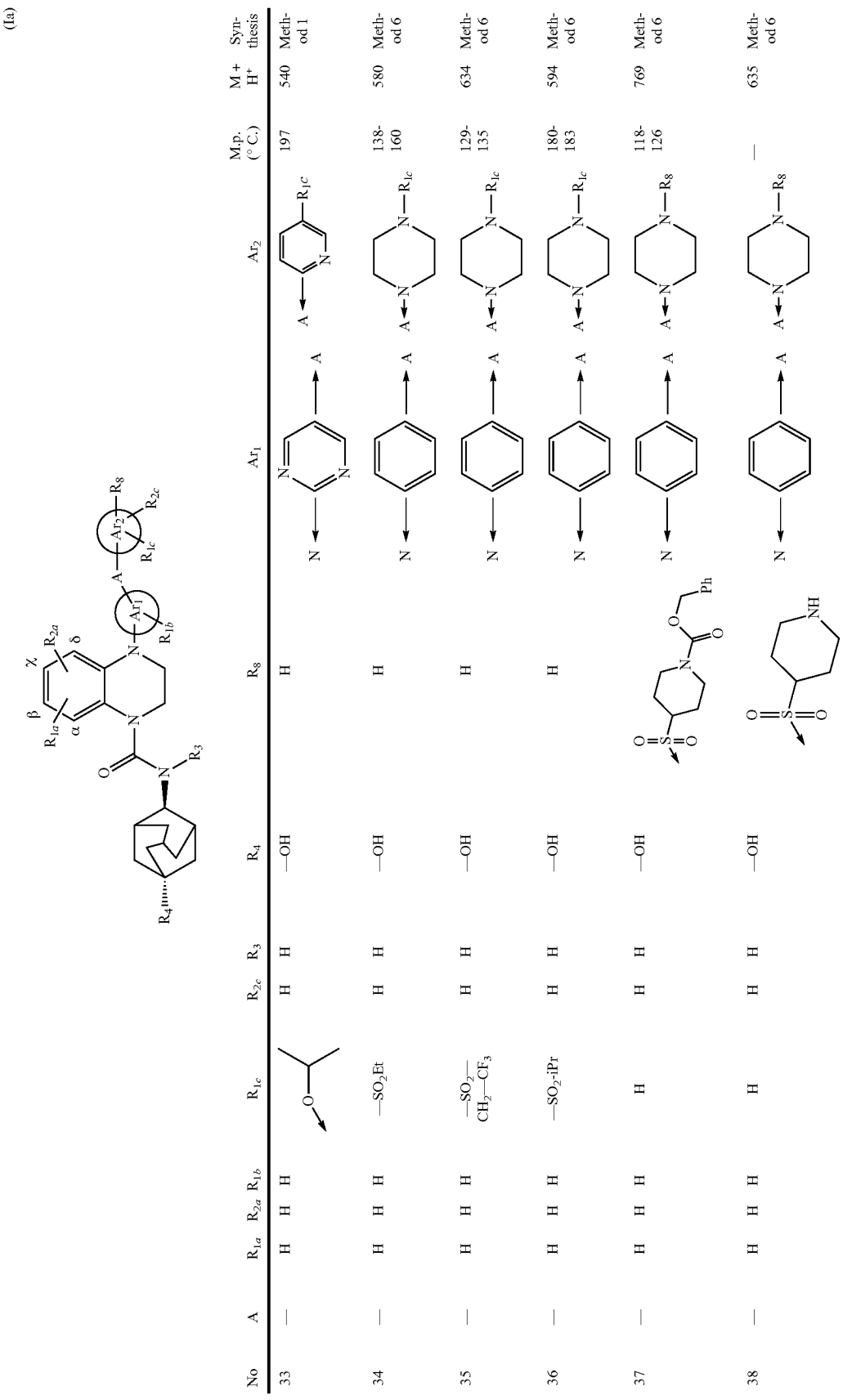

TABLE-continued (Ia)

| No | A | $R_{1a}$ | $R_{2a}$ | $R_{1b}$ | $R_{1c}$ | $R_{2c}$ | $R_3$ | $R_4$ | $R_8$ | Ar$_1$ | Ar$_2$ | M.p. (°C.) | M + H$^+$ | Synthesis |
|----|---|------|------|------|------|------|----|----|----|-----|-----|------|-----|------|
| 39 | — | H | H | H | cyclopropyl-SO$_2$— | H | H | —OH | H | phenyl (N) | piperazinyl-N-R$_{1c}$ | 134-139 | 592 | Method 6 |
| 40 | — | H | H | H | —SO$_2$Me | H | H | F | H | phenyl (N) | piperazinyl-N-R$_{1c}$ | 165-200 | 568 | Method 7 |
| 41 | — | H | H | H | cyclobutyl-SO$_2$— | H | H | —OH | H | phenyl (N) | piperazinyl-N-R$_{1c}$ | 175-178 | 606 | Method 6 |
| 42 | — | H | H | H | nPr-SO$_2$— | H | H | —OH | H | phenyl (N) | piperazinyl-N-R$_{1c}$ | — | 594 | Method 6 |
| 43 | — | H | H | H | nBu-SO$_2$— | H | H | —OH | H | phenyl (N) | piperazinyl-N-R$_{1c}$ | 110-114 | 608 | Method 6 |
| 44 | — | H | H | H | H | H | H | —OH | morpholinyl-SO$_2$— | phenyl (N) | piperazinyl-N-R$_8$ | 118-122 | 637 | Method 6 |

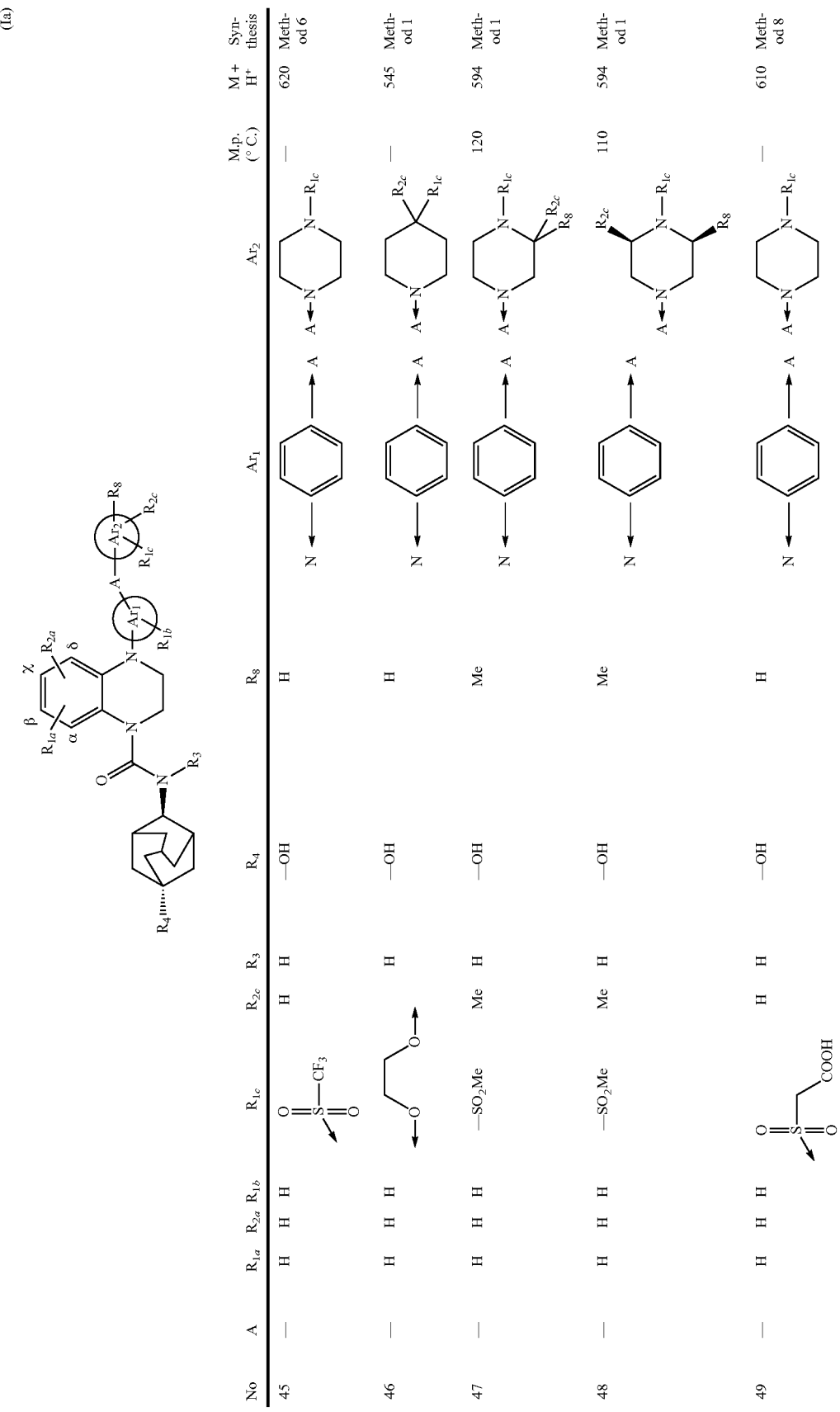

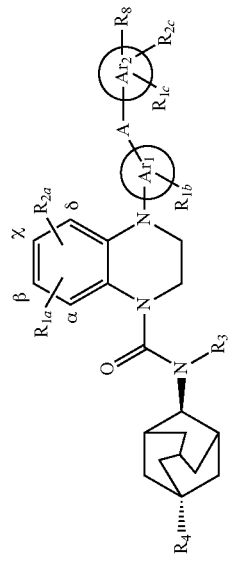

TABLE-continued (Ia)

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M + H⁺ | Synthesis |
|---|---|---|---|---|---|---|---|---|---|---|---|---|---|---|
| 50 | — | H | H | H | —S(=O)₂—CH₂—COOEt | H | H | —OH | H | phenyl (N, A) | piperazine N–$R_{1c}$ | 82 | 638 | Method 6 |
| 51 | — | H | H | H | —OH | H | H | —OH | H | phenyl (N, A) | piperazine N–$R_{1c}$ | 131 | 503 | Method 9 |
| 52 | — | H | H | H | —SO₂Me | H | H | —OH | H | phenyl (N, A) | azepane N–$R_{1c}$ | 185 | 580 | Method 1 |
| 53 | — | H | H | H | —C(CH₃)₂—CO₂Et | H | H | —OH | H | phenyl (N, A) | piperazine N–$R_{1c}$ | — | 602 | Method 6 |
| 54 | — | H | H | H | —S(=O)₂—CH₂CH₂—CO₂Me | H | H | —OH | H | phenyl (N, A) | piperazine N–$R_{1c}$ | — | 638 | Method 6 |
| 55 | — | H | H | H | —OMe | H | H | —OH | H | phenyl (N, A) | pyrimidine $R_{1c}$ | 118 | 512 | Method 1 |
| 56 | — | H | H | H | H | H | H | —OH | —CH₂CH₂—S(=O)₂—CH₂CH₂—morpholine | phenyl (N, A) | piperazine N–$R_8$ | — | 665 | Method 1 |

TABLE-continued (Ia)

| No | A | R1a | R2a | R1b | R1c | R2c | R3 | R4 | R8 | Ar1 | Ar2 | M.p. (°C.) | M + H+ | Synthesis |
|---|---|---|---|---|---|---|---|---|---|---|---|---|---|---|
| 57 | — | H | H | H | —SO$_2$Me | H | H | —OH | H | pyridazine (N=N) | piperazine (N-R1c) | 145 | 568 | Method 1 |
| 58 | — | H | H | H | —SO$_2$Me | H | Me | —OH | H | phenyl | piperazine (N-R1c) | 160 | 580 | Method 1 |
| 59 | — | H | H | H | —SO$_2$Me | Me | H | —OH | Me | phenyl | piperidine (R2c, N-R1c, R8) | 135 | 594 | Method 1 |
| 60 | — | H | H | H | —CH$_2$CH$_2$S(O)$_2$N(Et)$_2$ | H | H | —OH | H | phenyl | piperazine (N-R1c) | — | 651 | Method 1 |
| 61 | — | H | H | H | —SO$_2$Me | H | H | —OH | H | phenyl | 2,5-diazabicyclic (N-R1c) | 144-153 | 592 | Method 1 |
| 62 | — | H | H | H | —OMe | H | H | —CONH$_2$ | H | pyrimidine | phenyl-R1c | 196-197 | 539 | Method 1 |

TABLE-continued (Ia)

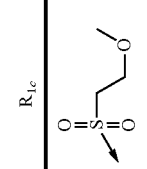

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+H+ | Synthesis |
|---|---|---|---|---|---|---|---|---|---|---|---|---|---|---|
| 63 | — | H | H | H | —S(=O)₂CH₂CH₂OMe | H | H | —OH | H | phenyl-N→A | piperazinyl-N-R₁c | — | 610 | Method 1 |
| 64 | — | H | H | H | —OiPr | H | H | —OH | H | phenyl-N→A | piperidinyl-R₁c | 98 | 545 | Method 1 |
| 65 | — | H | H | H | —OH | H | H | —OH | H | pyrimidinyl-N→A | phenyl-R₁c | 220 | 498 | Method 1 |
| 66 | — | H | H | H | —H | H | H | —OH | H | phenyl-N→A | piperazinyl-N-R₁c | 179-180 | 515 | Method 1 |
| 67 | —O— | H | H | H | —Br | H | H | —H | H | pyrimidinyl-N→A | piperazinyl-N-R₁c | 199-200 | 576 | Method 1 |
| 68 | — | H | H | H | —S(=O)₂-cyclopropyl | H | H | —CONH₂ | H | phenyl-N→A | piperazinyl-N-R₁c | 143 | 619 | Method 1 |
| 69 | — | χ-Cl | H | H | —SO₂Me | H | H | —OH | H | phenyl-N→A | piperazinyl-N-R₁c | — | 660 | Method 1 |

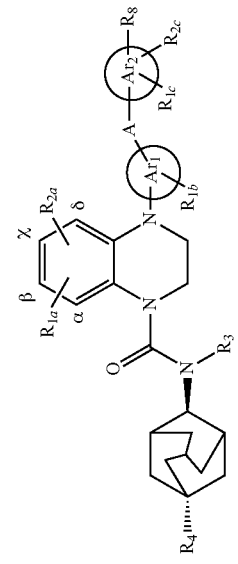

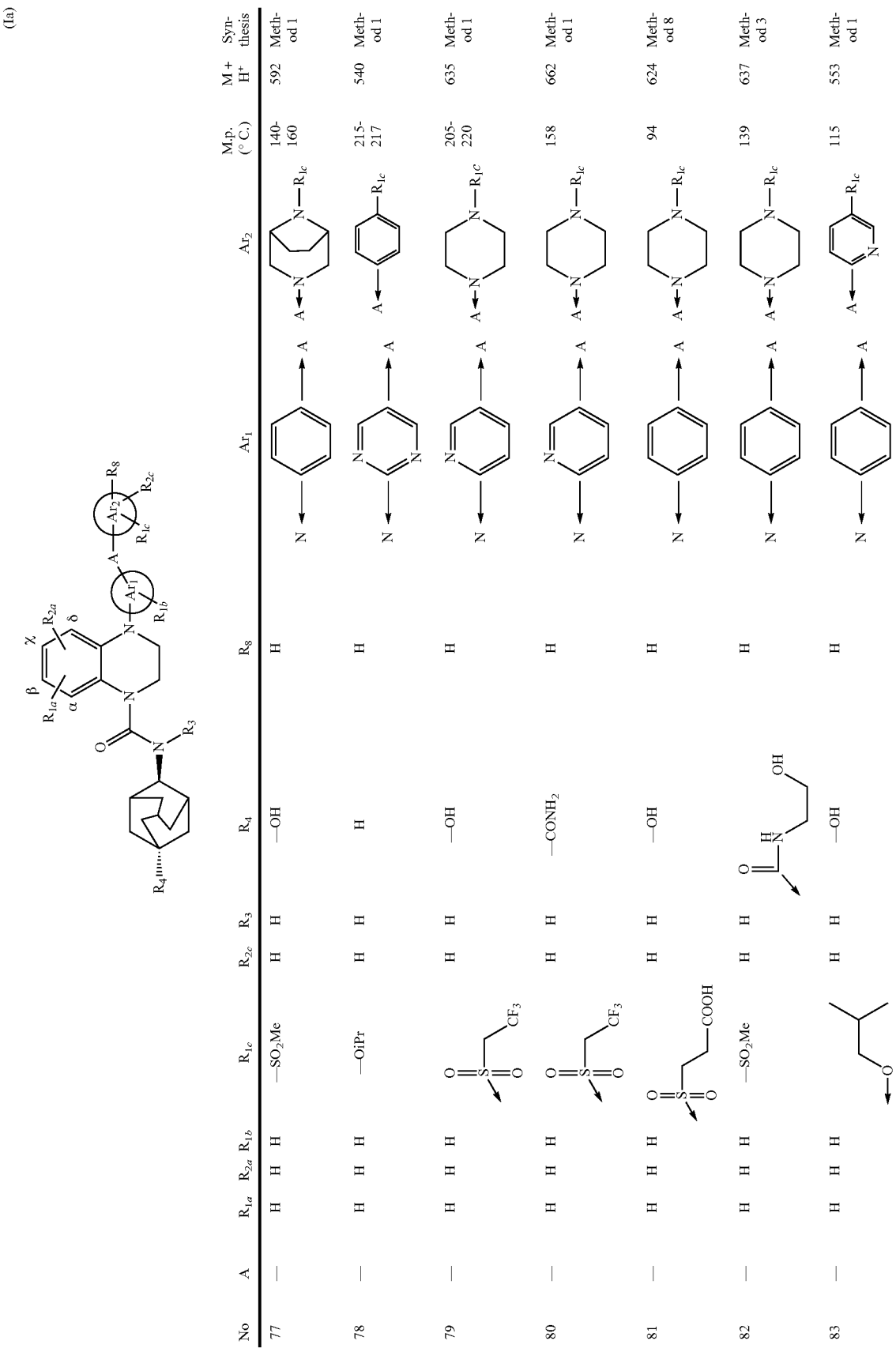

TABLE-continued

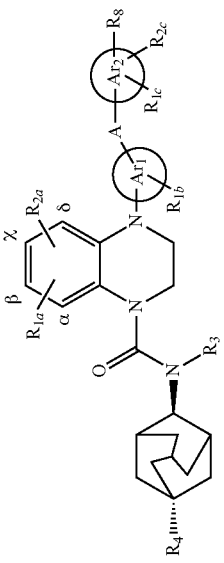

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+ H+ | Synthesis |
|---|---|---|---|---|---|---|---|---|---|---|---|---|---|---|
| 84 | — | H | H | H | sec-butoxy | H | H | —OH | H | phenyl-N,A | pyridyl-$R_{1c}$ | 110 | 553 | Method 1 |
| 85 | — | H | H | H | isopropoxy | H | H | —CONH$_2$ | H | phenyl-N,A | pyridyl-$R_{1c}$ | 193-194 | 566 | Method 1 |
| 86 | — | H | H | H | —SO$_2$Me | H | H | C(O)NH—OMe | H | phenyl-N,A | piperazinyl-$R_{1c}$ | 256-258 | 623 | Method 1 |
| 87 | — | H | H | H | —SO$_2$Et | H | H | —OH | H | pyridyl-N,A | piperazinyl-$R_{1c}$ | 105 | 581 | Method 1 |
| 88 | — | H | H | H | cyclopropyl-SO$_2$ | H | H | —OH | H | phenyl-N,A | piperazinyl-$R_{1c}$ | 194 | 593 | Method 1 |
| 89 | — | H | H | H | cyclopropyl-SO$_2$ | H | H | —CONH$_2$ | H | pyridyl-N,A | piperazinyl-$R_{1c}$ | 120 | 620 | Method 1 |

TABLE-continued (Ia)

| No | A | R1a | R2a | R1b | R1c | R2c | R3 | R4 | R8 | Ar1 | Ar2 | M.p. (°C.) | M+H+ | Synthesis |
|---|---|---|---|---|---|---|---|---|---|---|---|---|---|---|
| 90 | — | H | H | H | iPr-SO2- | H | H | —OH | H | pyridinyl-N | piperazinyl N-R1c | 176 | 595 | Method 1 |
| 91 | — | H | H | H | H | H | H | —OH | 4-methoxy-pyridinyl | phenyl | — | 580 | Method 1 |
| 92 | — | H | H | H | MeO-CH2CH2-SO2- | H | H | —CONH2 | H | phenyl | piperazinyl N-R1c | — | 637 | Method 1 |
| 93 | — | H | H | H | H2N-CH2CH2-SO2- | H | H | —CONH2 | H | phenyl | piperazinyl N-R1c | — | 622 | Method 1 |
| 94 | — | H | H | H | (Et)2N-CH2CH2-SO2- | H | H | —CONH2 | H | phenyl | piperazinyl N-R1c | — | 678 | Method 1 |
| 95 | — | H | H | H | H | H | H | —CONH2 | 4-(methylsulfonyl)piperidinyl | phenyl | piperazinyl N-R8 | 230 | 662 | Method 1 |
| 96 | — | H | H | H | -tBu | H | H | —CONH2 | H | phenyl | piperazinyl N-R1c | 228 | 571 | Method 1 |

TABLE-continued (Ia)

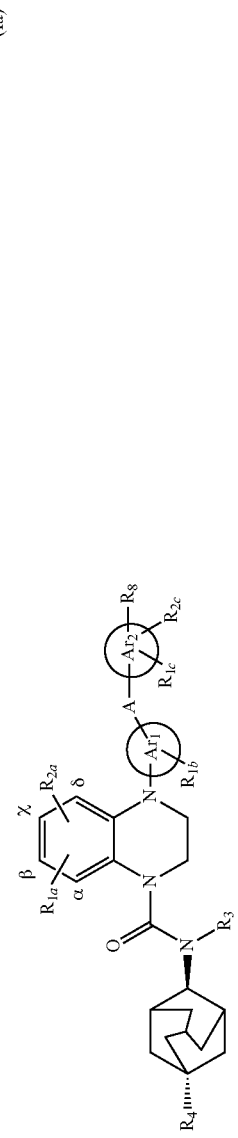

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (° C.) | M + H⁺ | Synthesis |
|----|---|----------|----------|----------|----------|----------|-------|-------|-------|--------|--------|-------------|--------|-----------|
| 97 | — | H | H | H | —SO₂Me | H | H | —CONH₂ | H | pyridine-N | piperazine-$R_{1c}$ | 235 | 594 | Method 1 |
| 98 | — | H | H | H | propylsulfonyl | H | H | —OH | H | pyridine-N | piperazine-$R_{1c}$ | 170 | 595 | Method 1 |
| 99 | — | H | H | H | isobutylsulfonyl | H | H | —OH | H | pyridine-N | piperazine-$R_{1c}$ | 205 | 609 | Method 1 |
| 100 | — | H | H | H | H | H | H | —OH | H | pyridine-N | morpholine | 182 | 490 | Method 1 |
| 101 | — | H | H | H | hydroxyethylsulfonyl | H | H | —CONH₂ | H | phenyl-N | piperazine-$R_{1c}$ | — | 623 | Method 1 |
| 102 | — | H | H | H | H | H | H | —OH | 4-methoxy-piperidine | phenyl-N | piperidine-$R_8$ | — | 586 | Method 11 |

TABLE-continued

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+H+ | Synthesis |
|---|---|---|---|---|---|---|---|---|---|---|---|---|---|---|
| 103 | — | H | H | H | —C(O)N(CH₃)₂ | H | H | —OH | H | phenyl (N) | piperazine N-$R_{1c}$ | 86 | 559 | Method 6 |
| 104 | — | H | H | H | cyclopropyl-SO₂— | H | H | —CONH₂ | H | pyridyl (N) | piperazine N-$R_{1c}$ | 152-155 | 620 | Method 1 |
| 105 | — | H | H | H | —SO₂Et | H | H | —CONH₂ | H | phenyl (N) | piperazine N-$R_{1c}$ | 162-171 | 607 | Method 1 |
| 106 | — | H | H | H | CF₃CH₂SO₂— | H | H | —CONH₂ | H | phenyl (N) | piperazine N-$R_{1c}$ | 145-153 | 661 | Method 1 |
| 107 | — | H | H | H | —C(O)CH₂NH₂ | H | H | —OH | H | phenyl (N) | piperazine N-$R_{1c}$ | 190-203 | 572 | Method 6 |
| 108 | — | H | H | H | —CH₂CH₂OH | H | H | —CONH₂ | H | phenyl (N) | pyridyl-$R_{1c}$ | 206 | 538 | Method 1 |

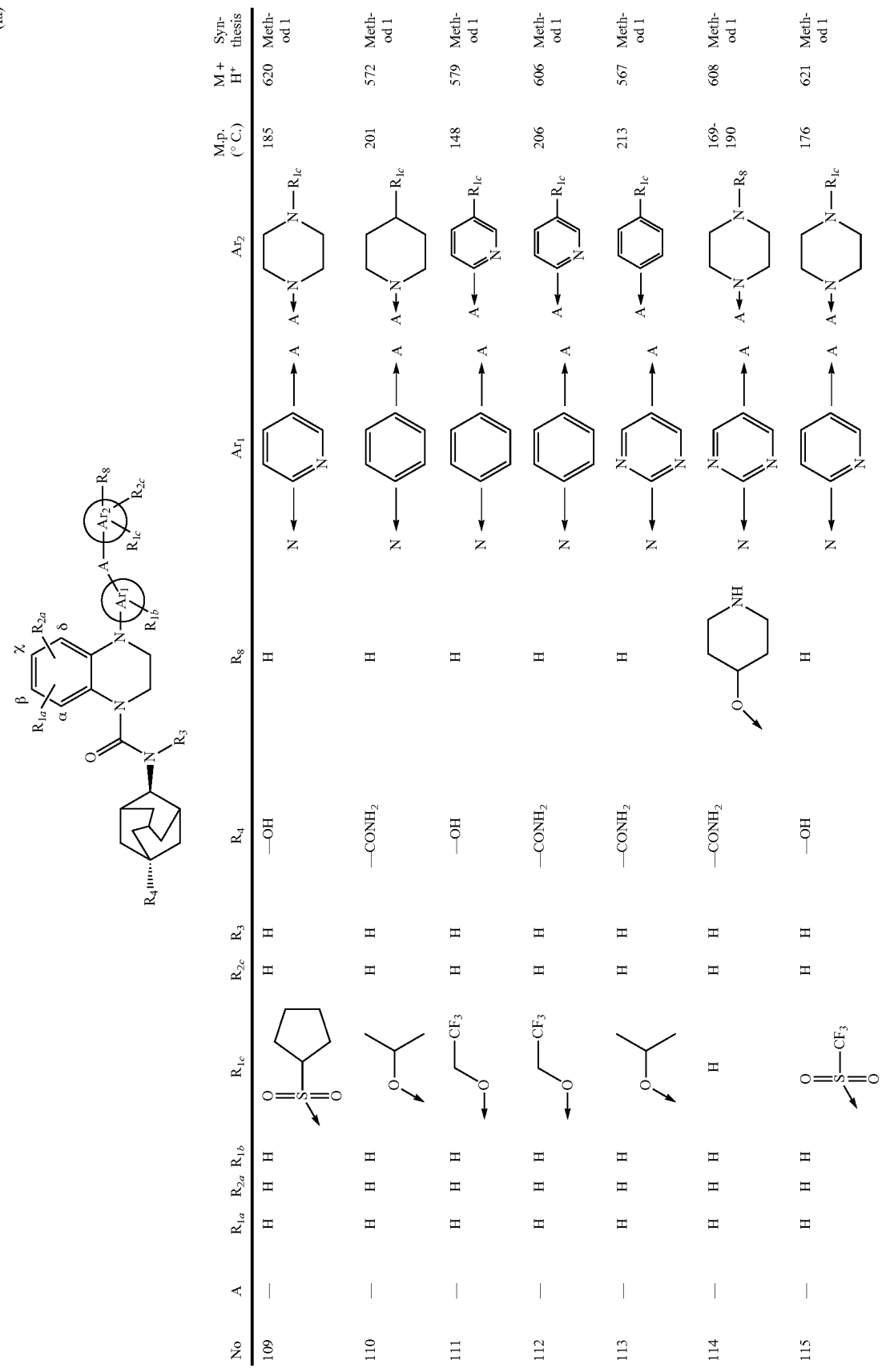

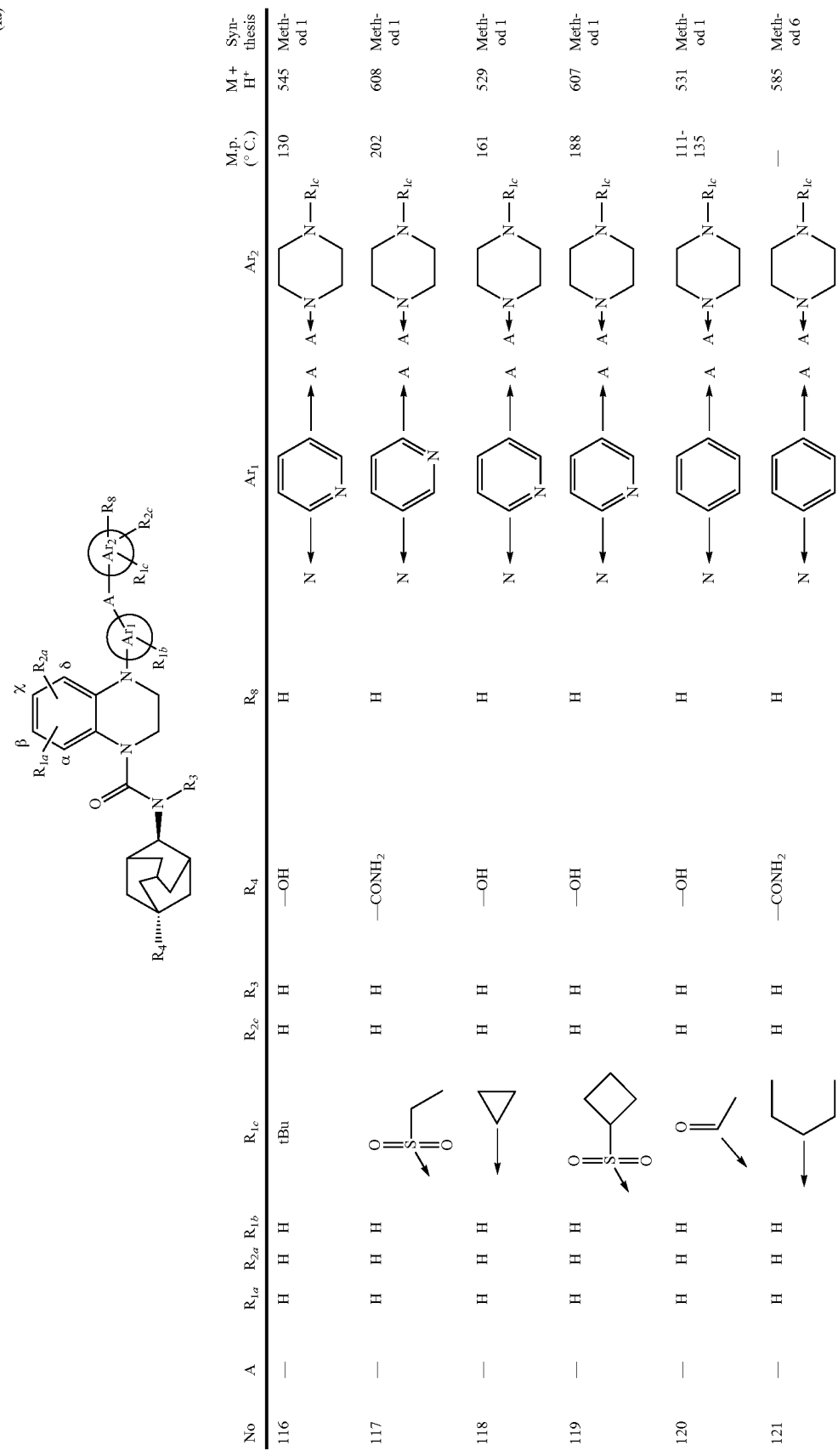

TABLE-continued (Ia)

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+H+ | Synthesis |
|---|---|---|---|---|---|---|---|---|---|---|---|---|---|---|
| 122 | — | H | H | H | isobutyl-sulfonyl | H | H | —CONH$_2$ | H | pyridine-N | piperazine-N-R$_{1c}$ | 204 | 636 | Method 1 |
| 123 | — | H | H | H | CF$_3$(CH$_2$)$_2$-sulfonyl | H | H | —OH | H | pyridine-N | piperazine-N-R$_{1c}$ | 194-200 | 649 | Method 1 |
| 124 | — | H | H | H | CF$_3$CH$_2$- | H | H | —CONH$_2$ | H | phenyl | piperazine-N-R$_{1c}$ | >200 | 597 | Method 6 |
| 125 | — | H | H | H | 2-methoxyethoxy-ethylsulfonyl | H | H | —CONH$_2$ | H | phenyl | piperazine-N-R$_{1c}$ | — | 681 | Method 1 |
| 126 | — | H | H | H | isopropoxyethyl-sulfonyl | H | H | —CONH$_2$ | H | pyridine-N | piperazine-N-R$_{1c}$ | 173 | 666 | Method 1 |
| 127 | — | H | H | H | cyclopropylmethyl-sulfonyl | H | H | —OH | H | pyridine-N | piperazine-N-R$_{1c}$ | 197 | 606 | Method 1 |

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+H+ | Synthesis |
|---|---|---|---|---|---|---|---|---|---|---|---|---|---|---|
| 128 | — | H | H | H | tBu | H | H | —CONH₂ | H | pyridine | piperazine | 189-192 | 572 | Method 1 |
| 129 | — | H | H | H | cyclopropyl | H | H | —CONH₂ | H | pyridine | piperazine | 190-197 | 556 | Method 1 |
| 130 | — | H | H | H | H | H | H | —CONH₂ | tetrahydropyran | benzene | piperazine | — | 589 | Method 6 |
| 131 | — | H | H | H | CH₂CH₂SO₂- (OMe) | H | H | —CONH₂ | H | pyridine | piperazine | 135 | 638 | Method 1 |
| 132 | — | H | H | H | H | H | H | —OH | N-SO₂Me pyrrolidine | benzene | dimethylpyrrolidine | 127 | 606 | Method 1 |
| 133 | — | H | H | H | neopentyl | H | H | —OH | H | pyridine | piperazine | — | 559 | Method 1 |
| 134 | — | H | H | H | CH(CH₂OMe)₂ | H | H | —OH | H | pyridine | piperazine | — | 591 | Method 1 |

TABLE-continued (Ia)

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+H+ | Synthesis |
|---|---|---|---|---|---|---|---|---|---|---|---|---|---|---|
| 135 | — | H | H | H | ~~~OMe (propyl-OMe) | H | H | —OH | H | pyridyl | piperazinyl-N-R_{1c} | 152 | 561 | Method 1 |
| 136 | — | H | H | H | isobutyl ketone | H | H | —OH | H | pyridyl | piperazinyl-N-R_{1c} | 155-160 | 573 | Method 1 |
| 137 | — | H | H | H | methylsulfonyl | H | H | —NHC(O)CH_3 | H | pyridyl | piperazinyl-N-R_{1c} | 250 | 607 | Method 12 |
| 138 | — | H | H | H | ethylsulfonyl-OMe | H | H | —OH | H | pyridyl | piperazinyl-N-R_{1c} | 151 | 611 | Method 1 |
| 139 | — | H | H | H | tBu ketone | H | H | —OH | H | pyridyl | piperazinyl-N-R_{1c} | 100-120 | 573 | Method 1 |
| 140 | — | H | H | H | F | F | H | —OH | H | pyridyl | piperidinyl-R_{2c},R_{1c} | 100-125 | 524 | Method 1 |

TABLE-continued (Ia)

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+H+ | Synthesis |
|----|---|----------|----------|----------|----------|----------|-------|-------|-------|--------|--------|------------|------|-----------|
| 141 | — | H | H | H | H | H | H | —OH | pyrrolidinyl | pyridine | piperazine | 100-125 | 557 | Method 1 |
| 142 | — | H | H | H | cyclopropylsulfonyl | H | H | —OH | H | pyridine | piperazine | 160 | 605 | Method 1 |
| 143 | — | H | H | H | tert-butoxycarbonyl | H | H | —OH | H | pyridine | piperazine | 105 | 589 | Method 6 |
| 144 | — | H | H | H | CH2CH2OMe | H | H | —CONH2 | H | phenyl | piperazine | 175-182 | 100 | Method 1 |
| 145 | — | H | H | Me | methylsulfonyl | H | H | —CONH2 | H | pyridine | piperazine | 179-182 | 608 | Method 1 |
| 146 | — | H | H | H | tert-butyl-COOH | H | H | —CONH2 | H | phenyl | piperazine | — | 601 | Method 13 |

TABLE-continued

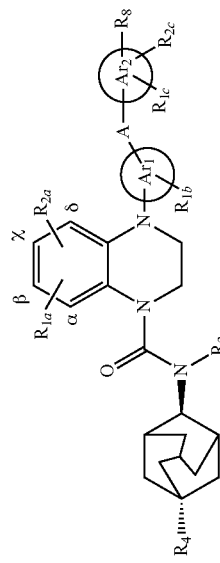

(Ia)

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+H+ | Synthesis |
|---|---|---|---|---|---|---|---|---|---|---|---|---|---|---|
| 147 | — | H | H | H | tBu | H | H | —CONH$_2$ | H | pyridyl | piperidyl-R$_{1c}$ | 225 | 571 | Method 1 |
| 148 | — | H | H | H | H | H | H | —CONH$_2$ | pyrrolidinyl | pyridyl | piperidyl-R$_8$ | 219° | 584 | Method 1 |
| 149 | — | H | H | H | EtSO$_2$ | H | H | —CONH$_2$ | H | pyridyl | piperazinyl-R$_{1c}$ | 175° | 608 | Method 1 |
| 150 | — | H | H | Me | MeSO$_2$ | H | H | —CONH$_2$ | H | pyridyl | piperazinyl-R$_{1c}$ | 150-152 | 608 | Method 1 |
| 151 | — | H | H | H | F | F | H | —CONH$_2$ | H | pyridyl | piperidyl-R$_{1c}$R$_{2c}$ | 222 | 551 | Method 1 |
| 152 | — | H | H | H | CH$_2$C(CH$_3$)$_2$OH | H | H | —CONH$_2$ | H | phenyl | piperazinyl-R$_{1c}$ | 194-200 | 587 | Method 14 |

TABLE-continued (Ia)

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M+H+ | Synthesis |
|----|---|----|----|----|----|----|----|----|----|----|----|----|----|----|
| 153 | — | H | H | H | isopropylsulfonyl | H | H | —CONH$_2$ | H | pyridyl | N-piperazinyl-$R_{1c}$ | 195 | 622 | Method 1 |
| 154 | — | H | H | H | H | H | H | —CONH$_2$ | H | pyridyl | morpholinyl | 215 | 517 | Method 1 |
| 155 | — | H | H | Me | methylsulfonyl | H | H | —CONH$_2$ | H | pyridyl | N-piperazinyl-$R_{1c}$ | — | 608 | Method 1 |
| 156 | — | H | H | H | CF$_3$ | H | H | —CONH$_2$ | H | pyridyl | N-piperidinyl-$R_{1c}$ | 220 | 583 | Method 1 |
| 157 | — | H | H | H | t-Bu | H | H | —OH | H | pyridyl | N-piperidinyl-$R_{1c}$ | 135 | 544 | Method 1 |
| 158 | — | H | H | H | isobutyl | H | H | —OH | H | pyridyl | N-piperidinyl-$R_{1c}$ | 209 | 572 | Method 1 |

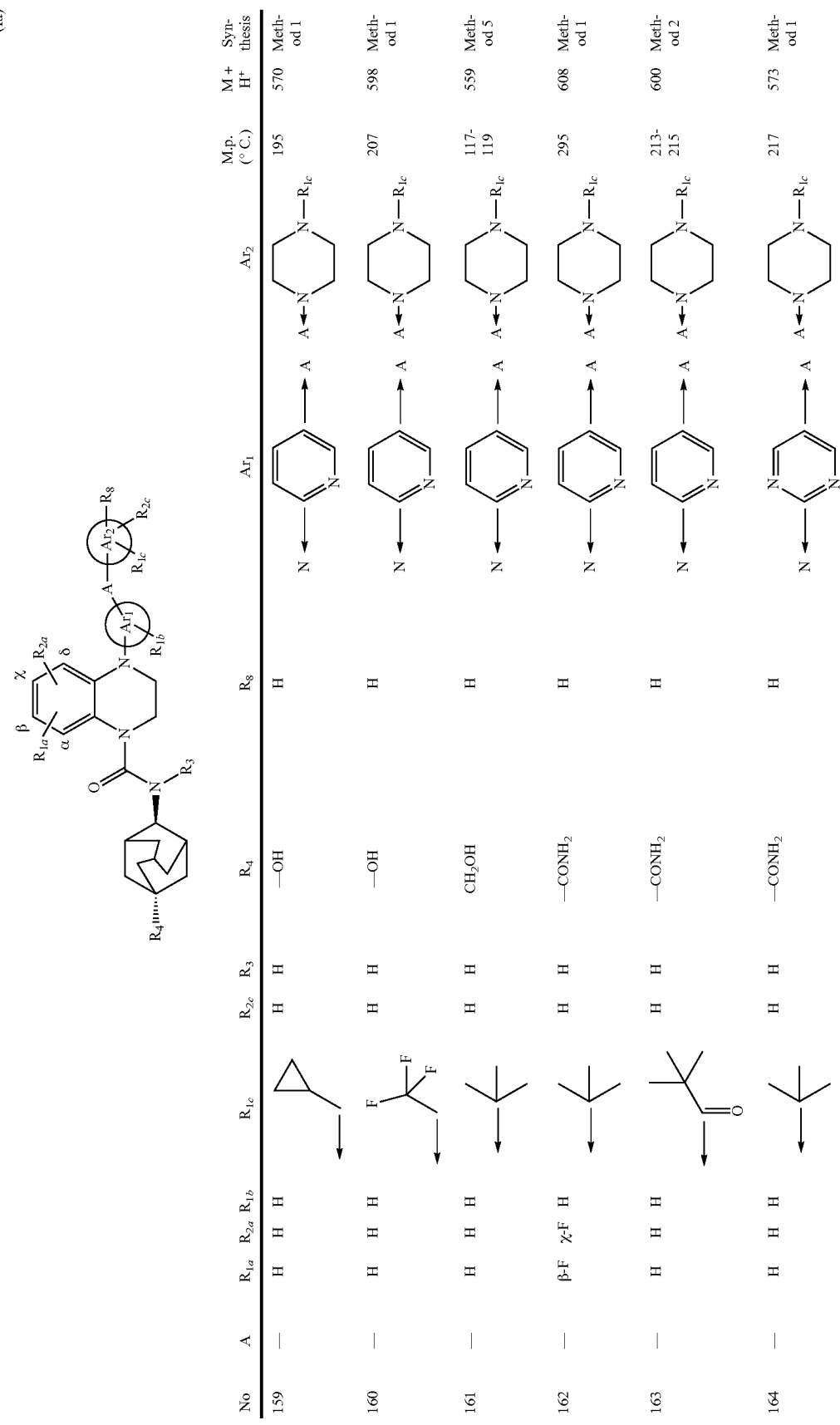

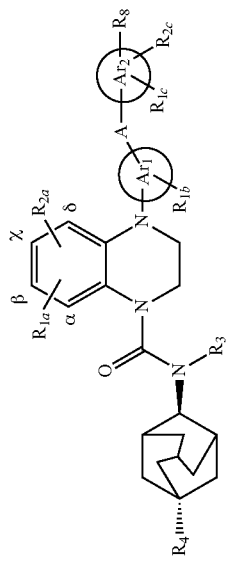

TABLE-continued

| No | A | $R_{1a}$ | $R_{2a}$ | $R_{1b}$ | $R_{1c}$ | $R_{2c}$ | $R_3$ | $R_4$ | $R_8$ | $Ar_1$ | $Ar_2$ | M.p. (°C.) | M + H⁺ | Synthesis |
|---|---|---|---|---|---|---|---|---|---|---|---|---|---|---|
| 172 | — | H | H | H | —COOH | H | H | —CONH₂ | H | pyridine | piperidine-N-R₁c | 250 | 559 | Method 14 |
| 173 | — | H | H | H | C(Me)₂COOEt | H | H | —CONH₂ | H | pyridine | piperidine-N-R₁c | 97 | 630 | Method 1 |
| 174 | — | H | H | H | Me | Me | H | —CONH₂ | H | pyridine | piperidine-N-R₁c, R₂c | 235 | 543 | Method 1 |
| 175 | — | H | H | H | difluorocyclopropylmethyl | H | H | —CONH₂ | H | pyridine | piperidine-N-R₁c | 206 | 606 | Method 1 |
| 176 | — | H | H | Me | —SO₂CF₃ | H | H | —CONH₂ | H | pyridine | piperidine-N-R₁c | 204 | 630 | Method 1 |
| 177 | — | H | H | H | CH₂CH₂CF₃ | H | H | —CONH₂ | H | pyridine | piperidine-N-R₁c | 208 | 612 | Method 1 |

TABLE-continued (Ia)

| No | A | R$_{1a}$ | R$_{2a}$ | R$_{1b}$ | R$_{1c}$ | R$_{2c}$ | R$_3$ | R$_4$ | R$_8$ | Ar$_1$ | A | Ar$_2$ | M.p. (°C.) | M+H$^+$ | Synthesis |
|---|---|---|---|---|---|---|---|---|---|---|---|---|---|---|---|
| 178 | — | H | H | H | ethylsulfonyl | H | H | —CONH$_2$ | H | pyridyl | A | piperazine-N-R$_{1c}$ | 204 | 622 | Method 1 |
| 179 | — | H | H | Me | t-butyl | H | H | —CONH$_2$ | H | pyridyl (R$_{1b}$) | A | piperazine-N-R$_{1c}$ | 189-199 | 586 | Method 1 |
| 180 | — | H | H | H | isopropyl | H | H | —CONH$_2$ | H | pyridyl | A | piperazine-N-R$_{1c}$ | 207 | 586 | Method 1 |
| 181 | — | H | H | H | H | H | H | —CONH$_2$ | H | pyridyl | A | thiomorpholine-1,1-dioxide | 118-160 | 565 | Method 1 |
| 182 | — | H | H | H | H | H | H | —CONH$_2$ | tetrahydropyran-4-yl | pyridyl | A | piperazine-N-R$_8$ | 220 | 600 | Method 1 |
| 183 | — | H | H | Me | cyclopropylsulfonyl | H | H | —CONH$_2$ | H | pyridyl (R$_{1b}$) | A | piperazine-N-R$_{1c}$ | 152-154 | 634 | Method 1 |

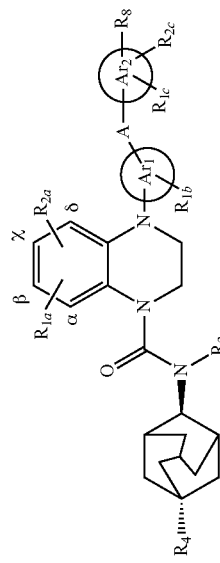

TABLE-continued
(Ia)
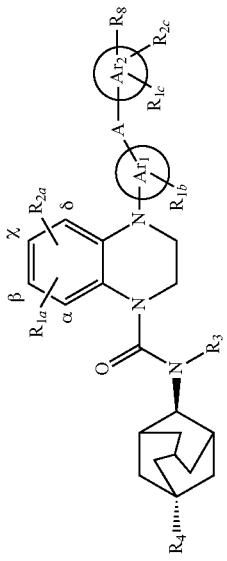
| No | A | R1a | R2a | R1b | R1c | R2c | R3 | R4 | R8 | Ar1 | Ar2 | M.p. (°C.) | M + H+ | Synthesis |
|---|---|---|---|---|---|---|---|---|---|---|---|---|---|---|
| 190 | — | H | H | F | cyclopropyl-S(O)₂— | H | H | —CONH₂ | H | pyridine (R1b, A) | piperazine (A, R1c) | 148 | 637 | Method 1 |
| 191 | — | H | H | H | —O-CH₂CH₂-O-CH₃ | H | H | —CONH₂ | H | pyridine (A) | piperazine (A, R1c) | 159 | 589 | Method 1 |
| 192 | — | H | H | H | —O-CH₂CH₂-O-CH₃ | H | H | —CONH₂ | H | pyridine (A) | piperazine (A, R1c) | 190 | 574 | Method 1 |

The compounds according to the invention formed the subject of pharmacological assays which make it possible to determine their inhibiting effect on the enzyme 11βHSD1, which is involved in the metabolism of lipids and the metabolism of glucose.

These assays consisted in measuring the in vitro inhibiting activity of the compounds of the invention on the enzyme 11βHSD1 by virtue of an SPA (Scintillation Proximity Assay) test in 384-well format. The recombinant 11βHSD1 protein was produced in the yeast S. cerevisiae. The reaction was carried out by incubating the enzyme in the presence of $^3$H-cortisone and of NADPH, in the absence or in the presence of an increasing concentration of inhibitor. SPA beads coupled to an antimouse antibody, which are preincubated with an anticortisol antibody, made it possible to measure the amount of cortisol formed during the reaction.

The inhibiting activity with regard to the enzyme 11βHSD1 is given by the concentration which inhibits 50% of the activity of 11βHSD1 ($IC_{50}$).

The $IC_{50}$ values of the compounds according to the invention are less than 1 μM. For example, the $IC_{50}$ values of the compounds Nos. 3, 6, 9, 14, 15, 16, 27, 30, 31, 85, 89, 95, 96, 118, 119, 125, 128, 132 and 137 are respectively 0.405, 0.624, 0.052, 0.028, 0.049, 0.028, 0.017, 0.094, 0.023, 0.007, 0.004, 0.008, 0.019, 0.008, 0.007, 0.007, 0.004, 0.187 and 0.130 μM.

In order to evaluate the pharmacodynamic properties of 11βHSD1 inhibitors, use was made of an ex vivo test which makes it possible to measure the activity of this enzyme in intact animal tissues. The compound to be evaluated is administered orally to C57bl/6J mice at the dose of 10 mg/kg. 16 h after the treatment, the animals are euthanasized by cervical dislocation. 50 mg of liver and 200 mg of subcutaneous adipose tissue are removed from each animal and placed on ice in a 24-well plate in 500 μl of PBS comprising 2 mM of EDTA and protease inhibitors. The tissues are subsequently cut with scissors into pieces with a size of approximately 3 mm$^3$ and are then preincubated at 37° C. for 10 minutes. 500 μl of PBS additivated with 2 mM of EDTA, with protease inhibitors and with 1.5 μCi of $^3$H-cortisone (at 50 Ci/mmol) are subsequently added per well. The tissues are thus incubated at 37° C. with gentle agitation in the presence of radiolabelled substrate for 15 minutes, in the case of the livers, or 2 h, in the case of the adipose tissues. The enzymatic reaction is halted by addition of 500 μl of methanol/1N HCl (1:1). The reaction supernatant is collected and frozen over dry ice, then centrifuged (20 minutes at 20000 g) after defrosting in order to remove as much cell debris as possible. The samples are filtered (through Acroprep 24 type GHP 0.2 μm filters) before analysis on an HPLC line (Alliance 2695 from Waters), coupled to a radioactivity detector (Radioamatic 625TR from Perkin-Elmer). The analysis is carried out on 100 μl of sample injected onto a C18 column (4.6×75; 3.5 μm SUNFIRE from Waters), then eluted with an isocratic solvent composed of H$_2$O/trifluoroacetic acid/methanol (44.95/0.05/55) for 8 minutes at a flow rate of 1 ml/minute. The retention times of the cortisone and cortisol peaks are 3.5 and 4.5 minutes respectively under these conditions. The Empower Pro2 software developed by Waters was used for the analysis of the chromatograms. The radiolabelled tracer peaks are converted into "μmol of cortisol formed/μg of tissue" in order to calculate the inhibition of the conversion of the cortisone to cortisol by 11βHSD1.

For example, compounds 92 and 99 exhibit, in the target tissues, the following degrees of inhibition:

| ex vivo 16 h inhib. | Liver | Subcutaneous fat |
|---|---|---|
| Compound No. 99 | 85% | 80% |
| Compound No. 92 | 85% | 60% |

It thus appears that the compounds according to the invention have an inhibiting activity for the enzyme 11βHSD1. The compounds according to the invention can thus be used in the preparation of medicaments, in particular of medicaments which inhibit the enzyme 11βHSD1.

Thus, according to another of its aspects, a subject-matter of the invention is medicaments which comprise a compound of formula (I) or an addition salt of the latter with a pharmaceutically acceptable acid or base or also a hydrate or a solvate of the compound of formula (I).

These medicaments are employed therapeutically, in particular in the treatment and prevention of obesity, diabetes, microcirculatory disorders, insulin resistance, the metabolic syndrome, Cushing's syndrome, hypertension, atherosclerosis, cognition and dementia, glaucoma, osteoporosis, lipodystrophy, cardiac hypertrophy, cardiac insufficiency, liver diseases and some infectious diseases by increasing the effectiveness of the immune system or also for promoting the healing of wounds.

According to another of its aspects, the present invention relates to pharmaceutical compositions comprising, as active principle, a compound according to the invention. These pharmaceutical compositions comprise an effective dose of at least one compound according to the invention or a pharmaceutically acceptable salt, a hydrate or a solvate of the said compound, and at least one pharmaceutically acceptable excipient. The said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in unit administration form, as a mixture with conventional pharmaceutical excipients, to animals and to human beings, for the prophylaxis or the treatment of the above disorders or diseases.

The appropriate unit administration forms comprise oral forms, such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. For topical application, the compounds according to the invention can be used in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

We claim:
1. A compound of formula (I):

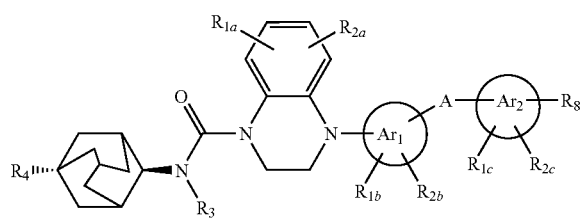

wherein:
A is a bond, oxygen atom or —CH$_2$—;
Ar$_1$ is phenyl or heteroaryl;
Ar$_2$ is phenyl, heteroaryl or heterocycloalkyl;
R$_{1a}$, R$_{1b}$, R$_{1c}$, R$_{2a}$, R$_{2b}$ and R$_{2c}$ are, independently, hydrogen, halogen, alkyl, cycloalkyl, -alkylcycloalkyl optionally substituted by one or more halogen atoms, hydroxy, alkoxy, hydroxyalkyl, alkoxyalkyl, alkoxyalkoxy, haloalkyl, —O-haloalkyl, oxo, —CO-alkyl, —CO-alkyl-NR$_6$R$_7$, —CO-haloalkyl, —COOR$_5$, -alkyl-COOR$_5$, —O-alkyl-COOR$_5$, —SO$_2$-alkyl, —SO$_2$-cycloalkyl, —SO$_2$-alkylcycloalkyl, —SO$_2$-alkyl-OR$_5$, —SO$_2$-alkyl-COOR$_5$, —SO$_2$-alkyl-NR$_6$R$_7$, —SO$_2$-haloalkyl, -alkyl-SO$_2$-alkyl, —SO$_2$—NR$_6$R$_7$, —SO$_2$-alkylalkoxyalkoxy, —CONR$_6$R$_7$, -alkyl-CONR$_6$R$_7$ or —O-alkyl-NR$_6$R$_7$;
R$_3$ is hydrogen or alkyl;
R$_4$ is hydrogen, halogen, cyano, —OR$_5$, hydroxyalkyl, —COOR$_5$, —NR$_6$R$_7$, —CONR$_6$R$_7$, —SO$_2$-alkyl, —SO$_2$—NR$_6$R$_7$, —NR$_6$—COOR$_5$, —NR$_6$—COR$_5$ or —CO—NR$_6$-alkyl-OR$_5$ group;
R$_5$, R$_6$ and R$_7$ are, independently, hydrogen, alkyl or -alkylphenyl;
R$_8$ is hydrogen, alkyl, or —B-Het;
B is a bond, oxygen atom, —CO— or —SO$_2$—(CH$_2$)$_n$—;
n is 0, 1 or 2; and
Het is heteroaryl or heterocycloalkyl optionally substituted by 1 to 3 groups chosen from alkyl, —SO$_2$-alkyl and —COOR$_5$;
or a pharmaceutically acceptable salt thereof.

2. The compound according to claim 1, wherein A is a bond; or a pharmaceutically acceptable salt thereof.

3. The compound according to claim 1, wherein Ar$_1$ is phenyl, pyridinyl, pyrimidinyl, pyridazinyl or thiazolyl; or a pharmaceutically acceptable salt thereof.

4. The compound according to claim 1, wherein Ar$_2$ is phenyl, pyridinyl, pyrimidinyl, piperidinyl, piperazinyl, homopiperazinyl, 3,8-diazabicyclo[3.2.1]octyl, morpholinyl, thiomorpholinyl, octahydropyrrolo[3,4-c]pyrrolyl, 1,2,3,6-tetrahydropyridinyl or 2,5-diazabicyclo[2.2.1]heptyl; or a pharmaceutically acceptable salt thereof.

5. The compound according to claim 1, wherein R$_{1a}$, R$_{2a}$, R$_{1b}$ and R$_{2b}$ are, independently, hydrogen, halogen, alkyl or alkoxy; or a pharmaceutically acceptable salt thereof.

6. The compound according to claim 1, wherein R$_{1c}$ and R$_{2c}$ are, independently, hydrogen, halogen, alkyl, alkoxy, —SO$_2$-alkyl or —SO$_2$-cycloalkyl; or a pharmaceutically acceptable salt thereof.

7. The compound according to claim 1, wherein R$_3$ is hydrogen; or a pharmaceutically acceptable salt thereof.

8. The compound according to claim 1, wherein R$_4$ is hydrogen, halogen, cyano, hydroxy, hydroxyalkyl, —COOR$_5$, or —CONH$_2$; or a pharmaceutically acceptable salt thereof.

9. The compound according to claim 1, wherein Het is pyrrolidinyl, piperidinyl, piperazinyl, tetrahydropyranyl, morpholinyl or pyridinyl, each of which is optionally substituted by alkyl, —SO$_2$-alkyl or —COOR$_5$; or a pharmaceutically acceptable salt thereof.

10. The compound according to claim 1, wherein:
Ar$_2$ is phenyl;
R$_{1a}$, R$_{1b}$, R$_{1c}$, R$_{2a}$, R$_{2b}$ and R$_{2c}$ are, independently, hydrogen, halogen, alkyl, cycloalkyl, -alkylcycloalkyl optionally substituted by one or more halogen atoms, hydroxy, alkoxy, hydroxyalkyl, alkoxyalkyl, haloalkyl, —O-haloalkyl, oxo, —CO-alkyl, —CO-alkyl-NR$_6$R$_7$, —COOR$_5$, -alkyl-COOR$_5$, —SO$_2$-alkyl, —SO$_2$-cycloalkyl, —SO$_2$-alkylcycloalkyl, —SO$_2$-alkyl-OR$_5$, —SO$_2$-alkyl-COOR$_5$, —SO$_2$-alkyl-NR$_6$R$_7$, —SO$_2$-haloalkyl, -alkyl-SO$_2$-alkyl, —SO$_2$-alkylalkoxyalkoxy, —CONR$_6$R$_7$ or —O-alkyl-NR$_6$R$_7$ group;
R$_4$ is hydrogen, halogen, cyano, —OR$_5$, hydroxyalkyl, —COOR$_5$, —CONR$_6$R$_7$, —NR$_6$—COOR$_5$, —NR$_6$—COR$_5$ or —CO—NR$_6$-alkyl-OR$_5$; and
Het is pyrrolidinyl, piperidinyl, piperazinyl, tetrahydropyranyl, morpholinyl or pyridinyl, each of which is optionally substituted by 1 to 3 groups chosen from alkyl, —SO$_2$-alkyl and —COOR$_5$ groups,
or a pharmaceutically acceptable salt thereof.

11. The compound according to claim 1, wherein:
Ar$_2$ is heteroaryl;
R$_{1a}$, R$_{1b}$, R$_{1c}$, R$_{2a}$, R$_{2b}$ and R$_{2c}$ are, independently, hydrogen, halogen, alkyl, cycloalkyl, -alkylcycloalkyl optionally substituted by one or more halogen atoms, hydroxy, alkoxy, hydroxyalkyl, alkoxyalkyl, haloalkyl, —O-haloalkyl, oxo, —CO-alkyl, —CO-alkyl-NR$_6$R$_7$, —COOR$_5$, -alkyl-COOR$_5$, —SO$_2$-alkyl, —SO$_2$-cycloalkyl, —SO$_2$-alkylcycloalkyl, —SO$_2$-alkyl-OR$_5$, —SO$_2$-alkyl-COOR$_5$, —SO$_2$-alkyl-NR$_6$R$_7$, —SO$_2$-haloalkyl, -alkyl-SO$_2$-alkyl, —SO$_2$-alkylalkoxyalkoxy, —CONR$_6$R$_7$ or —O-alkyl-NR$_6$R$_7$;
R$_3$ is hydrogen or alkyl;
R$_4$ is hydrogen, halogen, cyano, —OR$_5$, hydroxyalkyl, —COOR$_5$, —CONR$_6$R$_7$, —NR$_6$—COOR$_5$, —NR$_6$—COR$_5$ or —CO—NR$_6$-alkyl-OR$_5$; and
Het is pyrrolidinyl, piperidinyl, piperazinyl, tetrahydropyranyl, morpholinyl or pyridinyl, each of which is optionally substituted by 1 to 3 groups chosen from alkyl, —SO$_2$-alkyl and —COOR$_5$ groups;
or a pharmaceutically acceptable salt thereof.

12. The compound according to claim 1, wherein:
Ar$_2$ is heterocycloalkyl;
R$_{1a}$, R$_{1b}$, R$_{1c}$, R$_{2a}$, R$_{2b}$ and R$_{2c}$ are, independently, hydrogen, halogen, alkyl, cycloalkyl, -alkylcycloalkyl optionally substituted by one or more halogen atoms, hydroxy, alkoxy, hydroxyalkyl, alkoxyalkyl, haloalkyl, —O-haloalkyl, oxo, —CO-alkyl, —CO-alkyl-NR$_6$R$_7$, —COOR$_5$, -alkyl-COOR$_5$, —SO$_2$-alkyl, —SO$_2$-cycloalkyl, —SO$_2$-alkylcycloalkyl, —SO$_2$-alkyl-OR$_5$, —SO$_2$-alkyl-COOR$_5$, —SO$_2$-alkyl-NR$_6$R$_7$, —SO$_2$-haloalkyl, -alkyl-SO$_2$-alkyl, —SO$_2$-alkylalkoxyalkoxy, —CONR$_6$R$_7$ or —O-alkyl-NR$_6$R$_7$;

R$_4$ is hydrogen, halogen, cyano, —OR$_5$, hydroxyalkyl, —COOR$_5$, —CONR$_6$R$_7$, —NR$_6$—COOR$_5$, —NR$_6$—COR$_5$ or —CO—NR$_6$-alkyl-OR$_5$; and Het is pyrrolidinyl, piperidinyl, piperazinyl, tetrahydropyranyl, morpholinyl or pyridinyl, each of which is optionally substituted by 1 to 3 groups chosen from alkyl, —SO$_2$-alkyl and —COOR$_5$ groups;

or a pharmaceutically acceptable salt thereof.

13. The compound according to claim 12, wherein Ar$_2$ is a piperidinyl, piperazinyl, homopiperazinyl, 3,8-diazabicyclo[3.2.1]octyl, morpholinyl, thiomorpholinyl, octahydropyrrolo[3,4-c]pyrrolyl, 1,2,3,6-tetrahydropyridinyl or 2,5-diazabicyclo[2.2.1]heptyl; or a pharmaceutically acceptable salt thereof.

14. The compound of claim 1 wherein
A is a bond;
Ar$_1$ is pyridinyl;
Ar$_2$ is piperazinyl;
R$_{1a}$ is H;
R$_{2a}$ is H;
R$_{1b}$ is H;
R$_{2b}$ is H;
R$_4$ is CONH$_2$ or OH;
R$_8$ is H;
R$_{2c}$ is H; and
R$_{1c}$ is (C$_1$-C$_5$)-alkyl.

15. The compound according to claim 1, which is:
4-(4-(Pyridin-2-yl)phenyl)-3-4-dihydro-2H-quinoxaline-1-carboxylic acid adamantan-2-ylamide,
4-{4-[1-(Tetrahydropyran-4-carbonyl)piperidin-4-yloxy]phenyl}-3,4-dihydro-2H-quinoxaline-1-carboxylic acid adamantan-2-ylamide,
4-[4-(Pyrimidin-2-ylmethoxy)phenyl]-3,4-dihydro-2H-quinoxaline-1-carboxylic acid adamantan-2-ylamide,
4-{4-[1-(Morpholine-4-carbonyl)piperidin-4-yl]phenyl}-3,4-dihydro-2H-quinoxaline-1-carboxylic acid adamantan-2-ylamide,
4-[4-(4-Methoxypyrimidin-2-yloxy)phenyl]-3,4-dihydro-2H-quinoxaline-1-carboxylic acid adamantan-2-ylamide,
4-{4-[4-(Morpholine-4-carbonyl)phenyl]thiazol-2-yl}-3,4-dihydro-2H-quinoxaline-1-carboxylic acid adamantan-2-ylamide,
4-[5-(4-Methoxyphenyl)pyrimidin-2-yl]-3,4-dihydro-2H-quinoxaline-1-carboxylic acid adamantan-2-ylamide,
4-[5-(4-Methoxyphenyl)pyrimidin-2-yl]-3,4-dihydro-2H-quinoxaline-1-carboxylic acid (5-hydroxyadamantan-2-yl)amide,
trans-4-[4-(4-(Methanesulphonyl)piperazin-1-yl)phenyl]-3,4-dihydro-2H-quinoxaline-1-carboxylic acid (5-hydroxyadamantan-2-yl)amide,
Methyl ester of 4-({4-[4-(4-(Methanesulphonyl)piperazin-1-yl)phenyl]-3,4-dihydro-2H-quinoxaline-1-carbonyl}amino)adamantane-1-carboxylic acid,
4-({4-[4-(4-(Methanesulphonyl)piperazin-1-yl)phenyl]-3,4-dihydro-2H-quinoxaline-1-carbonyl}amino)adamantane-1-carboxylic acid,
4-[4-(4-(Methanesulphonyl)piperazin-1-yl)phenyl]-3,4-dihydro-2H-quinoxaline-1-carboxylic acid (5-carbamoyladamantan-2-yl)amide,
trans-4-[4-(Pyridin-2-yloxy)phenyl]-3,4-dihydro-2H-quinoxaline-1-carboxylic acid (5-hydroxyadamantan-2-yl)amide,
trans-4-[4-(4-(Trifluoromethyl)pyrimidin-2-yloxy)phenyl]-3,4-dihydro-2H-quinoxaline-1-carboxylic acid (5-hydroxyadamantan-2-yl)amide,
trans-4-[4-(1-(Methanesulphonyl)-1,2,3,6-tetrahydropyridin-4-yl)phenyl]-3,4-dihydro-2H-quinoxaline-1-carboxylic acid (5-hydroxyadamantan-2-yl)amide,
trans-4-[4-(4-Hydroxy-1-(Methanesulphonyl)piperidin-4-yl)phenyl]-3,4-dihydro-2H-quinoxaline-1-carboxylic acid (5-hydroxyadamantan-2-yl)amide,
trans-4-[2-(4-(Methanesulphonyl)piperazin-1-yl)pyrimin-5-yl]-3,4-dihydro-2H-quinoxaline-1-carboxylic acid (5-hydroxyadamantan-2-yl)amide,
trans-4-[5-(4-(Methanesulphonyl)piperazin-1-yl)pyrimidin-2-yl]-3,4-dihydro-2H-quinoxaline-1-carboxylic acid (5-hydroxyadamantan-2-yl)amide,
trans-4-{4-[1-(Morpholine-4-carbonyl)piperidin-4-yl]phenyl}-3,4-dihydro-2H-quinoxaline-1-carboxylic acid (5-hydroxyadamantan-2-yl)amide,
trans-4-{4-[4-(5-Hydroxyadamantan-2-ylcarbamoyl)-3,4-dihydro-2H-quinoxalin-1-yl]phenyl}piperazine-1-carboxylic acid benzyl ester,
trans-4-[4-(4-(Methanesulphonyl)piperazin-1-yl)phenyl]-3,4-dihydro-2H-quinoxaline-1-carboxylic acid (5-(hydroxymethyl)adamantan-2-yl)amide,
trans-4-[4-(5-Fluoropyrimidin-2-yloxy)phenyl]-3,4-dihydro-2H-quinoxaline-1-carboxylic acid (5-hydroxyadamantan-2-yl)amide,
trans-4-[4-(1-(Methanesulphonyl)piperidin-4-yloxy)phenyl]-3,4-dihydro-2H-quinoxaline-1-carboxylic acid (5-hydroxyadamantan-2-yl)amide,
trans-4-(4-(Morpholin-4-yl)phenyl)-3,4-dihydro-2H-quinoxaline-1-carboxylic acid (5-hydroxyadamantan-2-yl)amide,
trans-4-[4-(1,1-Dioxo-1λ$^6$-thiomorpholin-4-yl)phenyl]-3,4-dihydro-2H-quinoxaline-1-carboxylic acid (5-hydroxyadamantan-2-yl)amide,
trans-4-[4-(5-Isopropoxypyridin-2-yl)phenyl]-3,4-dihydro-2H-quinoxaline-1-carboxylic acid (5-hydroxyadamantan-2-yl)amide,
trans-4-{4-[5-(4-Isopropylpiperazine-1-carbonyl)pyridin-2-yl]phenyl}-3,4-dihydro-2H-quinoxaline-1-carboxylic acid (5-hydroxyadamantan-2-yl)amide,
trans-4-[6-(4-(Methanesulphonyl)piperazin-1-yl)pyridin-3-yl]-3,4-dihydro-2H-quinoxaline-1-carboxylic acid (5-hydroxyadamantan-2-yl)amide,
trans-4-(4-(Piperazin-1-yl)phenyl)-3,4-dihydro-2H-quinoxaline-1-carboxylic acid (5-hydroxyadamantan-2-yl)amide,
trans-4-[4-(4,4-Difluoropiperidin-1-yl)phenyl]-3,4-dihydro-2H-quinoxaline-1-carboxylic acid (5-hydroxyadamantan-2-yl)amide,
trans-4-[5-(4-(Methanesulphonyl)piperazin-1-yl)pyridin-2-yl]-3,4-dihydro-2H-quinoxaline-1-carboxylic acid (5-hydroxyadamantan-2-yl)amide,
trans-4-[5-(4-(Methanesulphonyl)piperazin-1-yl)pyridin-2-yl]-3,4-dihydro-2H-quinoxaline-1-carboxylic acid (5-hydroxyadamantan-2-yl)amide,
trans-4-[2-(1-(Methanesulphonyl)piperidin-4-yloxy)pyrimidin-5-yl]-3,4-dihydro-2H-quinoxaline-1-carboxylic acid (5-hydroxyadamantan-2-yl)amide,
trans-4-[5-(5-Isopropoxypyridin-2-yl)pyrimidin-2-yl]-3,4-dihydro-2H-quinoxaline-1-carboxylic acid (5-hydroxyadamantan-2-yl)amide,
trans-4-[4-(4-(Ethanesulphonyl)piperazin-1-yl)phenyl]-3,4-dihydro-2H-quinoxaline-1-carboxylic acid (5-hydroxyadamantan-2-yl)amide, trans-4-{4-[4-(2,2,2-Trifluoroethanesulphonyl)piperazin-1-yl]phenyl}-3,4-dihydro-2H-quinoxaline-1-carboxylic acid (5-hydroxyadamantan-2-yl)amide,
trans-4-{4-[4-(Propane-2-sulphonyl)piperazin-1-yl]phenyl}-3,4-dihydro-2H-quinoxaline-1-carboxylic acid (4-hydroxyadamantan-1-yl)amide,
trans-4-(4-{4-[4-(5-Hydroxyadamantan-2-ylcarbamoyl)-3,4-dihydro-2H-quinoxalin-1-yl]phenyl}piperazine-1-sulphonyl)piperidine-1-carboxylic acid benzyl ester,
trans-4-{4-[4-(Piperidine-4-sulphonyl)piperazin-1-yl]phenyl}-3,4-dihydro-2H-quinoxaline-1-carboxylic acid (5-hydroxyadamantan-2-yl)amide,
trans-4-[4-(4-(Cyclopropanesulphonyl)piperazin-1-yl)phenyl]-3,4-dihydro-2H-quinoxaline-1-carboxylic acid (5-hydroxyadamantan-2-yl)amide,
trans-4-[4-(4-(Methanesulphonyl)piperazin-1-yl)phenyl]-3,4-dihydro-2H-quinoxaline-1-carboxylic acid (5-fluoroadamantan-2-yl)amide,
trans-4-[4-(4-(Cyclobutanesulphonyl)piperazin-1-yl)phenyl]-3,4-dihydro-2H-quinoxaline-1-carboxylic acid (5-hydroxyadamantan-2-yl)amide,
trans-4-{4-[4-(Propane-1-sulphonyl)piperazin-1-yl]phenyl}-3,4-dihydro-2H-quinoxaline-1-carboxylic acid (5-hydroxyadamantan-2-yl)amide,
trans-4-{4-[4-(Butane-1-sulphonyl)piperazin-1-yl]phenyl}-3,4-dihydro-2H-quinoxaline-1-carboxylic acid (5-hydroxyadamantan-2-yl)amide,
trans-4-{4-[4-(Morpholine-4-sulphonyl)piperazin-1-yl]phenyl}-3,4-dihydro-2H-quinoxaline-1-carboxylic acid (5-hydroxyadamantan-2-yl)amide,
trans-4-[4-(4-(Trifluoromethanesulphonyl)piperazin-1-yl)phenyl]-3,4-dihydro-2H-quinoxaline-1-carboxylic acid (5-hydroxyadamantan-2-yl)amide,
trans-4-[4-(1,4-Dioxa-8-azaspiro[4.5]dec-8-yl)phenyl]-3,4-dihydro-2H-quinoxaline-1-carboxylic acid (5-hydroxyadamantan-2-yl)amide,
trans-4-[4-(4-Methanesulphonyl-3,3-dimethylpiperazin-1-yl)phenyl]-3,4-dihydro-2H-quinoxaline-1-carboxylic acid (5-hydroxyadamantan-2-yl)amide,
trans-4-[4-((3R,5S)-4-Methanesulphonyl-3,5-dimethylpiperazin-1-yl)phenyl]-3,4-dihydro-2H-quinoxaline-1-carboxylic acid (5-hydroxyadamantan-2-yl)amide,
trans-(4-{4-[4-(5-Hydroxyadamantan-2-ylcarbamoyl)-3,4-dihydro-2H-quinoxalin-1-yl]phenyl}piperazine-1-sulphonyl)acetic acid,
trans-(4-{4-[4-(5-Hydroxyadamantan-2-ylcarbamoyl)-3,4-dihydro-2H-quinoxalin-1-yl]phenyl}piperazine-1-sulphonyl)acetic acid ethyl ester,
trans-4-[4-(4-Hydroxypiperidin-1-yl)phenyl]-3,4-dihydro-2H-quinoxaline-1-carboxylic acid (5-hydroxyadamantan-2-yl)amide,
trans-4-[4-(4-Methanesulphonyl-1,4-diazepan-1-yl)phenyl]-3,4-dihydro-2H-quinoxaline-1-carboxylic acid (5-hydroxyadamantan-2-yl)amide,
trans-2-(4-{4-[4-(5-Hydroxyadamantan-2-ylcarbamoyl)-3,4-dihydro-2H-quinoxalin-1-yl]phenyl}piperazin-1-yl)-2-methylpropionic acid ethyl ester,
trans-3-(4-{4-[4-(5-Hydroxyadamantan-2-ylcarbamoyl)-3,4-dihydro-2H-quinoxalin-1-yl]phenyl}piperazine-1-sulphonyl)propionic acid methyl ester,
trans-4-[4-(5-Methoxypyrimidin-2-yl)phenyl]-3,4-dihydro-2H-quinoxaline-1-carboxylic acid (5-hydroxyadamantan-2-yl)amide,
trans-4-{4-[4-(2-(Morpholin-4-yl)ethanesulphonyl)piperazin-1-yl]phenyl}-3,4-dihydro-2H-quinoxaline-1-carboxylic acid (5-hydroxyadamantan-2-yl)amide,
trans-4-[6-(4-(Methanesulphonyl)piperazin-1-yl)pyridazin-3-yl]-3,4-dihydro-2H-quinoxaline-1-carboxylic acid (5-hydroxyadamantan-2-yl)amide,
trans-4-[4-(4-(Methanesulphonyl)piperazin-1-yl)phenyl]-3,4-dihydro-2H-quinoxaline-1-carboxylic acid (5-hydroxyadamantan-2-yl)(methyl)amide,
trans-4-[4-(4-Methanesulphonyl-3,5-dimethylpiperazin-1-yl)phenyl]-3,4-dihydro-2H-quinoxaline-1-carboxylic acid (5-hydroxyadamantan-2-yl)amide,
trans-4-{4-[4-(2-(Diethylamino)ethanesulphonyl)piperazin-1-yl]phenyl}-3,4-dihydro-2H-quinoxaline-1-carboxylic acid (5-hydroxyadamantan-2-yl)amide,
trans-4-[4-(3-Methanesulphonyl-3,8-diazabicyclo[3.2.1]oct-8-yl)phenyl]-3,4-dihydro-2H-quinoxaline-1-carboxylic acid (5-hydroxyadamantan-2-yl)amide,
trans-4-[5-(4-Methoxyphenyl)pyrimidin-2-yl]-3,4-dihydro-2H-quinoxaline-1-carboxylic acid (5-carbamoyladamantan-2-yl)amide,
trans-4-{4-[4-(2-Methoxyethanesulphonyl)piperazin-1-yl]phenyl}-3,4-dihydro-2H-quinoxaline-1-carboxylic acid (5-hydroxyadamantan-2-yl)amide,
trans-4-[4-(4-Isopropoxypiperidin-1-yl)phenyl]-3,4-dihydro-2H-quinoxaline-1-carboxylic acid (5-hydroxyadamantan-2-yl)amide,
trans-4-[5-(4-Hydroxyphenyl)pyrimidin-2-yl]-3,4-dihydro-2H-quinoxaline-1-carboxylic acid (5-hydroxyadamantan-2-yl)amide,
trans-4-(4-(Piperazin-1-yl)phenyl)-3,4-dihydro-2H-quinoxaline-1-carboxylic acid (5-carbamoyladamantan-2-yl)amide,
trans-4-[4-(5-Bromopyrimidin-2-yloxy)phenyl]-3,4-dihydro-2H-quinoxaline-1-carboxylic acid (5-hydroxyadamantan-2-yl)amide,
trans-4-[4-(4-(Cyclopropanesulphonyl)piperazin-1-yl)phenyl]-3,4-dihydro-2H-quinoxaline-1-carboxylic acid (5-carbamoyladamantan-2-yl)amide,
trans-4-[4-(4-(Cyclopropanesulphonyl)piperazin-1-yl)phenyl]-3,4-dihydro-2H-quinoxaline-1-carboxylic acid (5-carbamoyladamantan-2-yl)amide,
trans-6-Chloro-4-[4-(4-(Methanesulphonyl)piperazin-1-yl)phenyl]-3,4-dihydro-2H-quinoxaline-1-carboxylic acid (5-hydroxyadamantan-2-yl)amide,
trans-4-[4-(5-(Methanesulphonyl)hexahydropyrrolo[3,4-c]pyrrol-2-yl)phenyl]-3,4-dihydro-2H-quinoxaline-1-carboxylic acid (5-hydroxyadamantan-2-yl)amide,
trans-4-{4-[4-(2-Aminoethanesulphonyl)piperazin-1-yl]phenyl}-3,4-dihydro-2H-quinoxaline-1-carboxylic acid (5-hydroxyadamantan-2-yl)amide,
trans-4-(4-(Morpholin-4-yl)phenyl)-3,4-dihydro-2H-quinoxaline-1-carboxylic acid (5-carbamoyladamantan-2-yl)amide,
trans-4-{4-[5-(Piperidin-4-yloxy)pyridin-2-yl]phenyl}-3,4-dihydro-2H-quinoxaline-1-carboxylic acid (5-hydroxyadamantan-2-yl)amide,
trans-4-{4-[5-(2-Aminoethoxy)pyridin-2-yl]phenyl}-3,4-dihydro-2H-quinoxaline-1-carboxylic acid (5-hydroxyadamantan-2-yl)amide,
trans-4-{4-[4-(2-Hydroxyethanesulphonyl)piperazin-1-yl]phenyl}-3,4-dihydro-2H-quinoxaline-1-carboxylic acid (5-hydroxyadamantan-2-yl)amide,
trans-4-[4-(8-Methanesulphonyl-3,8-diazabicyclo[3.2.1]oct-3-yl)phenyl]-3,4-dihydro-2H-quinoxaline-1-carboxylic acid (5-carbamoyladamantan-2-yl)amide,
trans-4-[4-(8-Methanesulphonyl-3,8-diazabicyclo[3.2.1]oct-3-yl)phenyl]-3,4-dihydro-2H-quinoxaline-1-carboxylic acid (5-hydroxyadamantan-2-yl)amide, trans-4-[5-(4-Isopropoxyphenyl)pyrimidin-2-yl]-3,4-dihydro-2H-quinoxaline-1-carboxylic acid (5-hydroxyadamantan-2-yl)amide,
trans-4-{5-[4-(2,2,2-Trifluoroethanesulphonyl)piperazin-1-yl]pyridin-2-yl}-3,4-dihydro-2H-quinoxaline-1-carboxylic acid (5-hydroxyadamantan-2-yl)amide,
trans-4-{5-[4-(2,2,2-Trifluoroethanesulphonyl)piperazin-1-yl]pyridin-2-yl}-3,4-dihydro-2H-quinoxaline-1-carboxylic acid (5-carbamoyladamantan-2-yl)amide,
trans-3-(4-{4-[4-(5-Hydroxyadamantan-2-ylcarbamoyl)-3,4-dihydro-2H-quinoxalin-1-yl]phenyl}piperazine-1-sulphonyl)propionic acid,
trans-4-[4-(4-(Methanesulphonyl)piperazin-1-yl)phenyl]-3,4-dihydro-2H-quinoxaline-1-carboxylic acid [5-(2-hydroxyethylcarbamoyl)adamantan-2-yl]amide,
trans-4-[4-(5-Isobutoxypyridin-2-yl)phenyl]-3,4-dihydro-2H-quinoxaline-1-carboxylic acid (5-hydroxyadamantan-2-yl)amide,
trans-4-[4-(5-(sec-Butoxy)pyridin-2-yl)phenyl]-3,4-dihydro-2H-quinoxaline-1-carboxylic acid (5-hydroxyadamantan-2-yl)amide,
trans-4-[4-(5-Isopropoxypyridin-2-yl)phenyl]-3,4-dihydro-2H-quinoxaline-1-carboxylic acid (5-carbamoyladamantan-2-yl)amide,
trans-[4-({4-[4-(4-(Methanesulphonyl)piperazin-1-yl)phenyl]-3,4-dihydro-2H-quinoxaline-1-carbonyl}amino)adamantan-1-yl]carbamic acid methyl ester,
trans-4-[5-(4-(Ethanesulphonyl)piperazin-1-yl)pyridin-2-yl]-3,4-dihydro-2H-quinoxaline-1-carboxylic acid (5-hydroxyadamantan-2-yl)amide,
trans-4-[5-(4-(Cyclopropanesulphonyl)piperazin-1-yl)pyridin-2-yl]-3,4-dihydro-2H-quinoxaline-1-carboxylic acid (5-hydroxyadamantan-2-yl)amide,
trans-4-[5-(4-(Cyclopropanesulphonyl)piperazin-1-yl)pyridin-2-yl]-3,4-dihydro-2H-quinoxaline-1-carboxylic acid (5-carbamoyladamantan-2-yl)amide,
trans-4-{5-[4-(Propane-2-sulphonyl)piperazin-1-yl]pyridin-2-yl}-3,4-dihydro-2H-quinoxaline-1-carboxylic acid (5-hydroxyadamantan-2-yl)amide,
trans-4-{4-[4-(Pyridin-4-yloxy)piperidin-1-yl]phenyl}-3,4-dihydro-2H-quinoxaline-1-carboxylic acid (5-hydroxyadamantan-2-yl)amide,
trans-4-{4-[4-(2-Methoxyethanesulphonyl)piperazin-1-yl]phenyl}-3,4-dihydro-2H-quinoxaline-1-carboxylic acid (5-carbamoyladamantan-2-yl)amide,
trans-4-{4-[4-(2-Aminoethanesulphonyl)piperazin-1-yl]phenyl}-3,4-dihydro-2H-quinoxaline-1-carboxylic acid (5-carbamoyladamantan-2-yl)amide,
trans-4-{4-[4-(2-(Diethylamino)ethanesulphonyl)piperazin-1-yl]phenyl}-3,4-dihydro-2H-quinoxaline-1-carboxylic acid (5-carbamoyladamantan-2-yl)amide,
trans-4-{4-[4-(Piperidine-4-sulphonyl)piperazin-1-yl]phenyl}-3,4-dihydro-2H-quinoxaline-1-carboxylic acid (5-carbamoyladamantan-2-yl)amide,
trans-4-[4-(4-(tert-Butyl)piperazin-1-yl)phenyl]-3,4-dihydro-2H-quinoxaline-1-carboxylic acid (5-carbamoyladamantan-2-yl)amide,
trans-4-[5-(4-(Methanesulphonyl)piperazin-1-yl)pyridin-2-yl]-3,4-dihydro-2H-quinoxaline-1-carboxylic acid (5-carbamoyladamantan-2-yl)amide,
trans-4-{5-[4-(Propane-1-sulphonyl)piperazin-1-yl]pyridin-2-yl}-3,4-dihydro-2H-quinoxaline-1-carboxylic acid (5-carbamoyladamantan-2-yl)amide,
trans-4-{5-[4-(2-Methylpropane-1-sulphonyl)piperazin-1-yl]pyridin-2-yl}-3,4-dihydro-2H-quinoxaline-1-carboxylic acid (5-hydroxyadamantan-2-yl)amide,
trans-4-(5-(Morpholin-4-yl)pyridin-2-yl)-3,4-dihydro-2H-quinoxaline-1-carboxylic acid (5-hydroxyadamantan-2-yl)amide,
trans-4-{4-[4-(2-Hydroxyethanesulphonyl)piperazin-1-yl]phenyl}-3,4-dihydro-2H-quinoxaline-1-carboxylic acid (5-carbamoyladamantan-2-yl)amide,
trans-4-{4-[4-(Piperidin-4-yloxy)piperidin-1-yl]phenyl}-3,4-dihydro-2H-quinoxaline-1-carboxylic acid (5-hydroxyadamantan-2-yl)amide,
trans-4-[4-(4-(Dimethylcarbamoyl)piperazin-1-yl)phenyl]-3,4-dihydro-2H-quinoxaline-1-carboxylic acid (5-hydroxyadamantan-2-yl)amide,
trans-4-[6-(4-(Cyclopropanesulphonyl)piperazin-1-yl)pyridin-3-yl]-3,4-dihydro-2H-quinoxaline-1-carboxylic acid (5-carbamoyladamantan-2-yl)amide,
trans-4-[4-(4-(Ethanesulphonyl)piperazin-1-yl)phenyl]-3,4-dihydro-2H-quinoxaline-1-carboxylic acid (5-carbamoyladamantan-2-yl)amide,
trans-4-{4-[4-(2,2,2-Trifluoroethanesulphonyl)piperazin-1-yl]phenyl}-3,4-dihydro-2H-quinoxaline-1-carboxylic acid (5-carbamoyladamantan-2-yl)amide,
trans-4-{4-[4-(2-Aminoacetyl)piperazin-1-yl]phenyl}-3,4-dihydro-2H-quinoxaline-1-carboxylic acid (5-carbamoyladamantan-2-yl)amide,
trans-4-[4-(5-(Hydroxymethyl)pyridin-2-yl)phenyl]-3,4-dihydro-2H-quinoxaline-1-carboxylic acid (5-carbamoyladamantan-2-yl)amide,
trans-4-[5-(4-(Cyclopentanesulphonyl)piperazin-1-yl)pyridin-2-yl]-3,4-dihydro-2H-quinoxaline-1-carboxylic acid (5-hydroxyadamantan-2-yl)amide,
trans-4-[4-(4-Isopropoxypiperidin-1-yl)phenyl]-3,4-dihydro-2H-quinoxaline-1-carboxylic acid (5-carbamoyladamantan-2-yl)amide,
trans-4-{4-[5-(2,2,2-Trifluoroethoxy)pyridin-2-yl]phenyl}-3,4-dihydro-2H-quinoxaline-1-carboxylic acid (5-hydroxyadamantan-2-yl)amide,
trans-4-{4-[5-(2,2,2-Trifluoroethoxy)pyridin-2-yl]phenyl}-3,4-dihydro-2H-quinoxaline-1-carboxylic acid (5-carbamoyladamantan-2-yl)amide,
trans-4-[5-(4-Isopropoxyphenyl)pyrimidin-2-yl]-3,4-dihydro-2H-quinoxaline-1-carboxylic acid (5-carbamoyladamantan-2-yl)amide,
trans-4-{5-[4-(Piperidin-4-yloxy)phenyl]pyrimidin-2-yl}-3,4-dihydro-2H-quinoxaline-1-carboxylic acid (5-carbamoyladamantan-2-yl)amide,
trans-4-[5-(4-(Trifluoromethanesulphonyl)piperazin-1-yl)pyridin-2-yl]-3,4-dihydro-2H-quinoxaline-1-carboxylic acid (5-hydroxyadamantan-2-yl)amide,
trans-4-[5-(4-(tert-Butyl)piperazin-1-yl)pyridin-2-yl]-3,4-dihydro-2H-quinoxaline-1-carboxylic acid (5-hydroxyadamantan-2-yl)amide,
trans-4-[6-(4-(Ethanesulphonyl)piperazin-1-yl)pyridin-3-yl]-3,4-dihydro-2H-quinoxaline-1-carboxylic acid (5-carbamoyladamantan-2-yl)amide,
trans-4-[5-(4-Cyclopropylpiperazin-1-yl)pyridin-2-yl]-3,4-dihydro-2H-quinoxaline-1-carboxylic acid (5-hydroxyadamantan-2-yl)amide,
trans-4-[5-(4-(Cyclobutanesulphonyl)piperazin-1-yl)pyridin-2-yl]-3,4-dihydro-2H-quinoxaline-1-carboxylic acid (5-hydroxyadamantan-2-yl)amide,
trans-4-[5-(4-Acetylpiperazin-1-yl)pyridin-2-yl]-3,4-dihydro-2H-quinoxaline-1-carboxylic acid (5-hydroxyadamantan-2-yl)amide,
trans-4-{4-[4-(1-Ethylpropyl)piperazin-1-yl]phenyl}-3,4-dihydro-2H-quinoxaline-1-carboxylic acid (5-carbamoyladamantan-2-yl)amide, trans-4-{5-[4-(2-Methylpropane-1-sulphonyl)piperazin-1-yl]pyridin-2-yl}-3,4-dihydro-2H-quinoxaline-1-carboxylic acid (5-carbamoyladamantan-2-yl)amide,
trans-4-{5-[4-(3,3,3-Trifluoropropane-1-sulphonyl)piperazin-1-yl]pyridin-2-yl}-3,4-dihydro-2H-quinoxaline-1-carboxylic acid (5-hydroxyadamantan-2-yl)amide,
trans-4-{4-[4-(2,2,2-Trifluoroethyl)piperazin-1-yl]phenyl}-3,4-dihydro-2H-quinoxaline-1-carboxylic acid (5-carbamoyladamantan-2-yl)amide,
trans-4-(4-{4-[2-(2-Methoxyethoxy)ethanesulphonyl]piperazin-1-yl}phenyl)-3,4-dihydro-2H-quinoxaline-1-carboxylic acid (5-carbamoyladamantan-2-yl)amide,
trans-4-{5-[4-(2-Isopropoxyethanesulphonyl)piperazin-1-yl]pyridin-2-yl}-3,4-dihydro-2H-quinoxaline-1-carboxylic acid (5-carbamoyladamantan-2-yl)amide,
4-[5-(4-(Cyclopropylmethanesulphonyl)piperazin-1-yl)pyridin-2-yl]-3,4-dihydro-2H-quinoxaline-1-carboxylic acid (5-hydroxyadamantan-2-yl)amide,
trans-4-[5-(4-(tert-Butyl)piperazin-1-yl)pyridin-2-yl]-3,4-dihydro-2H-quinoxaline-1-carboxylic acid (5-carbamoyladamantan-2-yl)amide,
trans-4-[5-(4-Cyclopropylpiperazin-1-yl)pyridin-2-yl]-3,4-dihydro-2H-quinoxaline-1-carboxylic acid (5-carbamoyladamantan-2-yl)amide,
trans-4-{4-[4-(Tetrahydropyran-4-yl)piperazin-1-yl]phenyl}-3,4-dihydro-2H-quinoxaline-1-carboxylic acid (5-carbamoyladamantan-2-yl)amide,
trans-4-{5-[4-(2-Methoxyethanesulphonyl)piperazin-1-yl]pyridin-2-yl}-3,4-dihydro-2H-quinoxaline-1-carboxylic acid (5-carbamoyladamantan-2-yl)amide,
trans-4-[4-(7-Methanesulphonyl-2,7-diazaspiro[4.4]non-2-yl)phenyl]-3,4-dihydro-2H-quinoxaline-1-carboxylic acid (5-hydroxyadamantan-2-yl)amide,
trans-4-{5-[4-(2,2-Dimethylpropyl)piperazin-1-yl]pyridin-2-yl}-3,4-dihydro-2H-quinoxaline-1-carboxylic acid (5-hydroxyadamantan-2-yl)amide,
trans-4-{5-[4-(2-Methoxy-1-(methoxymethyl)ethyl)piperazin-1-yl]pyridin-2-yl}-3,4-dihydro-2H-quinoxaline-1-carboxylic acid (5-hydroxyadamantan-2-yl)amide,
trans-4-{5-[4-(3-Methoxypropyl)piperazin-1-yl]pyridin-2-yl}-3,4-dihydro-2H-quinoxaline-1-carboxylic acid (5-hydroxyadamantan-2-yl)amide,
trans-4-{5-[4-(3-Methylbutyryl)piperazin-1-yl]pyridin-2-yl}-3,4-dihydro-2H-quinoxaline-1-carboxylic acid (5-hydroxyadamantan-2-yl)amide,
trans-4-[4-(4-(Methanesulphonyl)piperazin-1-yl)phenyl]-3,4-dihydro-2H-quinoxaline-1-carboxylic acid (5-(acetylamino)adamantan-2-yl)amide,
trans-4-{5-[4-(2-Methoxyethanesulphonyl)piperazin-1-yl]pyridin-2-yl}-3,4-dihydro-2H-quinoxaline-1-carboxylic acid (5-hydroxyadamantan-2-yl)amide,
trans-4-{5-[4-(2,2-Dimethylpropionyl)piperazin-1-yl]pyridin-2-yl}-3,4-dihydro-2H-quinoxaline-1-carboxylic acid (5-hydroxyadamantan-2-yl)amide,
trans-4-(4,4-Difluoro-3,4,5,6-tetrahydro-2H-1,3'-bipyridinyl-6'-yl)-3,4-dihydro-2H-quinoxaline-1-carboxylic acid (5-hydroxyadamantan-2-yl)amide,
trans-4-(4-(Pyrrolidin-1-yl)-3,4,5,6-tetrahydro-2H-1,3'-bipyridinyl-6'-yl)-3,4-dihydro-2H-quinoxaline-1-carboxylic acid (5-hydroxyadamantan-2-yl)amide,
trans-4-[5-(5-Cyclopropanesulphonyl-2,5-diazabicyclo[2.2.1]hept-2-yl)pyridin-2-yl]-3,4-dihydro-2H-quinoxaline-1-carboxylic acid (5-hydroxyadamantan-2-yl)amide,
trans-4-{6-[4-(5-Hydroxyadamantan-2-ylcarbamoyl)-3,4-dihydro-2H-quinoxalin-1-yl]-pyridin-3-yl}piperazine-1-carboxylic acid tert-butyl ester,
trans-4-{4-[4-(2-Methoxyethyl)piperazin-1-yl]phenyl}-3,4-dihydro-2H-quinoxaline-1-carboxylic acid (5-carbamoyladamantan-2-yl)amide,
trans-4-[5-(4-(Methanesulphonyl)piperazin-1-yl)-3-methylpyridin-2-yl]-3,4-dihydro-2H-quinoxaline-1-carboxylic acid (5-carbamoyladamantan-2-yl)amide,
trans-2-(4-{4-[4-(5-Carbamoyladamantan-2-ylcarbamoyl)-3,4-dihydro-2H-quinoxalin-1-yl]-phenyl}piperazin-1-yl)-2-methylpropionic acid,
trans-4-(4-(tert-Butyl)-3,4,5,6-tetrahydro-2H-1,3'-bipyridinyl-6'-yl)-3,4-dihydro-2H-quinoxaline-1-carboxylic acid (5-carbamoyladamantan-2-yl)amide,
trans-4-(4-(Pyrrolidin-1-yl)-3,4,5,6-tetrahydro-2H-1,3'-bipyridinyl-6'-yl)-3,4-dihydro-2H-quinoxaline-1-carboxylic acid (5-carbamoyladamantan-2-yl)amide,
trans-4-[5-(4-(Ethanesulphonyl)piperazin-1-yl)pyridin-2-yl]-3,4-dihydro-2H-quinoxaline-1-carboxylic acid (5-carbamoyladamantan-2-yl)amide,
trans-4-[5-(4-(Methanesulphonyl)piperazin-1-yl)-6-methylpyridin-2-yl]-3,4-dihydro-2H-quinoxaline-1-carboxylic acid (5-carbamoyladamantan-2-yl)amide,
trans-4-(4,4-Difluoro-3,4,5,6-tetrahydro-2H-1,3'-bipyridinyl-6'-yl)-3,4-dihydro-2H-quinoxaline-1-carboxylic acid (5-carbamoyladamantan-2-yl)amide,
trans-4-{4-[4-(2-Hydroxy-1,1-dimethylethyl)piperazin-1-yl]phenyl}-3,4-dihydro-2H-quinoxaline-1-carboxylic acid (5-carbamoyladamantan-2-yl)amide,
trans-4-{5-[4-(Propane-2-sulphonyl)piperazin-1-yl]-pyridin-2-yl}-3,4-dihydro-2H-quinoxaline-1-carboxylic acid (5-carbamoyladamantan-2-yl)amide,
trans-4-(5-(Morpholin-4-yl)-pyridin-2-yl)-3,4-dihydro-2H-quinoxaline-1-carboxylic acid (5-carbamoyladamantan-2-yl)amide,
trans-4-[5-(4-(Methanesulphonyl)piperazin-1-yl)-4-methylpyridin-2-yl]-3,4-dihydro-2H-quinoxaline-1-carboxylic acid (5-carbamoyladamantan-2-yl)amide,
trans-4-(4-Trifluoromethyl-3,4,5,6-tetrahydro-2H-1,3'-bipyridinyl-6'-yl)-3,4-dihydro-2H-quinoxaline-1-carboxylic acid (5-carbamoyladamantan-2-yl)amide,
trans-4-(4-(tert-Butyl)-3,4,5,6-tetrahydro-2H-1,3'-bipyridinyl-6'-yl)-3,4-dihydro-2H-quinoxaline-1-carboxylic acid (5-hydroxyadamantan-2-yl)amide,
trans-4-[5-(4-Isobutylpiperazin-1-yl)pyridin-2-yl]-3,4-dihydro-2H-quinoxaline-1-carboxylic acid (5-carbamoyladamantan-2-yl)amide,
trans-4-[5-(4-(Cyclopropylmethyl)piperazin-1-yl)pyridin-2-yl]-3,4-dihydro-2H-quinoxaline-1-carboxylic acid (5-carbamoyladamantan-2-yl)amide,
trans-4-{5-[4-(2,2,2-Trifluoroethyl)piperazin-1-yl]pyridin-2-yl}-3,4-dihydro-2H-quinoxaline-1-carboxylic acid (5-carbamoyladamantan-2-yl)amide,
trans-4-[5-(4-(tert-Butyl)piperazin-1-yl)pyridin-2-yl]-3,4-dihydro-2H-quinoxaline-1-carboxylic acid (5-(hydroxymethyl)adamantan-2-yl)amide,
trans-4-[5-(4-(tert-Butyl)piperazin-1-yl)pyridin-2-yl]-6,7-difluoro-3,4-dihydro-2H-quinoxaline-1-carboxylic acid (5-carbamoyladamantan-2-yl)amide,
trans-4-{5-[4-(2,2-Dimethylpropionyl)piperazin-1-yl]pyridin-2-yl}-3,4-dihydro-2H-quinoxaline-1-carboxylic acid (5-carbamoyladamantan-2-yl)amide,
trans-4-[5-(4-(tert-Butyl)piperazin-1-yl)pyrimidin-2-yl]-3,4-dihydro-2H-quinoxaline-1-carboxylic acid (5-carbamoyladamantan-2-yl)amide,
trans-4-[5-(4-(Cyclopropanesulphonyl)piperazin-1-yl)pyridin-2-yl]-3,4-dihydro-2H-quinoxaline-1-carboxylic acid (5-cyanoadamantane-2-yl)amide, trans-4-[5-(1-(tert-Butyl)piperidin-4-yloxy)pyridin-2-yl]-3,4-dihydro-2H-quinoxaline-1-carboxylic acid (5-carbamoyladamantan-2-yl)amide,
trans-{6'-[4-(5-Carbamoyladamantan-2-ylcarbamoyl)-3,4-dihydro-2H-quinoxalin-1-yl]-3,4,5,6-tetrahydro-2H-1,3'-bipyridinyl-4-yl}-acetic acid methyl ester,
trans-6'-[4-(5-Carbamoyladamantan-2-ylcarbamoyl)-3,4-dihydro-2H-quinoxalin-1-yl]3,4,5,6-tetrahydro-2H-1,3'-bipyridinyl-4-carboxylic acid ethyl ester,
trans-4-[5-(4-Isopropylpiperazin-1-yl)pyridin-2-yl]-3,4-dihydro-2H-quinoxaline-1-carboxylic acid (5-carbamoyladamantan-2-yl)amide,
trans-4-(1'-(tert-Butyl)-1',2',3',4',5',6'-hexahydro-3,4'-bipyridinyl-6-yl)-3,4-dihydro-2H-quinoxaline-1-carboxylic acid (5-carbamoyladamantan-2-yl)amide,
trans-{6'-[4-(5-Carbamoyladamantan-2-ylcarbamoyl)-3,4-dihydro-2H-quinoxalin-1-yl]-3,4,5,6-tetrahydro-2H-1,3'-bipyridinyl-4-yl}acetic acid,
trans-6'-[4-(5-Carbamoyladamantan-2-ylcarbamoyl)-3,4-dihydro-2H-quinoxalin-1-yl]-3,4,5,6-tetrahydro-2H-1,3'-bipyridinyl-4-carboxylic acid,
trans-2-(4-{6-[4-(5-Carbamoyladamantan-2-ylcarbamoyl)-3,4-dihydro-2H-quinoxalin-1-yl]-pyridin-3-yl}-piperazin-1-yl)-2-methylpropionic acid ethyl ester,
trans-4-(4,4-Dimethyl-3,4,5,6-tetrahydro-2H-1,3'-bipyridinyl-6'-yl)-3,4-dihydro-2H-quinoxaline-1-carboxylic acid (5-carbamoyladamantan-2-yl)amide,
trans-4-{5-[4-(2,2-Difluorocyclopropylmethyl)piperazin-1-yl]pyridin-2-yl}-3,4-dihydro-2H-quinoxaline-1-carboxylic acid (5-carbamoyladamantan-2-yl)amide,
trans-4-{5-[4-(Difluoromethanesulphonyl)piperazin-1-yl]pyridin-2-yl}-3,4-dihydro-2H-quinoxaline-1-carboxylic acid (5-carbamoyladamantan-2-yl)amide,
trans-4-{5-[4-(3,3,3-Trifluoropropyl)piperazin-1-yl]pyridin-2-yl}-3,4-dihydro-2H-quinoxaline-1-carboxylic acid (5-carbamoyladamantan-2-yl)amide,
trans-4-{5-[4-(2-(Methanesulphonyl)ethyl)piperazin-1-yl]pyridin-2-yl}-3,4-dihydro-2H-quinoxaline-1-carboxylic acid (5-carbamoyladamantan-2-yl)amide,
trans-4-{5-[4-(1-Ethylpropyl)piperazin-1-yl]pyridin-2-yl}-3,4-dihydro-2H-quinoxaline-1-carboxylic acid (5-carbamoyladamantan-2-yl)amide,
trans-4-[5-(1,1-Dioxo-1$\lambda^6$-thiomorpholin-4-yl)pyridin-2-yl]-3,4-dihydro-2H-quinoxaline-1-carboxylic acid (5-carbamoyladamantan-2-yl)amide,
trans-4-{5-[4-(Tetrahydropyran-4-yl)piperazin-1-yl]pyridin-2-yl}-3,4-dihydro-2H-quinoxaline-1-carboxylic acid (5-carbamoyladamantan-2-yl)amide,
trans-4-[5-(4-(Cyclopropanesulphonyl)piperazin-1-yl)-3-methylpyridin-2-yl]-3,4-dihydro-2H-quinoxaline-1-carboxylic acid (5-carbamoyladamantan-2-yl)amide,
trans-4-{5-[4-(2-Hydroxy-1,1-dimethylethyl)-piperazin-1-yl]pyridin-2-yl}-3,4-dihydro-2H-quinoxaline-1-carboxylic acid (5-carbamoyladamantan-2-yl)amide,
trans-4-{5-[4-(2-Fluoro-1,1-dimethylethyl)piperazin-1-yl]pyridin-2-yl}-3,4-dihydro-2H-quinoxaline-1-carboxylic acid (5-carbamoyladamantan-2-yl)amide, or
trans-4-[5-(4-(Trifluoromethanesulphonyl)piperazin-1-yl)pyridin-2-yl]-3,4-dihydro-2H-quinoxaline-1-carboxylic acid (5-carbamoyladamantan-2-yl)amide;
or a pharmaceutically acceptable salt thereof.

16. A pharmaceutical composition comprising the compound according to claim 1 or a pharmaceutically acceptable salt thereof, in combination with at least one pharmaceutically acceptable excipient.

17. A process for preparing the compound according to claim 1, comprising reacting a compound of formula (IV):

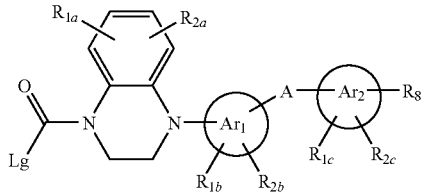

(IV)

wherein A, $Ar_1$, $Ar_2$, $R_{1a}$, $R_{1b}$, $R_{1c}$, $R_{2a}$, $R_{2b}$, $R_{2c}$ and $R_8$ are as defined in claim 1, and Lg is halogen or an activated hydroxy group selected from mesyl, tosyl, triflyl, acetyl and para-nitrophenyl, with a compound of formula (V):

(V)

wherein $R_3$ and $R_4$ are as defined claim 1.

18. A process for preparing the compound according to claim 1, wherein A is a bond, comprising reacting a compound of formula (XXVII):

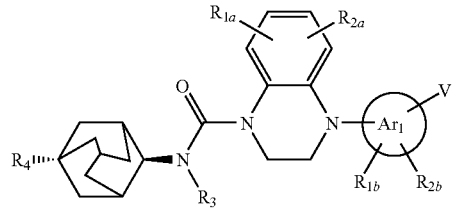

(XXVII)

wherein $Ar_1$, $R_{1a}$, $R_{1b}$, $R_{2a}$, $R_{2b}$, $R_3$ and $R_4$ are as defined in claim 1, and V is halogen or an activated hydroxy group selected from mesyl, tosyl, triflyl, acetyl and para-nitrophenyl, with a compound of formula (XVI):

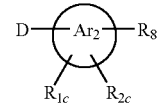

(XVI)

wherein $Ar_2$, $R_{1c}$, $R_{2c}$, and $R_8$ are as defined in claim 1, and D is a boron compound, a tin compound or a zinc compound, in the presence of a palladium catalyst, and a base.

19. A process for preparing the compound according to claim 1, wherein $R_4$ is $-CONR_6R_7$, comprising reacting a compound of formula (XXXIX):

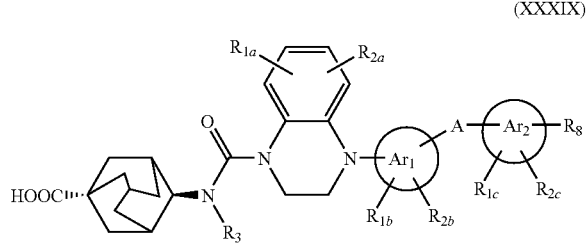

(XXXIX)

wherein A, Ar$_1$, Ar$_2$, R$_{1a}$, R$_{1b}$, R$_{1c}$, R$_{2a}$, R$_{2b}$, R$_{2c}$, R$_3$ and R$_8$ are as defined in claim 1, with a compound of formula (XXXVI), H—NR$_6$R$_7$, wherein R$_6$ and R$_7$ are as defined in claim 1, in the presence of dicyclohexylcarbodiimide, 1-(3-dimethylaminopropyl)-3-ethylcarbodiimide hydrochloride or bromotripyrrolidinophosphonium hexafluorophosphate, and a base.

20. A process for preparing the compound according to claim 1, comprising reacting a compound of formula (XLII):

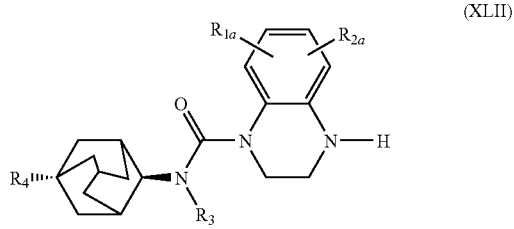

(XLII)

wherein R$_{1a}$, R$_{2a}$, R$_3$ and R$_4$ are as defined in claim 1, with a compound of formula (VII):

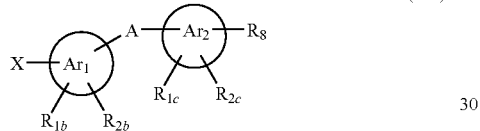

(VII)

wherein A, Ar$_1$, Ar$_2$, R$_{1b}$, R$_{1c}$, R$_{2b}$, R$_{2c}$ and R$_8$ are as defined in claim 1, and X is halogen or an activated hydroxy group selected from mesyl, tosyl, triflyl, acetyl and para-nitrophenyl, in the presence of a palladium catalyst and a base.

21. A process for preparing the compound according to claim 1, wherein Ar$_2$ is a piperazine group, A is a single bond directly connected to one of the two nitrogens of the piperazine and R$_{1c}$ is connected to the other nitrogen atom of the piperazine, comprising reacting a compound of formula (LII):

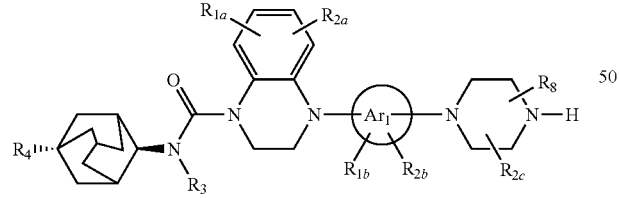

(LII)

wherein Ar$_1$, R$_{1a}$, R$_{1b}$, R$_{2a}$, R$_{2b}$, R$_{2c}$, R$_3$, R$_4$ and R$_8$ are as defined in claim 1, with a compound of formula (LIII), Lg-R$_{1c}$, where Lg is halogen or an activated hydroxy group selected from mesyl, tosyl, triflyl, acetyl and para-nitrophenyl, in the presence of a base, or with a compound (LIV), O—R$_{1c}$, in the presence of sodium borohydride, sodium triacetoxyborohydride, sodium cyanoborohydride, lithium aluminum hydride or diisobutyl aluminum hydride.

22. A process for preparing the compound according to claim 1, wherein R$_4$ is a halogen atom, comprising reacting a compound of formula (LVI):

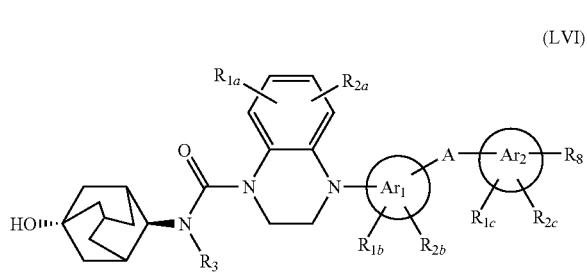

(LVI)

wherein A, Ar$_1$, Ar$_2$, R$_{1a}$, R$_{1b}$, R$_{1c}$, R$_{2a}$, R$_{2b}$, R$_{2c}$, R$_3$ and R$_8$ are as defined in claim 1, with (diethylamino)sulfur trifluoride or bis(2-methoxyethyl)aminosulphur trifluoride.

23. A compound of formula (II) or formula (IV):

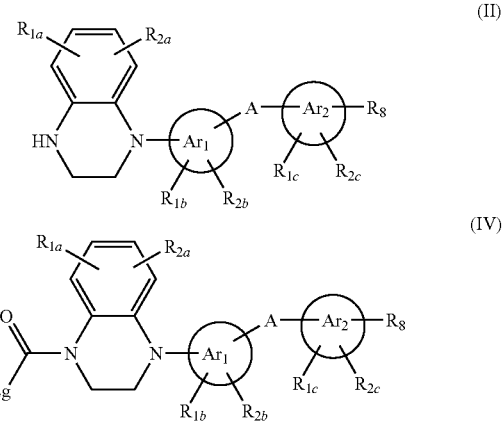

(II)

(IV)

wherein A, Ar$_1$, Ar$_2$, R$_{1a}$, R$_{1b}$, R$_{1c}$, R$_{2a}$, R$_{2b}$, R$_{2c}$ and R$_8$ are as defined in claim 1, and Lg is halogen or an activated hydroxy group selected from mesyl, tosyl, triflyl, acetyl and para-nitrophenyl.

24. A compound of formula (XXVII):

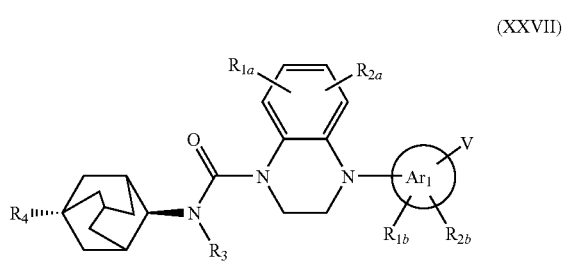

(XXVII)

wherein Ar$_1$, R$_{1a}$, R$_{1b}$, R$_{2a}$, R$_{2b}$, R$_3$ and R$_4$ are as defined in claim 1, and V is halogen or an activated hydroxy group selected from mesyl, tosyl, triflyl, acetyl and para-nitrophenyl.

* * * * *

UNITED STATES PATENT AND TRADEMARK OFFICE
CERTIFICATE OF CORRECTION

PATENT NO. : 8,211,892 B2  
APPLICATION NO. : 12/843124  
DATED : July 3, 2012  
INVENTOR(S) : Alain Jean Braun et al.

Page 1 of 1

It is certified that error appears in the above-identified patent and that said Letters Patent is hereby corrected as shown below:

In the Claims:

Column 155, line 24, claim 1 should read: A is a bond, oxygen atom or $-O-CH_2-$;

Signed and Sealed this  
Fourteenth Day of May, 2013

Teresa Stanek Rea  
*Acting Director of the United States Patent and Trademark Office*